(12) United States Patent
Cho et al.

(10) Patent No.: US 7,811,682 B2
(45) Date of Patent: *Oct. 12, 2010

(54) COMPOUND AND ORGANIC LIGHT EMITTING DEVICE USING THE SAME

(75) Inventors: Wook Dong Cho, Daejeon Metropolitan (KR); Ji Eun Kim, Daejeon Metropolitan (KR); Byung Sun Jeon, Seoul (KR); Seok Hee Yoon, Daejeon Metropolitan (KR); Jae Min Moon, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 808 days.

This patent is subject to a terminal disclaimer.

(21) Appl. No.: 11/658,994

(22) PCT Filed: Sep. 24, 2005

(86) PCT No.: PCT/KR2005/003181

§ 371 (c)(1),
(2), (4) Date: Jan. 31, 2007

(87) PCT Pub. No.: WO2006/033564

PCT Pub. Date: Mar. 30, 2006

(65) Prior Publication Data

US 2008/0303434 A1    Dec. 11, 2008

(30) Foreign Application Priority Data

Sep. 24, 2004    (KR) .................... 10-2004-0077214

(51) Int. Cl.
H01L 51/54    (2006.01)
C09K 11/06    (2006.01)

(52) U.S. Cl. ................ 428/690; 428/917; 313/504; 313/506; 252/301.16; 257/40; 257/E51.032; 556/408; 546/15; 546/16; 546/18

(58) Field of Classification Search .............. 556/408
See application file for complete search history.

(56) References Cited

U.S. PATENT DOCUMENTS

| | | | | |
|---|---|---|---|---|
| 6,329,082 | B1 * | 12/2001 | Kreuder et al. | 428/690 |
| 2003/0168970 | A1 * | 9/2003 | Tominaga et al. | 313/504 |
| 2004/0219386 | A1 | 11/2004 | Thoms | |

FOREIGN PATENT DOCUMENTS

| | | |
|---|---|---|
| JP | 2008-511155 | 4/2008 |
| JP | 2008-511156 | 4/2008 |
| JP | 2008-511161 | 4/2008 |
| JP | 2008-511162 | 4/2008 |
| WO | WO 93/09074 | 5/1993 |
| WO | WO 2004/020371 A1 | 3/2004 |
| WO | WO 2006/003564 | 3/2006 |
| WO | WO 2006/080637 | 8/2006 |
| WO | WO 2006/080638 | 8/2006 |
| WO | WO 2006/080645 | 8/2006 |
| WO | WO 2006/080646 | 8/2006 |

OTHER PUBLICATIONS

W. Tritschler, *Synthese un Konformation von Spiroacridanen*, Chem. Ber. 117, pp. 2703-2713; 1984.

* cited by examiner

*Primary Examiner*—D. L Tarazano
*Assistant Examiner*—Michael Wilson
(74) *Attorney, Agent, or Firm*—McKenna Long & Aldridge LLP

(57) ABSTRACT

Disclosed is a novel compound which is capable of significantly improving a lifespan, efficiency, and electrochemical and thermal stabilities of an organic light emitting device, the production of the compound, and an organic light emitting device in which the compound is contained in an organic compound layer.

10 Claims, 1 Drawing Sheet

[Fig. 1]
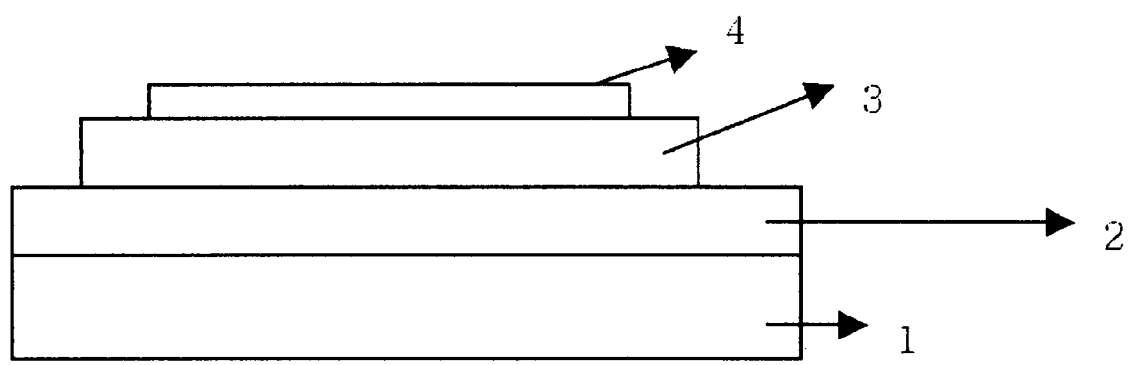
[Fig. 2]
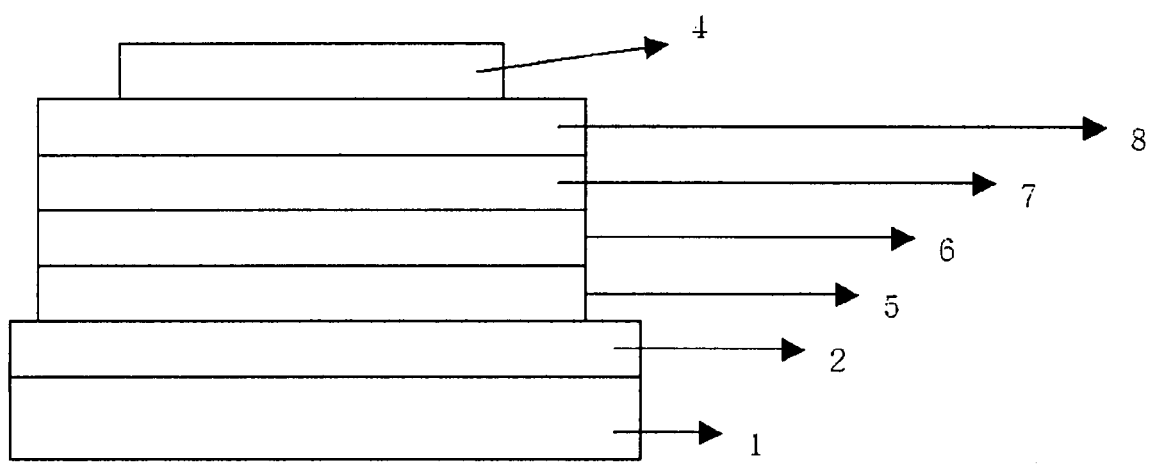

COMPOUND AND ORGANIC LIGHT EMITTING DEVICE USING THE SAME

This application claims priority to International Application No. PCT/KR2005/003181, filed on Sep. 24, 2005, and Korean Patent Application No. 10-2004-0077214, filed on Sep. 24, 2004, which are hereby incorporated by reference in their entirety.

TECHNICAL FIELD

The present invention relates to a novel compound which is capable of significantly improving a lifespan, efficiency, and electrochemical and thermal stabilities of an organic light emitting device, the production of the compound, and an organic light emitting device in which the compound is contained in an organic compound layer.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typically comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemically stable when it is oxidized, is mostly used as the hole injection material or the hole transport material. Meanwhile, an organic material having an n-type property, which is easily reduced and is electrochemically stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

DISCLOSURE OF INVENTION

Technical Problem

Accordingly, there is a need to develop an organic material having the above-mentioned requirements in the art.

Therefore, the present inventors provide an organic material which is capable of satisfying conditions required of a material which can be used for an organic light emitting device, for example, a proper energy level, electrochemical stability, and thermal stability, and which has a chemical structure capable of playing various roles required for the organic light emitting device, depending on a substituent group.

Furthermore, the present invention aims to provide the production of a novel organic light emitting material found by the present inventors, and an organic light emitting device using the same.

Technical Solution

The present invention provides a compound of Formula 1.

The present invention provides a method of producing the compound of Formula 1.

The present invention provides an organic light emitting device which comprises a first electrode, organic material layer(s) comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced:

[Formula 1]

(Structure showing a tricyclic system with nitrogen N at top and X at bottom center, with substituents R1 through R17 positioned around the ring system: R10, R9, R8 at top; R11, R7 on upper sides; R12, R6 on middle sides; R14, R13, R5, R4 around X; R15, R3 on lower sides; R16, R17, R1, R2 at bottom.)

In Formula 1, X is C or Si.

R1 to R8, and R10 to R17 are each independently selected from the group consisting of hydrogen; an alkyl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an alkoxy group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an alkenyl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an aryl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an arylamine group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; a hetero arylamine group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; a heterocyclic group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group and which includes O, N, or S as a heteroatom; an amino group, which is substituted with at least one substituent group selected from the group consisting of an alkyl group, an alkenyl group, a substituted or unsubstituted aryl group, a substituted or unsubstituted arylalkyl group, and a substituted or unsubstituted arylalkenyl group; a nitrile group; a nitro group; a halogen group; an amide group; and an ester group. They may form aliphatic or hetero condensation rings along with adjacent groups.

R9 is independently selected from the group consisting of hydrogen; an alkyl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an alkenyl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an aryl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; and a heterocyclic group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group and which includes O, N, or S as a heteroatom.

In connection with this, carbon at an ortho-position of the aryl or heterocyclic group and R8 or R10 independently may form a condensation ring along with a group selected from the group consisting of O, S, NR, PR, C=O, CRR', and SiRR', with the proviso that R9 is the substituted or unsubstituted aryl group or the substituted or unsubstituted heterocyclic group, and R and R' are each independently or collectively selected from the group consisting of hydrogen, oxygen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, and an ester group. R and R' may form a condensation ring to form a spiro compound.

A detailed description will be given of the substituent groups of Formula 1.

The carbon number of the alkyl, alkoxy, and alkenyl groups of R1 to R17 of Formula 1 is preferably 1-20.

Illustrative, but non-limiting, examples of the aryl group of R1 to R17 of Formula 1 include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the arylamine group of R1 to R17 of Formula 1 include a diphenylamine group, a dinaphthylamine group, a dibiphenylamine group, a phenylnaphthylamine group, a phenyldiphetylamine group, a ditolylamine group, a phenyltolylamine group, a carbazolyl group, and a triphenylamine group.

Illustrative, but non-limiting, examples of the heterocyclic group of R1 to R17 of Formula 1 include a thiophenyl group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

In a preferable example of the compound of Formula 1, any one of R1 to R4 and/or any one of R14 to R17 is the arylamine group, which is substituted or unsubstituted with at least one substituent group selected from the group consisting of the halogen group, the alkyl group, the alkenyl group, the alkoxy group, the substituted or unsubstituted arylamine group, the substituted or unsubstituted aryl group, the substituted or unsubstituted arylalkyl group, the substituted or unsubstituted arylalkenyl group, the substituted or unsubstituted heterocyclic group, the nitrile group, and the acetylene group.

According to a preferred embodiment of the present invention, R9 of Formula 1 is a substituted or unsubstituted aryl group or a substituted or unsubstituted heterocyclic group.

According to another preferred embodiment of the present invention, R9 of Formula 1 is a substituted or unsubstituted aryl or a substituted or unsubstituted heterocyclic group, and carbon at the ortho-position of the aryl or heterocyclic group and R8 or R10 form a condensation ring along with the group selected from the group consisting of O, S, NR, PR, C=O, CRR', and SiRR', with the proviso that R9 is the substituted or unsubstituted aryl group or the substituted or unsubstituted heterocyclic group (R and R' are as defined in Formula 1).

According to still another preferred embodiment of the present invention, R9 of Formula 1 is a substituted or unsubstituted aryl group or a substituted or unsubstituted heterocyclic group, and carbon at the ortho-position of the aryl or heterocyclic group and R8, and carbon at the ortho-position of the aryl or heterocyclic group and R10 form the condensation ring along with the group selected from the group consisting of O, S, NR, PR, C=O, CRR', and SiRR' (R and R' are as defined in Formula 1).

According to the preferred embodiment of the present invention, illustrative, but non-limiting, examples of the compound of Formula 1 include compounds of the following Formulae 2 to 119.

[Formulae 2 to 119]

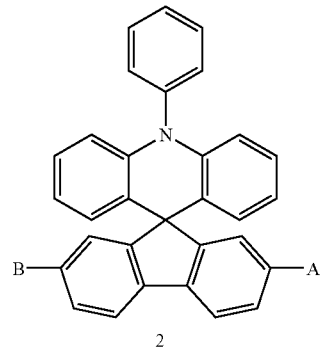

2

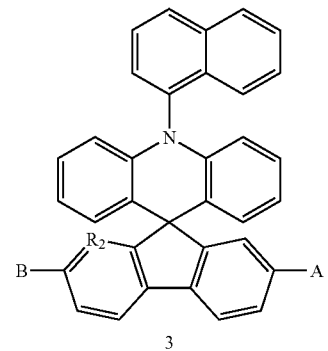

3

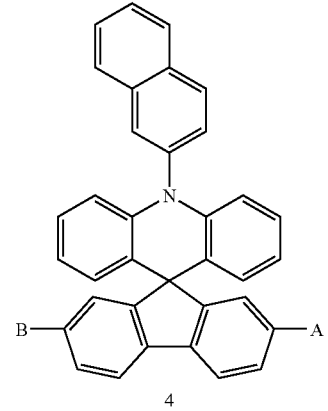

4

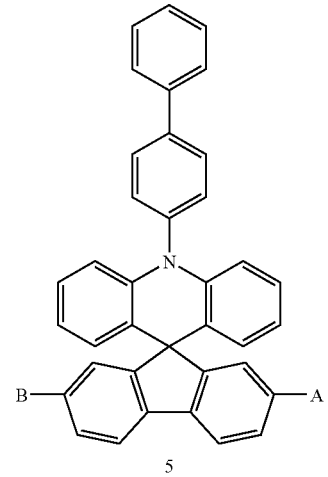

5

-continued

-continued
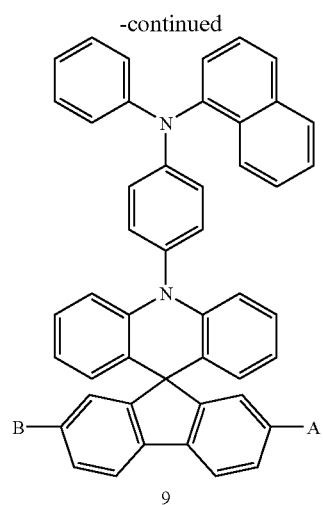
9
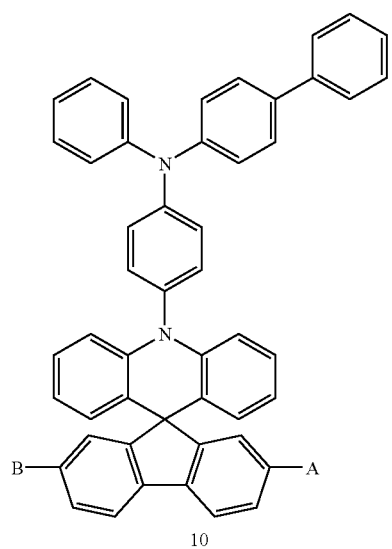
10
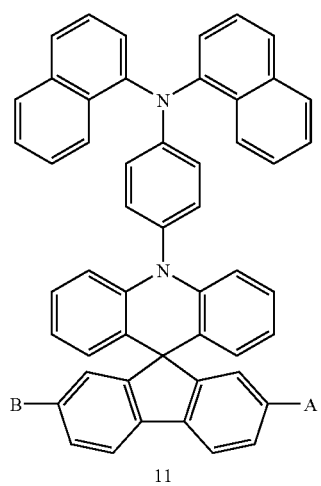
11
-continued
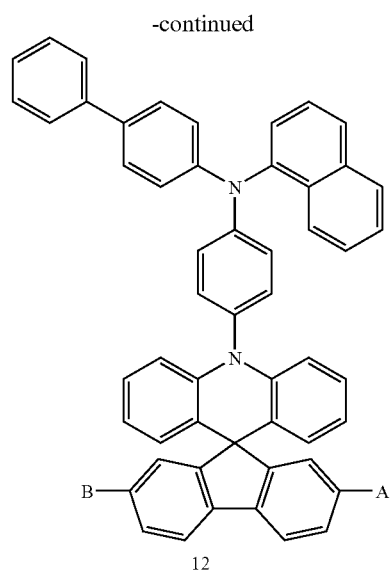
12
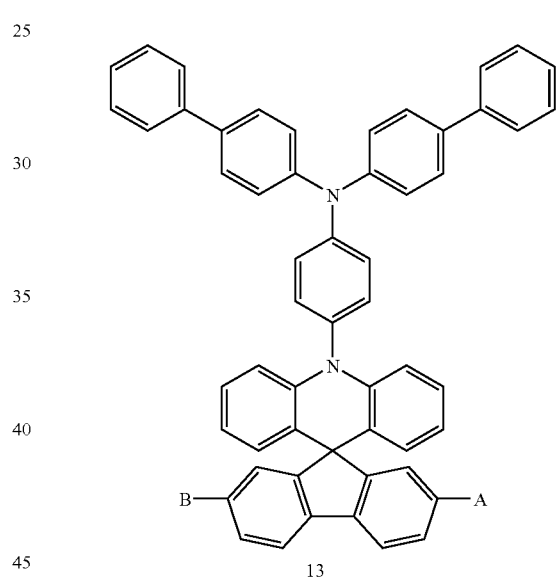
13
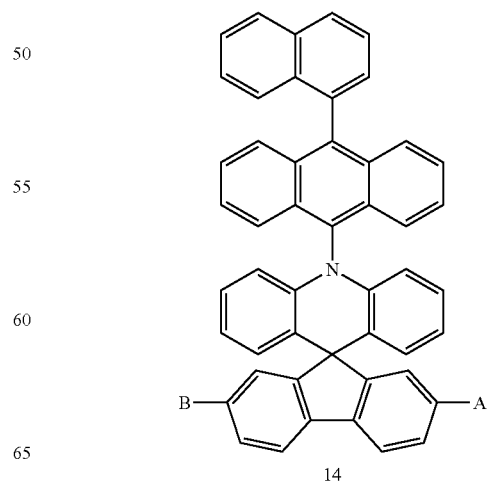
14

-continued
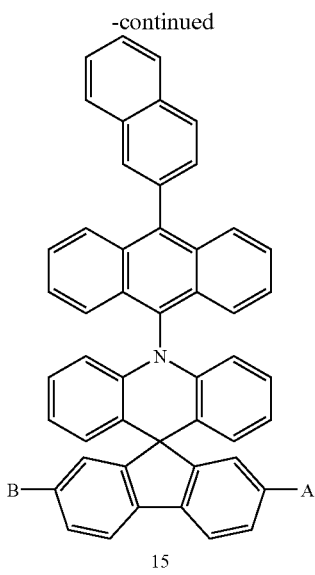
15
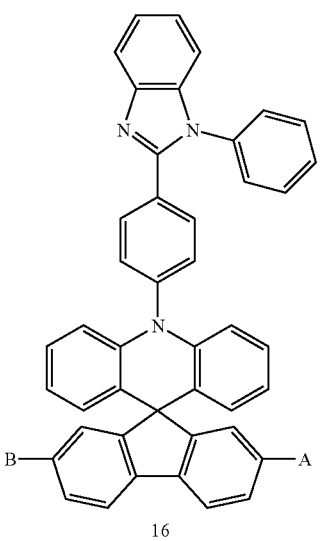
16
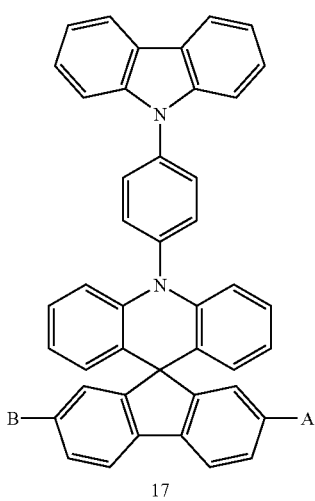
17
-continued
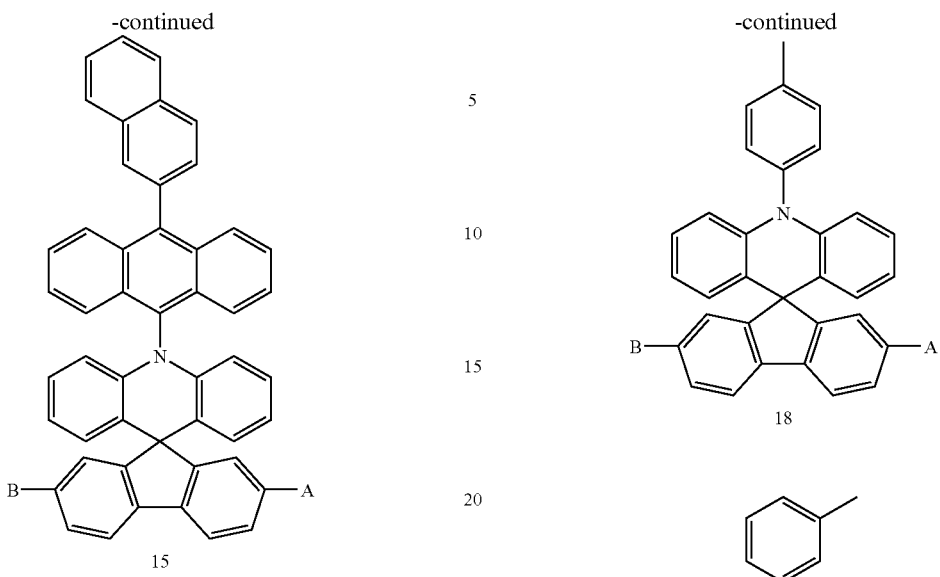
18
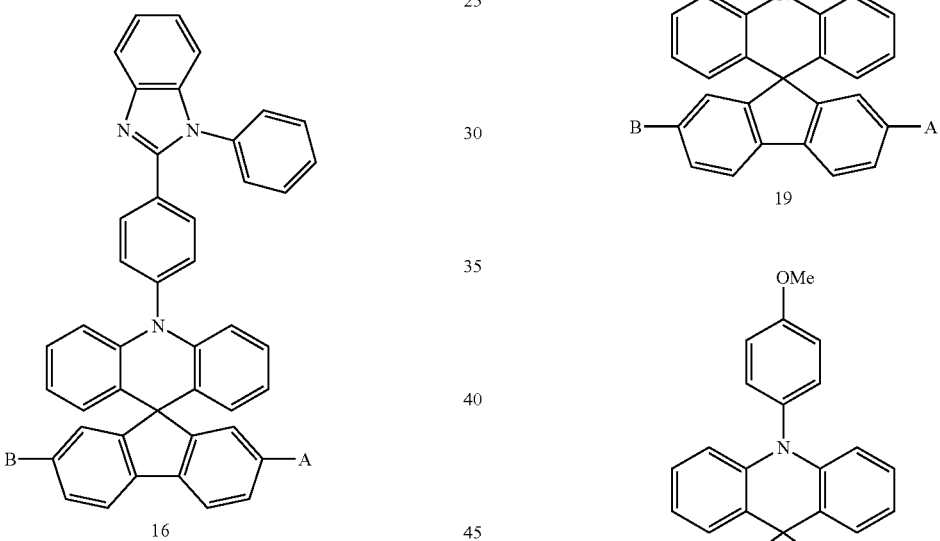
19
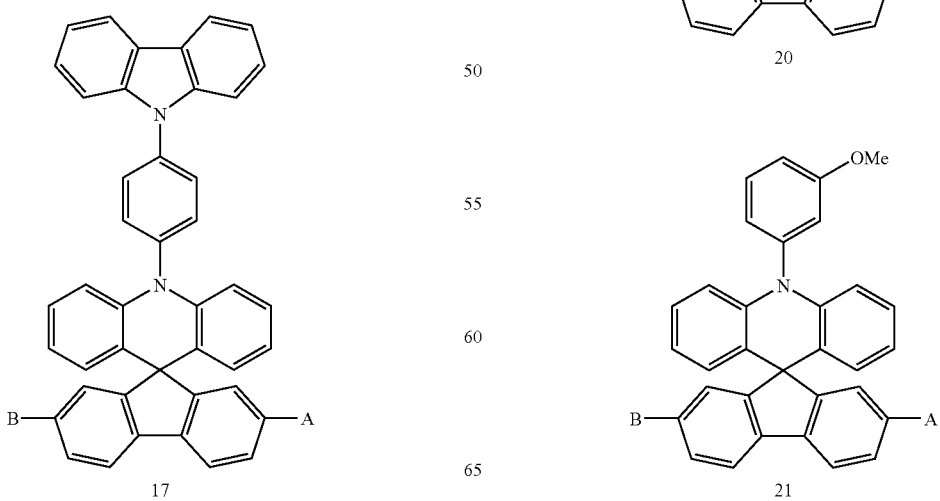
20
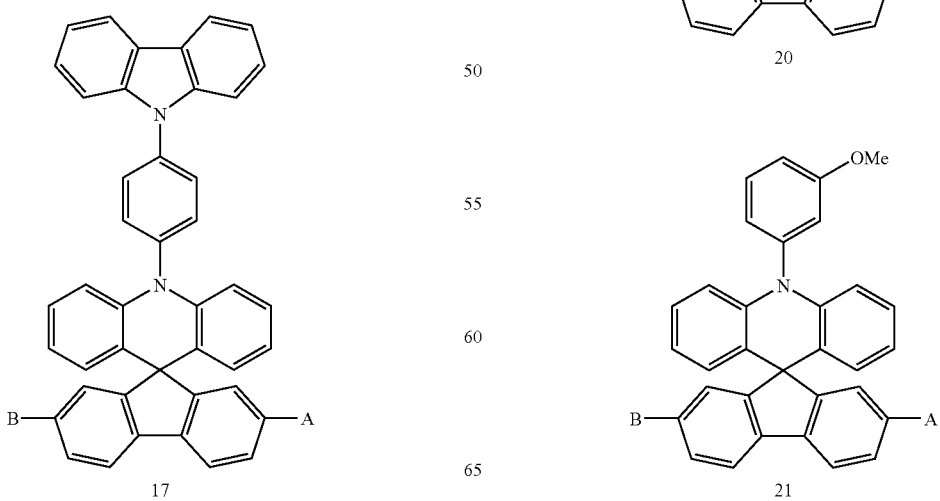
21

-continued
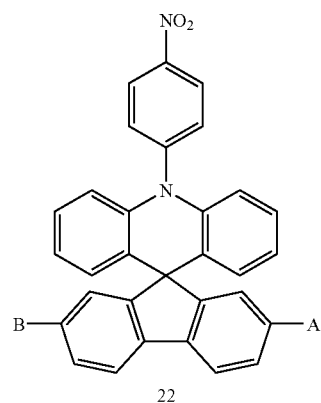
22
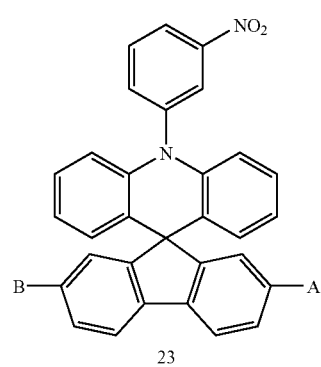
23
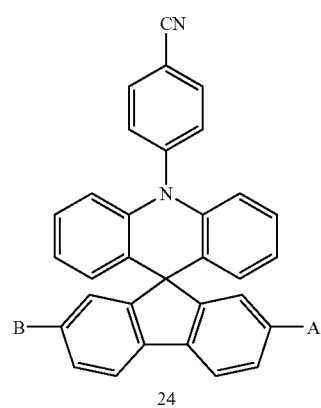
24
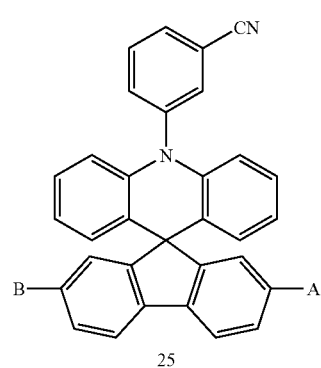
25
-continued
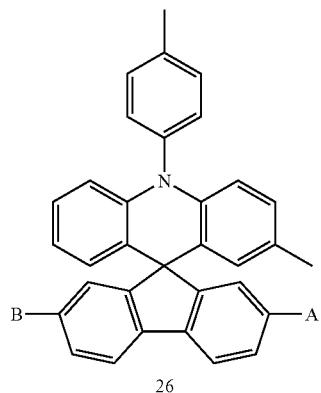
26
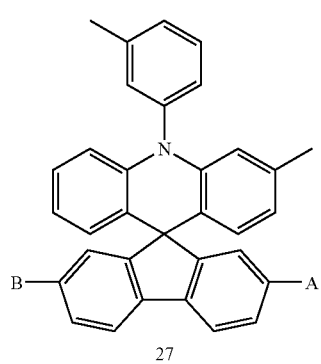
27
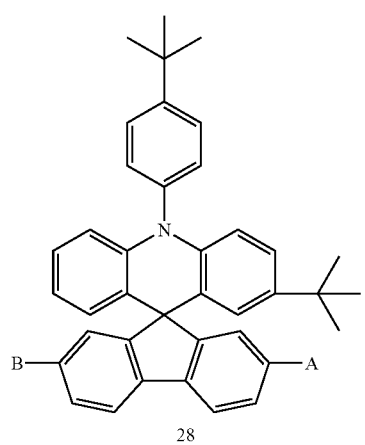
28
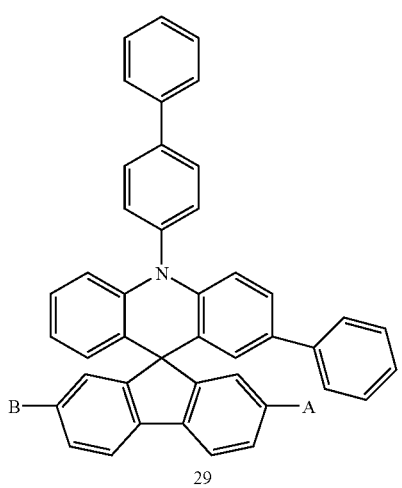
29

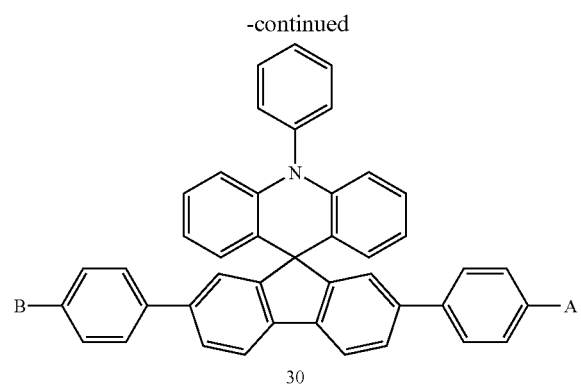
30
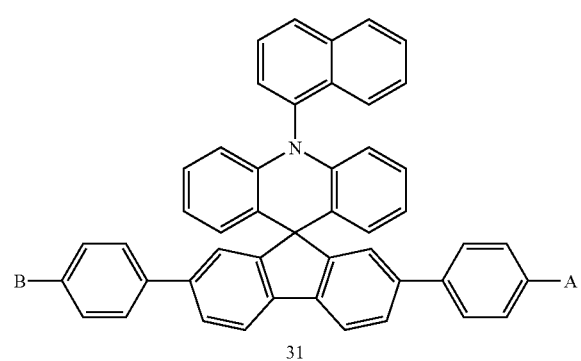
31
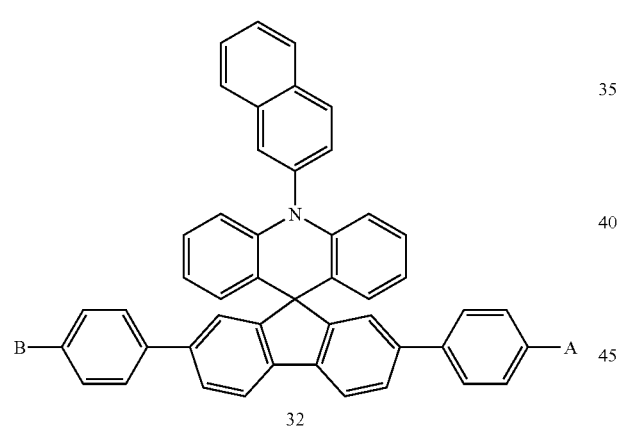
32
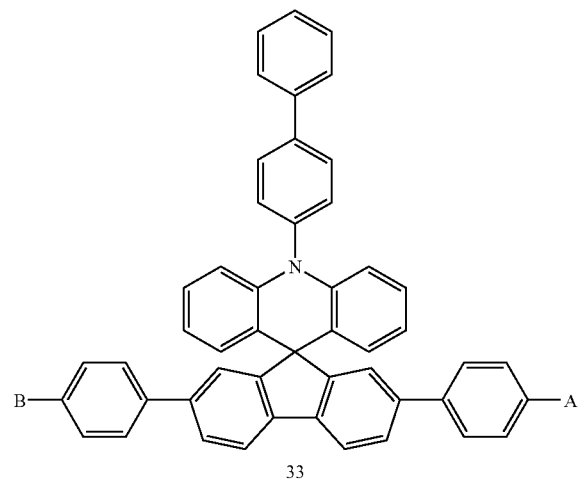
33
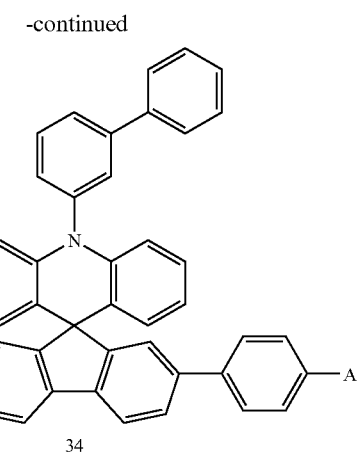
34
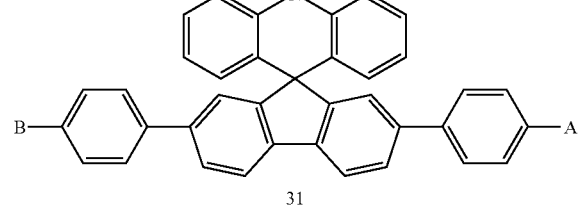
35
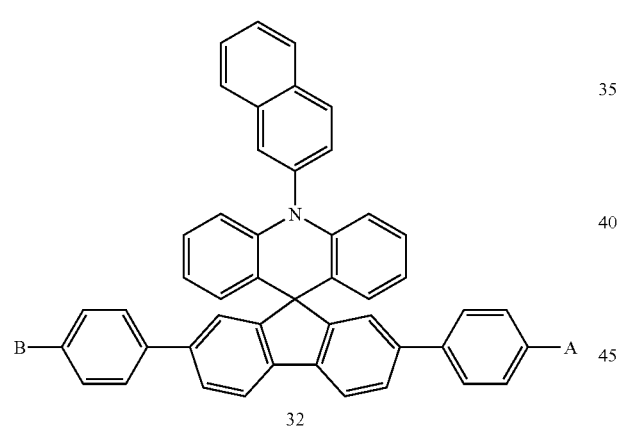
36
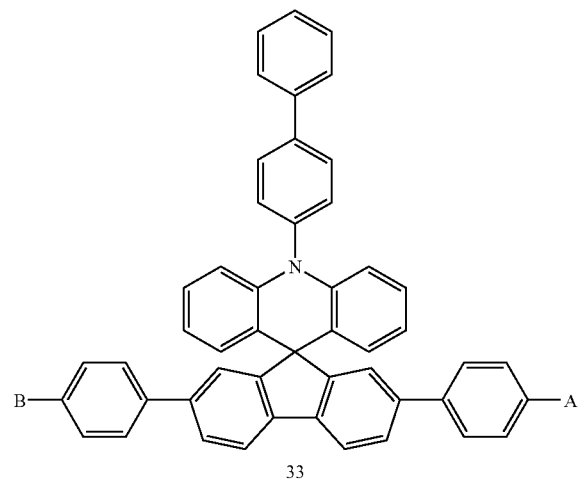
37

-continued
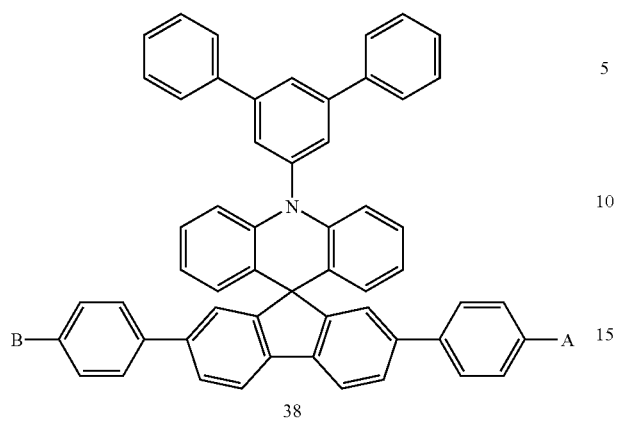
38
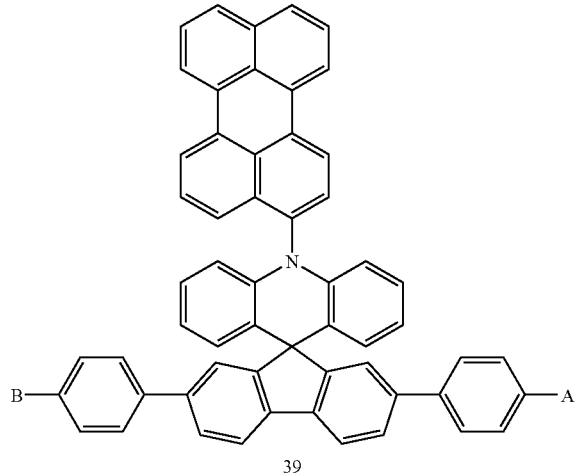
39
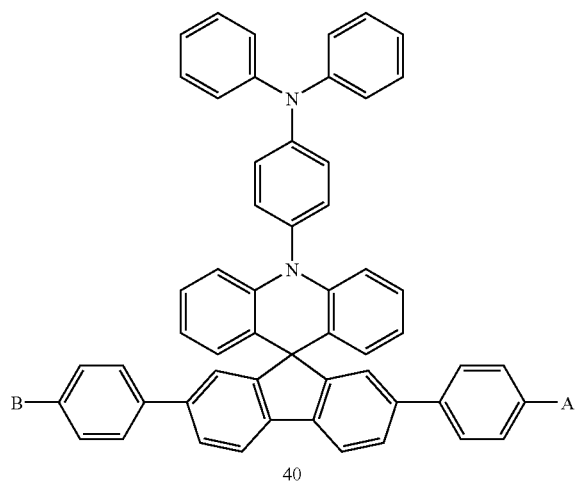
40
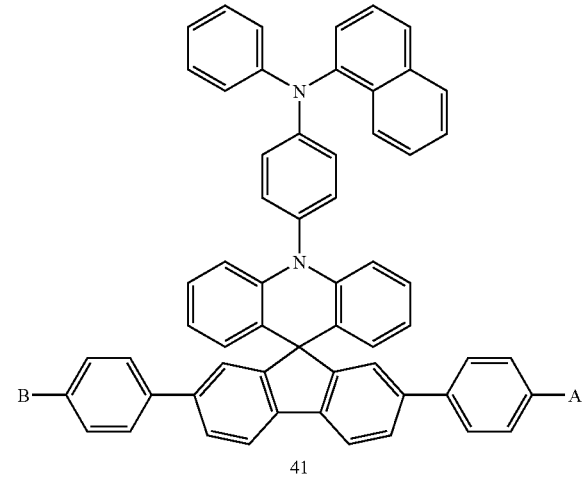
41
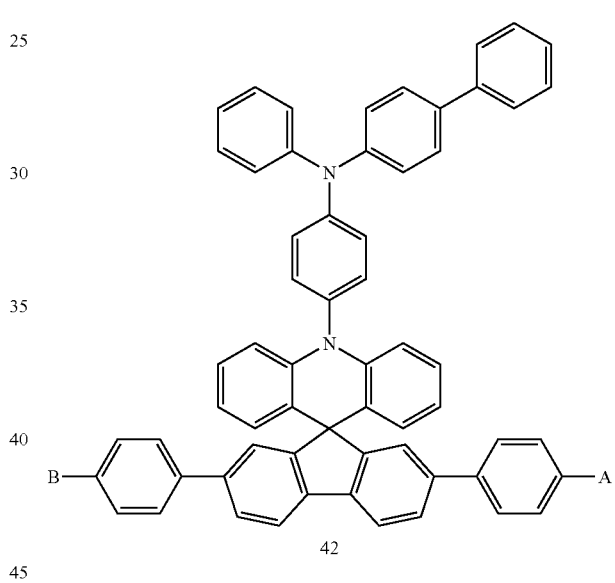
42
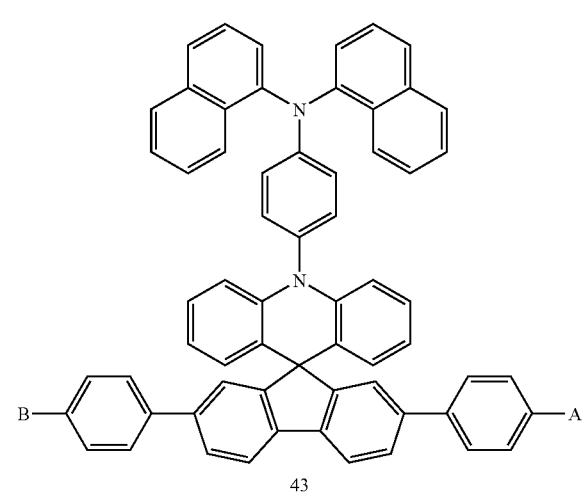
43

-continued
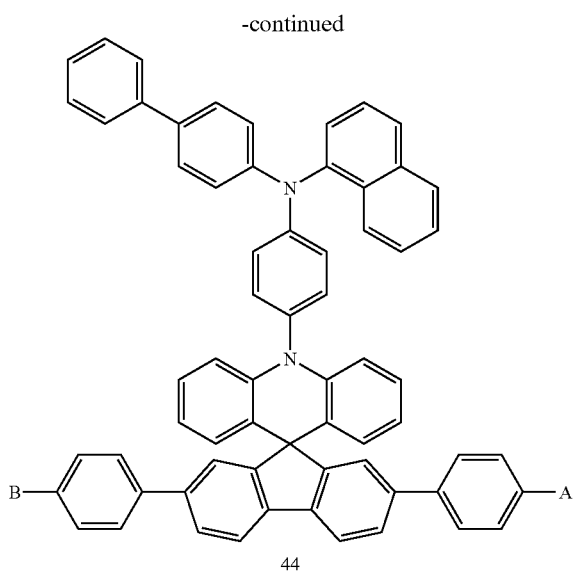
44
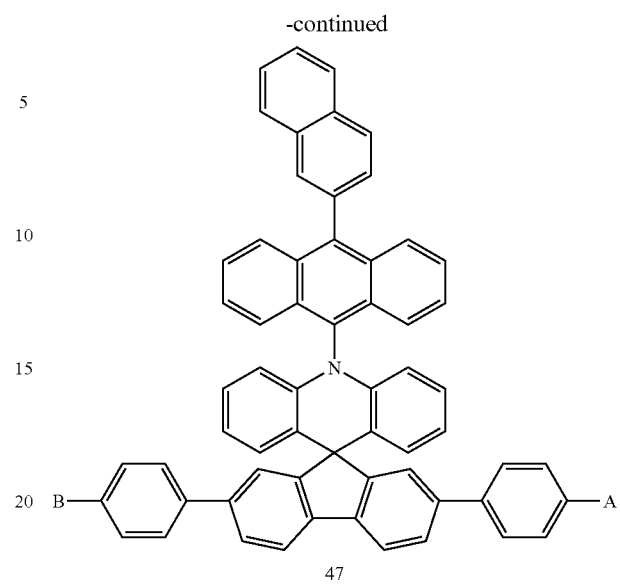
47
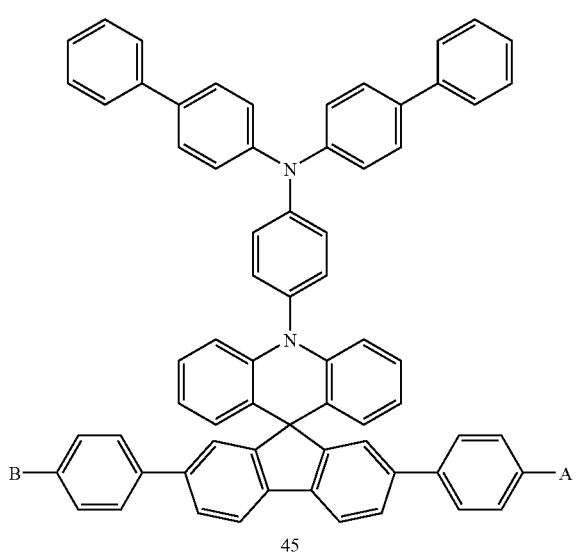
45
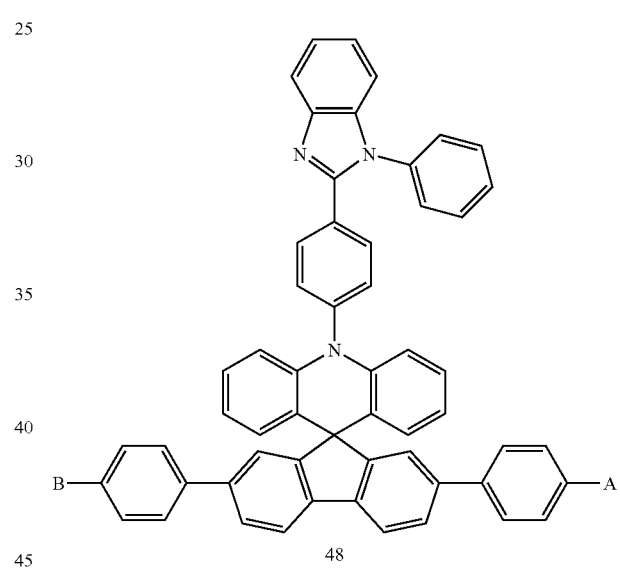
48
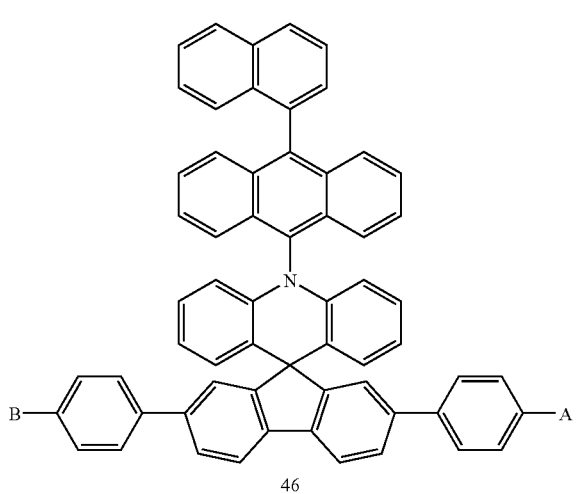
46
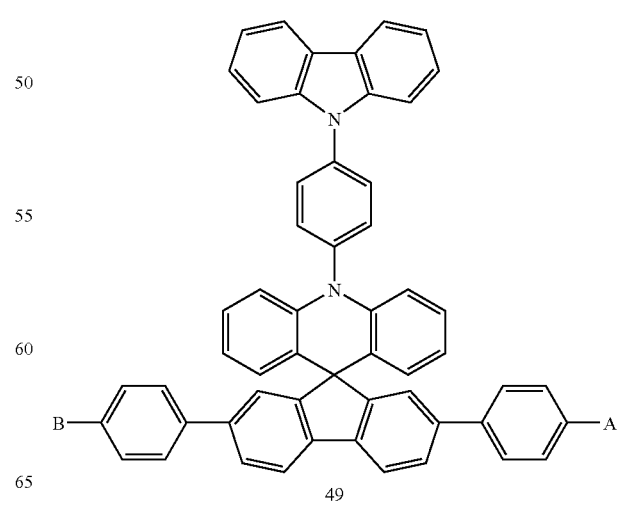
49

-continued
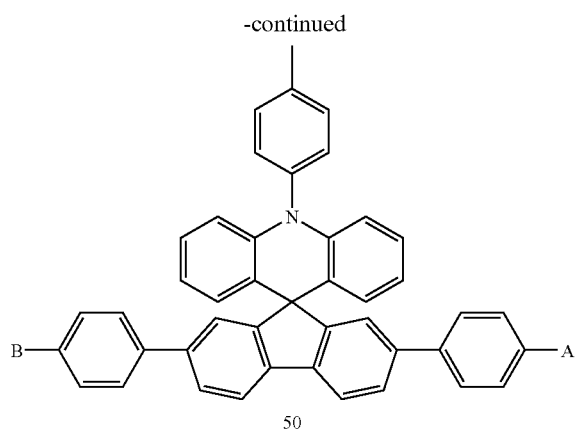
50
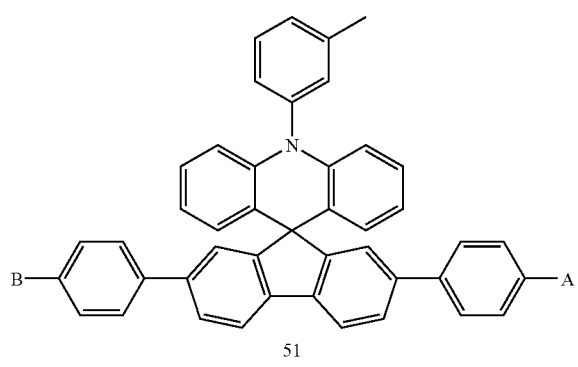
51
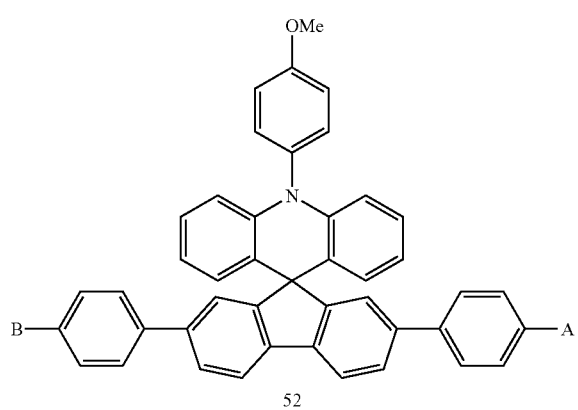
52
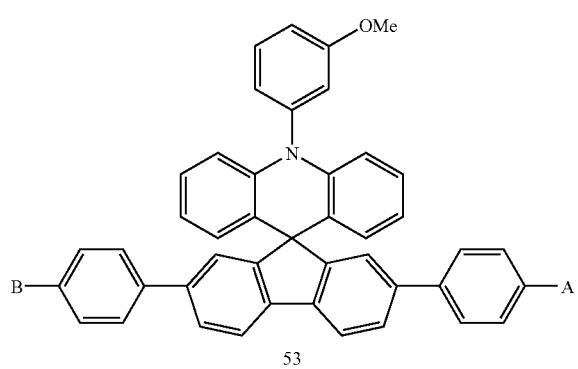
53
-continued
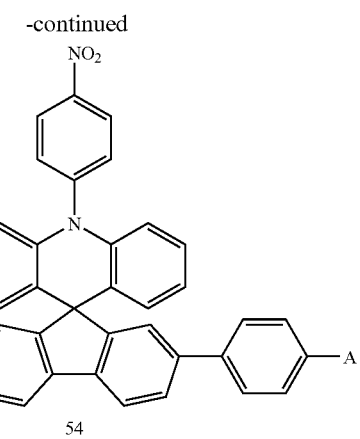
54
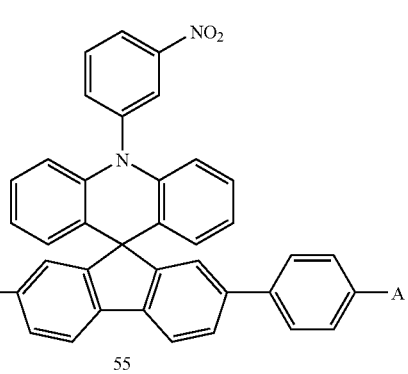
55
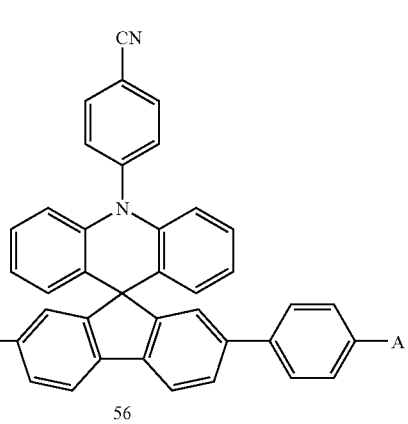
56
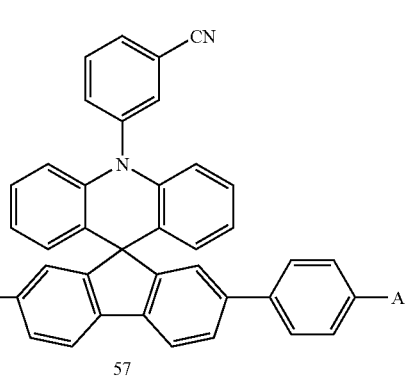
57

-continued
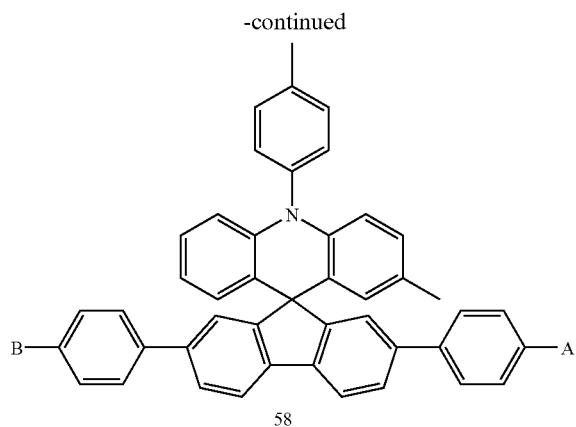
58
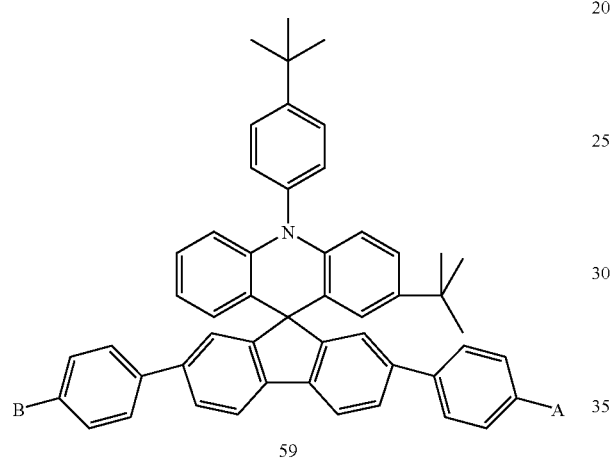
59
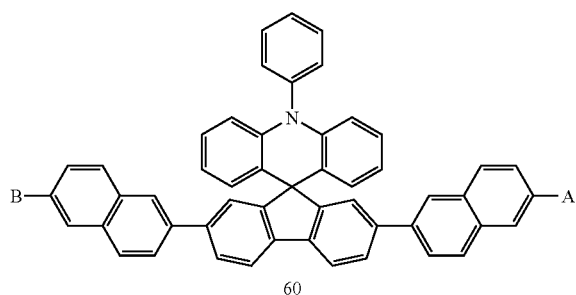
60
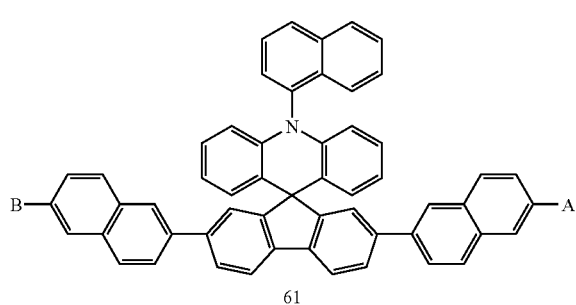
61
-continued
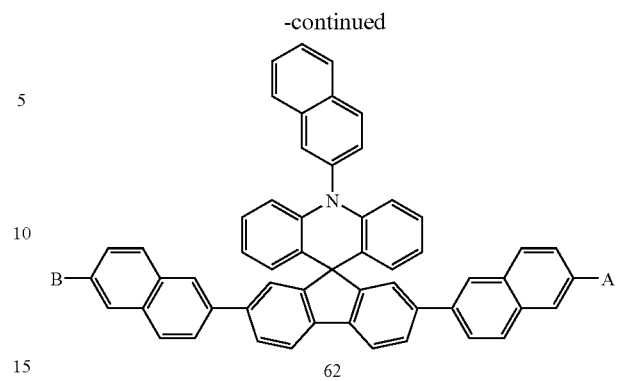
62
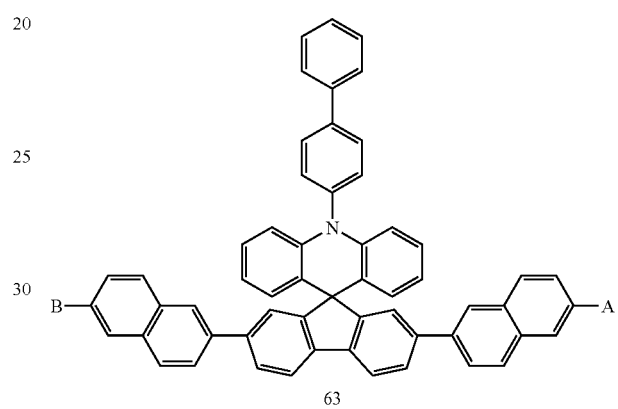
63
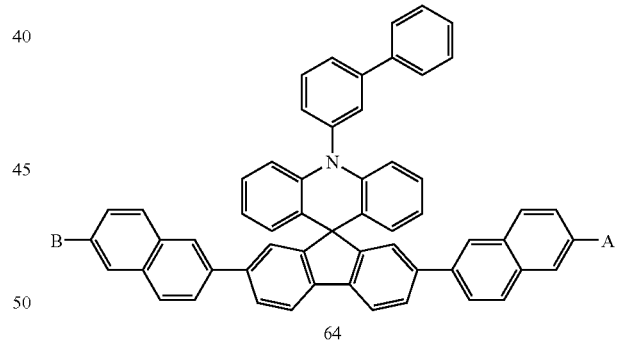
64
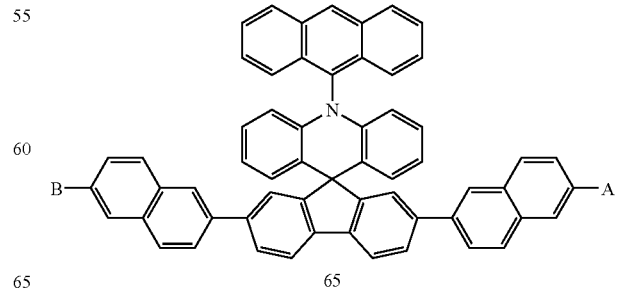
65

-continued
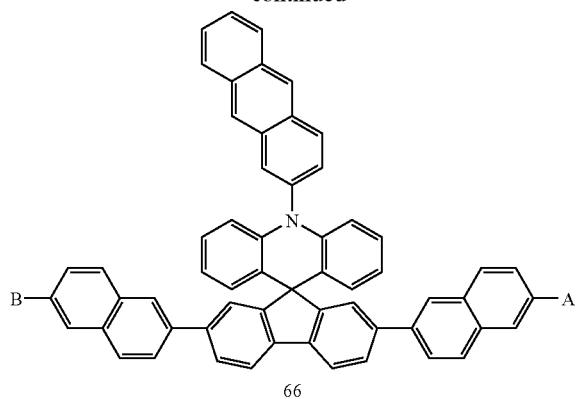
-continued
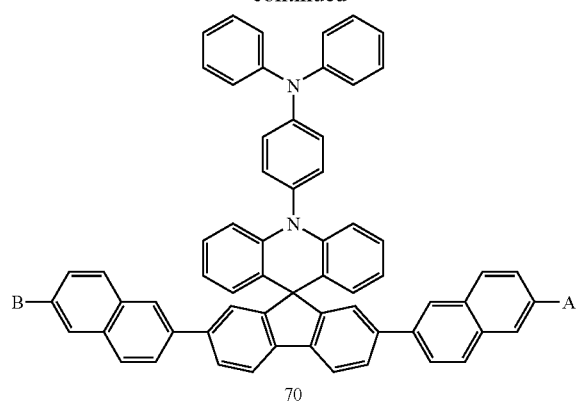

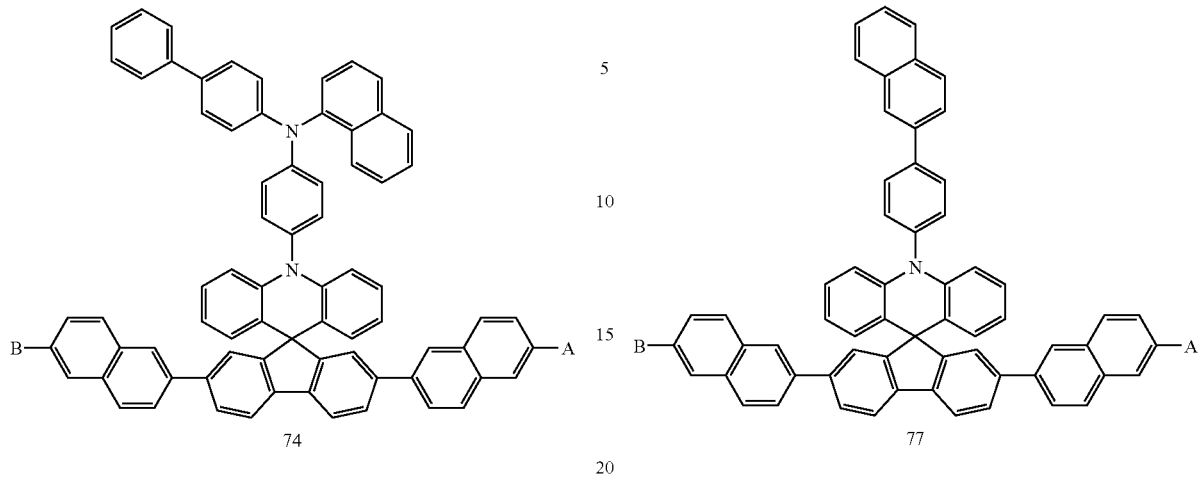
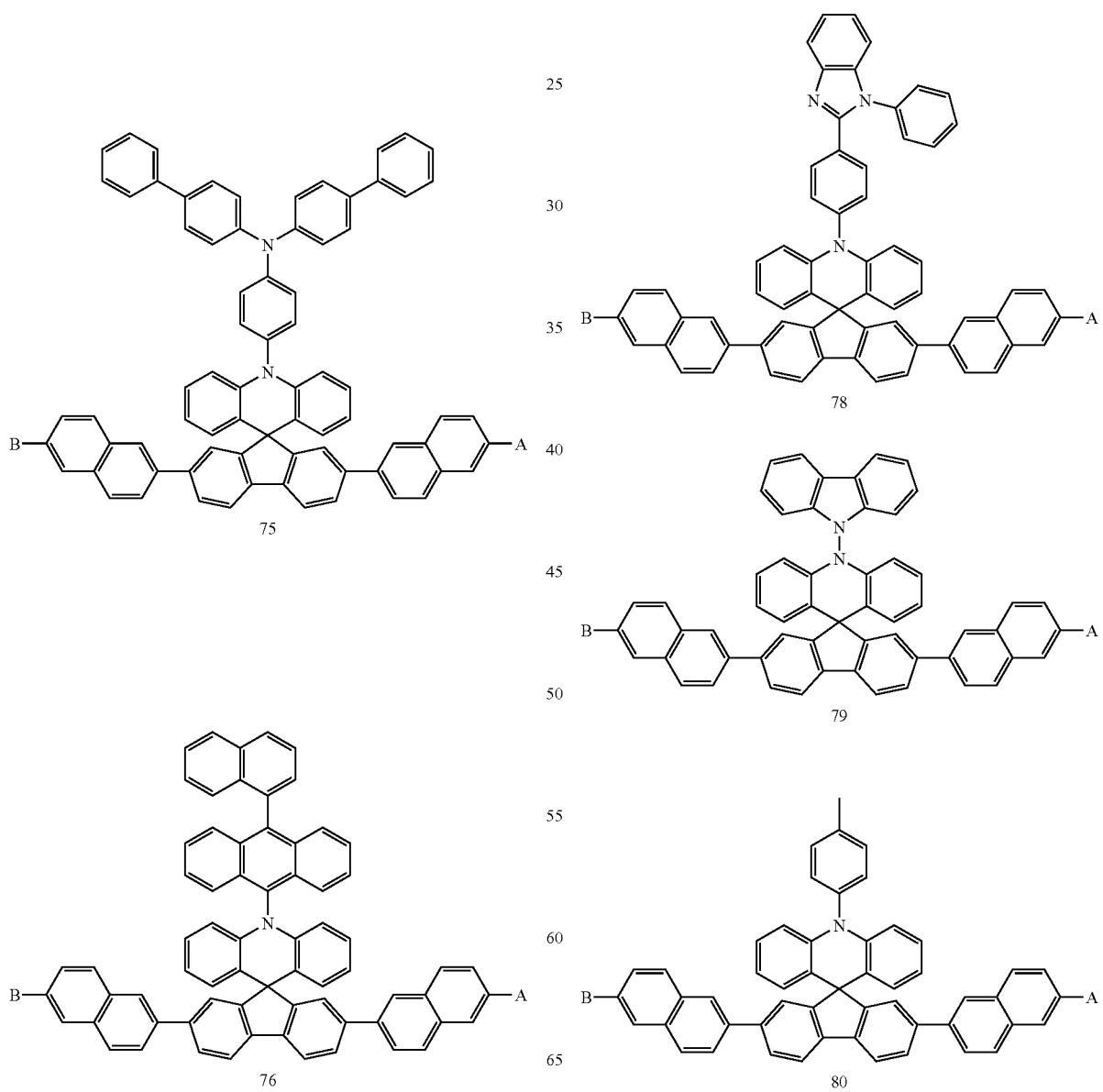

-continued
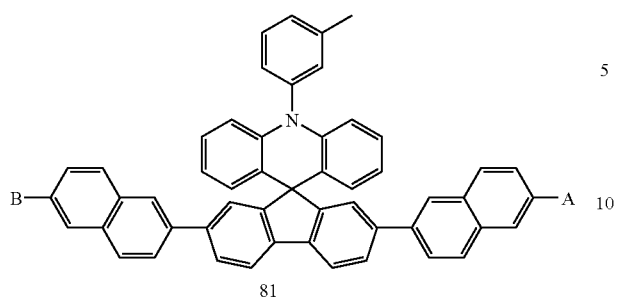
81
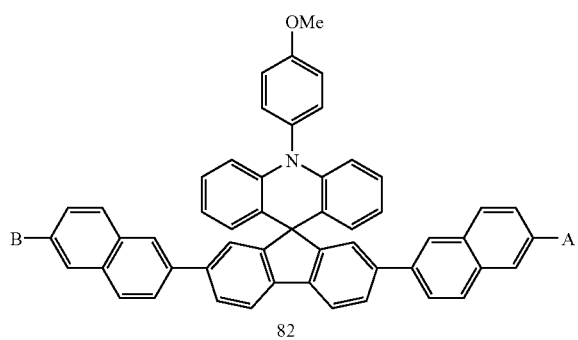
82
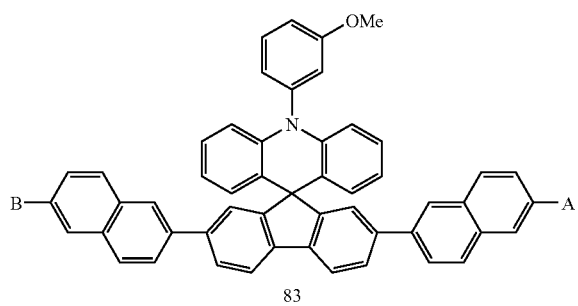
83
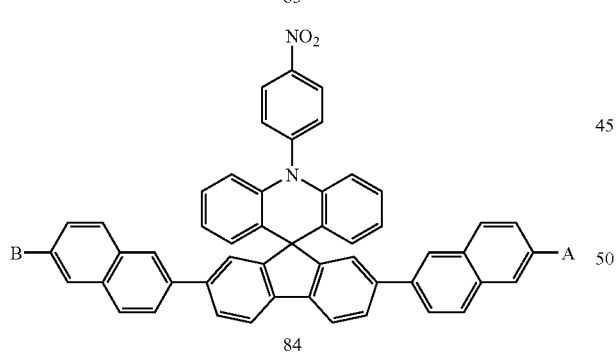
84
85
-continued
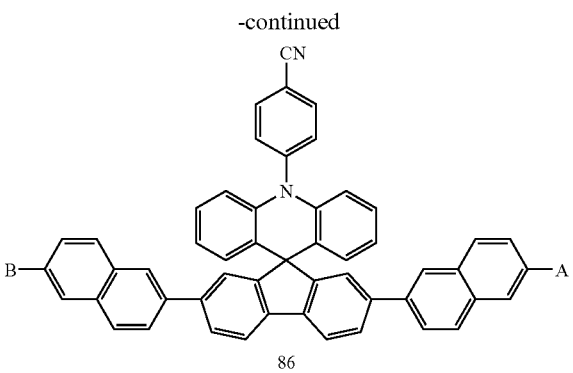
86
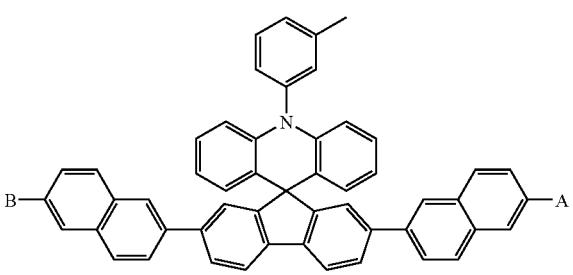
87
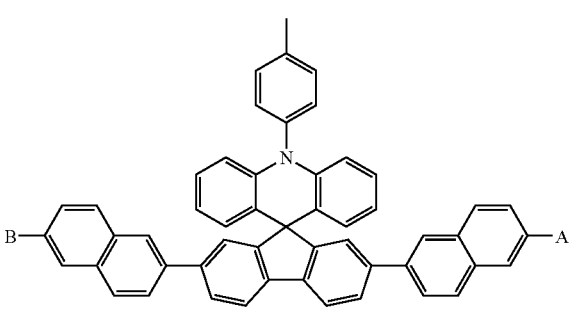
88
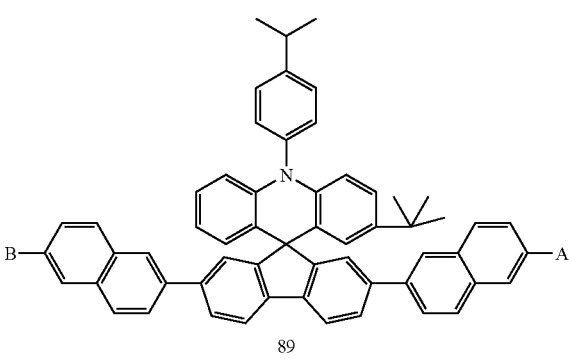
89

-continued
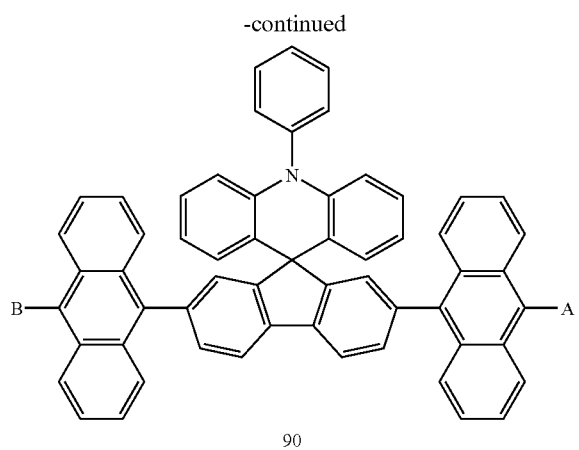
90
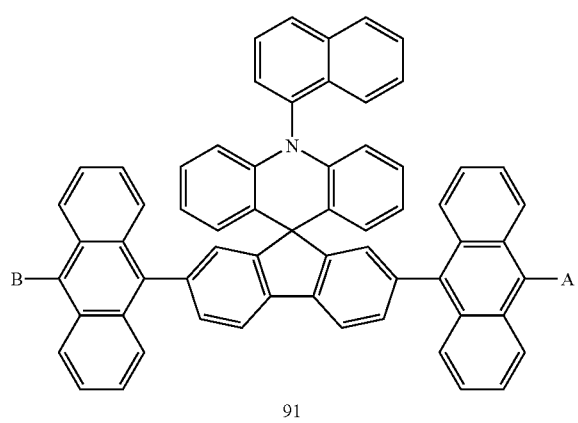
91
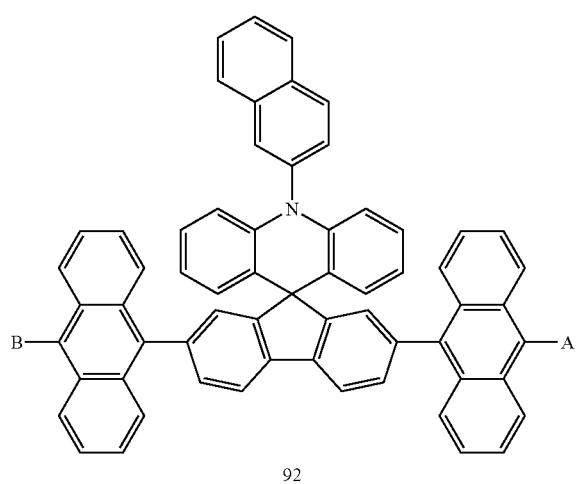
92
-continued
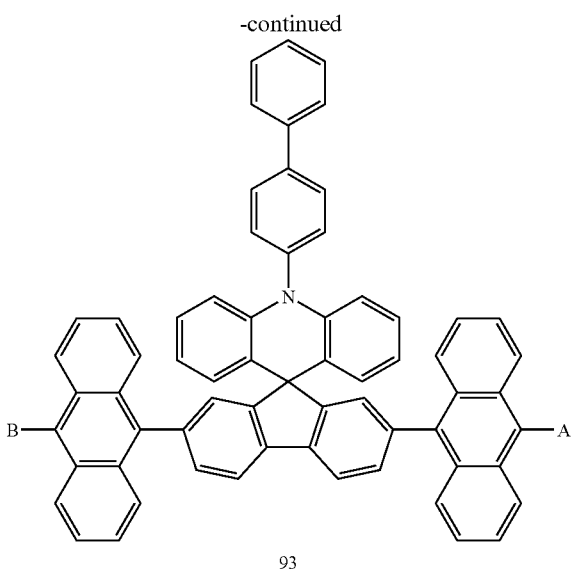
93
94
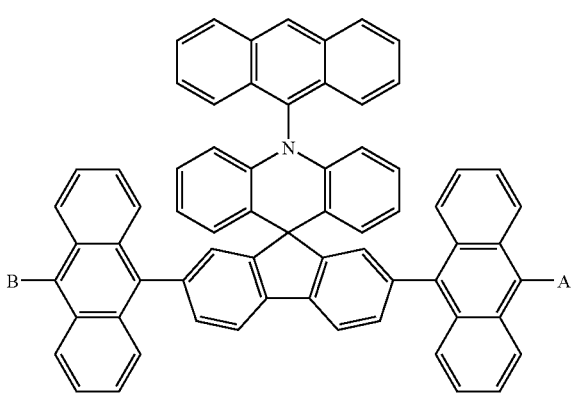
95

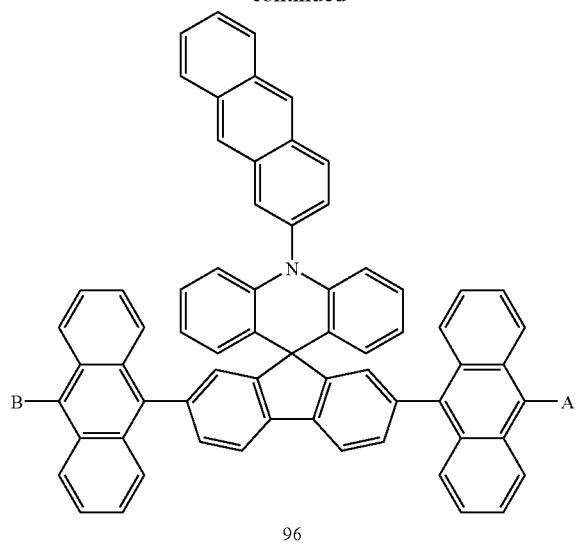
96
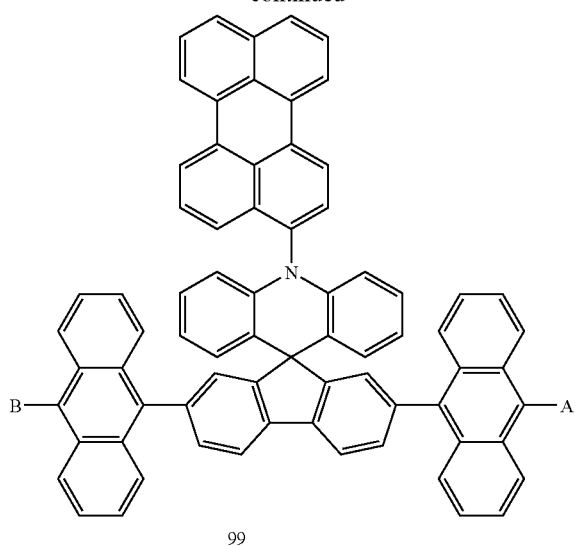
99
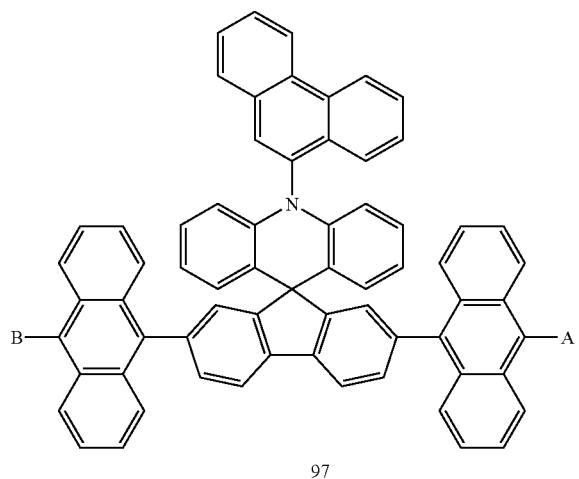
97
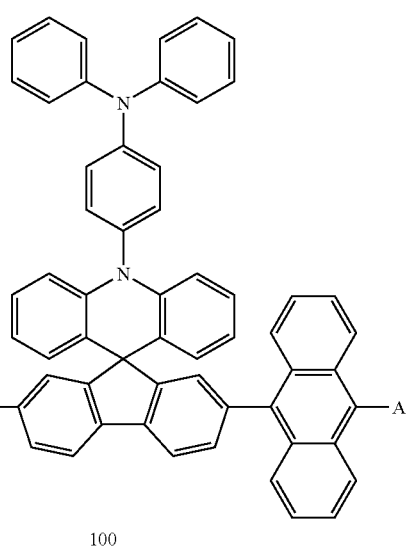
100
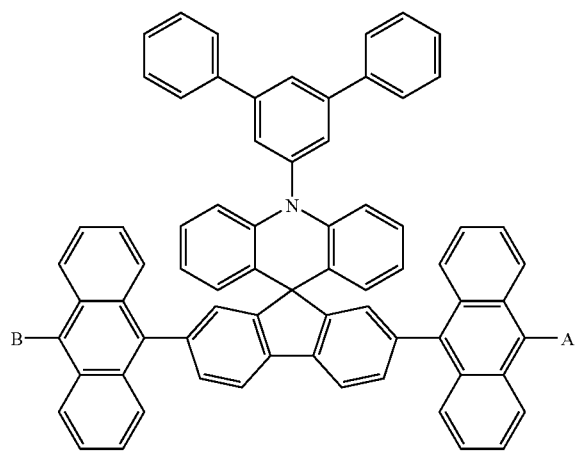
98
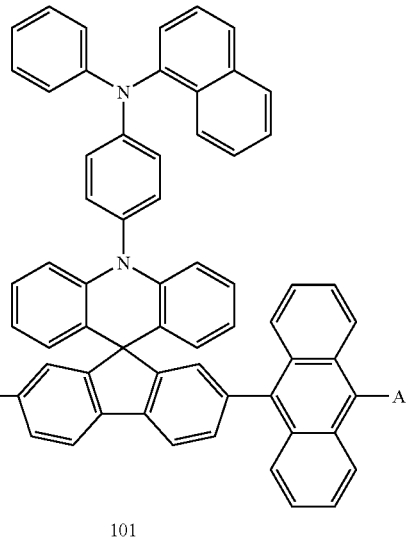
101

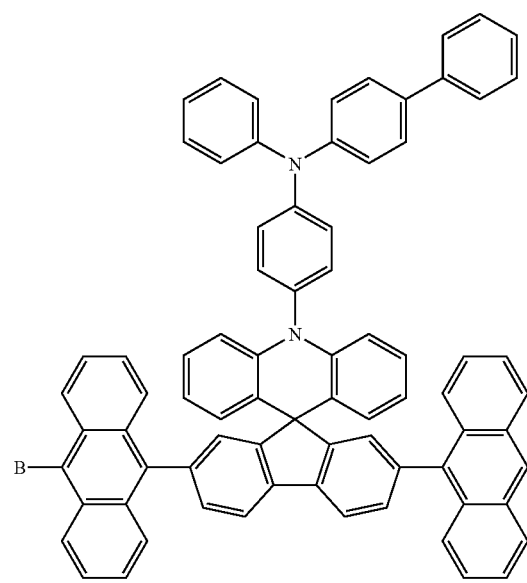
102
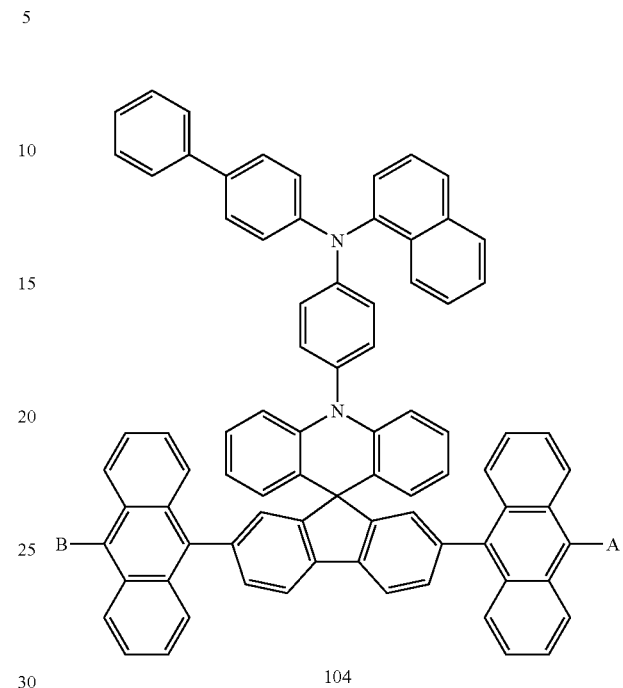
104
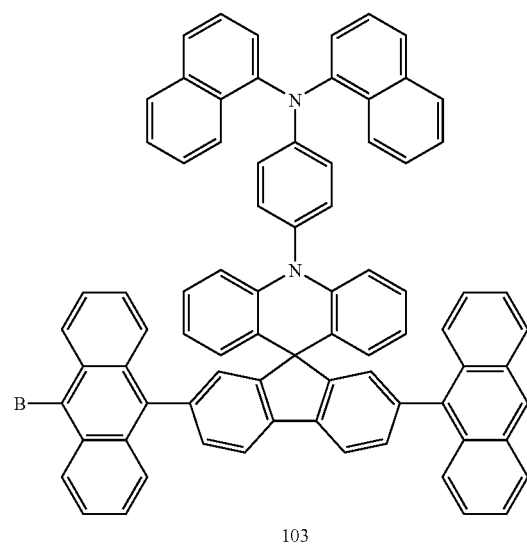
103
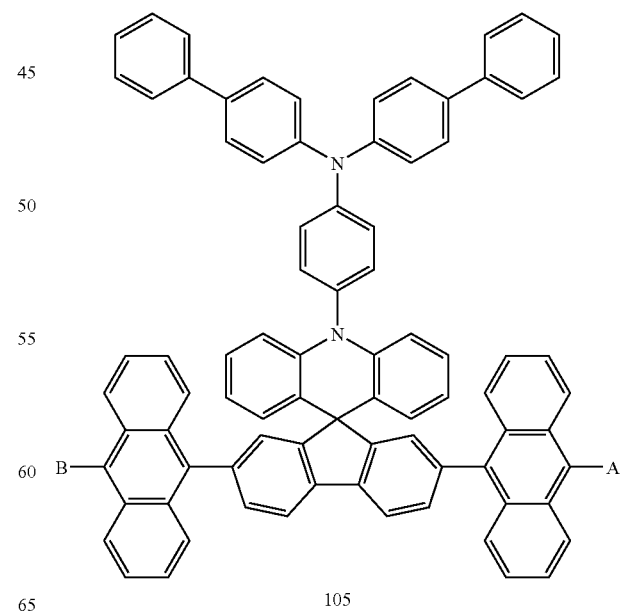
105

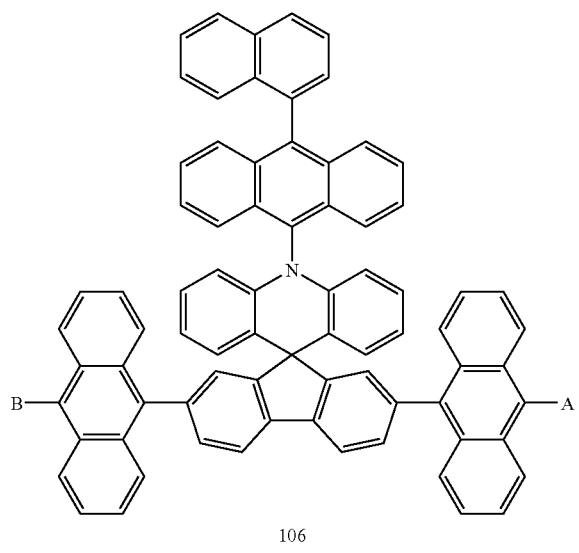
106
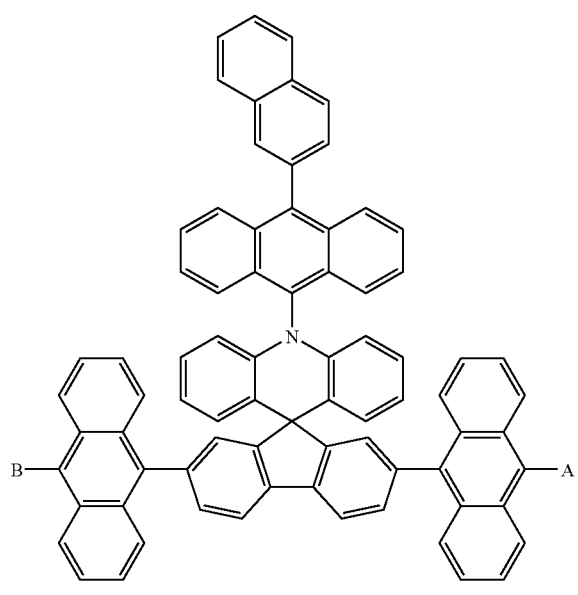
107
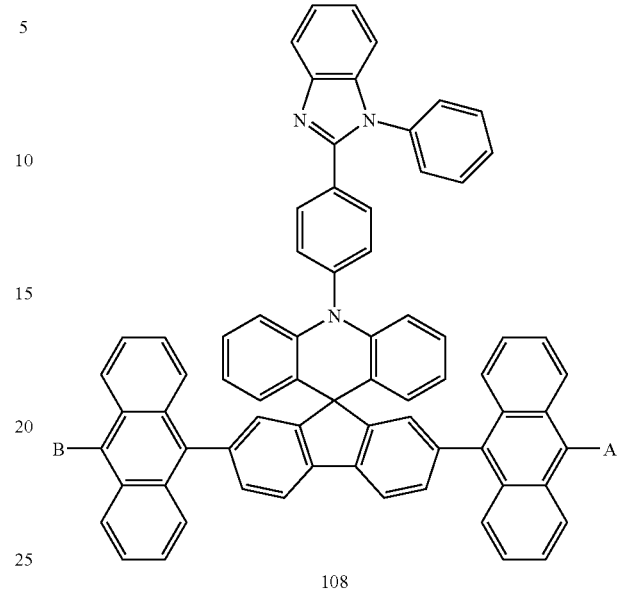
108
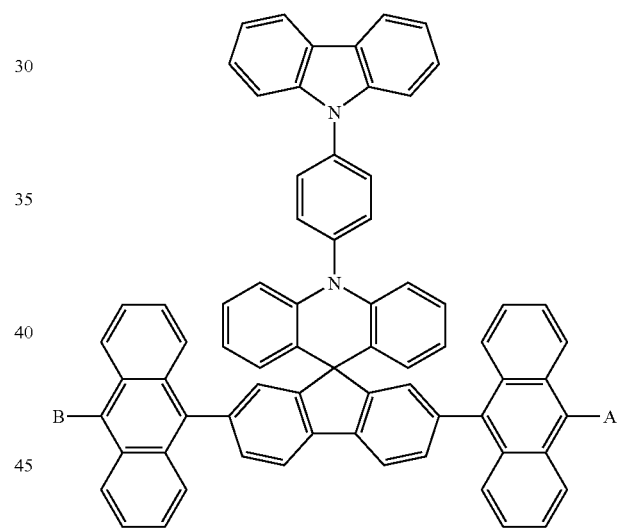
109
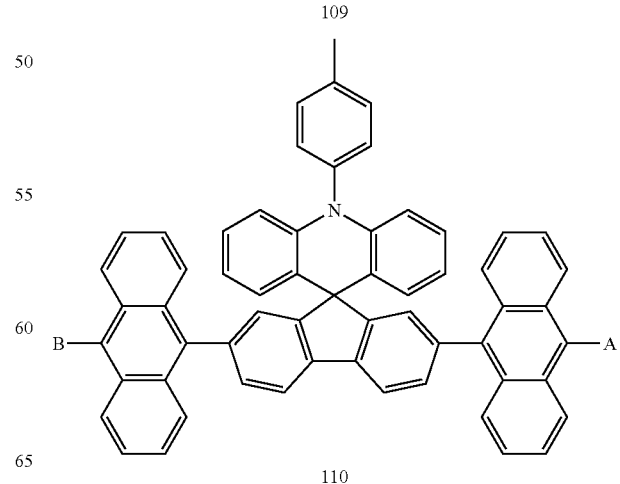
110

-continued
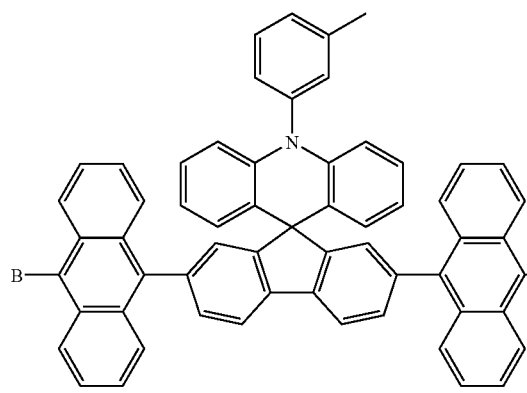
111
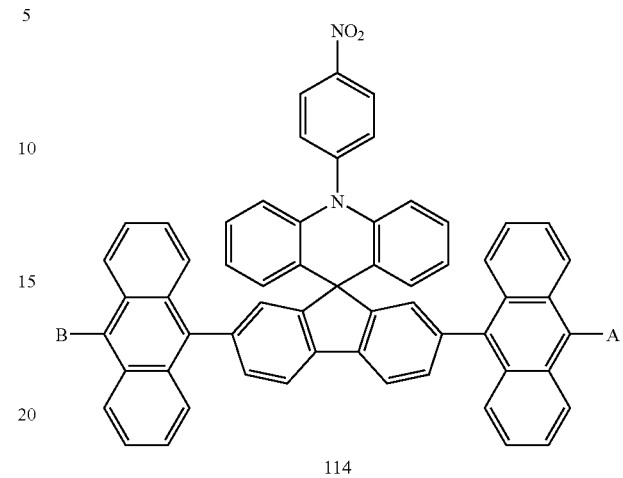
114
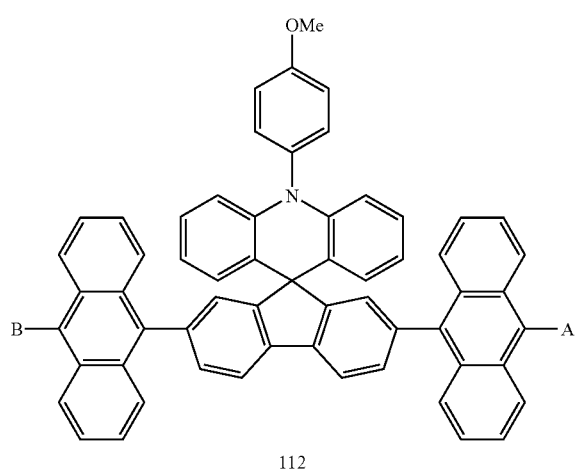
112
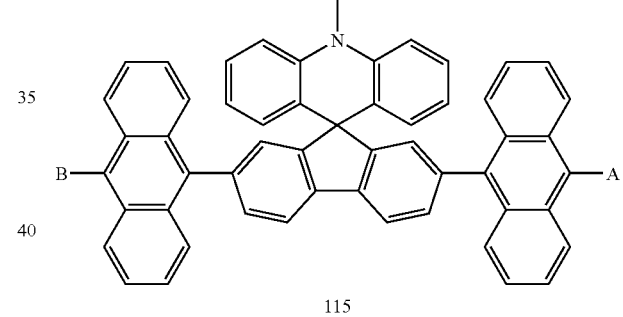
115
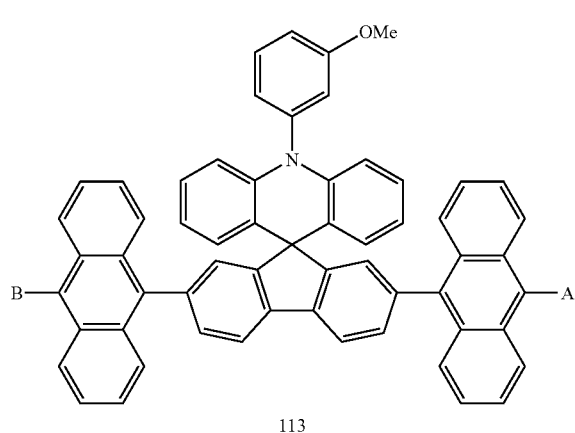
113
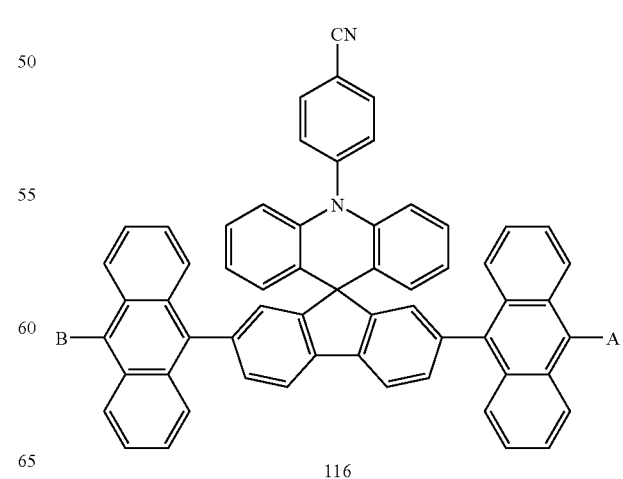
116

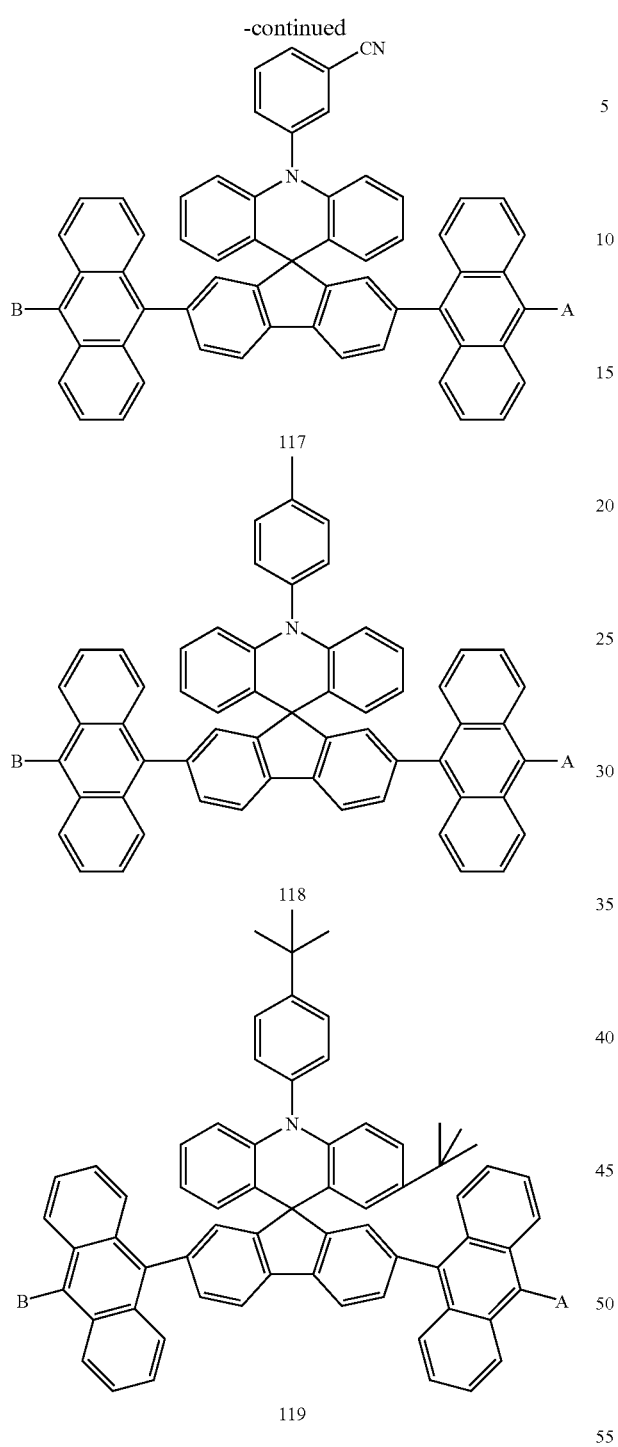

In the above Formulae, A or B is a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group, and preferably, the substituted or unsubstituted arylamine group.

Illustrative, but non-limiting, examples of A or B are as follows. Combination of the compounds of Formulae 2 to 119 and the following substituent groups A or B can form various derivative compounds. For example, if the compound of Formula 2 is combined with the substituent group 1, the resulting product will be designated by the compound of Formula 2-1.

A and B

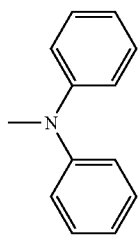

1

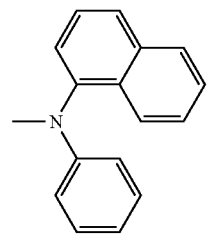

2

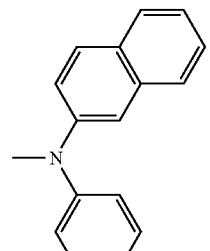

3

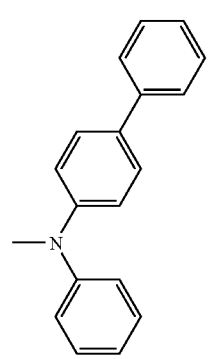

4

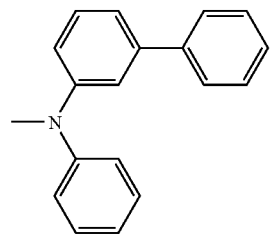

5

-continued
6
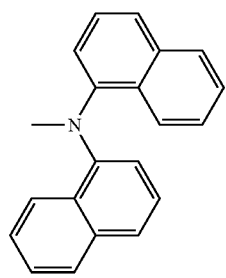
7
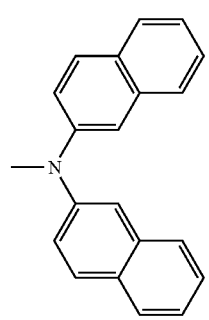
8
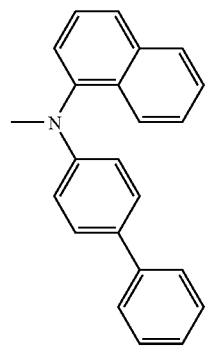
9
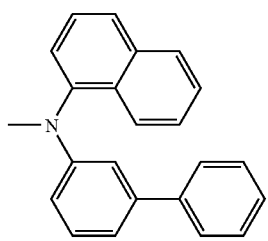
10
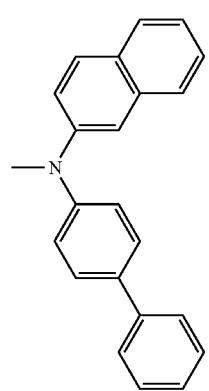
-continued
11
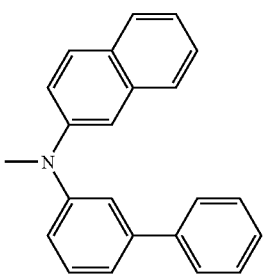
12
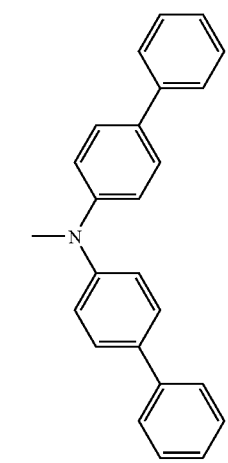
13
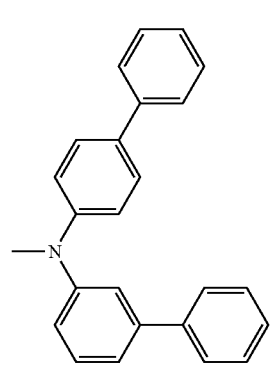
14
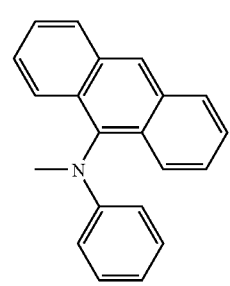

-continued
15
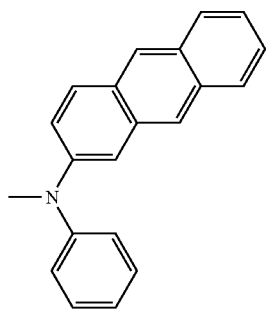
16
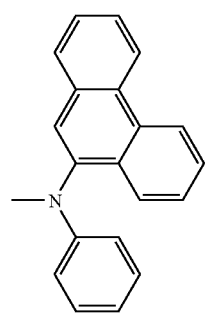
17
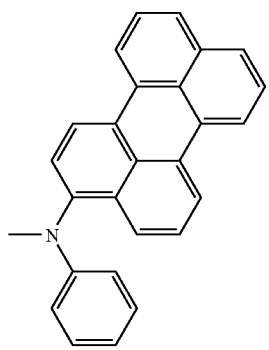
18
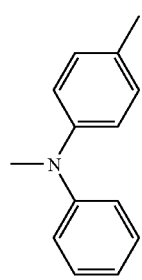
19
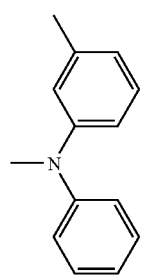
-continued
20
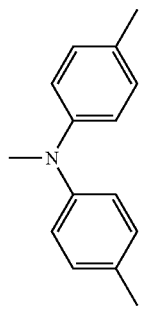
21
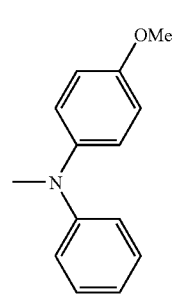
22
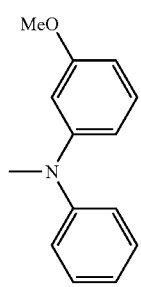
23
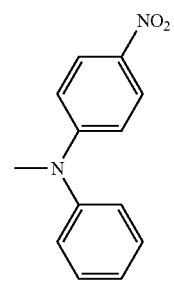
24
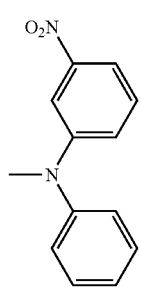

-continued
25
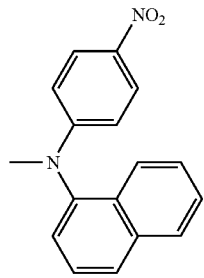
26
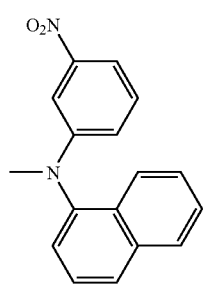
27
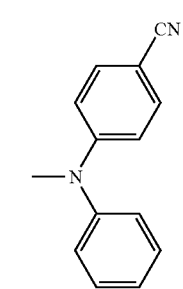
28
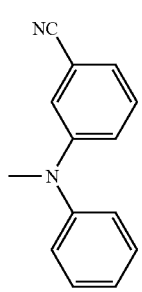
29
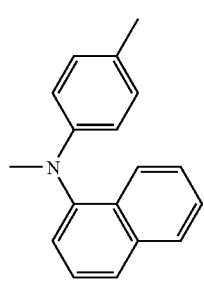
-continued
30
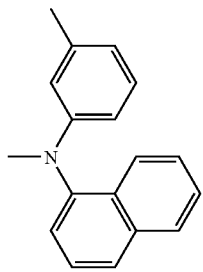
31
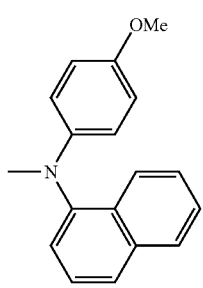
32
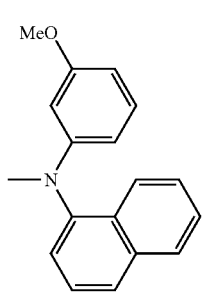
33
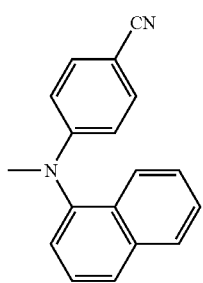
34
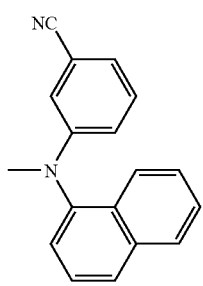

-continued
35
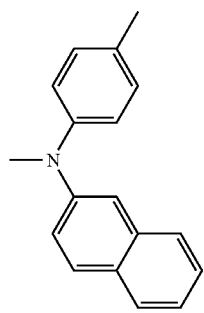
36
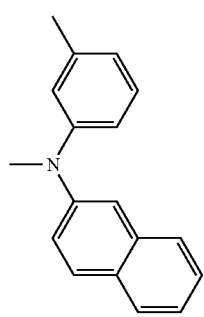
37
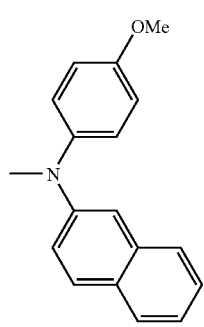
38
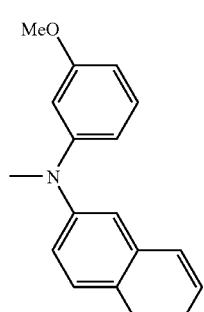
39
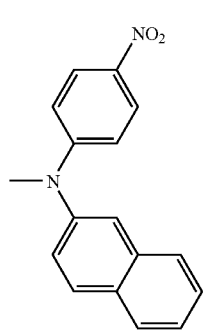
-continued
40
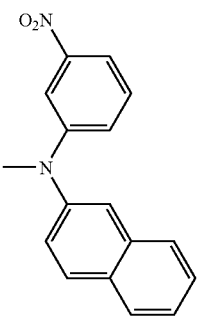
41
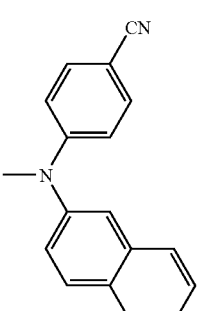
42
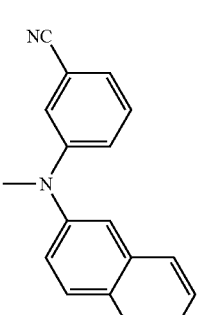
43
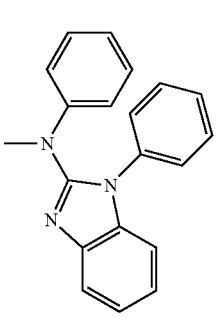
44

45
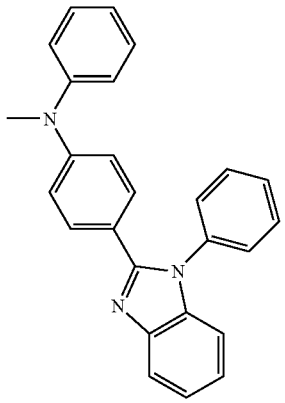
46
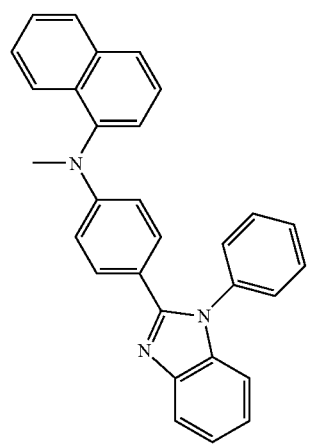
47
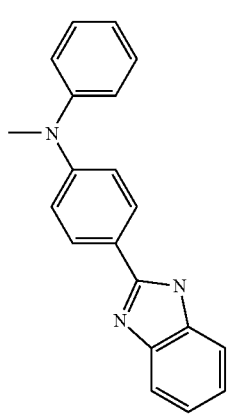
48
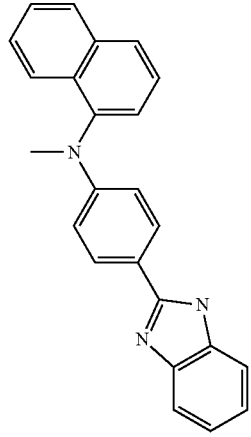
49
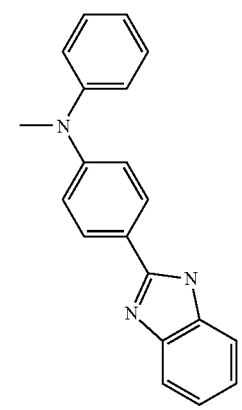
50
51
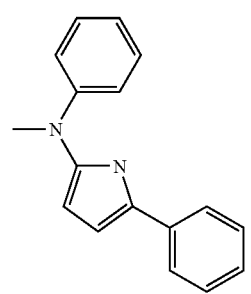

-continued
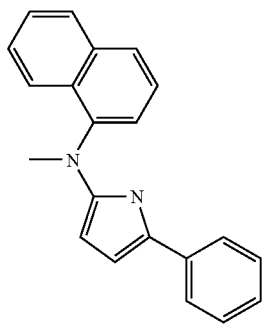
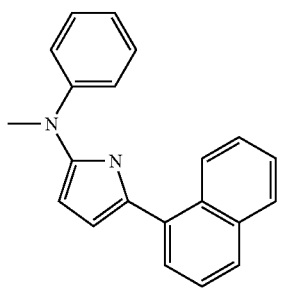
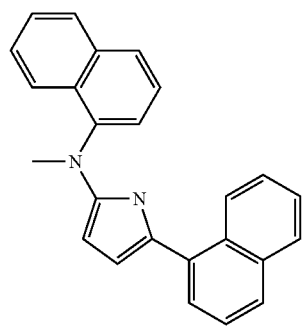
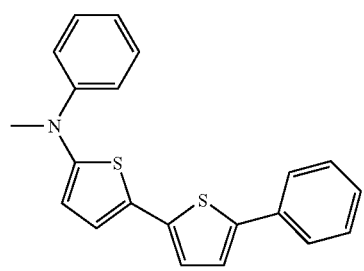
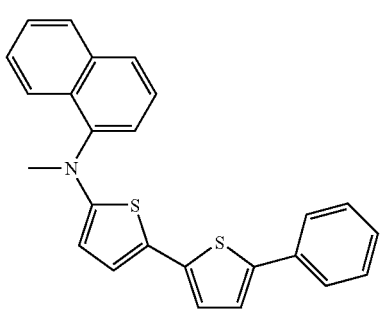
-continued
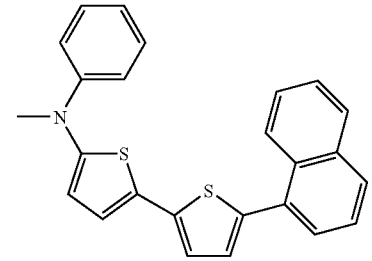
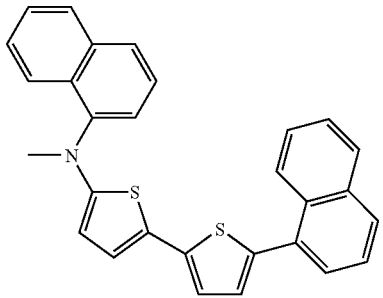
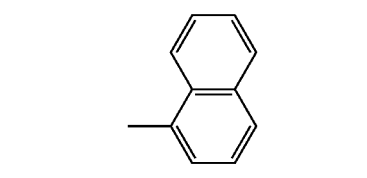
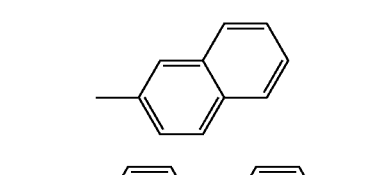
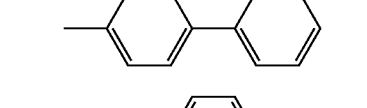
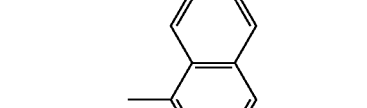
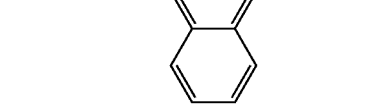
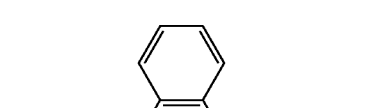
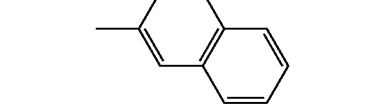
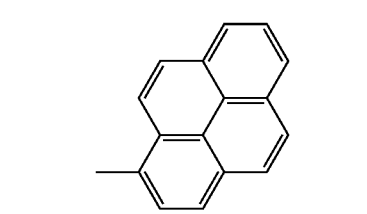

-continued
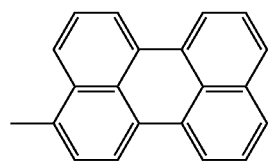
65
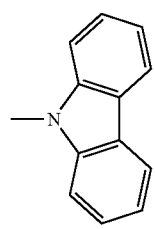
66
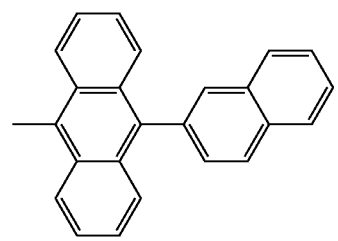
67
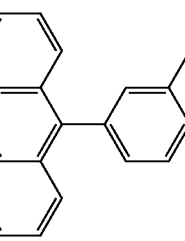
68
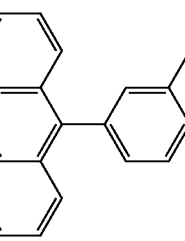
69
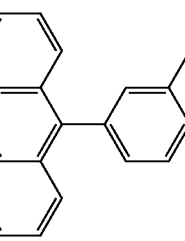
70
-continued
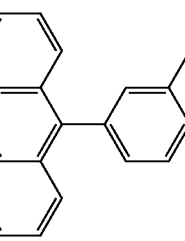
71
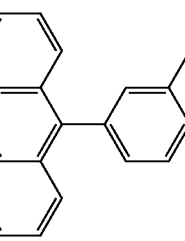
72
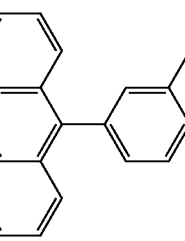
73
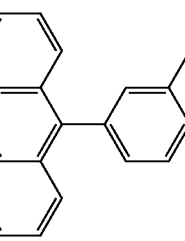
74
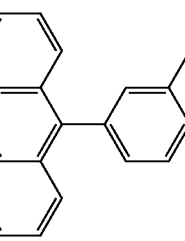
75

76
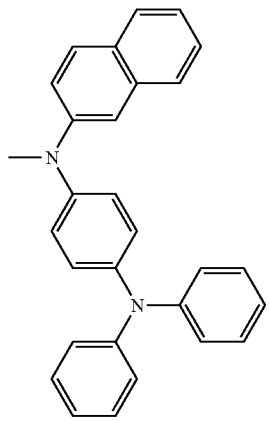
77
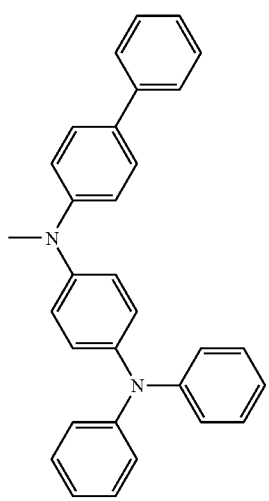
78
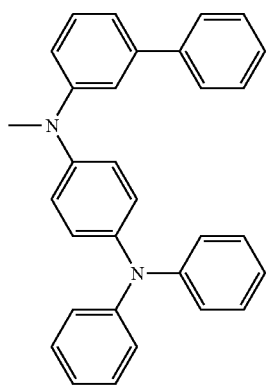
79
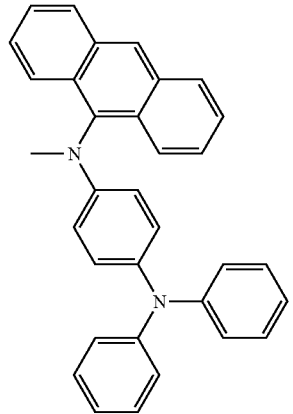
80
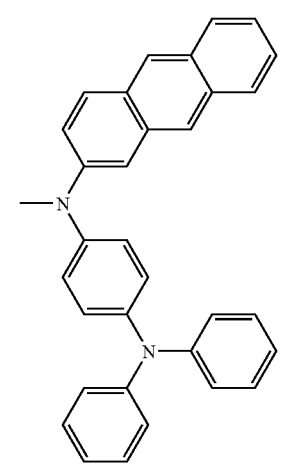
81
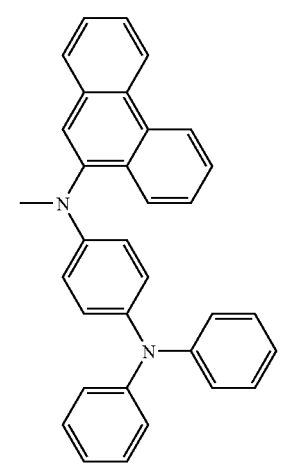

82
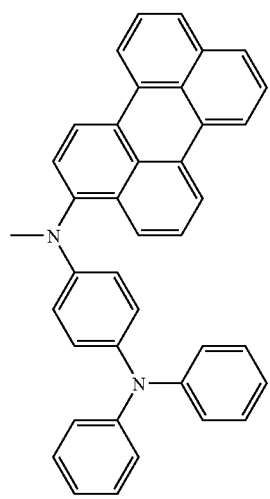
83
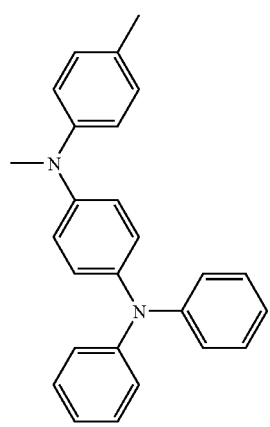
84
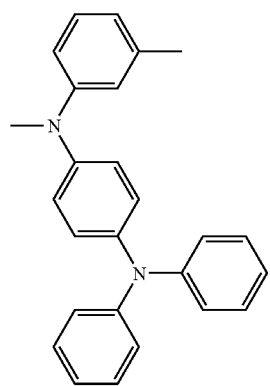
85
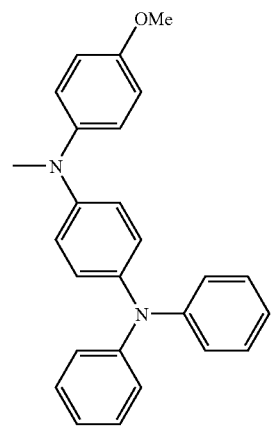
86
87
88

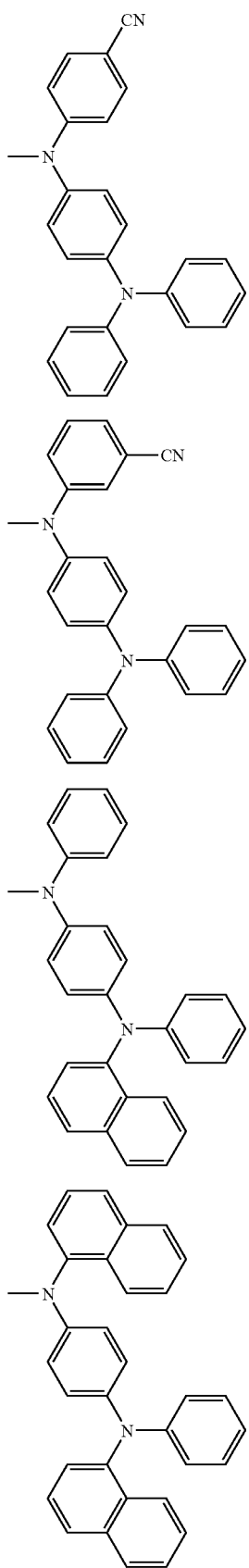
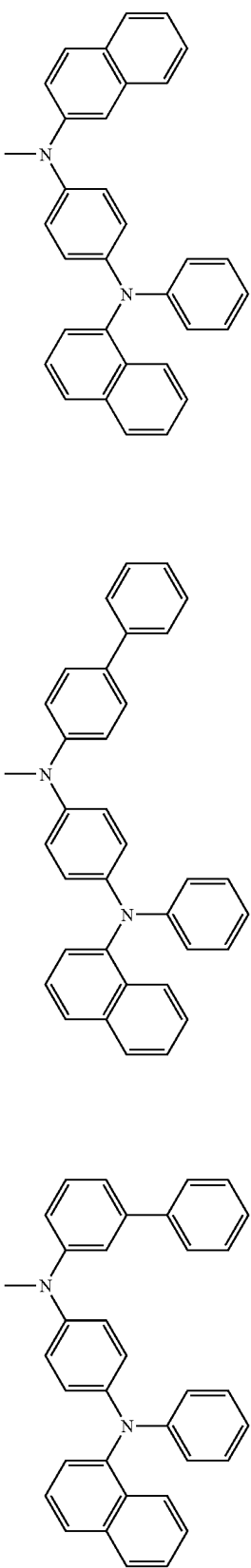

-continued
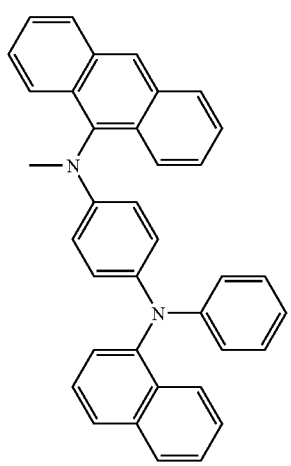
96
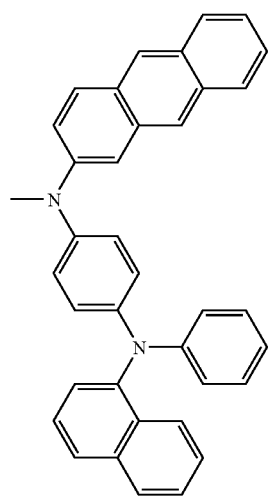
97
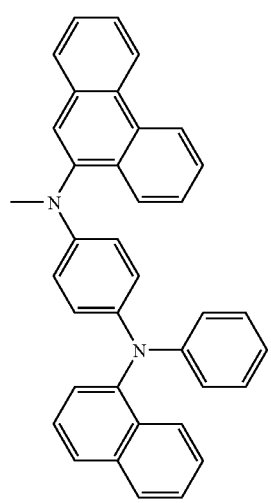
98
-continued
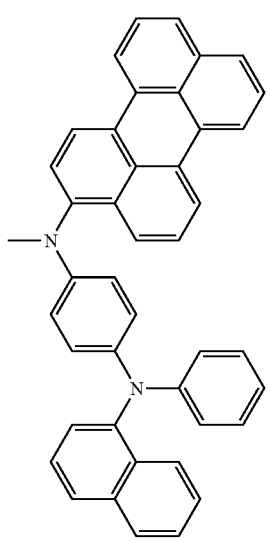
99
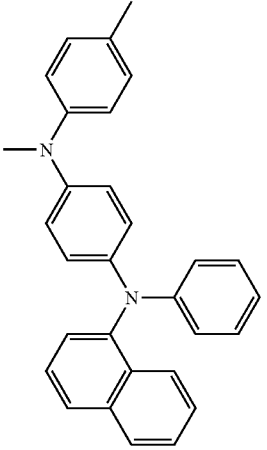
100
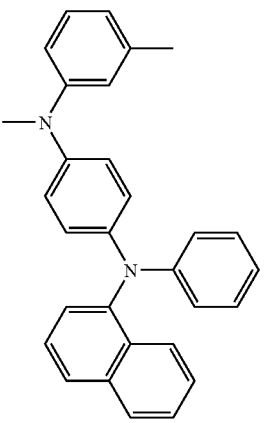
101

-continued
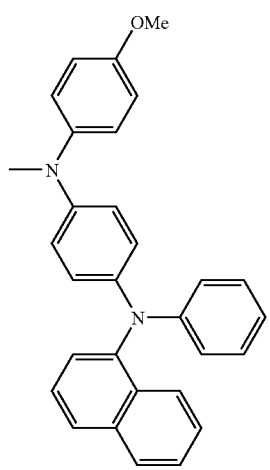
102
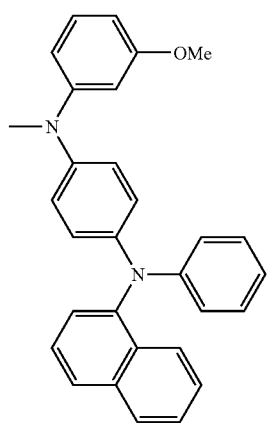
103
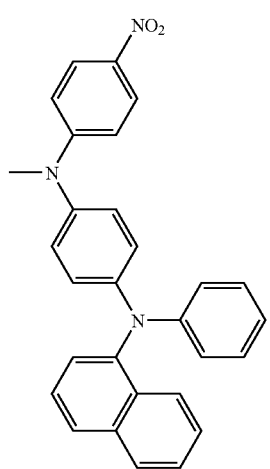
104
-continued
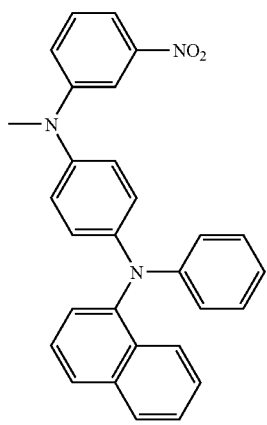
105
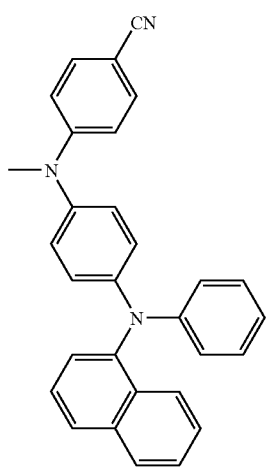
106
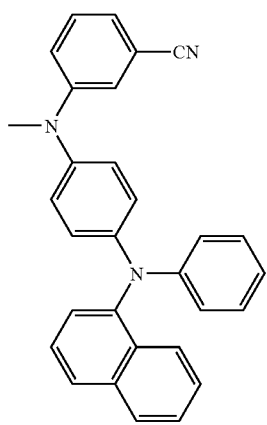
107

108
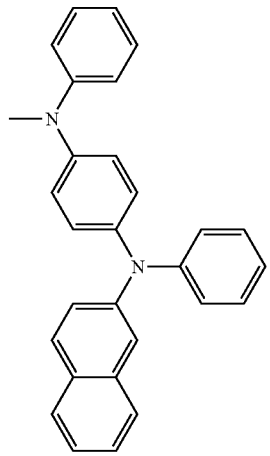
109
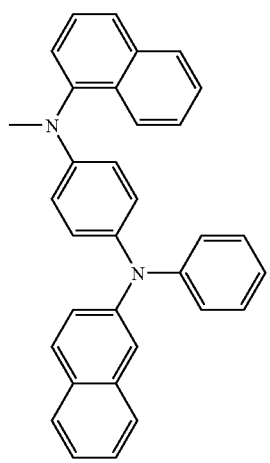
110
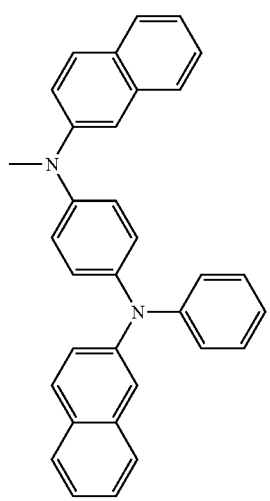
111
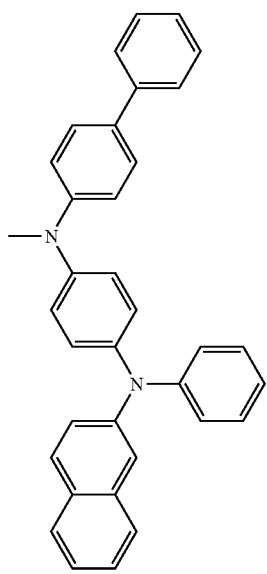
112
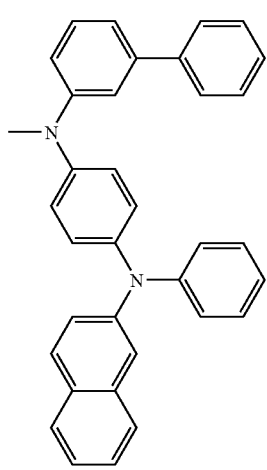
113
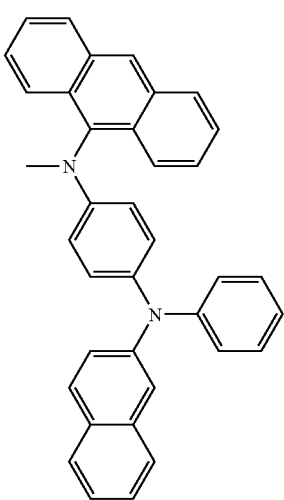

114
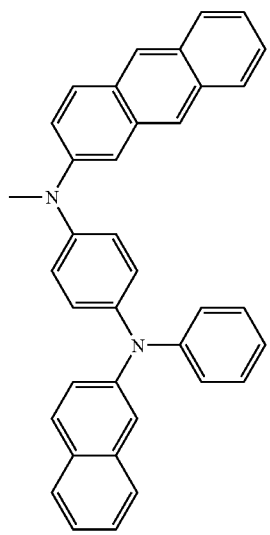
115
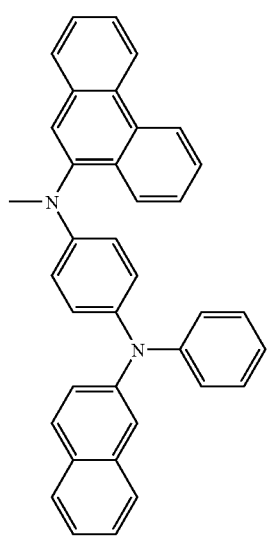
116
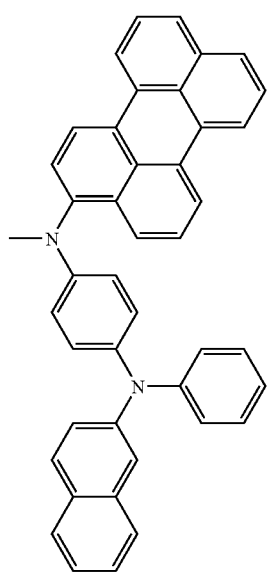
117
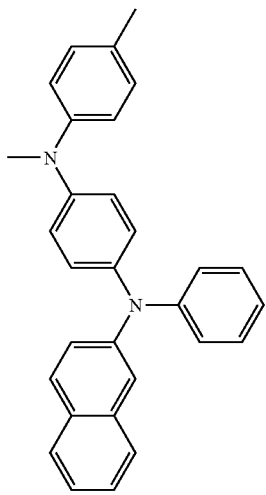
118
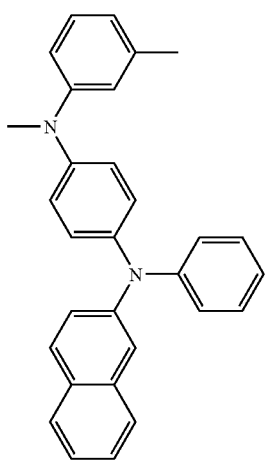
119
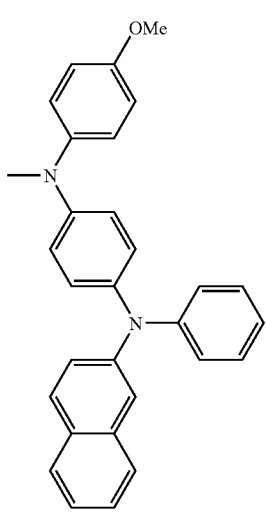

120
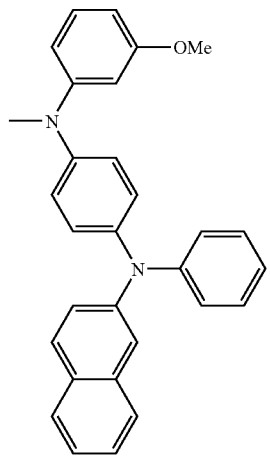
123
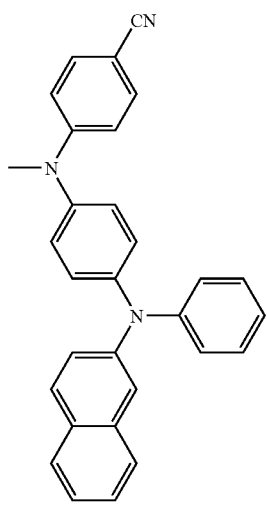
121
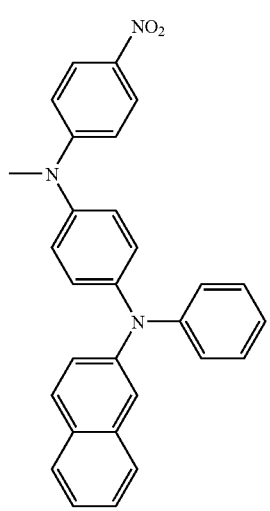
124
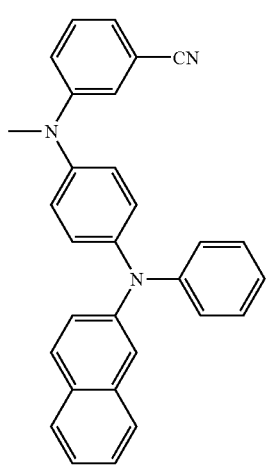
122
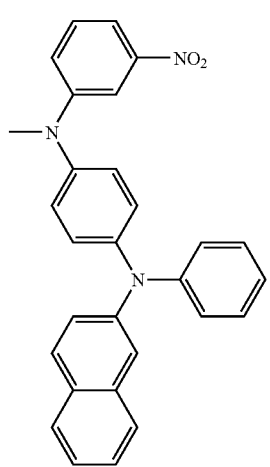
125
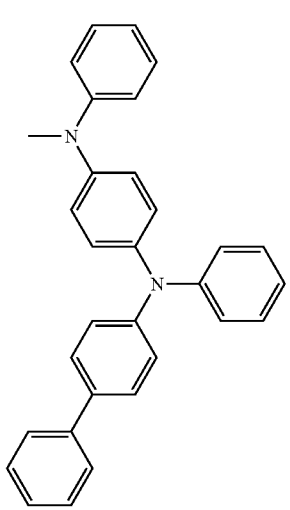

126 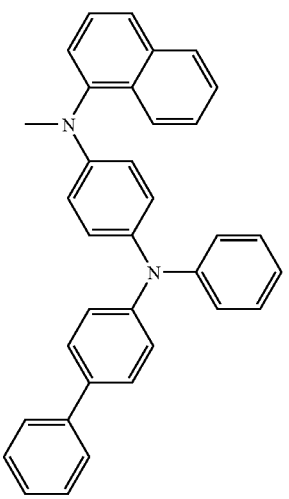
127 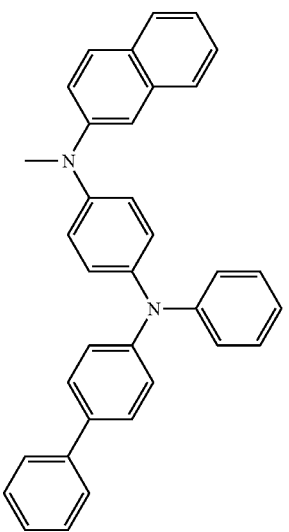
128 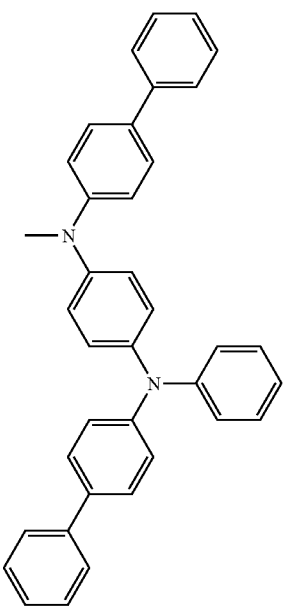
129 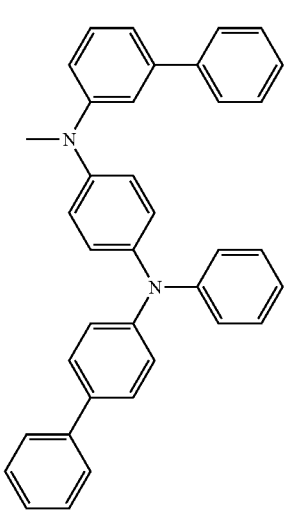
130 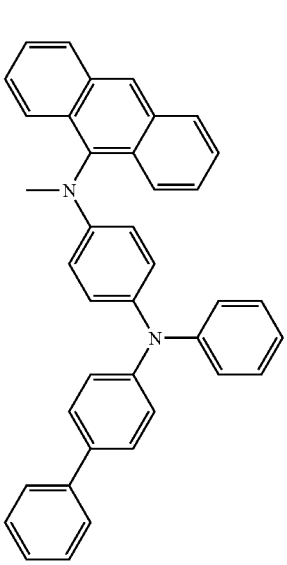
131 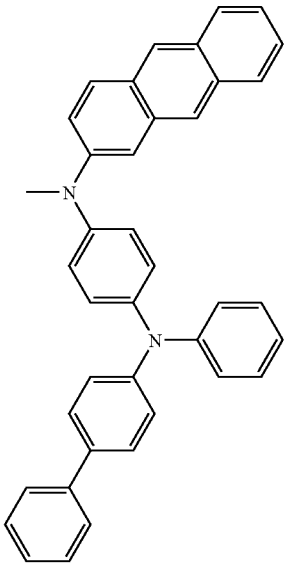

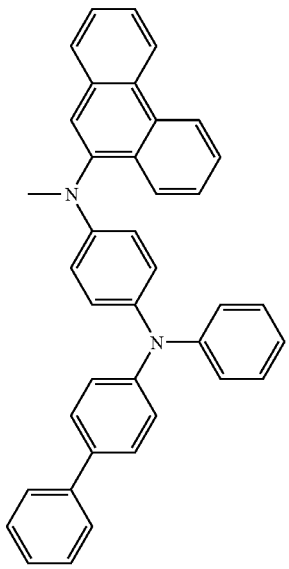
132
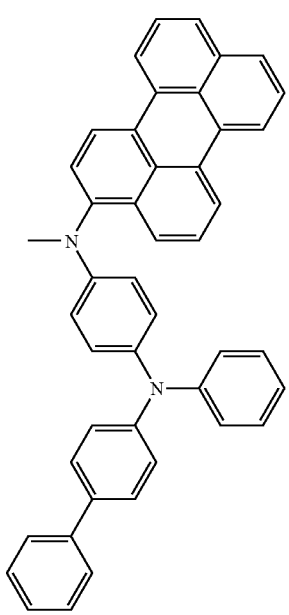
133
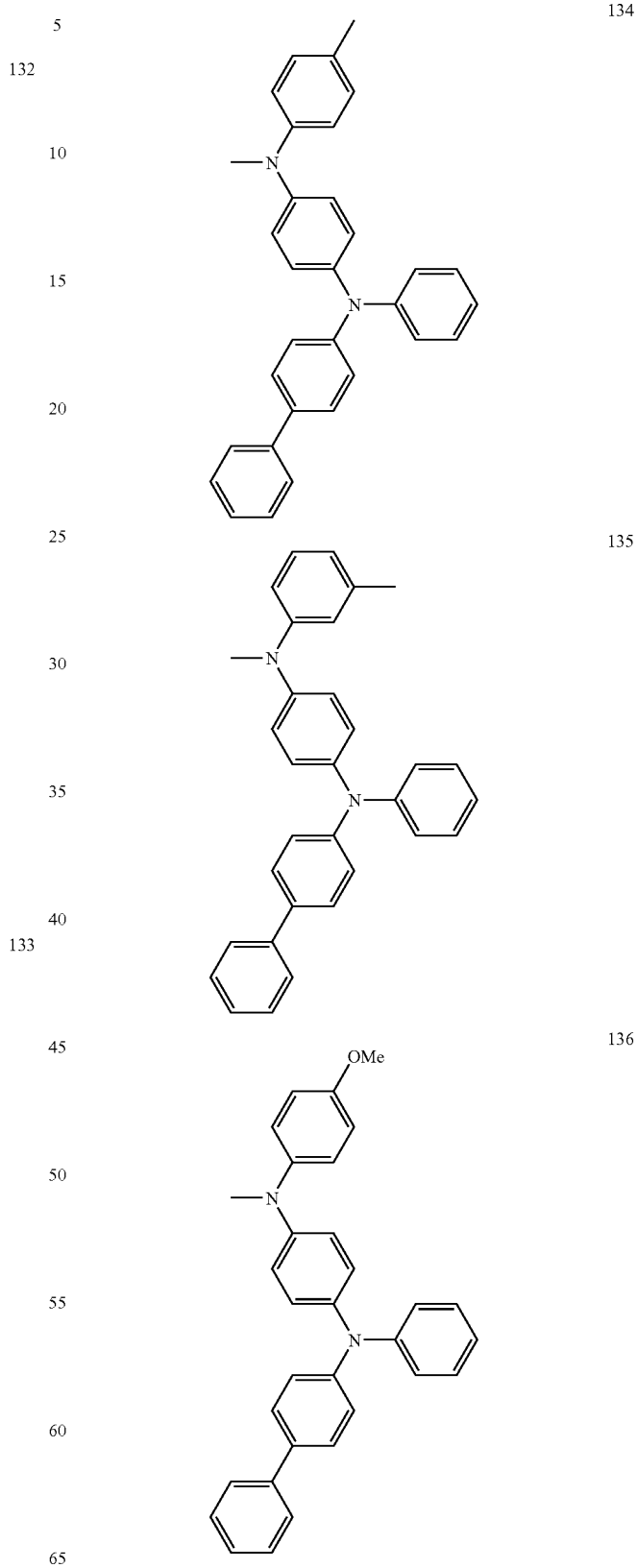

-continued
137
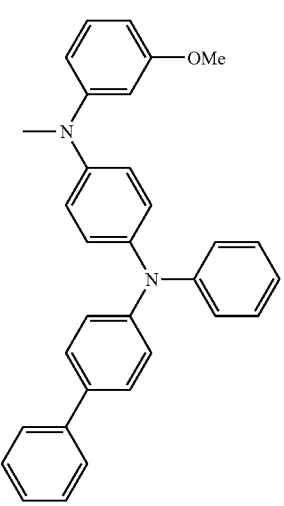
138
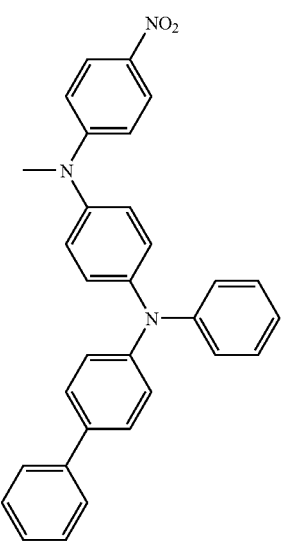
139
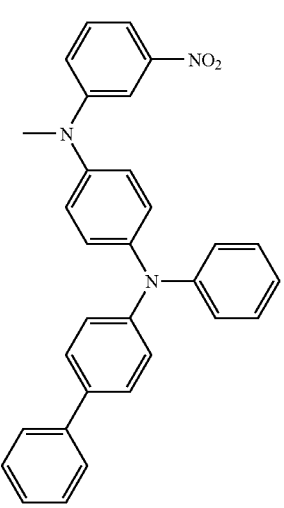
-continued
140
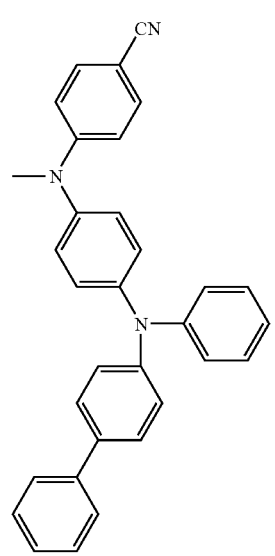
141
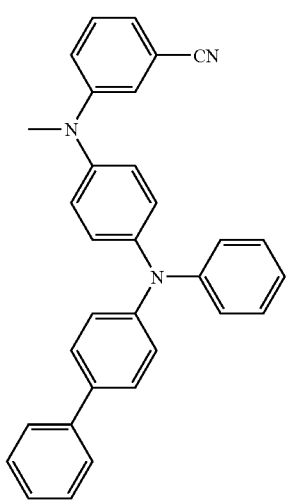
142

-continued
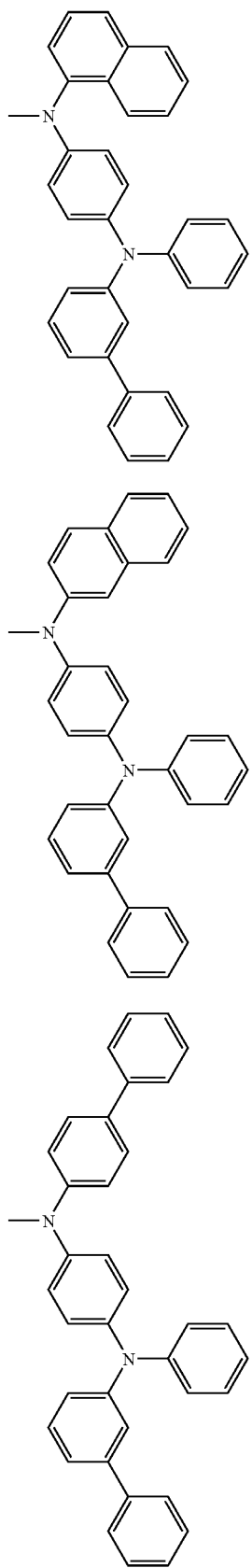
143
144
145
-continued
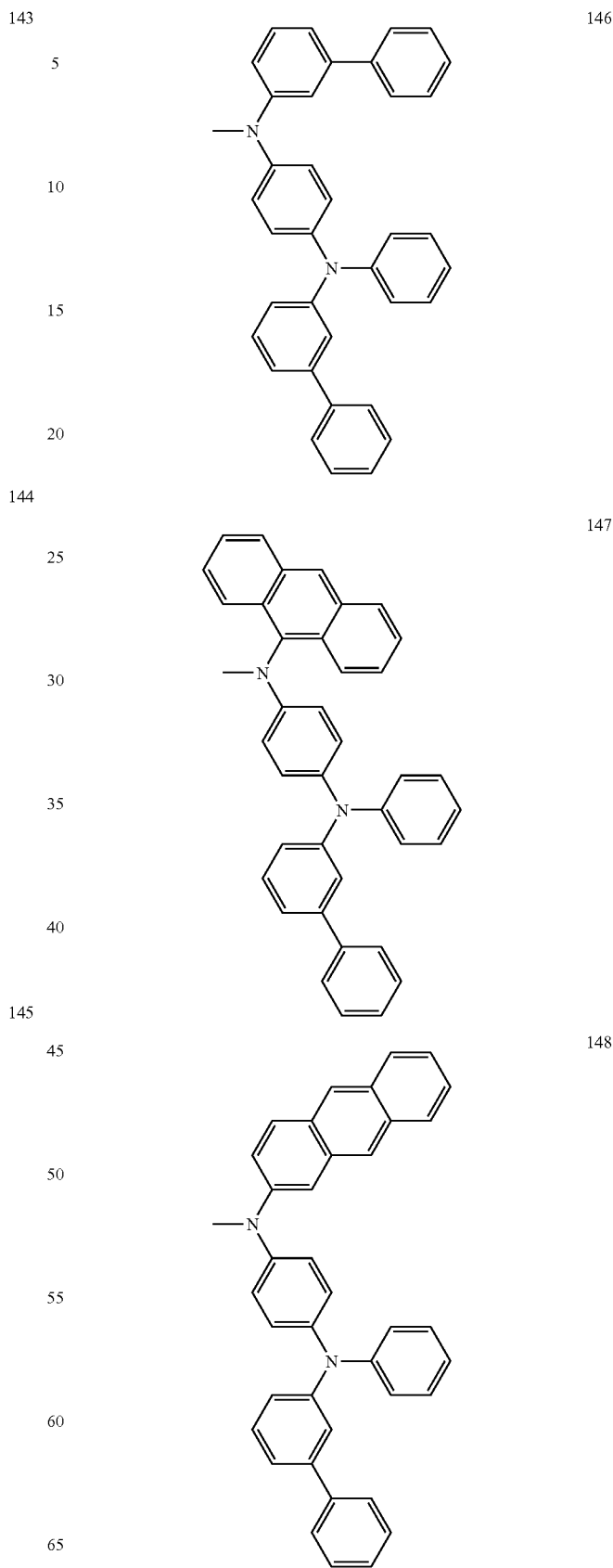
146
147
148

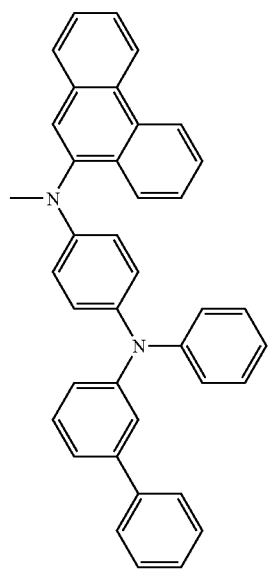
149
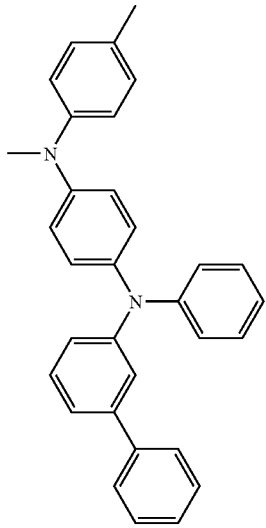
151
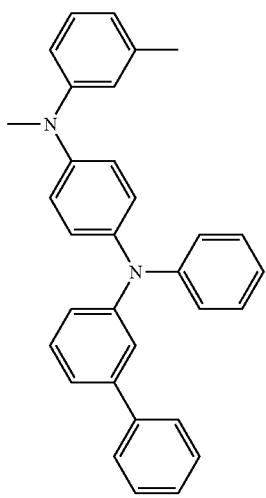
152
150
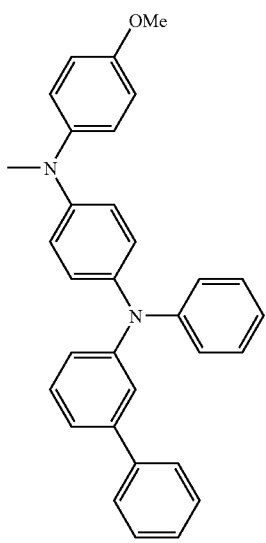
153

154
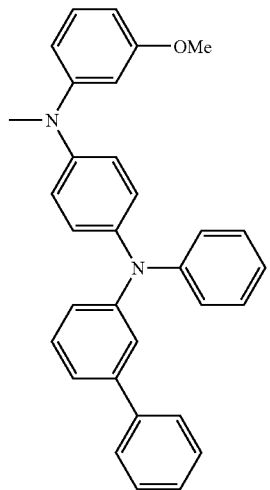
155
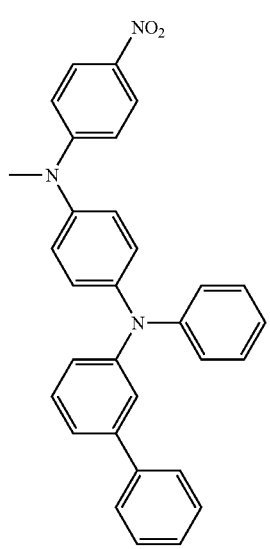
156
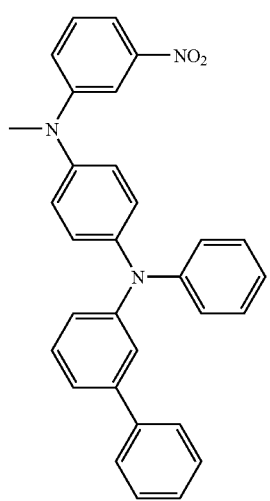
157
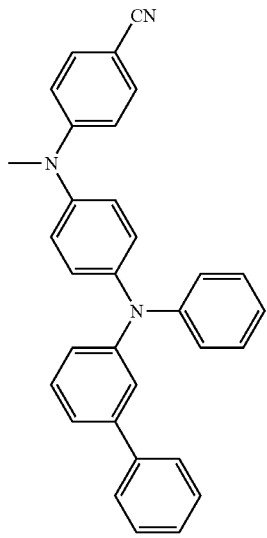
158
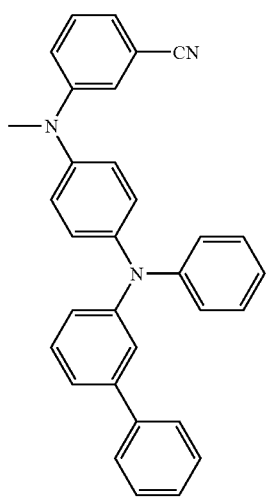
159
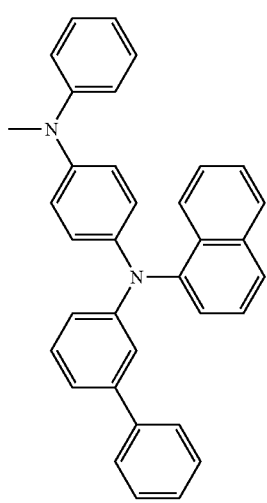

160
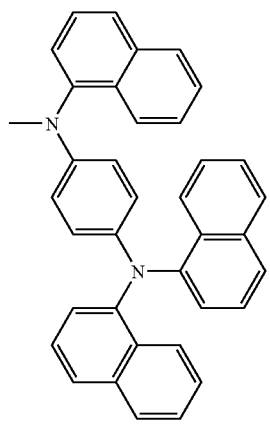
161
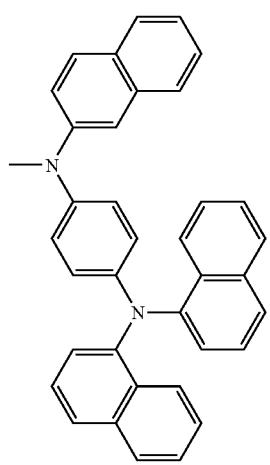
162
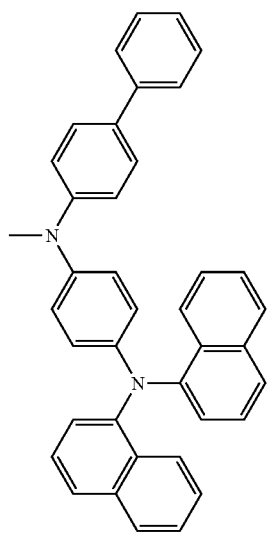
163
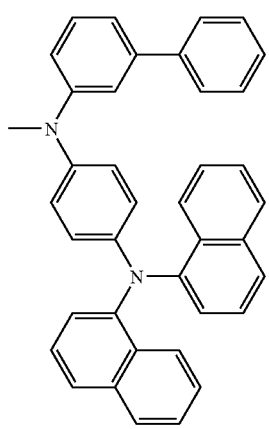
164
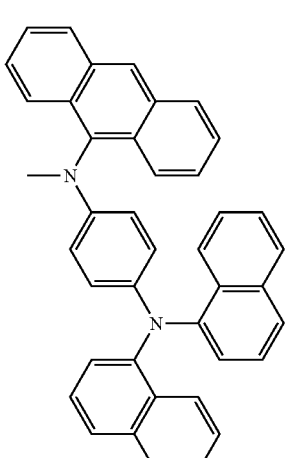
165
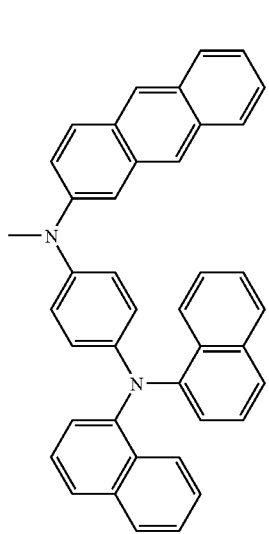

-continued
166
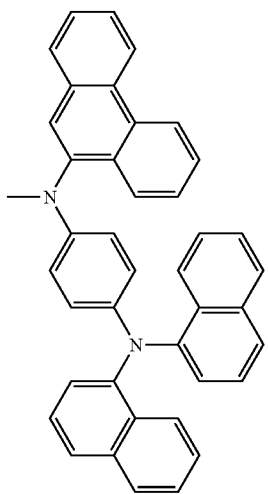
167
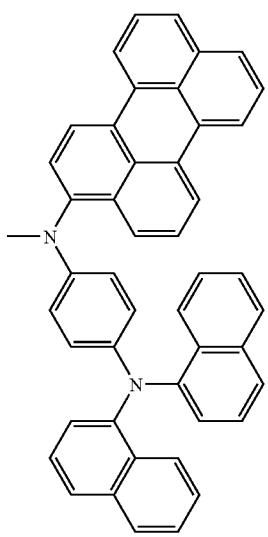
168
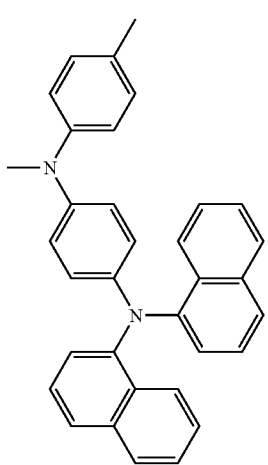
-continued
169
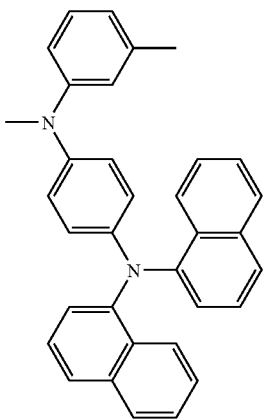
170
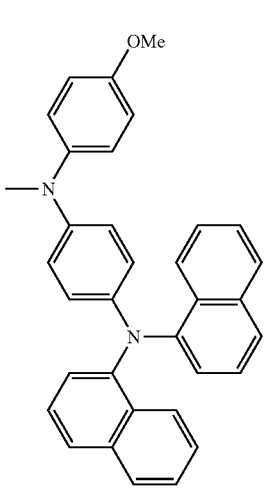
171
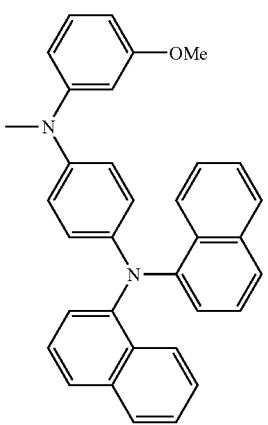

172

173

174

175

176

177

178
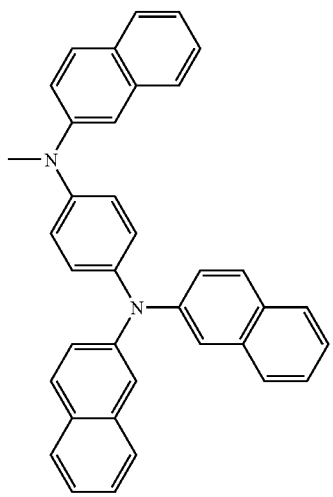
179
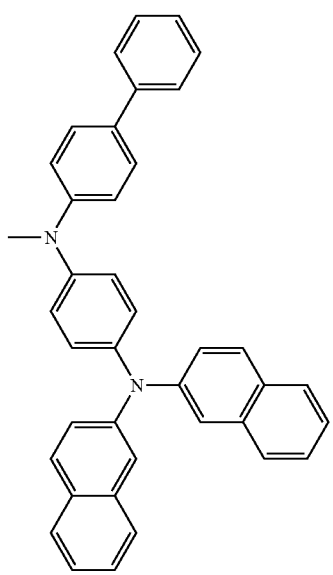
180
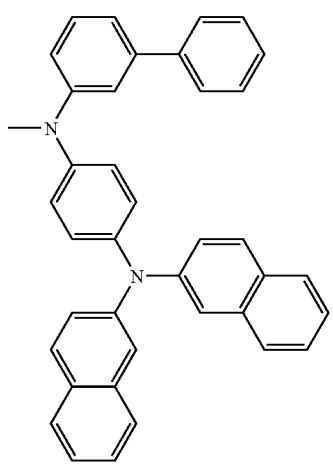
181
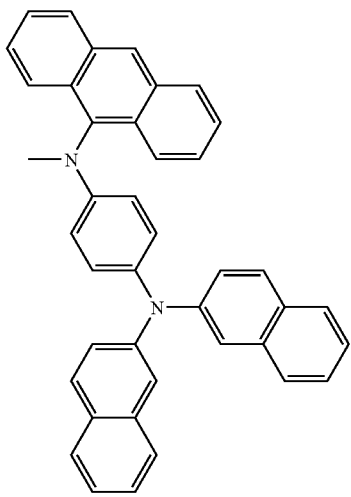
182
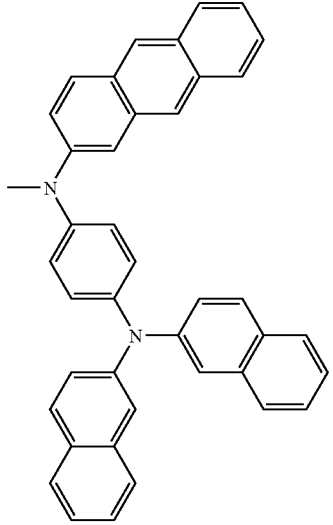
183
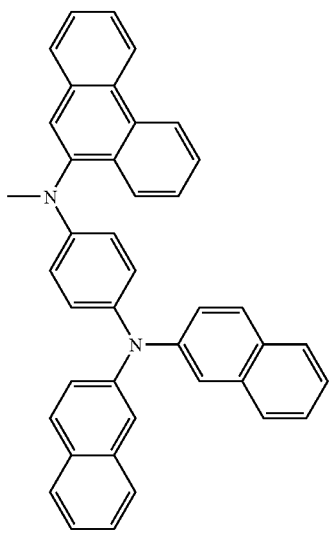

184
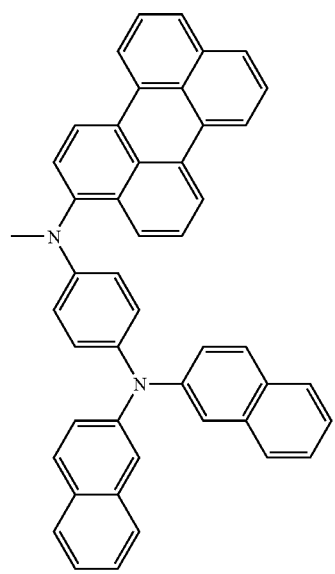
185
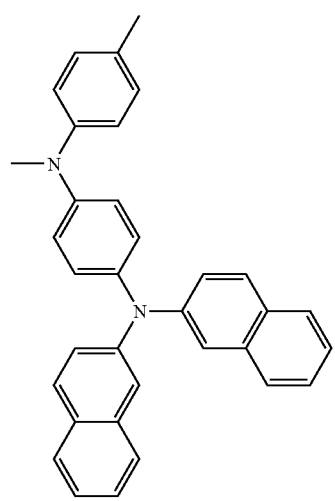
186
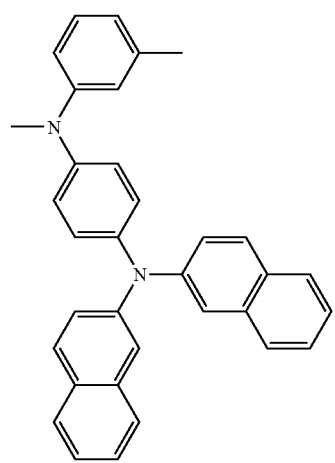
187
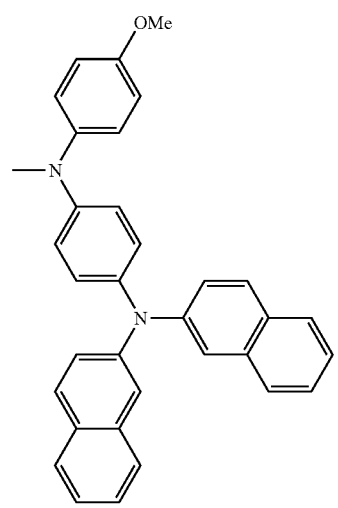
188
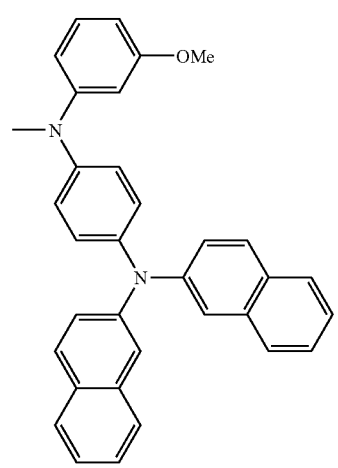
189
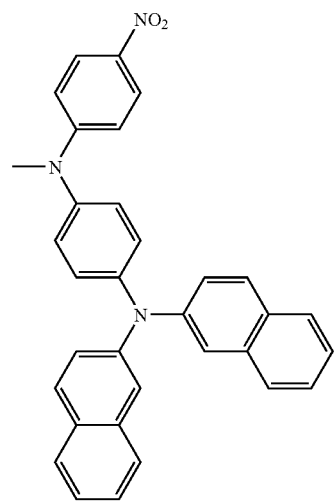

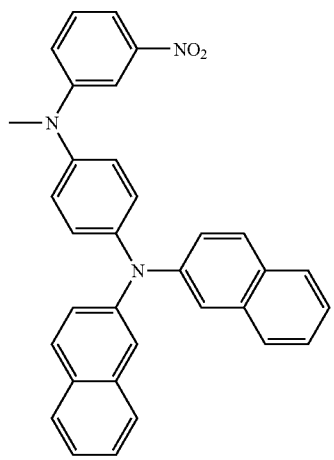
190
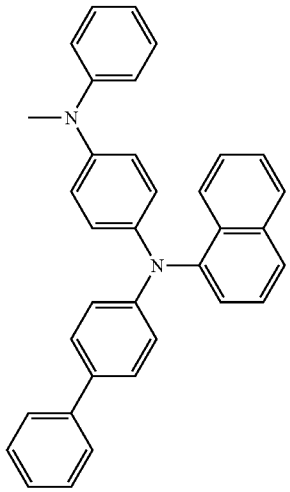
193
191
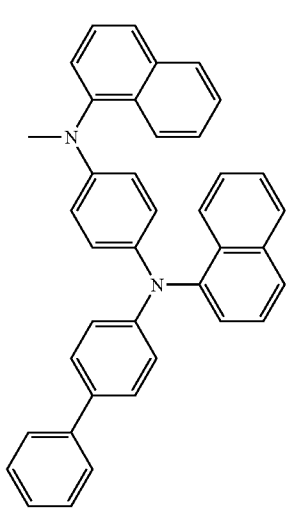
194
192
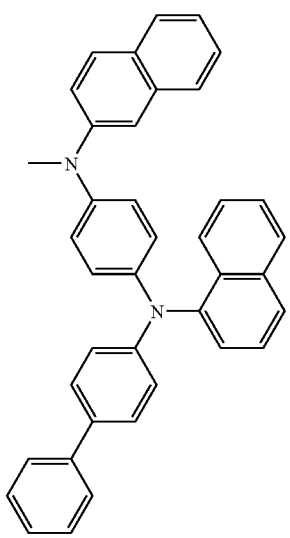
195

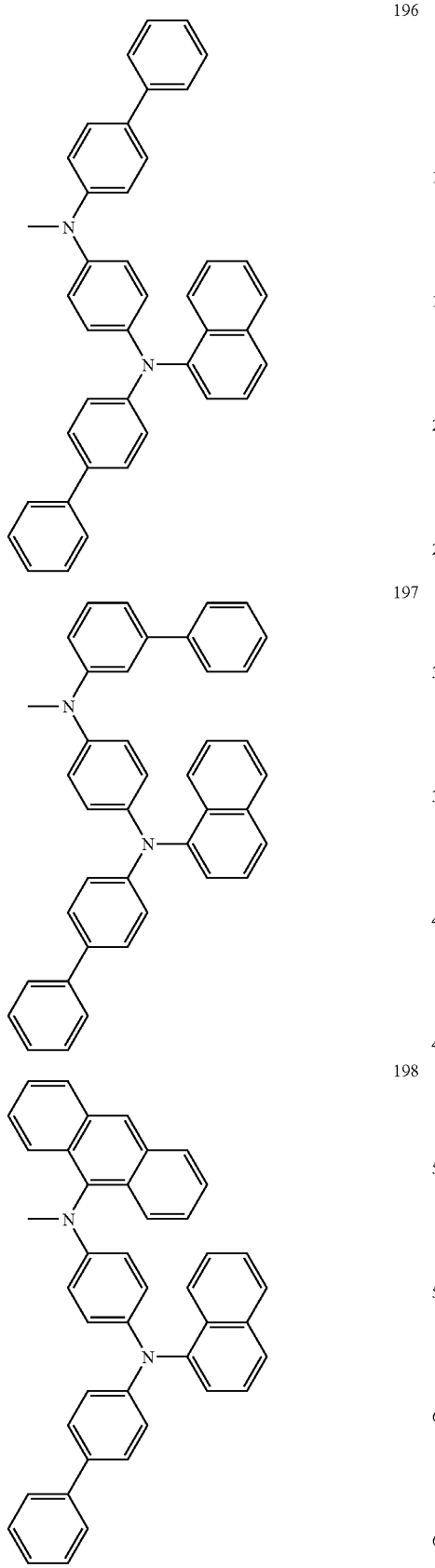
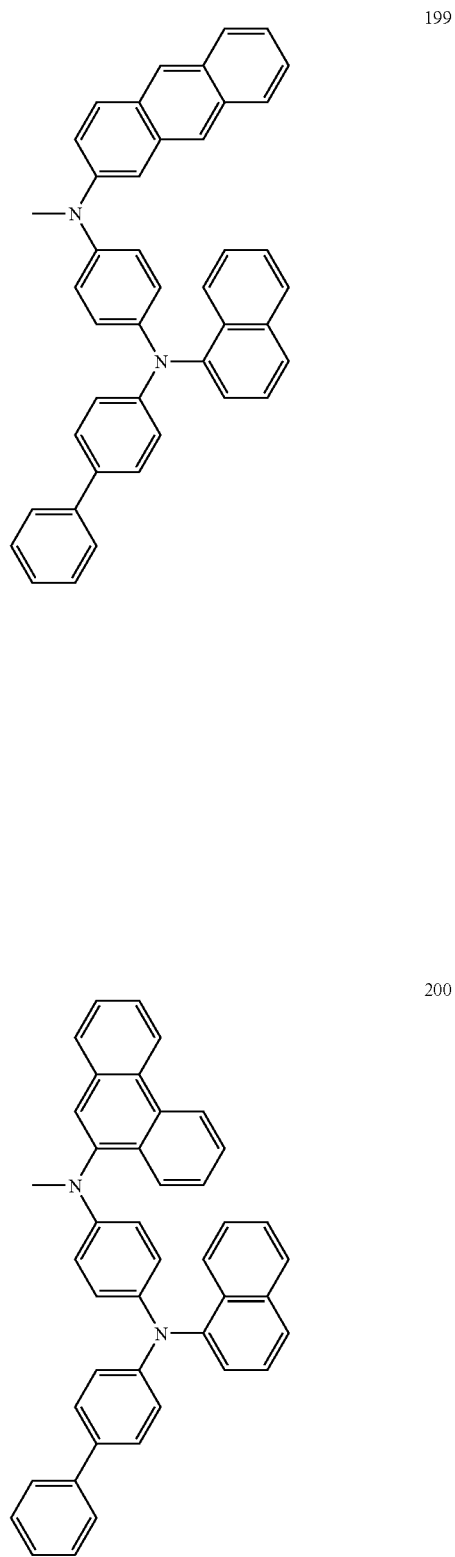

-continued
201
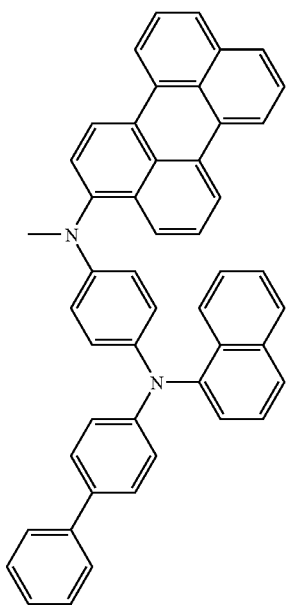
202
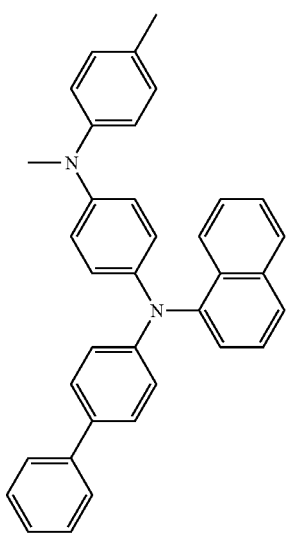
203
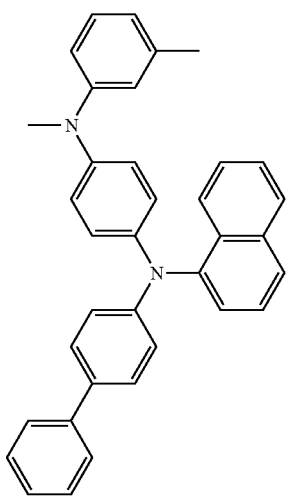
-continued
204
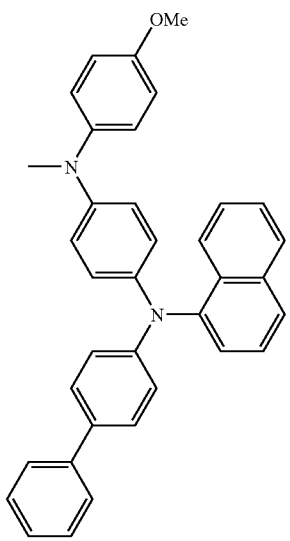
205
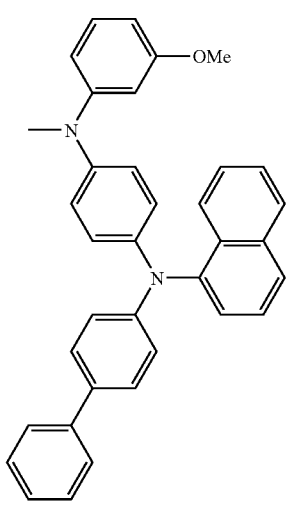
206
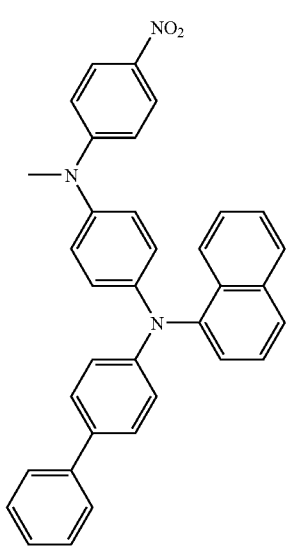

-continued
207
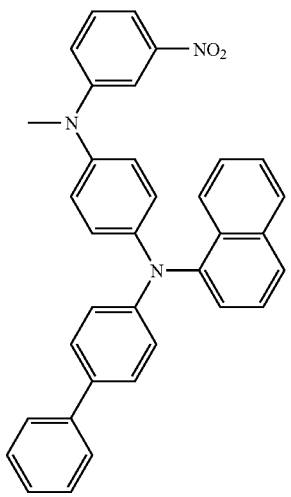
208
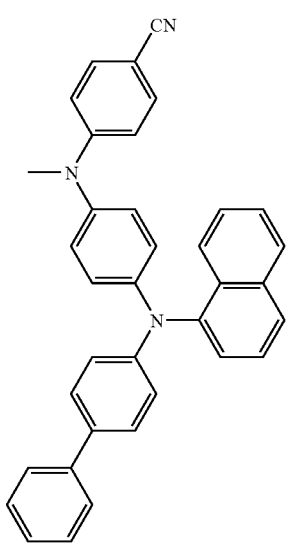
209
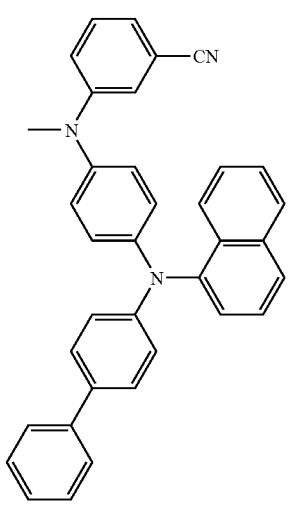
-continued
210
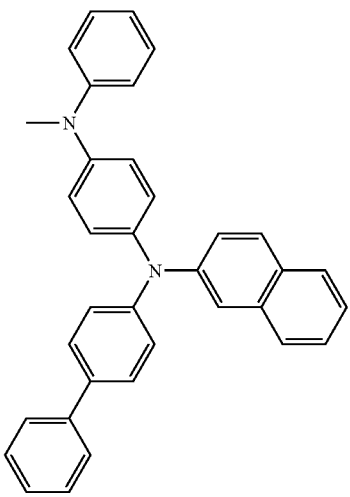
211
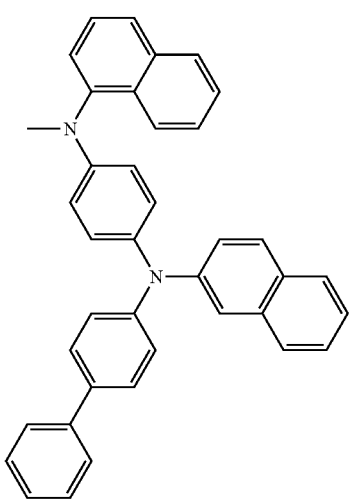
212
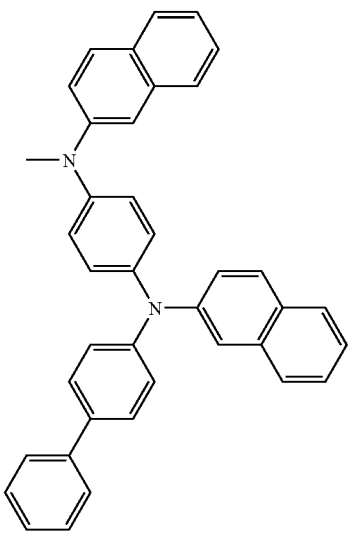

-continued
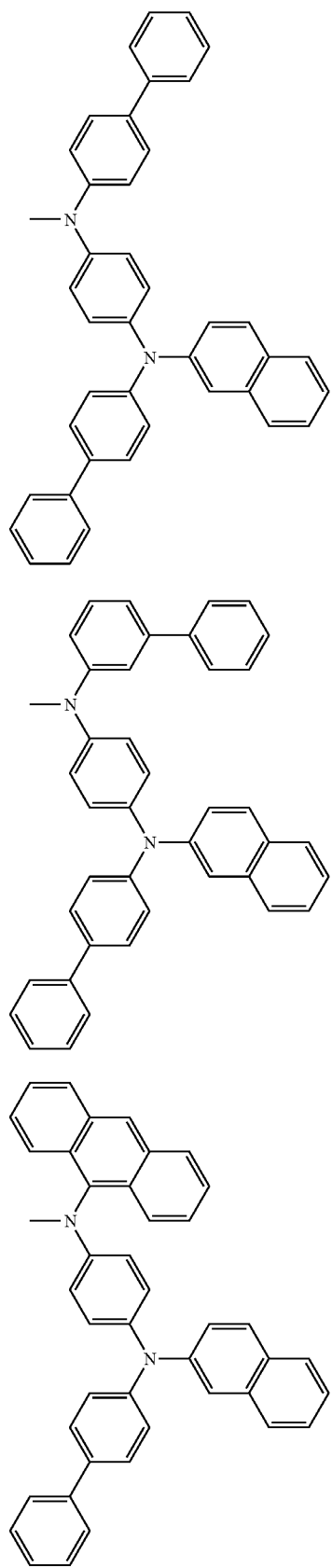
-continued
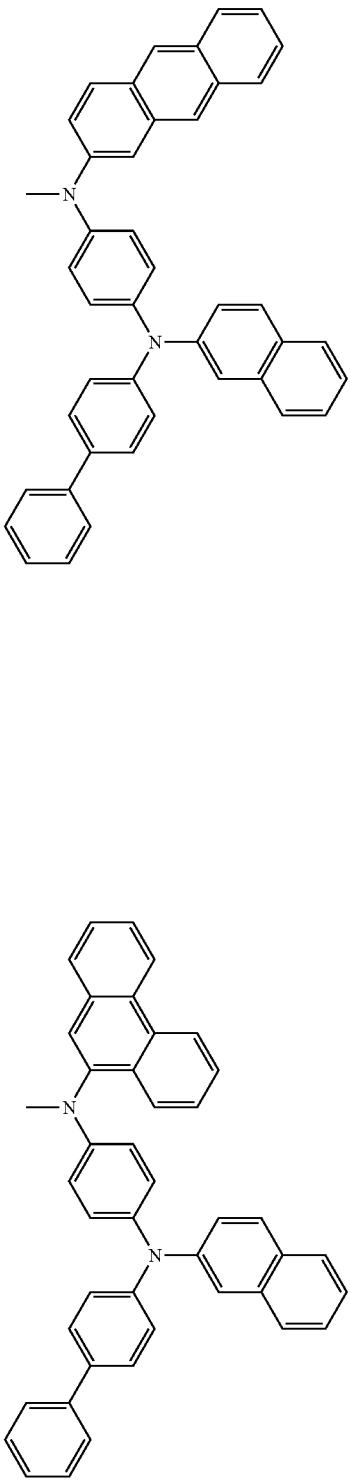

-continued
218
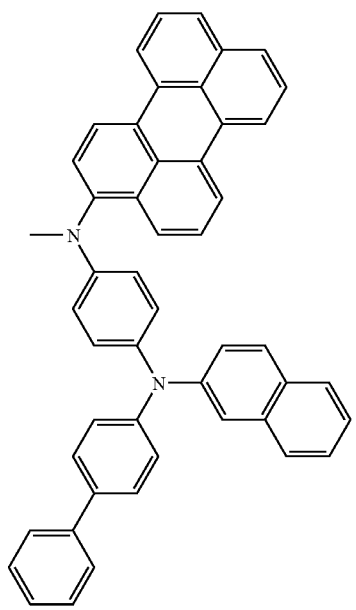
219
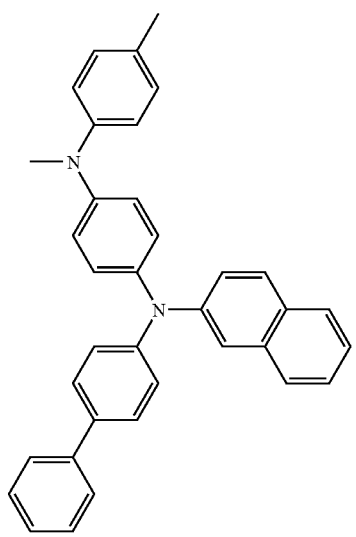
220
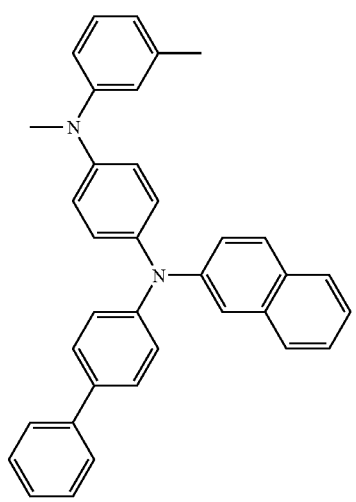
-continued
221
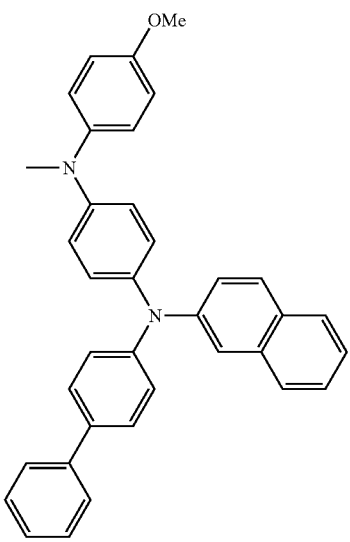
222
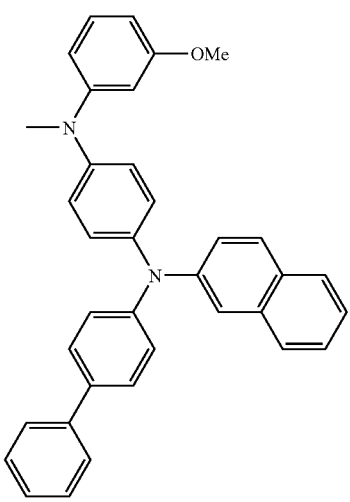
223
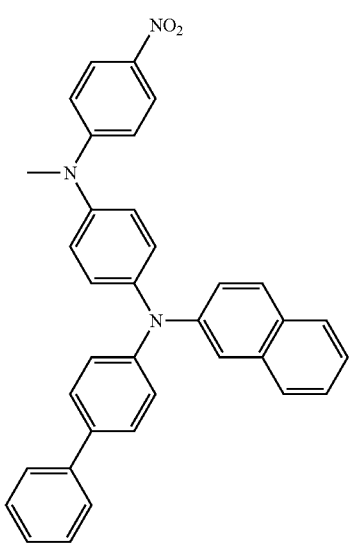

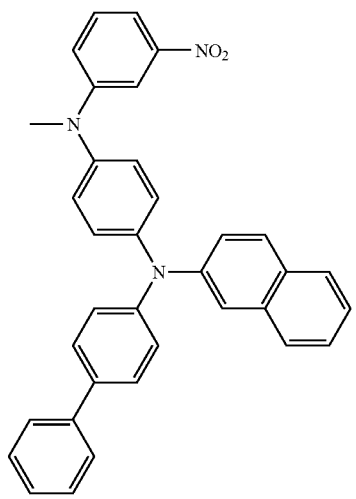
224
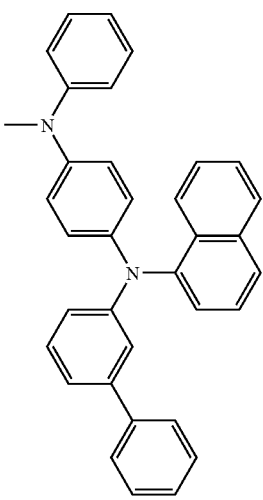
227
225
228
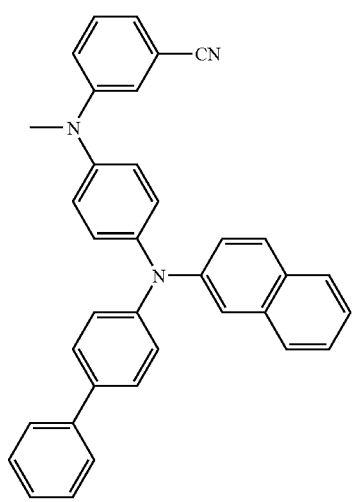
226
229

230
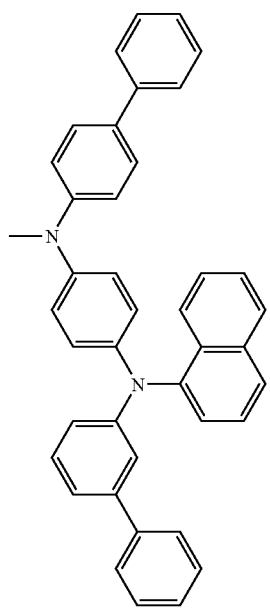
231
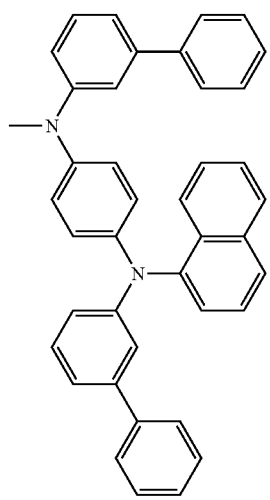
232
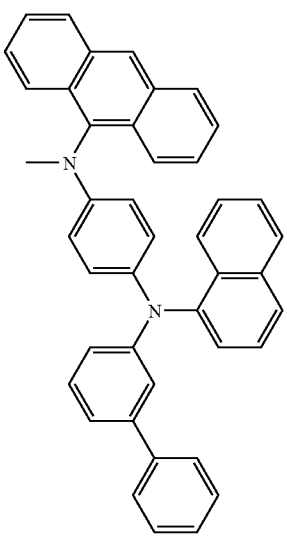
233
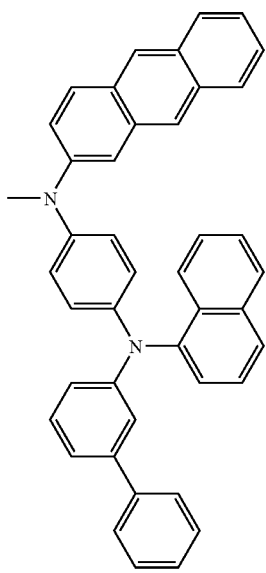
234
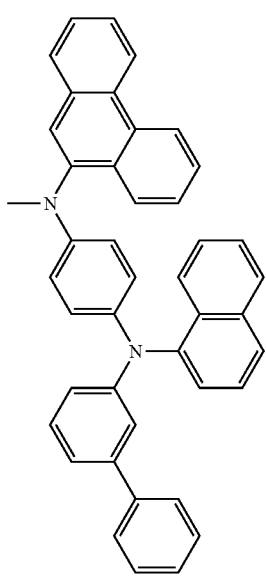

-continued
235
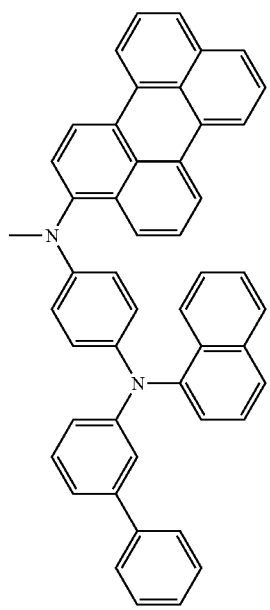
236
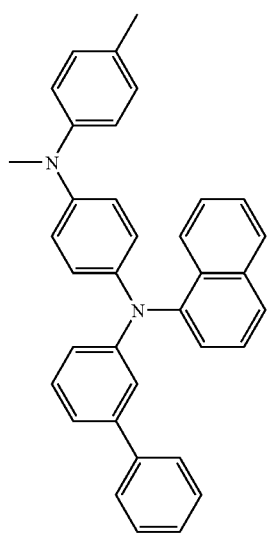
237
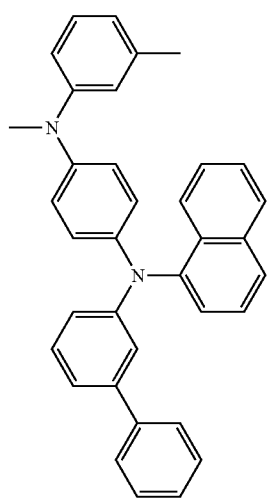
-continued
238
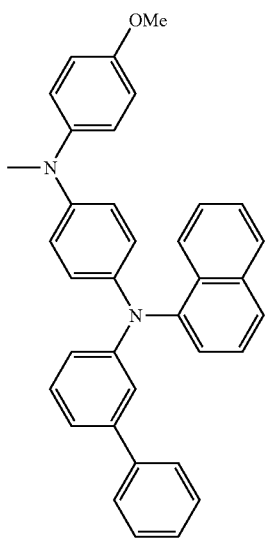
239
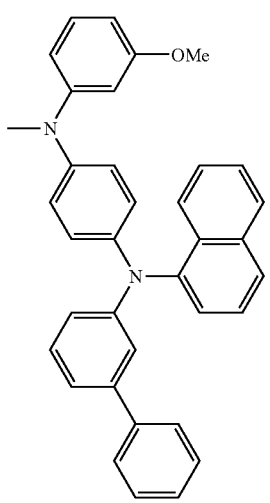
240
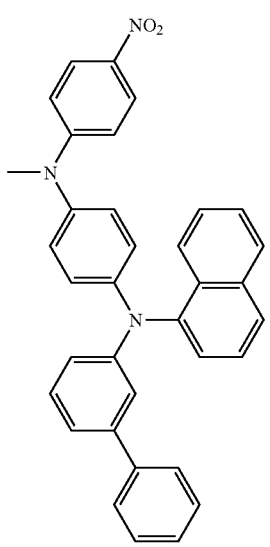

241 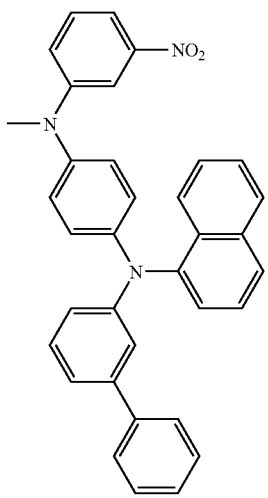
242 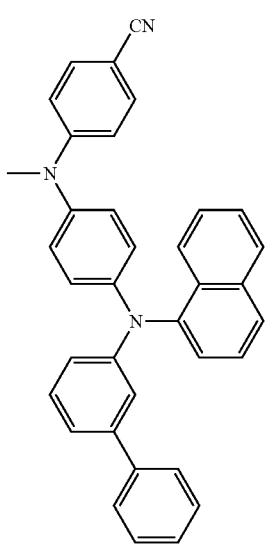
243 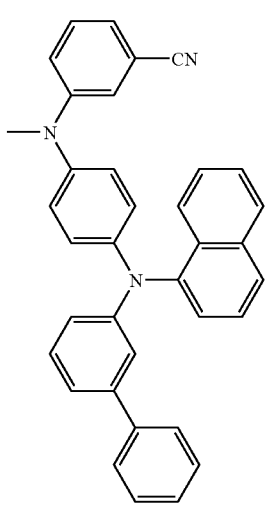
244 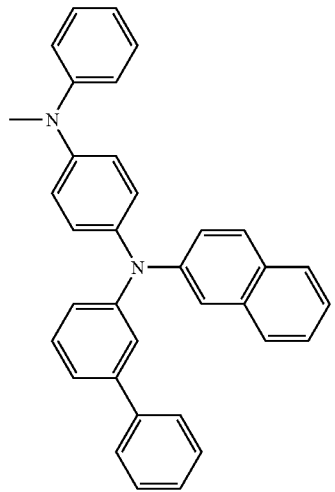
245 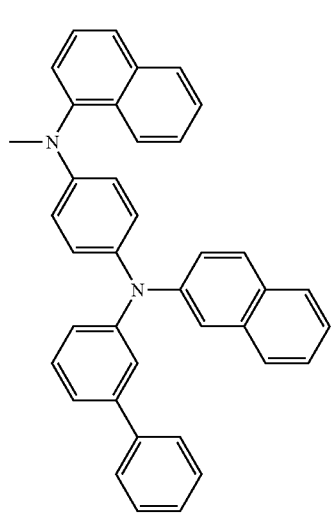
246 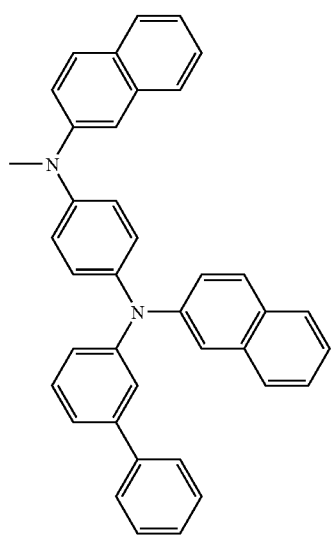

-continued
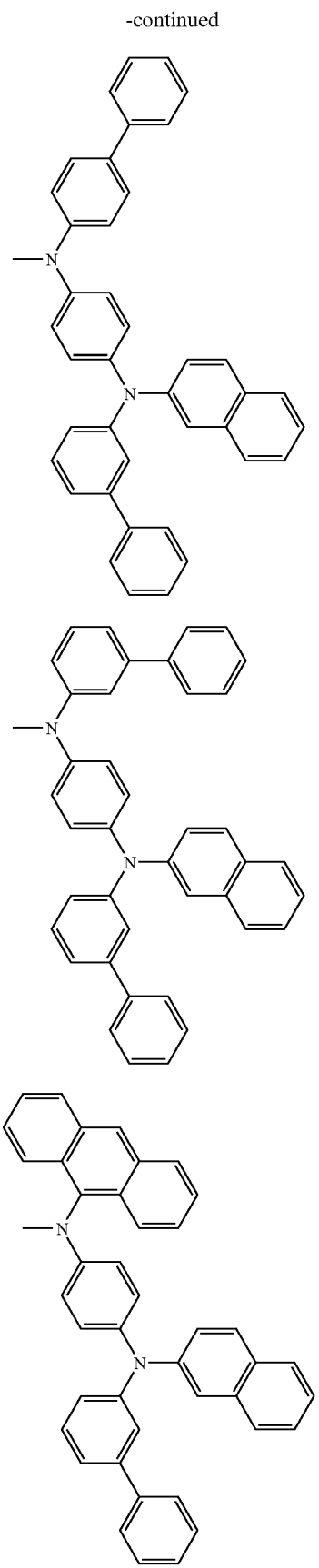
-continued
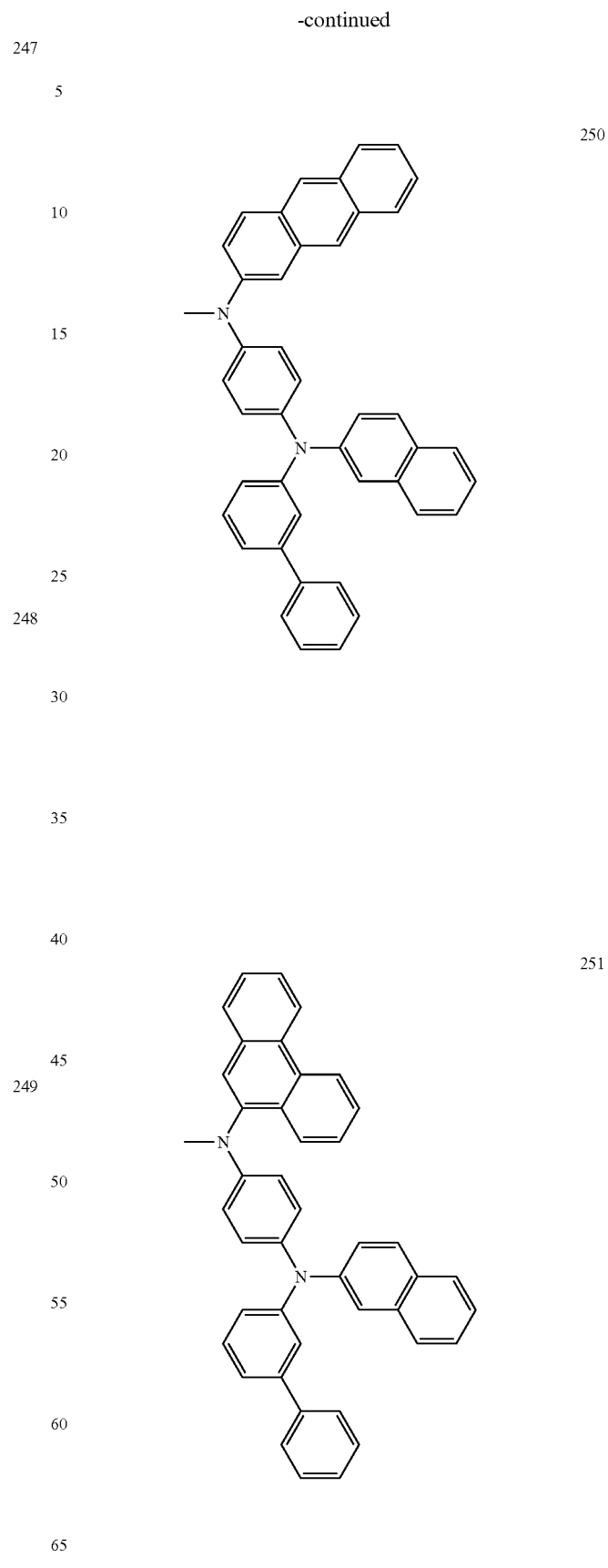

-continued
252
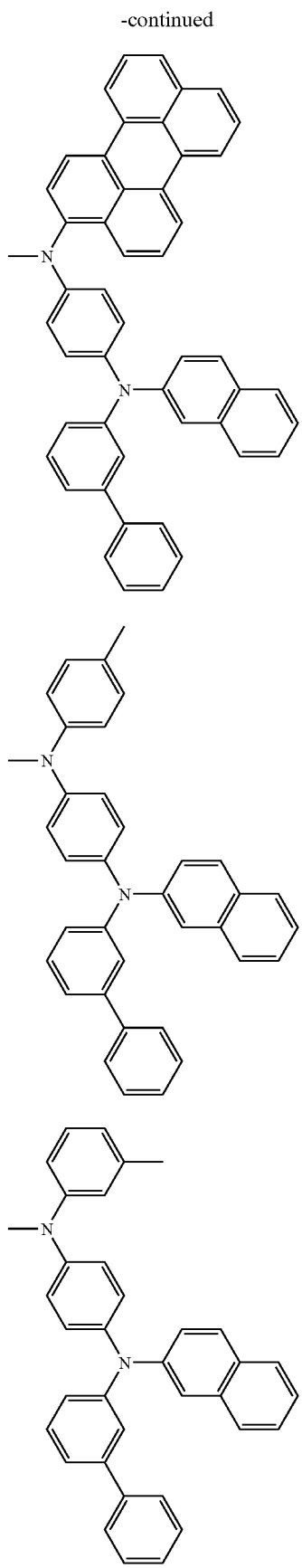
253
254
-continued
255
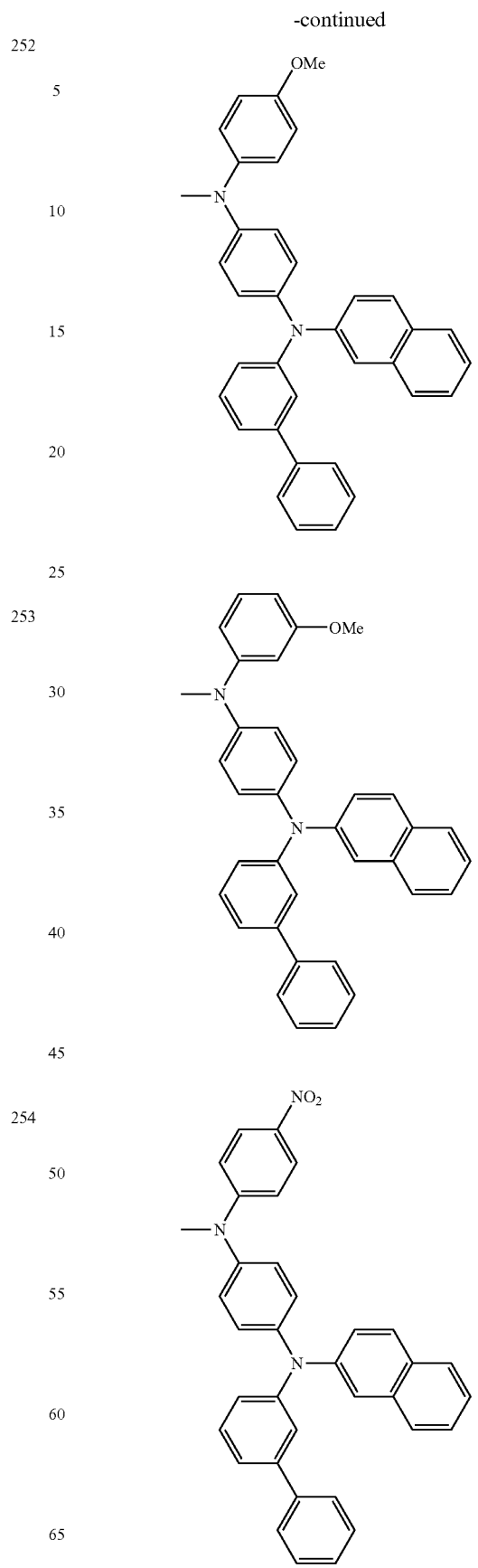
256
257

258
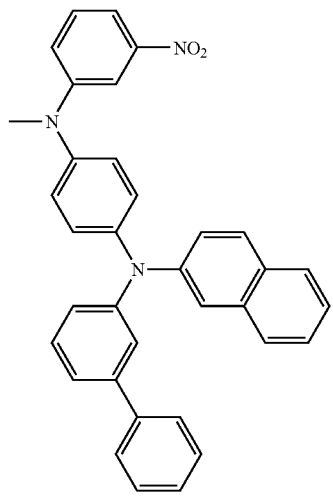
259
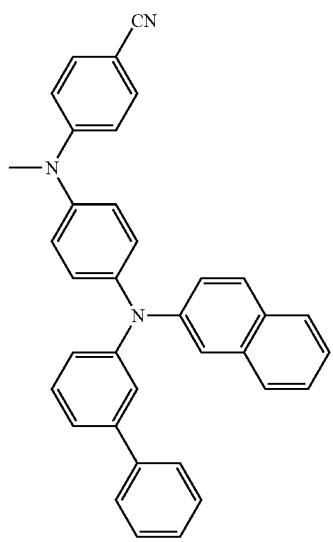
260
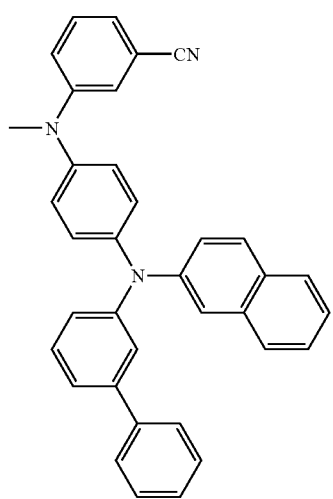
261
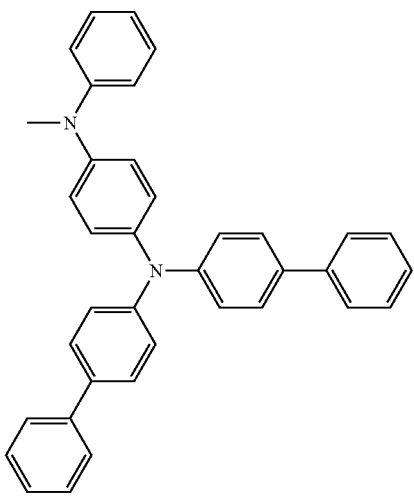
262
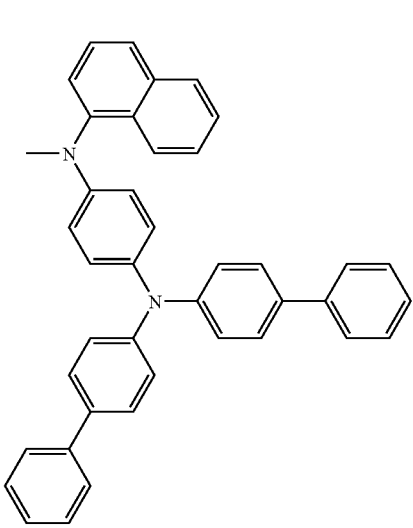
263
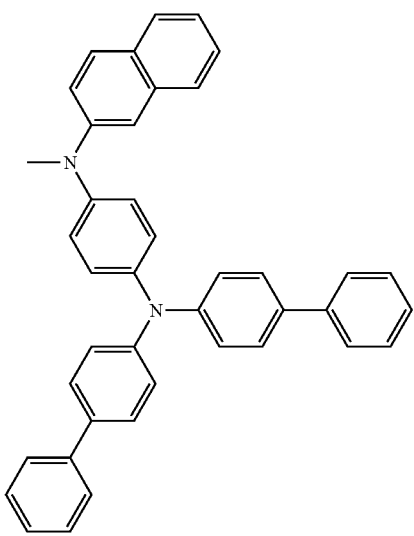

-continued
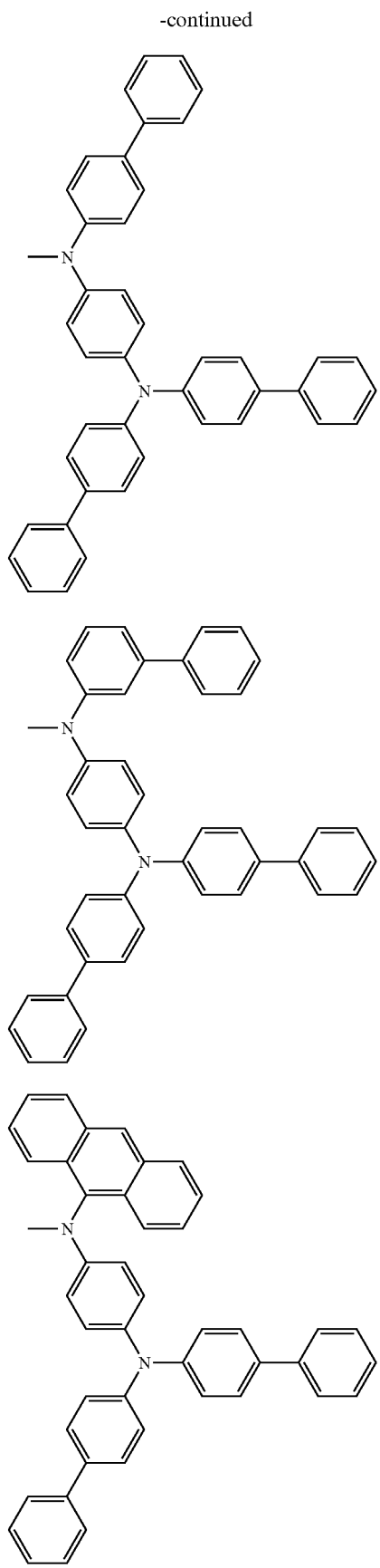
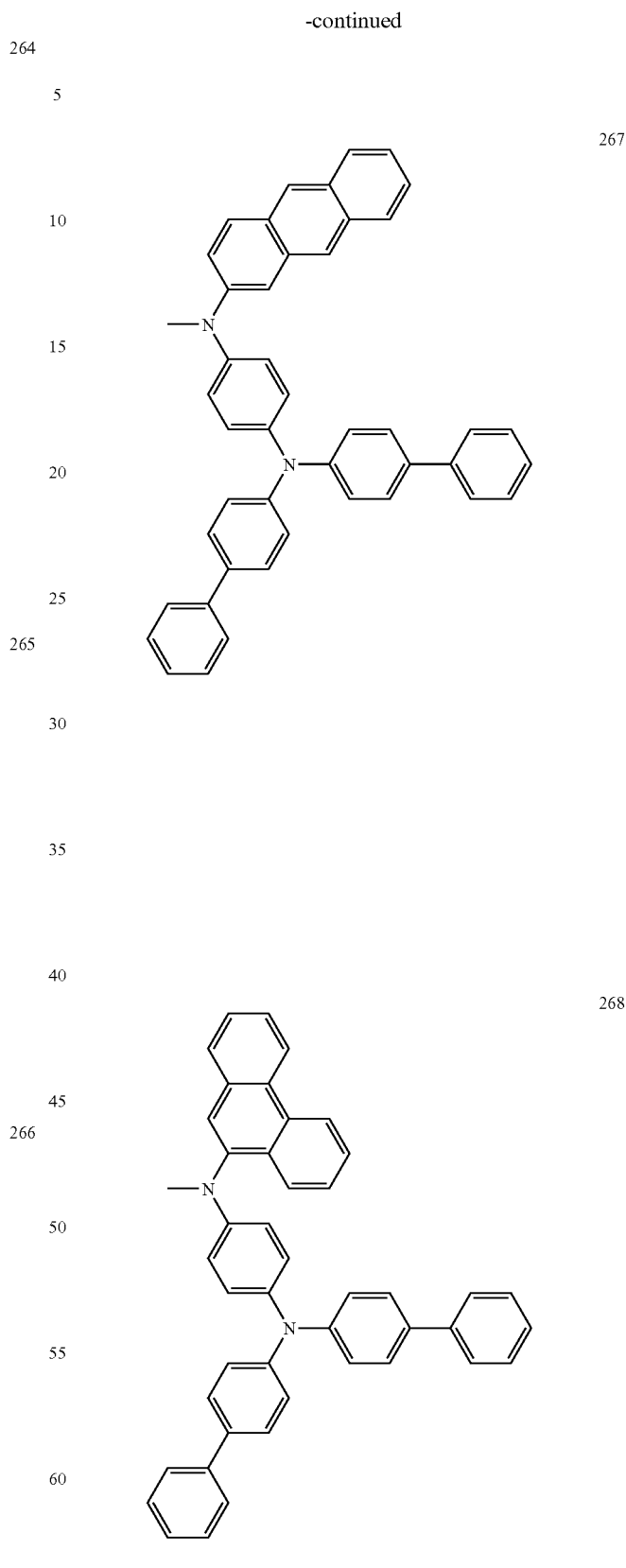

-continued
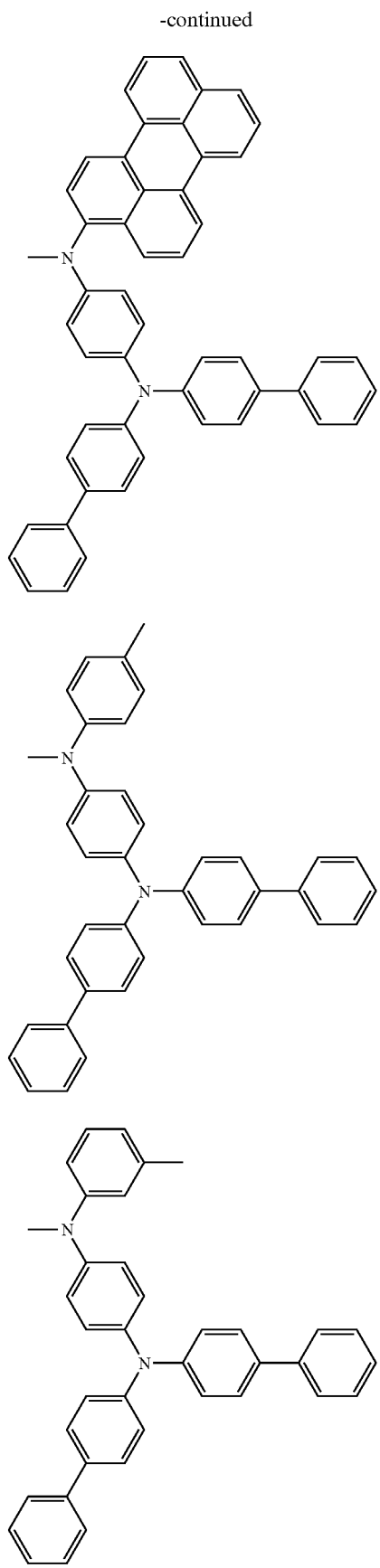
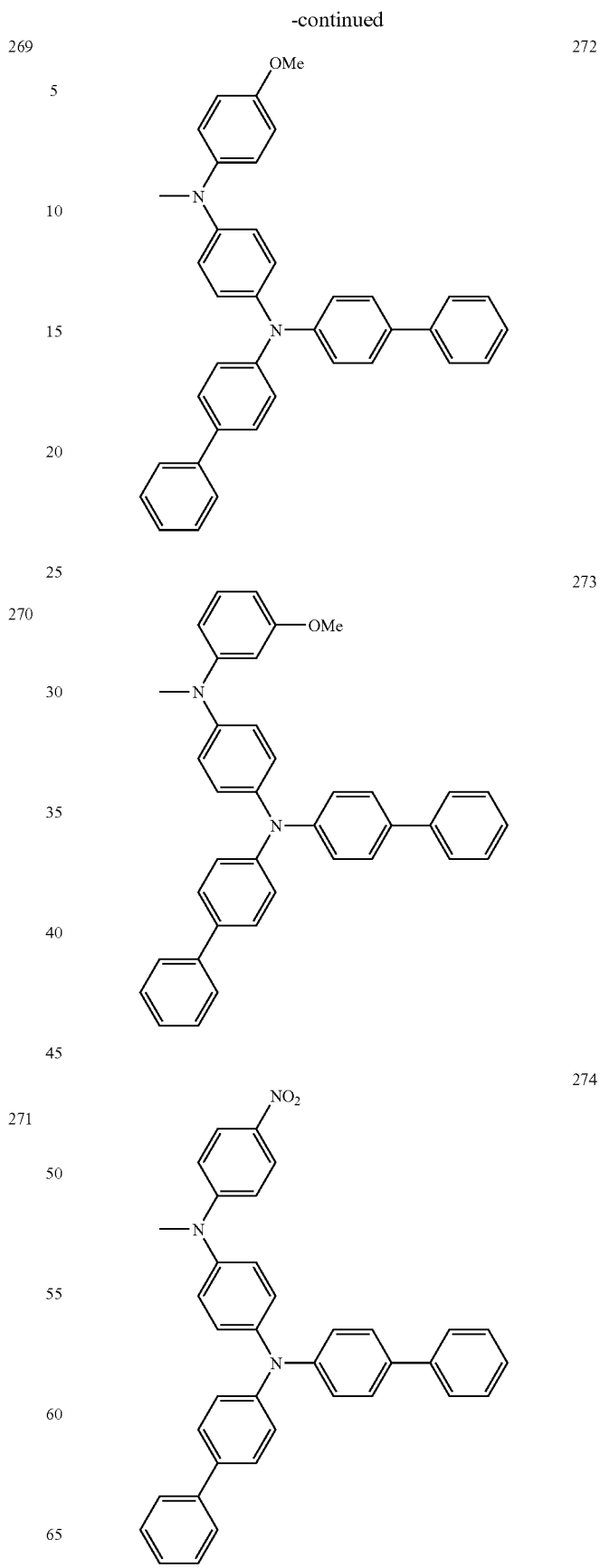

275
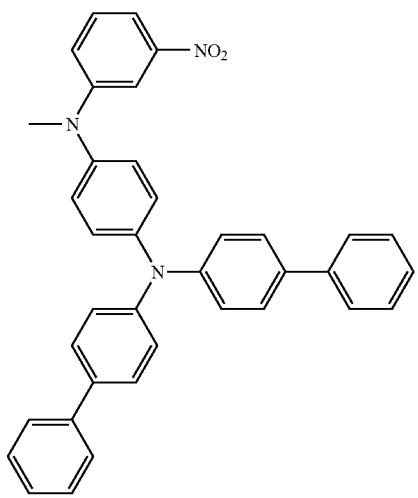
276
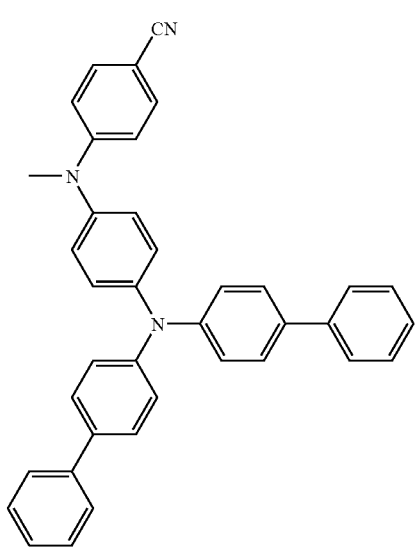
277
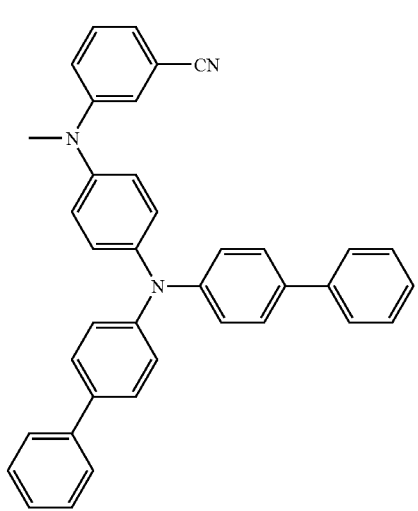
278
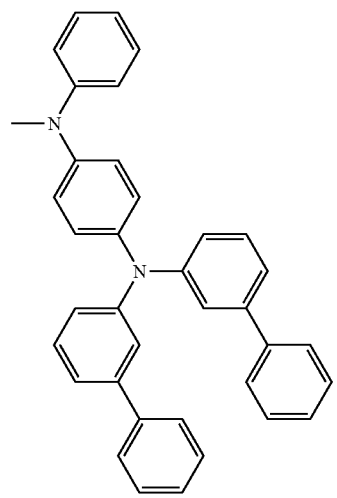
279
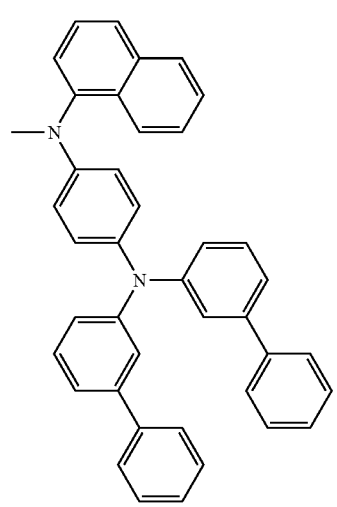
280
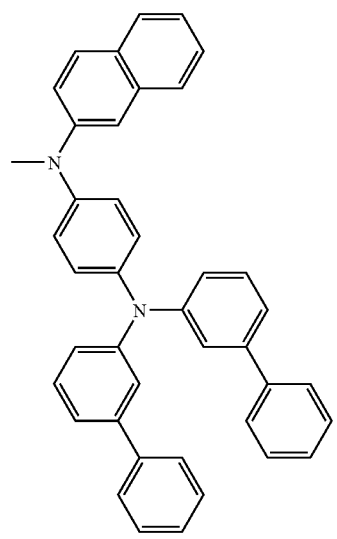

-continued
281
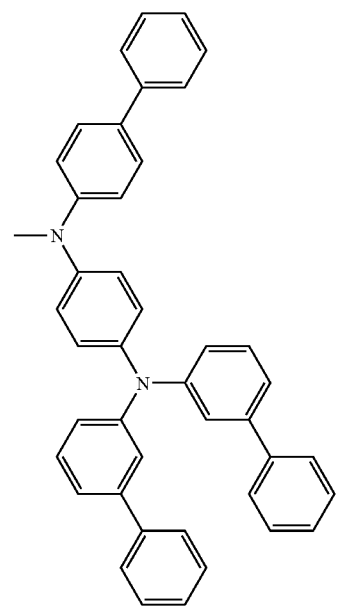
282
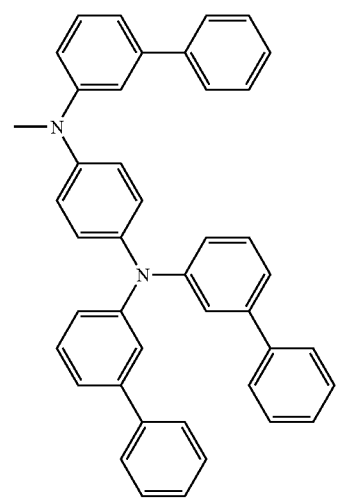
283
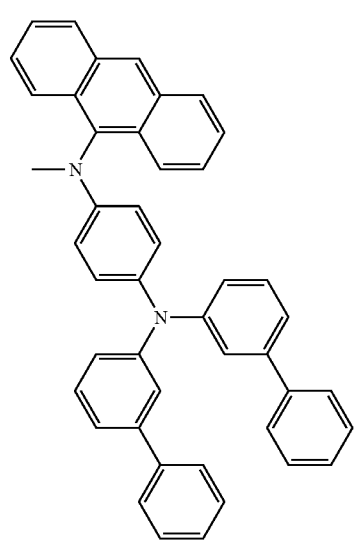
-continued
284
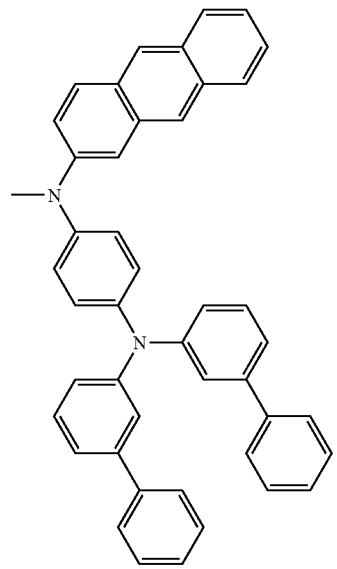
285
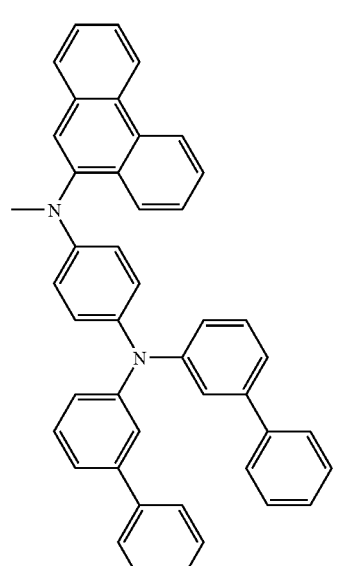

-continued
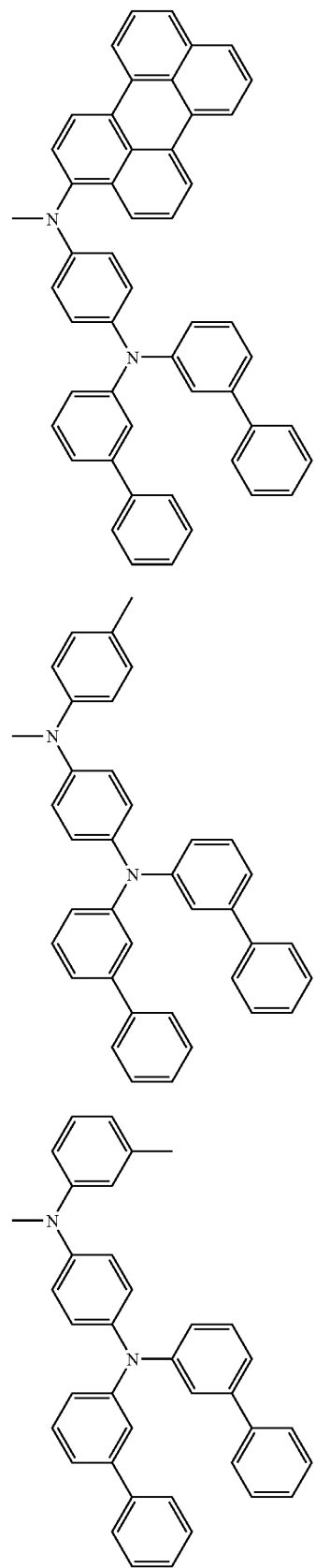
-continued
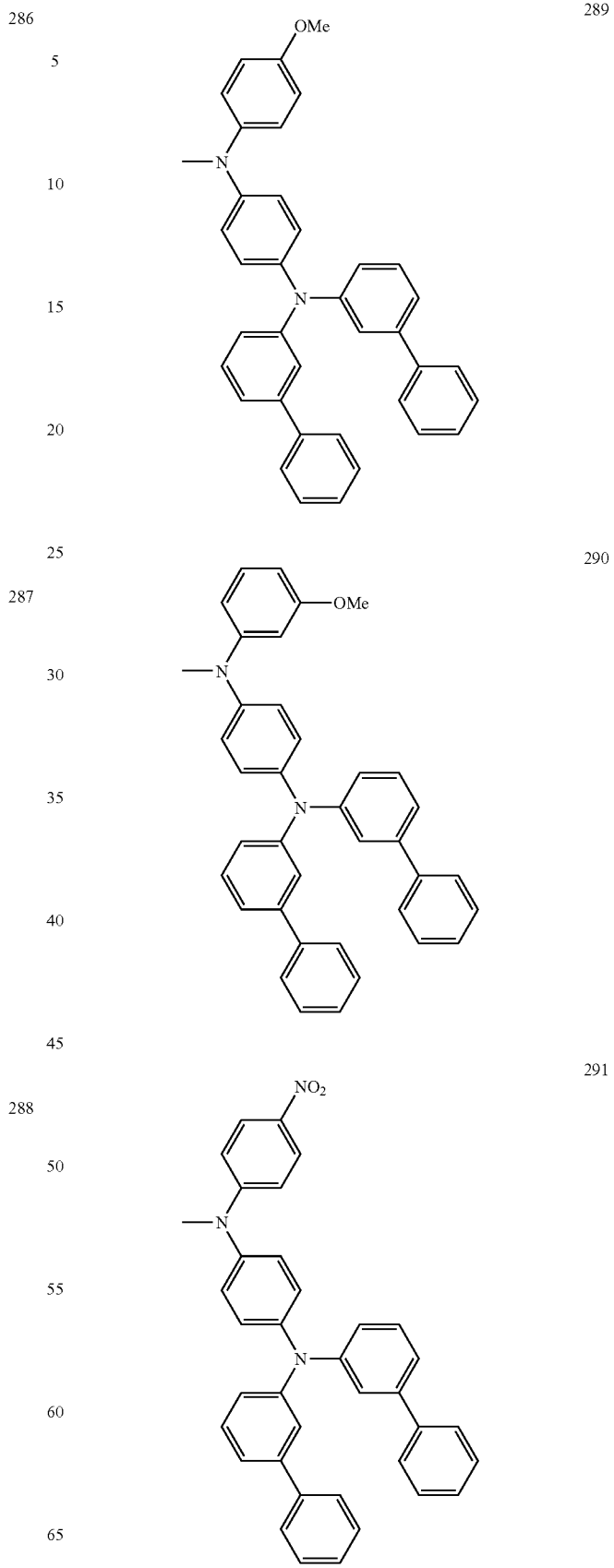

-continued
292
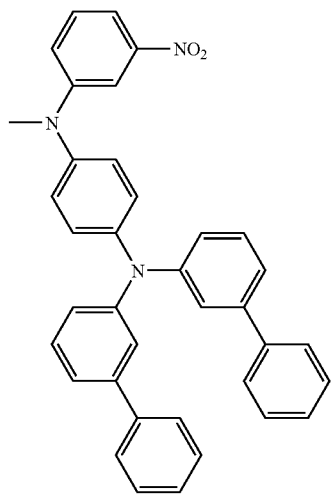
293
294
-continued
295
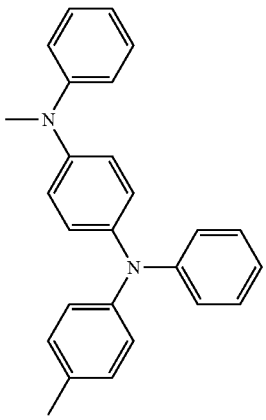
296
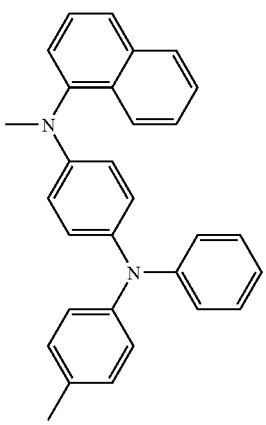
297
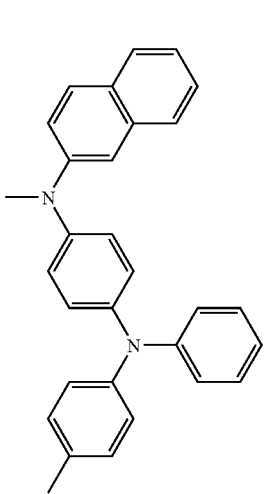

-continued
298
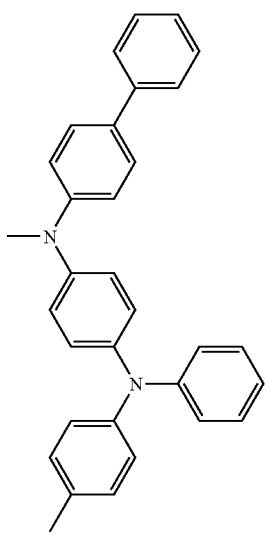
299
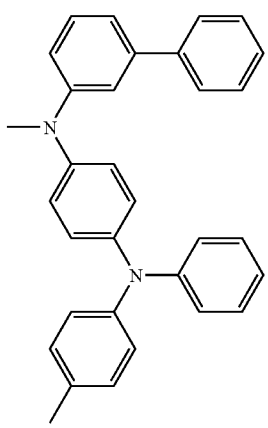
300
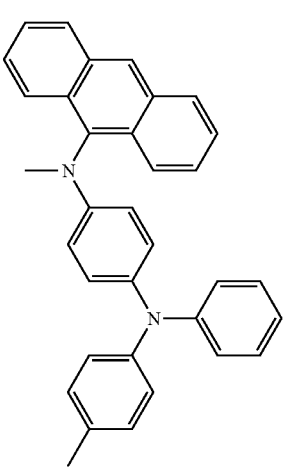
-continued
301
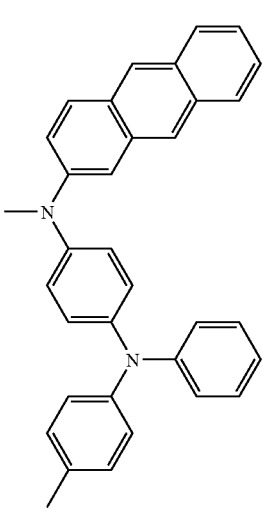
302
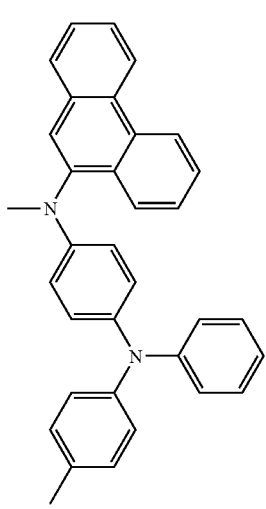
303
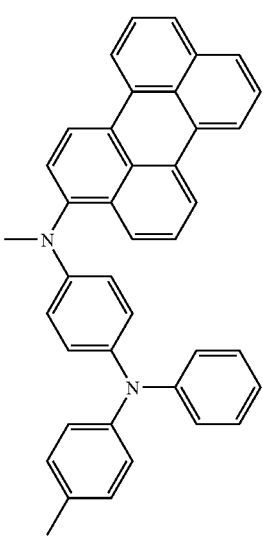

135 136
-continued -continued
304 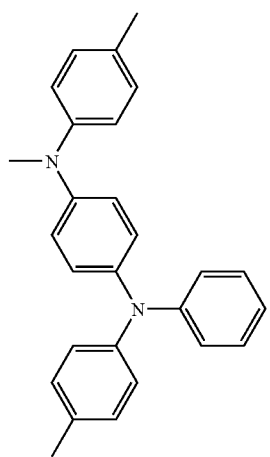
305 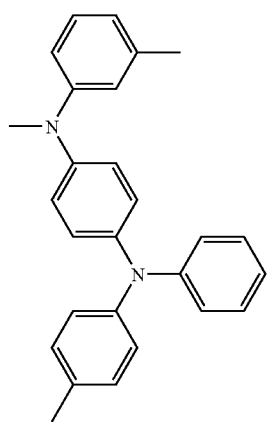
306 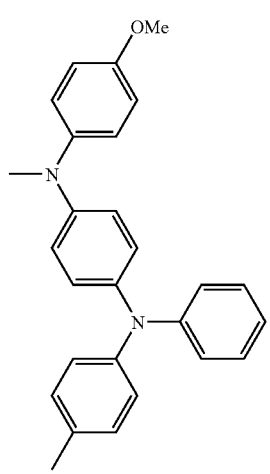
307 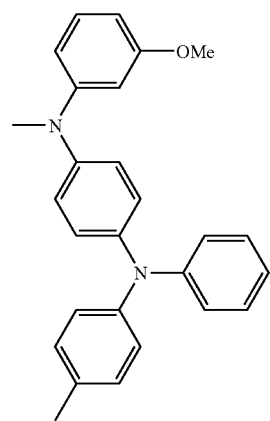
308 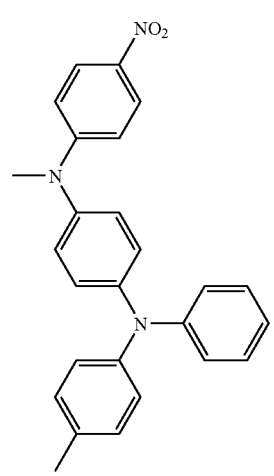
309 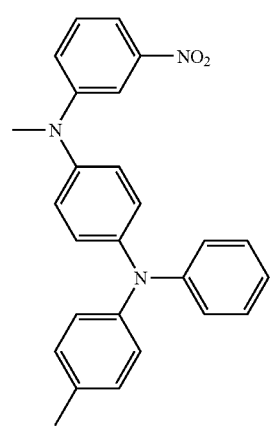

-continued
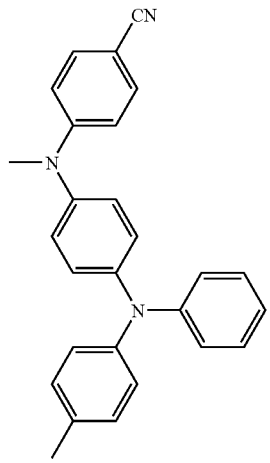
310
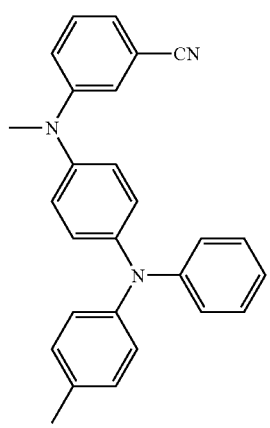
311
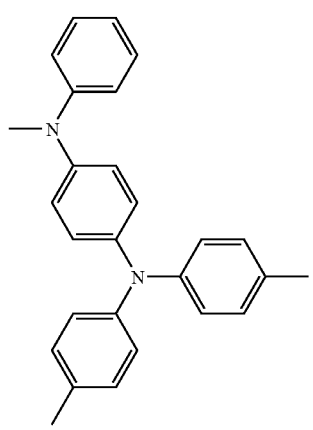
312
-continued
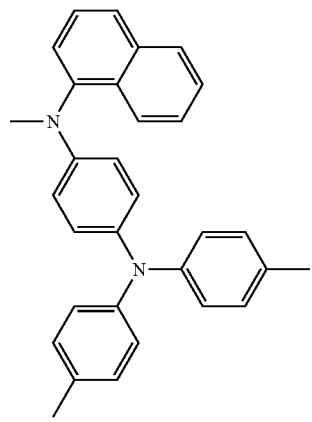
313
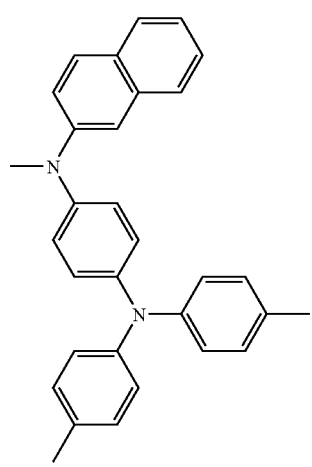
314
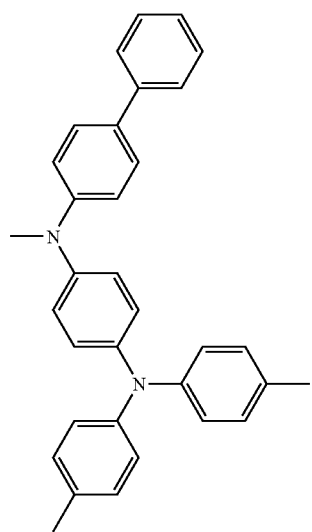
315

139 140
-continued -continued
316
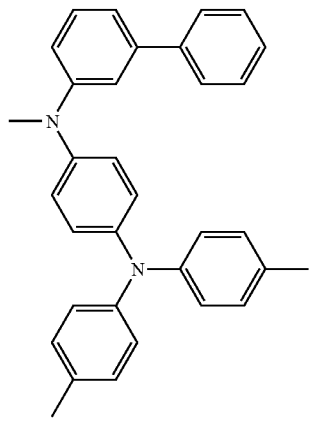
319
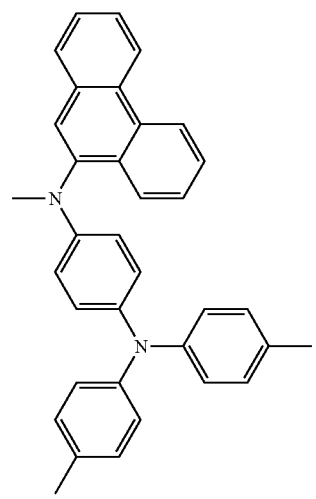
317
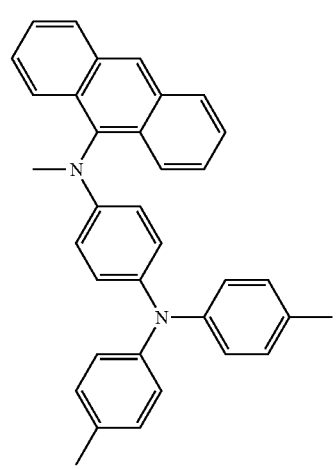
320
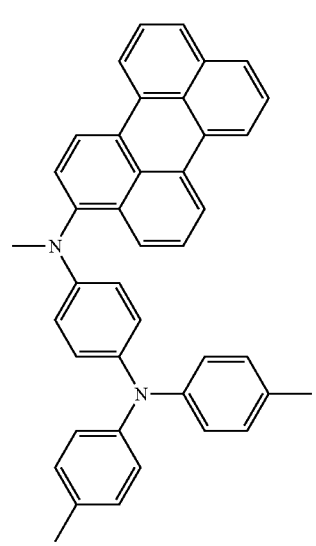
318
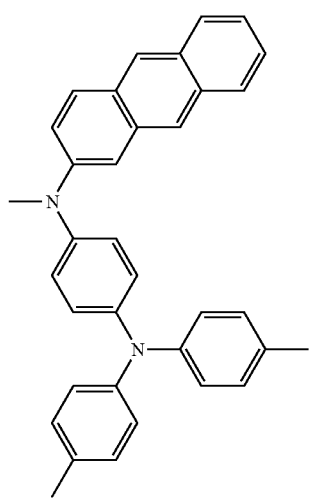
321
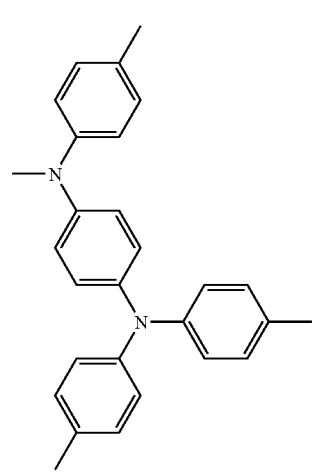

| 322 | 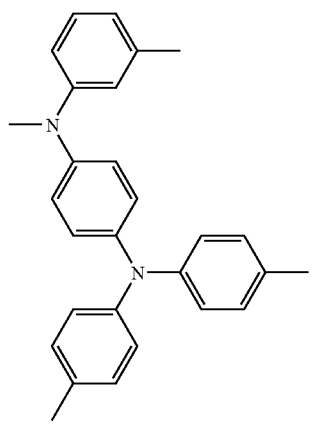 | 325 | 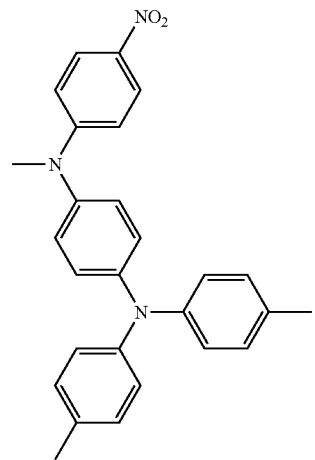 |
| 323 | 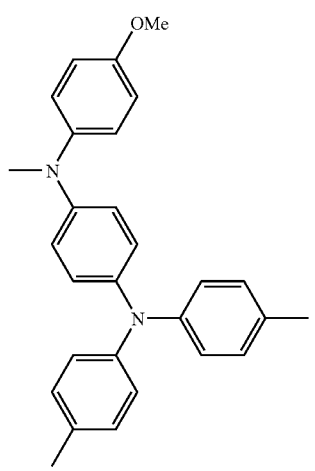 | 326 | 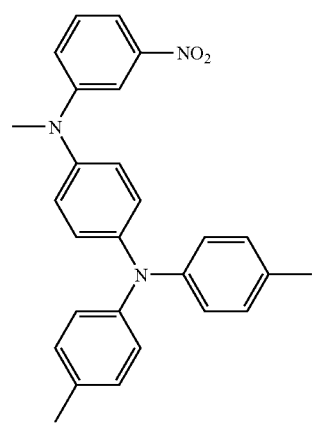 |
| 324 | 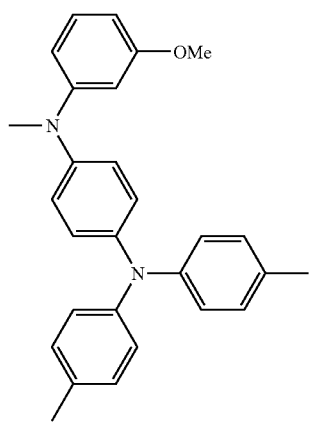 | 327 | 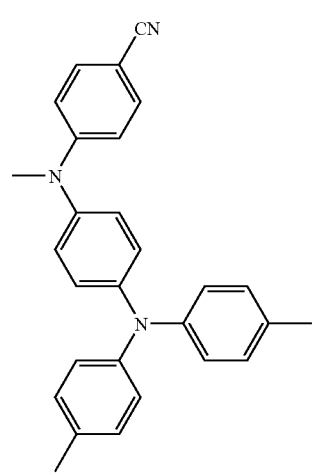 |

328
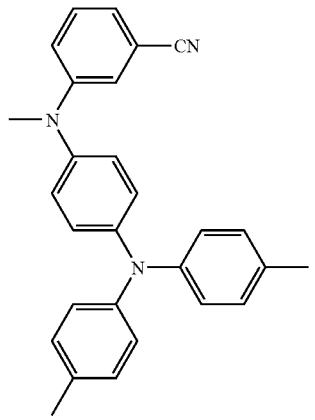
329
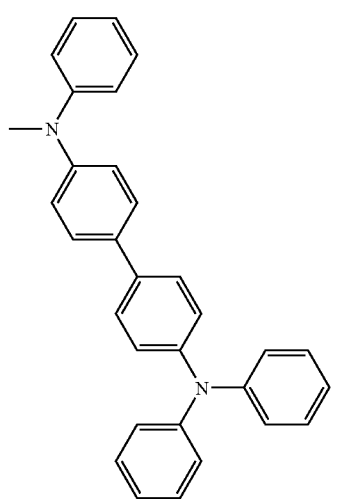
330
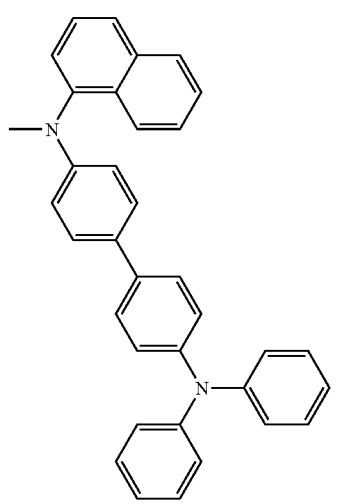
331
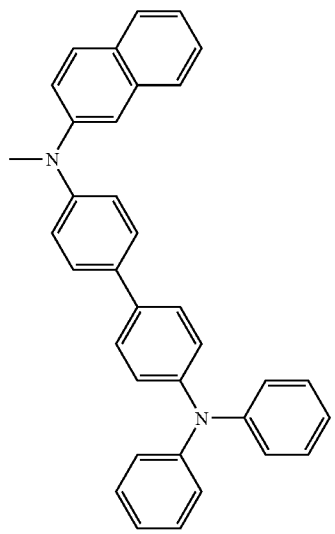
332
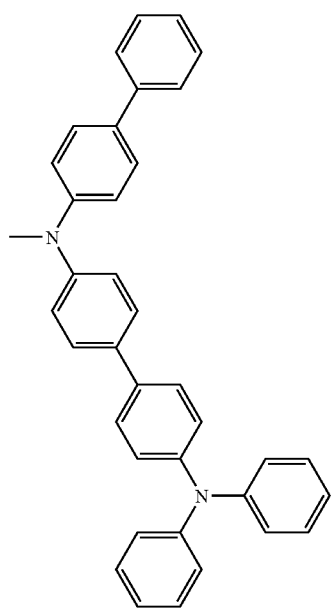
333
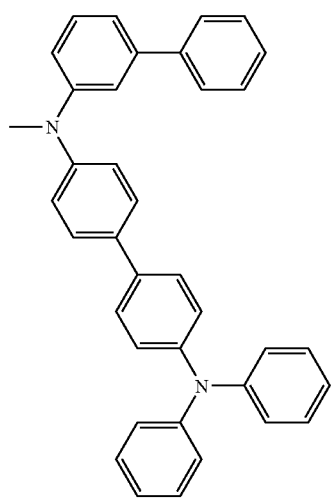

-continued
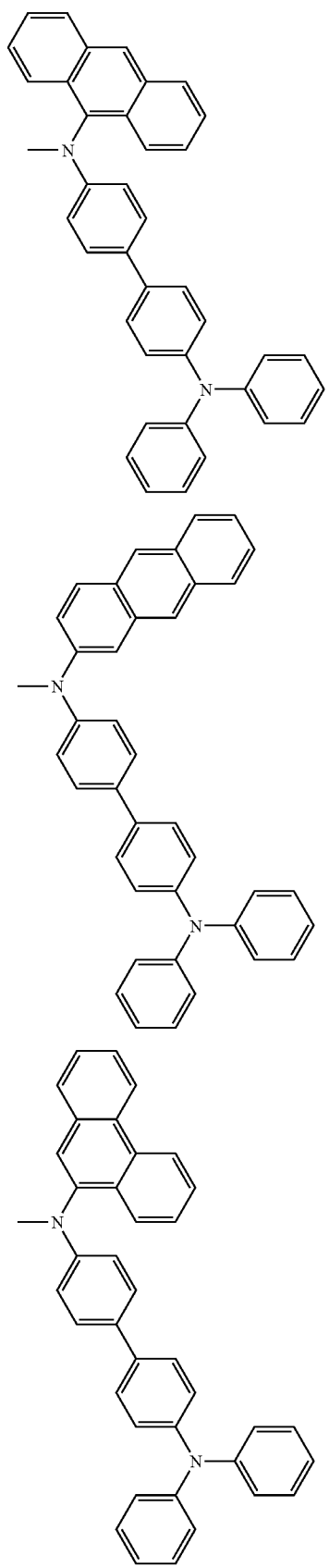
334
335
336
-continued
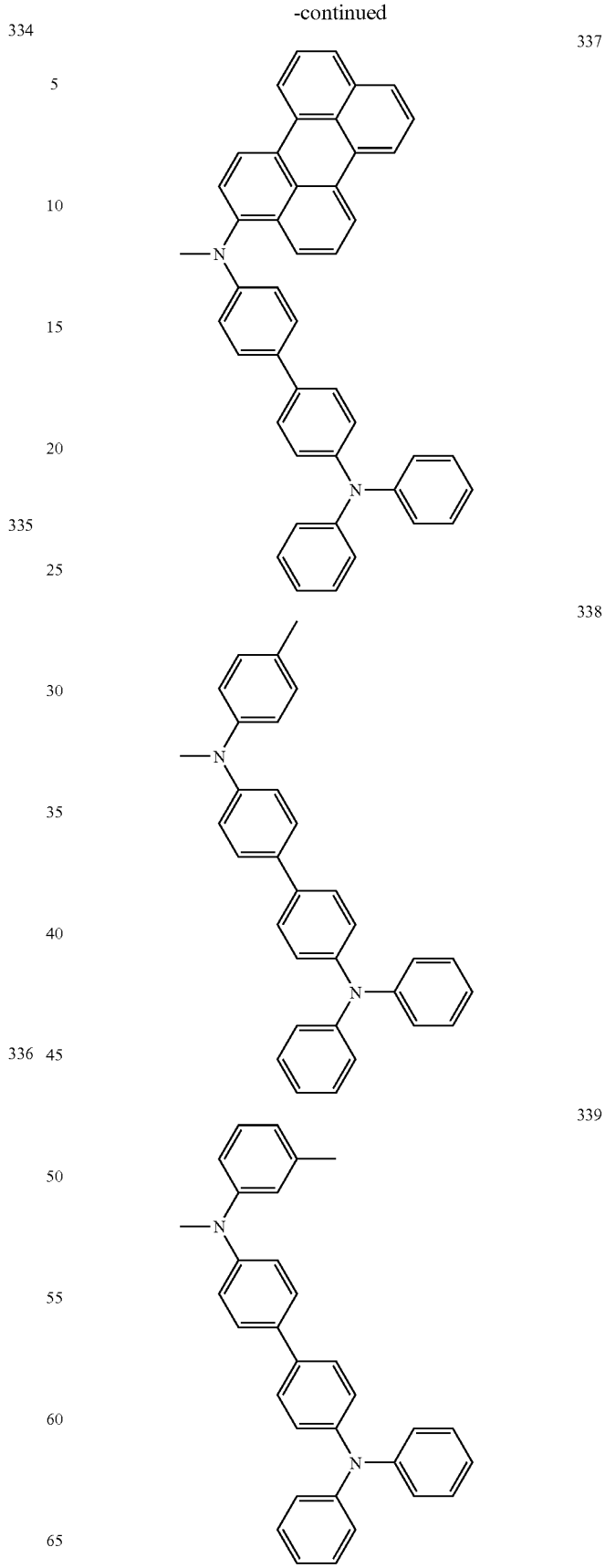
337
338
339

-continued
340
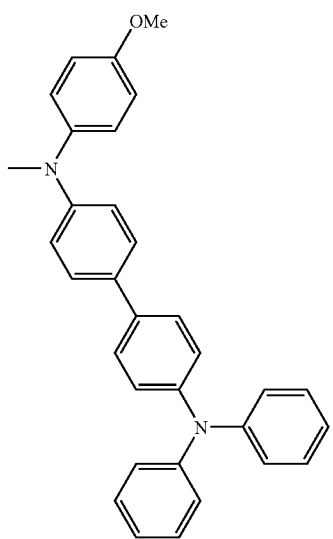
341
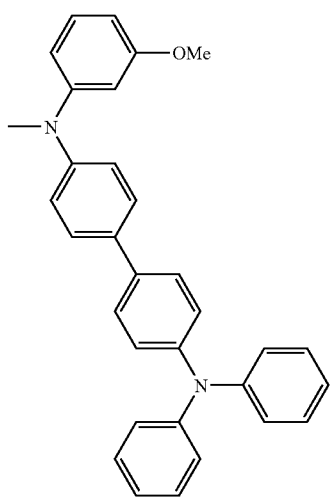
342
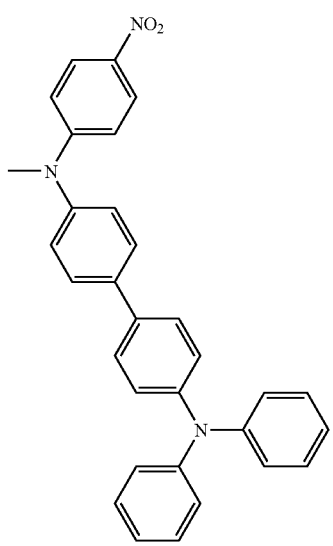
-continued
343
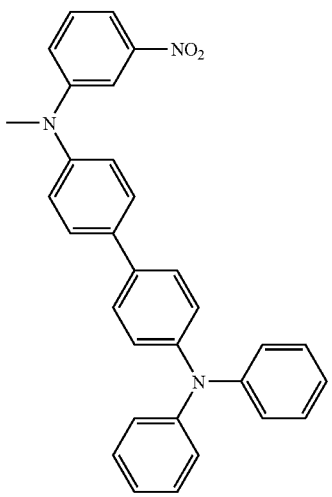
344
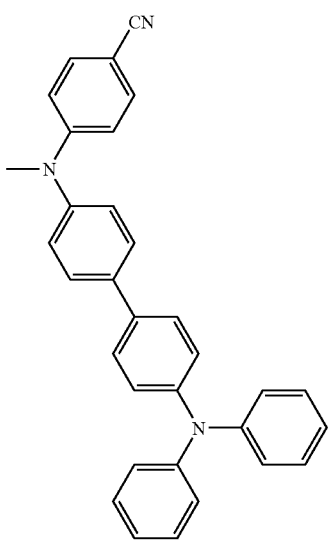
345
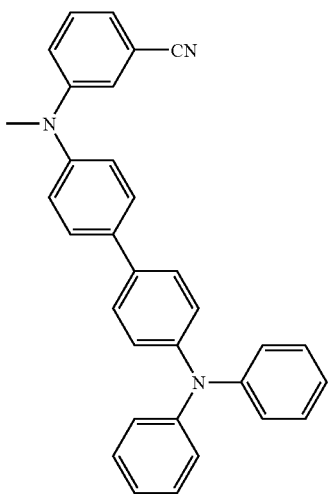

-continued
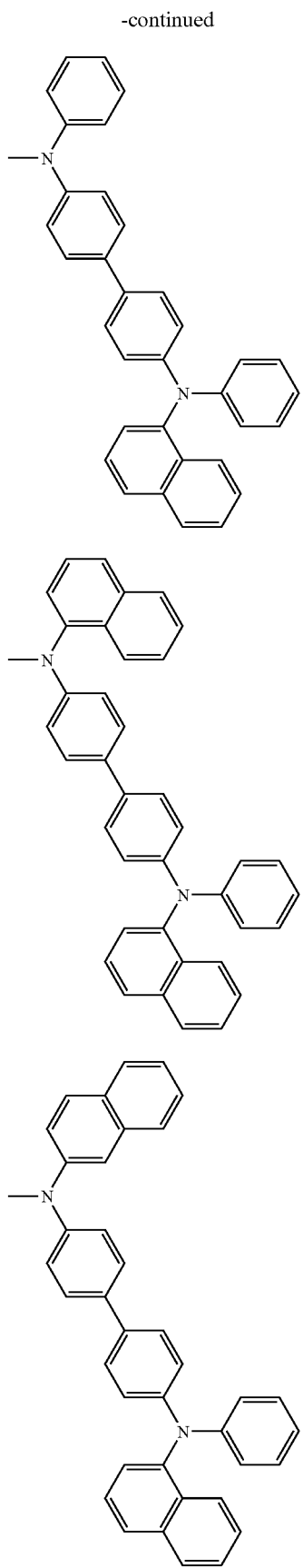
346
347
348
-continued
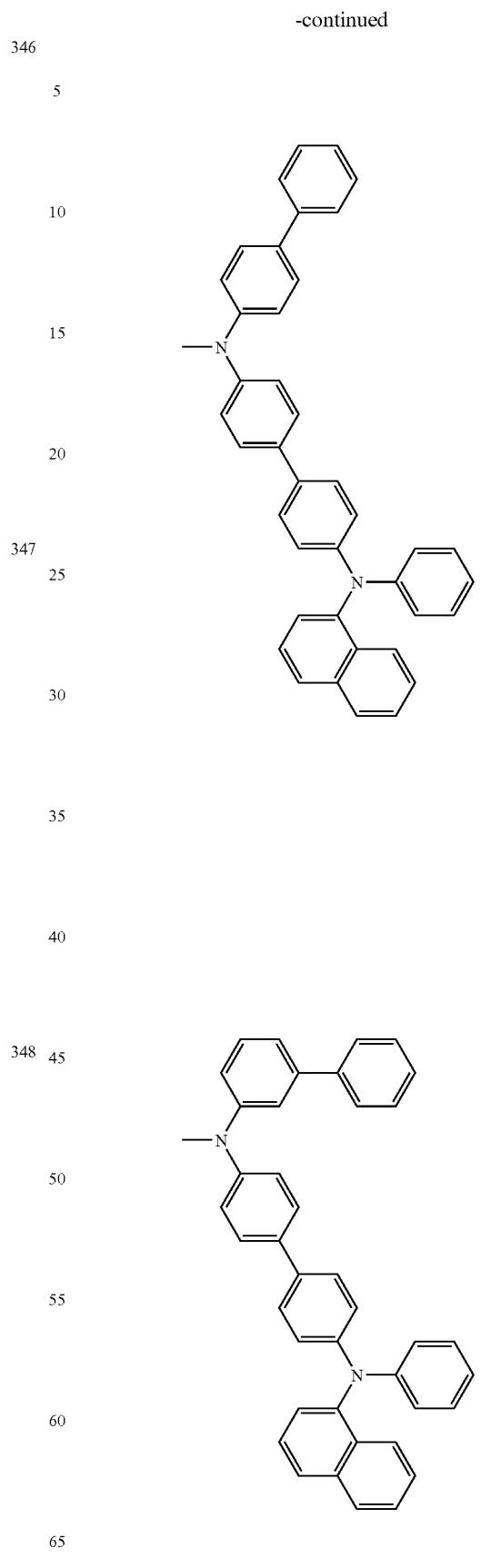
349
350

151
-continued
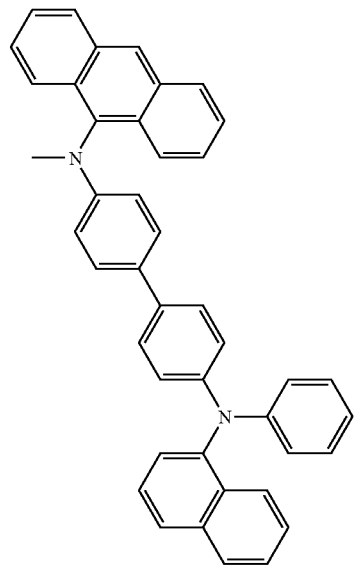
351
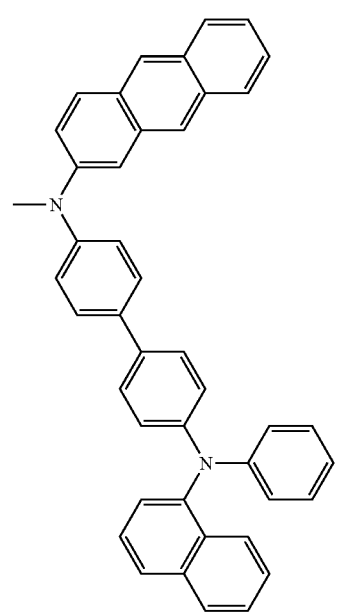
352
152
-continued
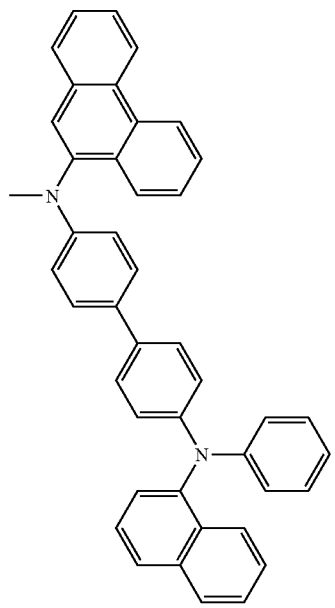
353
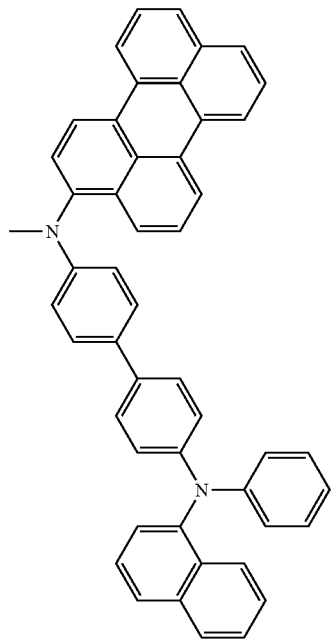
354

153
-continued
355
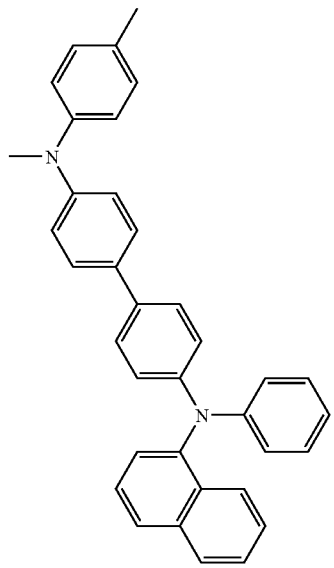
356
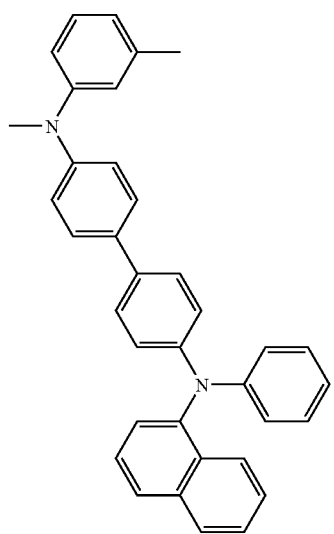
154
-continued
357
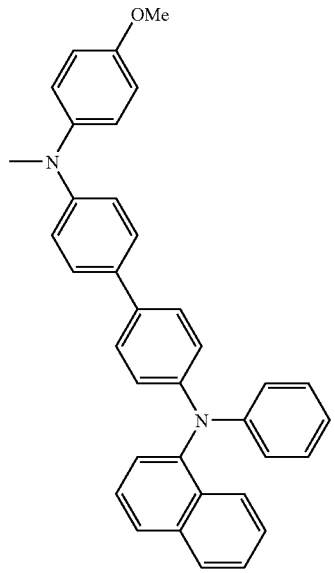
358
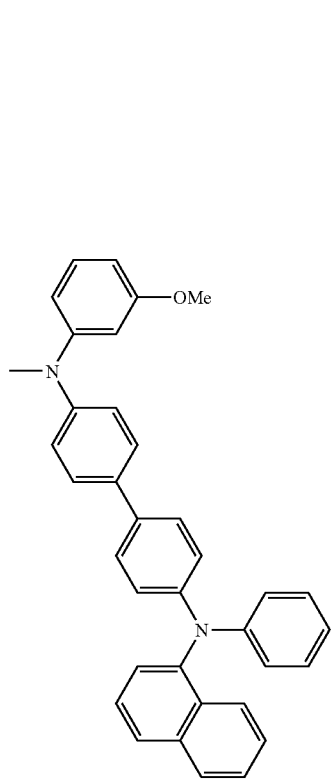

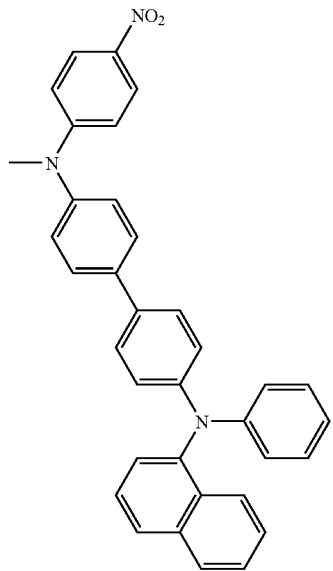
359
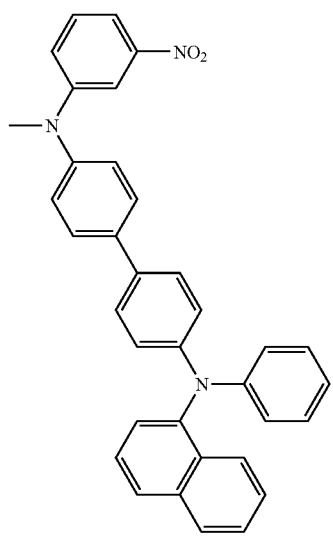
360
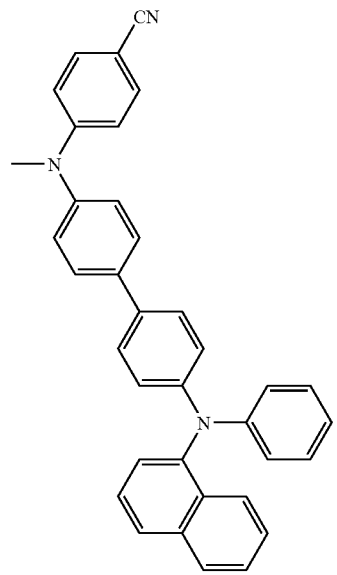
361
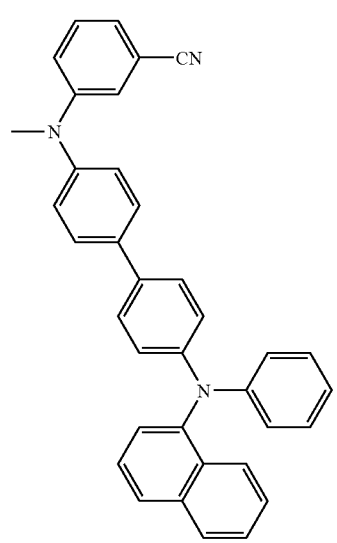
362
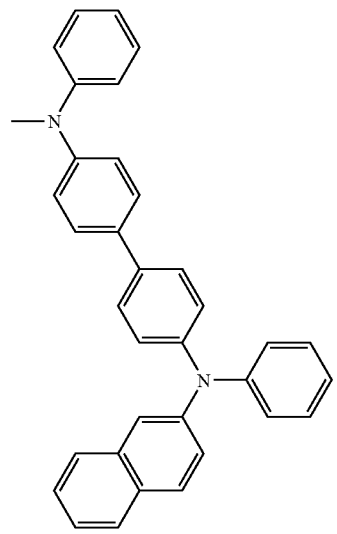
363

157
-continued
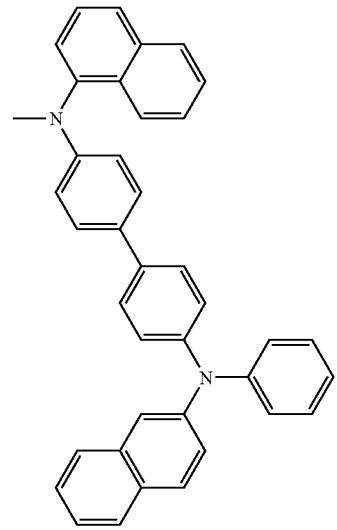
364
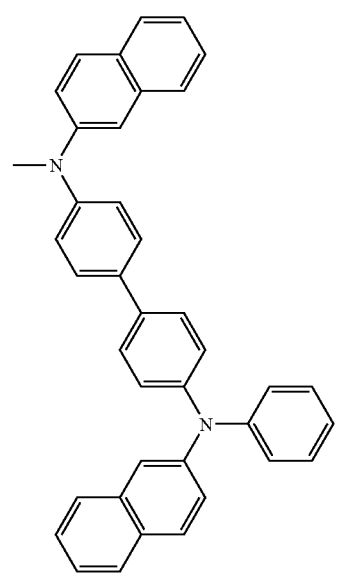
365
158
-continued
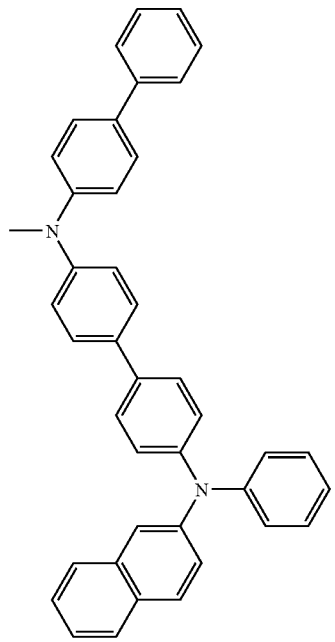
366
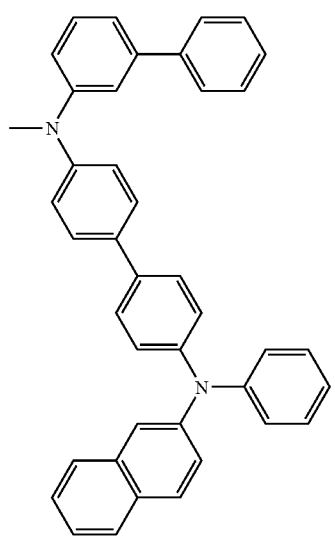
367

159
-continued
368
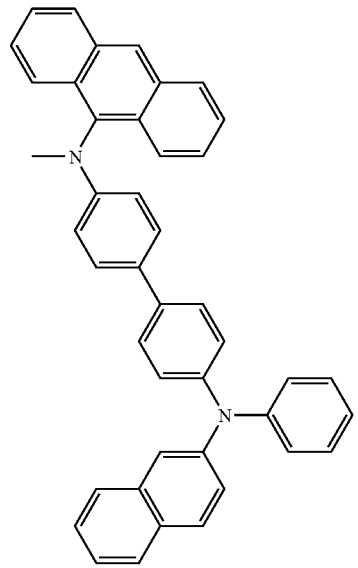
369
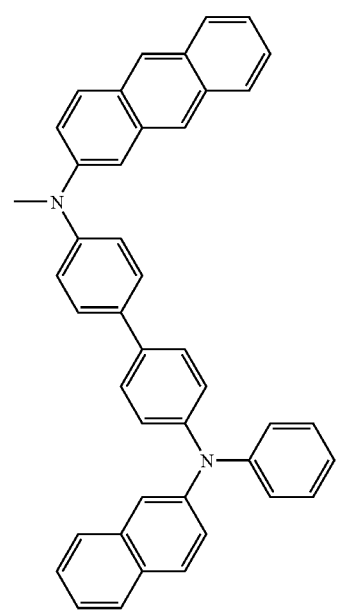
160
-continued
370
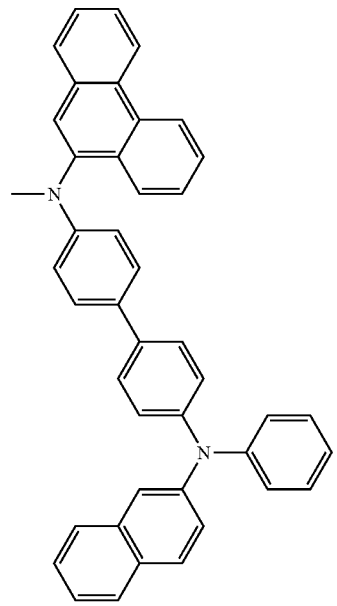
371
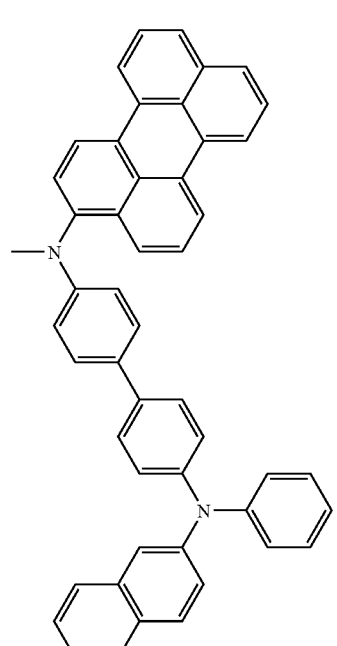

-continued
372
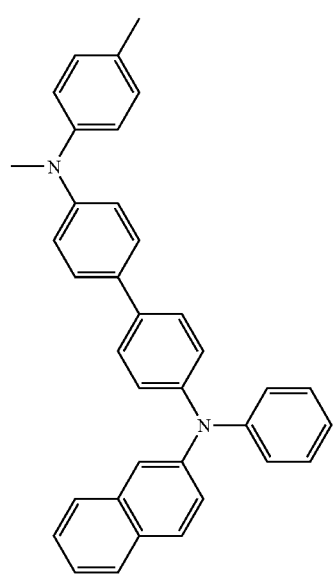
373
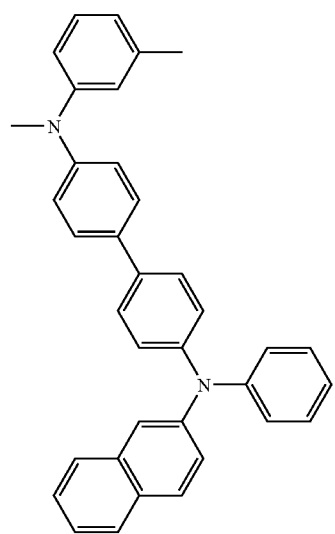
-continued
374
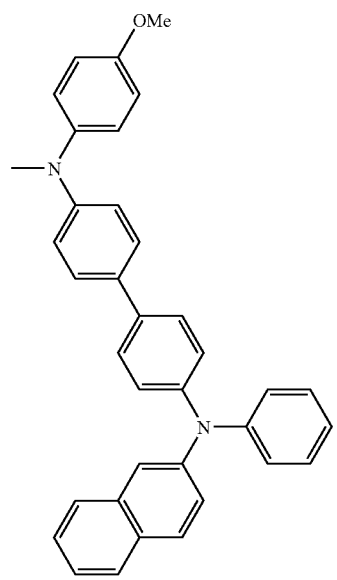
375
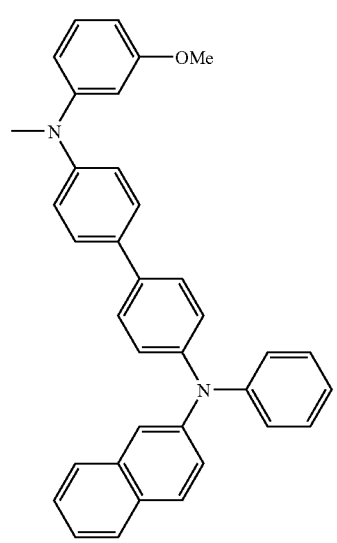

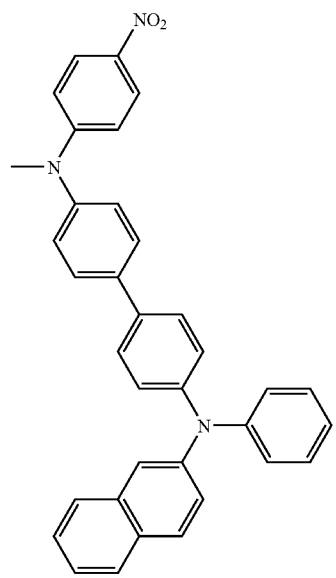
376
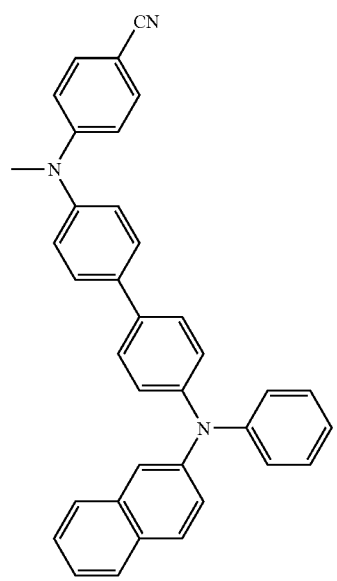
378
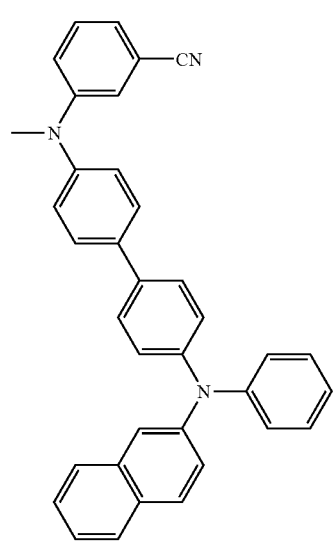
379

380
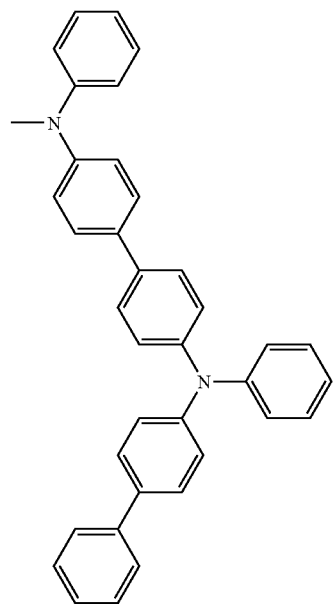
381
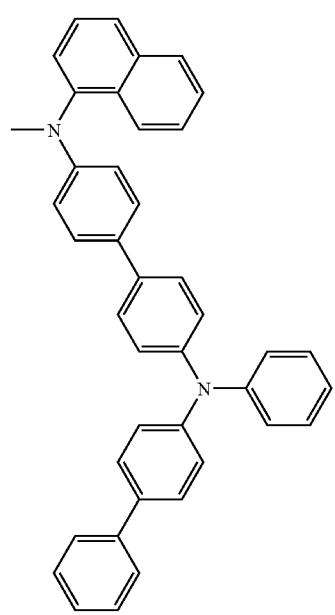
382
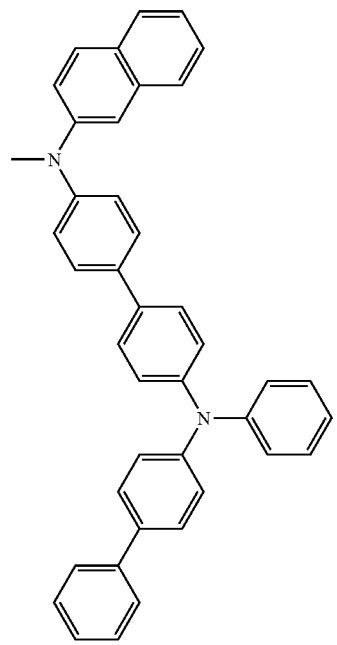
383
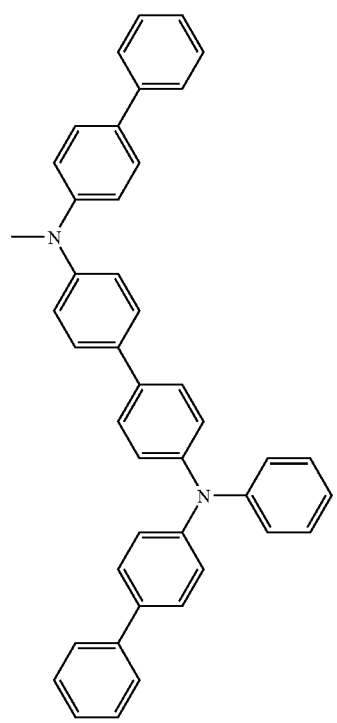

-continued
384
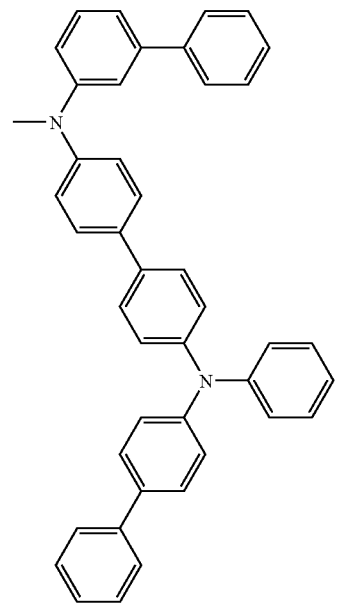
385
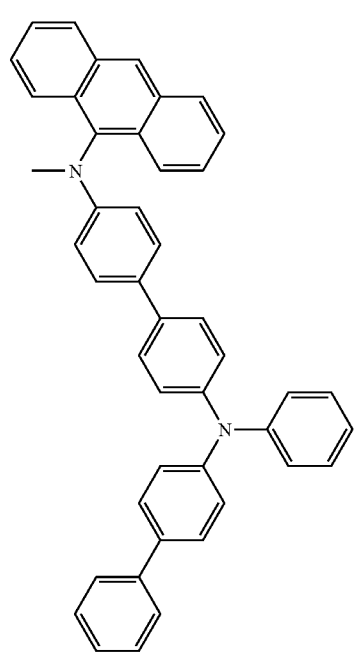
-continued
386
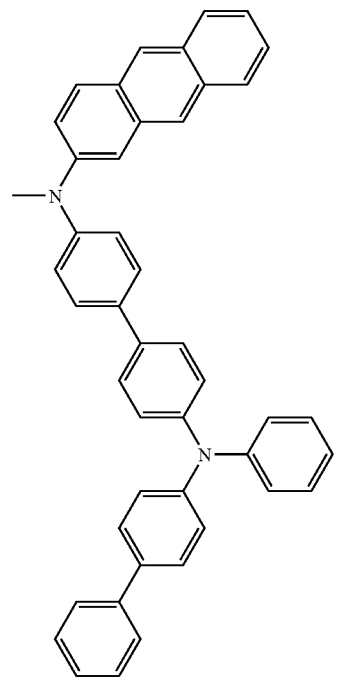
387
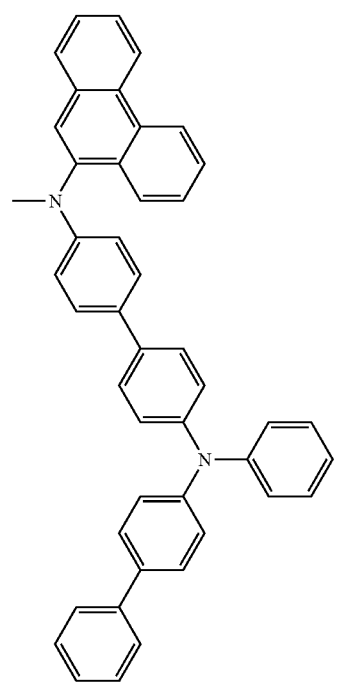

169 | 170
-continued | -continued
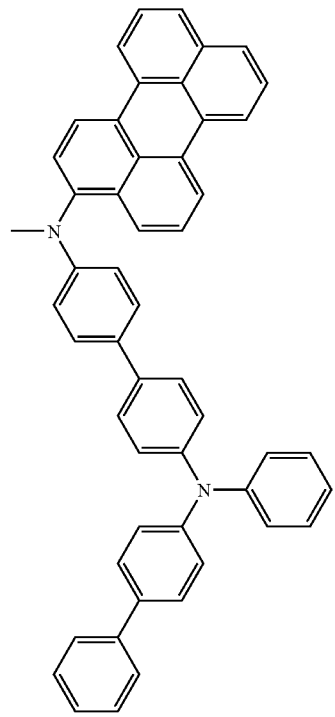
388
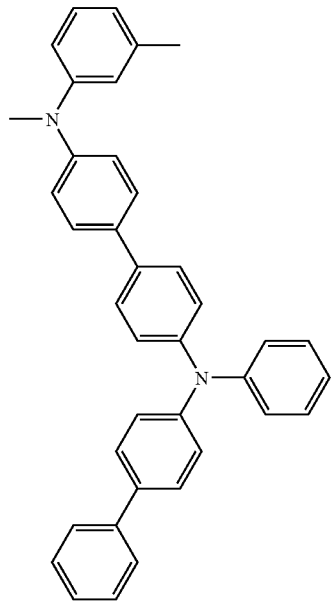
390
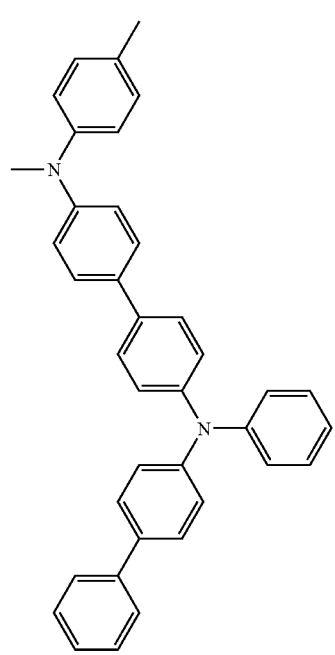
389
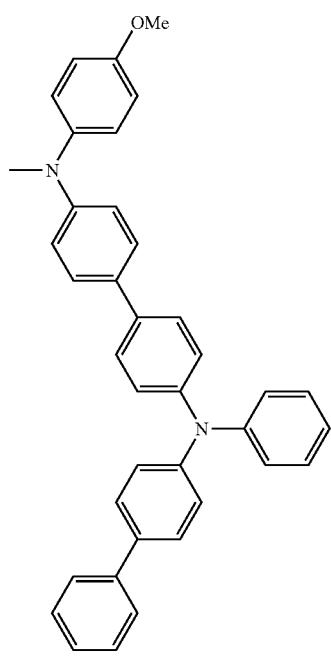
391

-continued
171
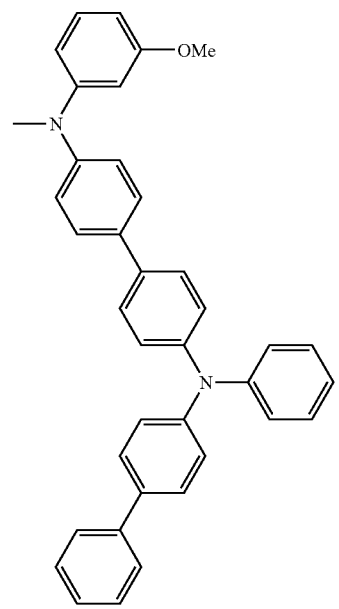
392
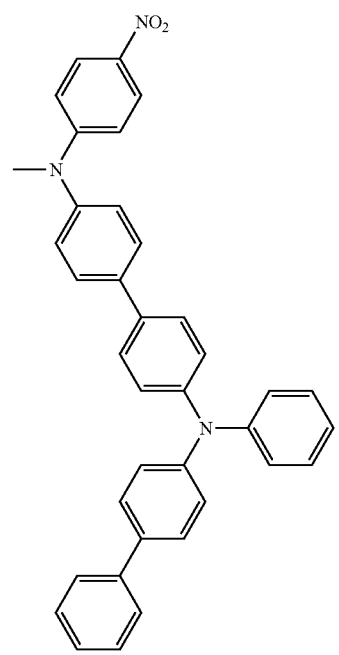
393
172
-continued
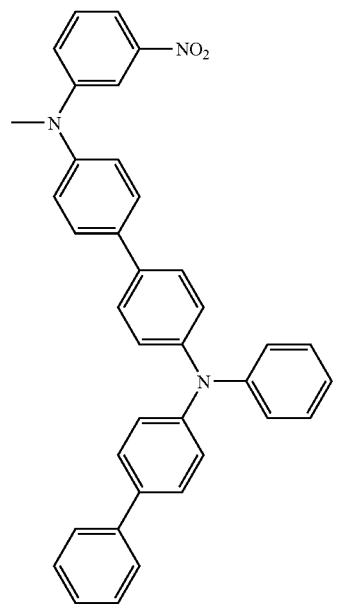
394
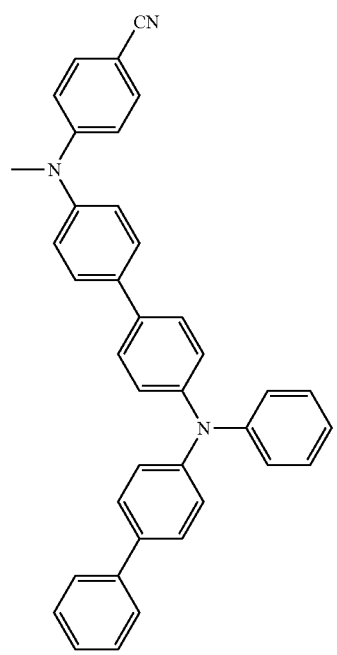
395

396
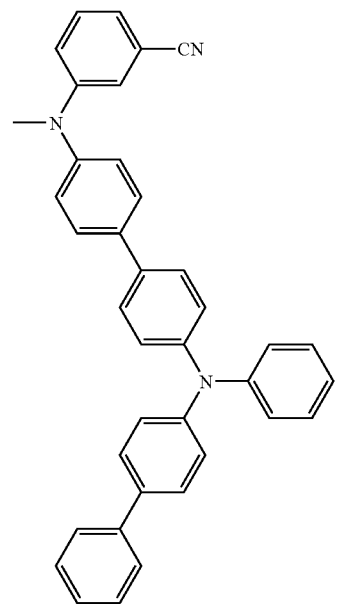
397
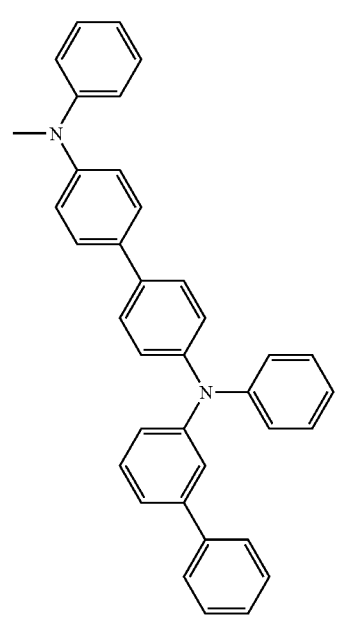
398
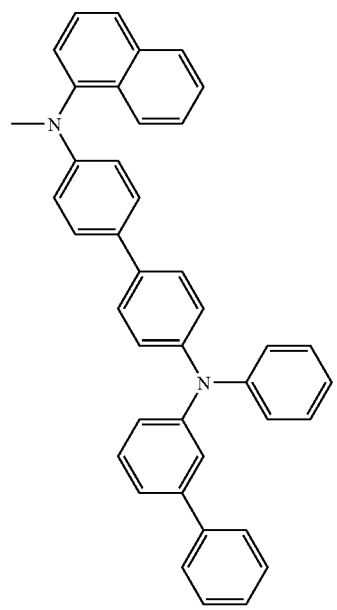
399
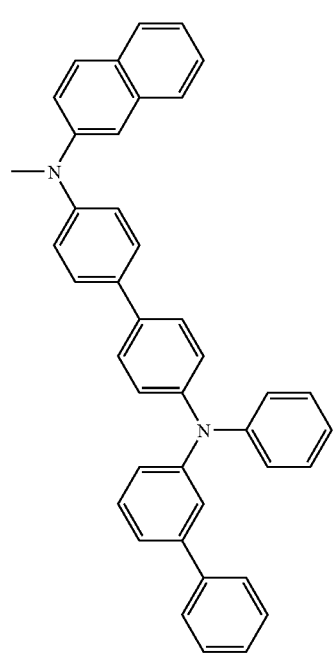

-continued
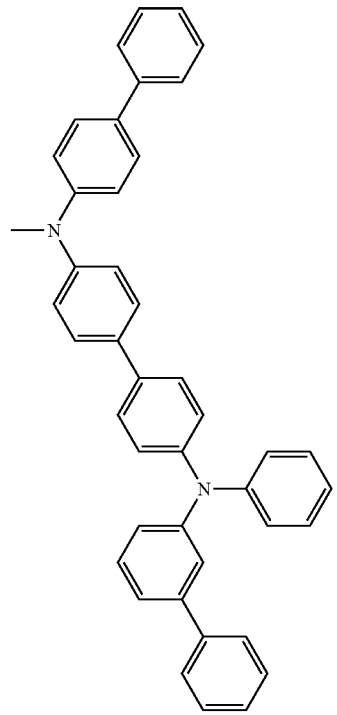
400
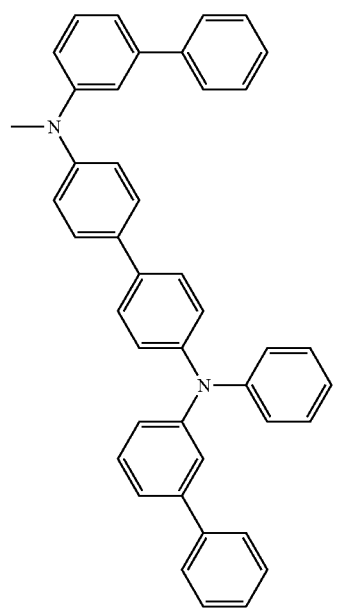
401
-continued
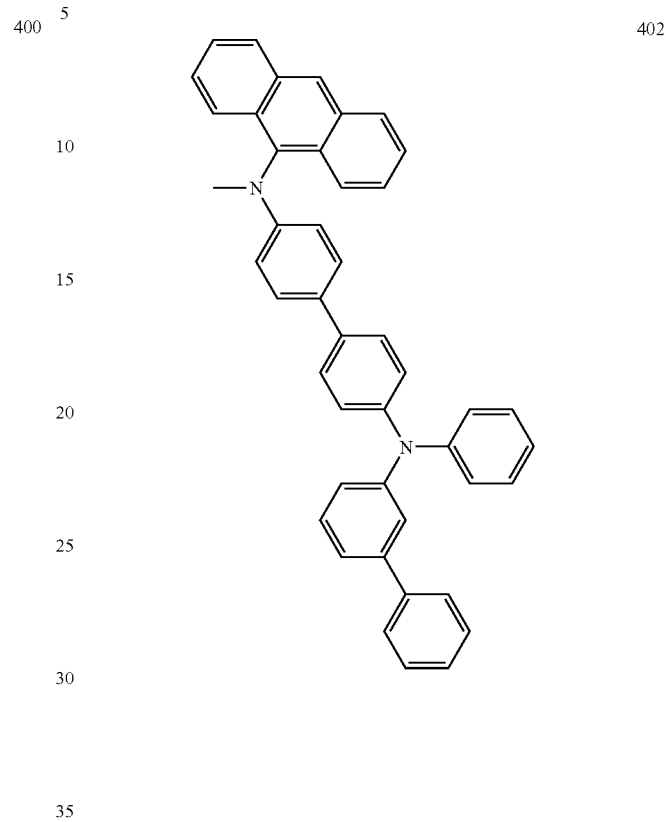
402
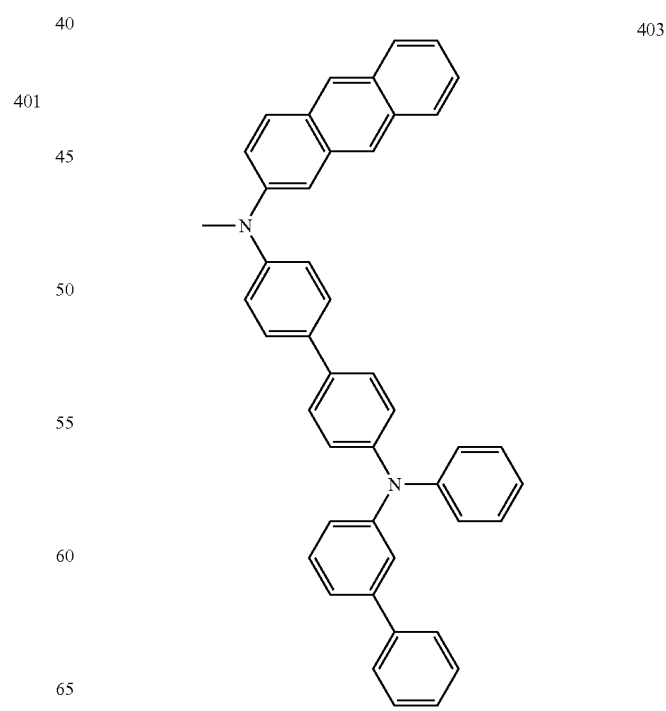
403

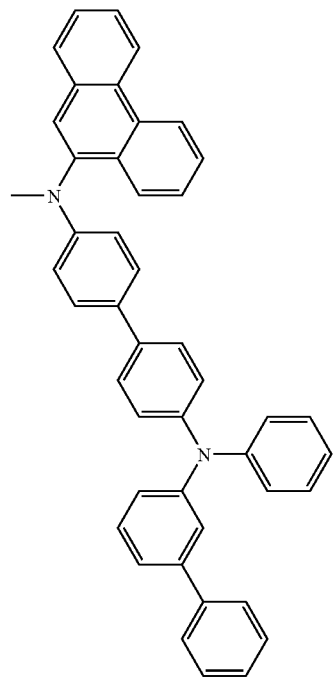
404
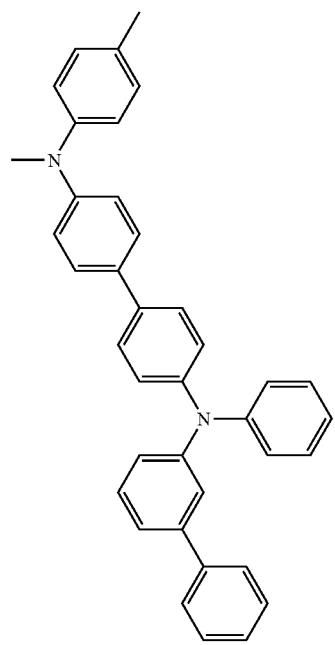
406
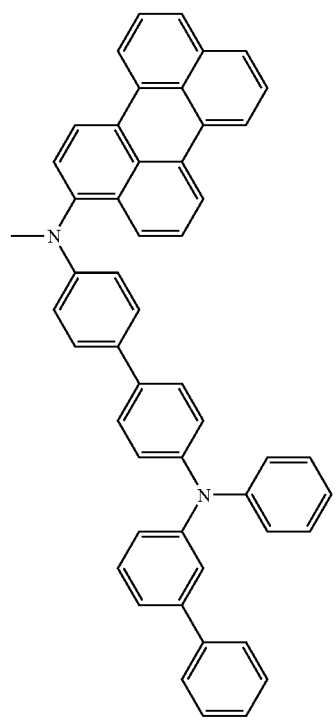
405
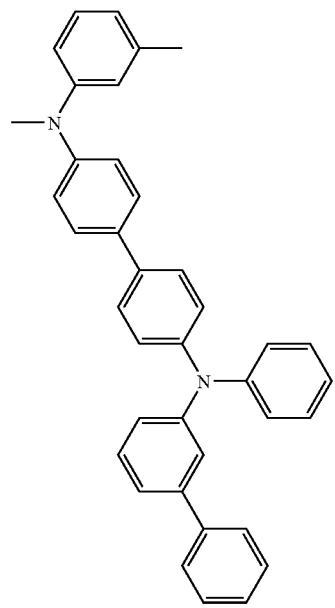
407

179 180
-continued -continued
408 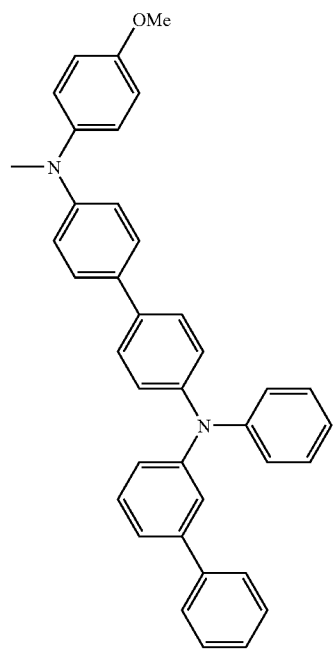 410 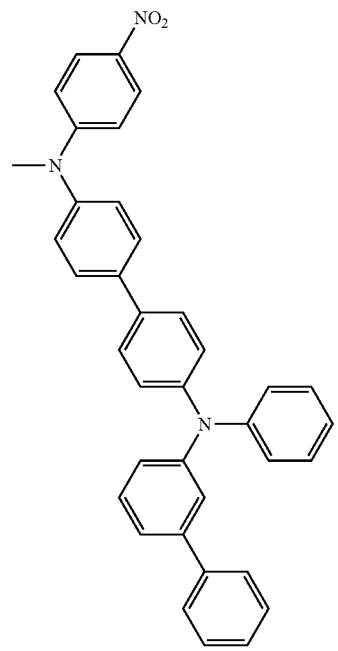
409 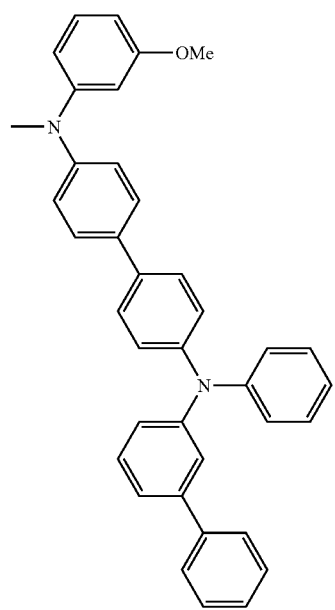 411 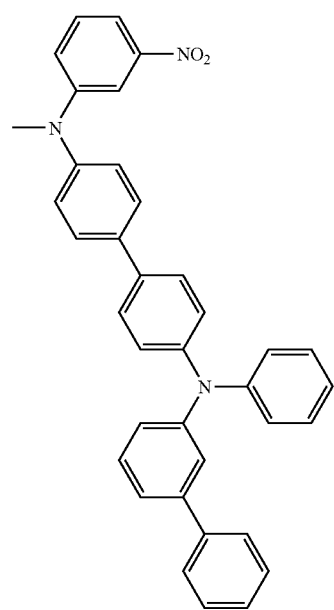

412
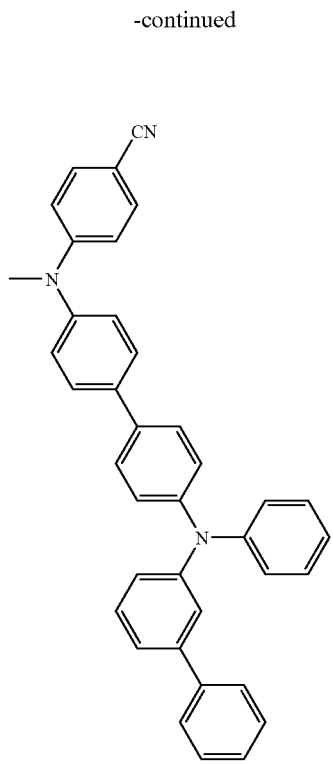
413
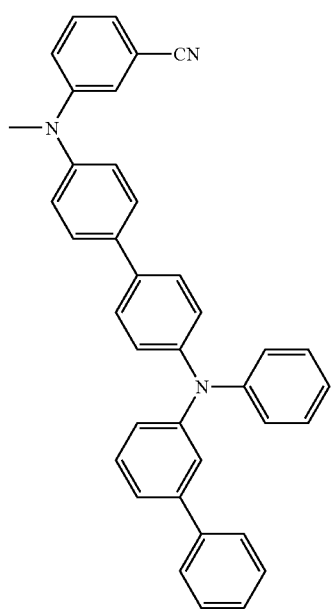
414
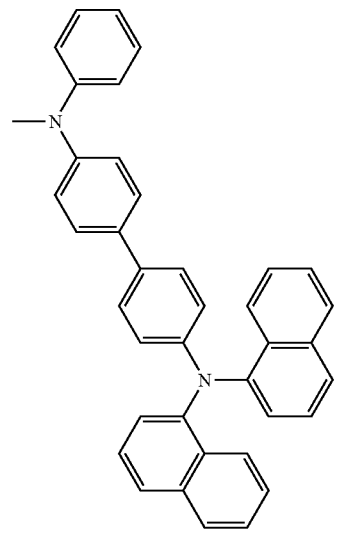
415
416
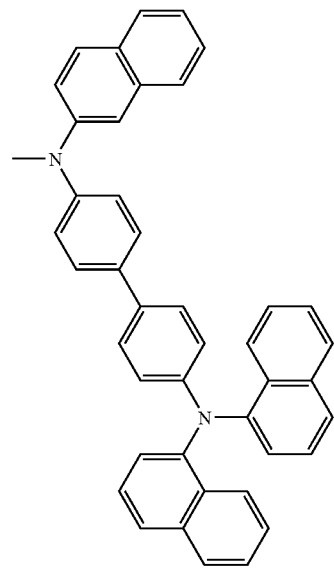

183
-continued
417
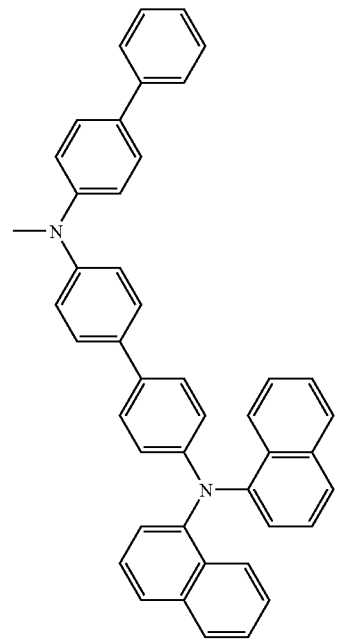
418
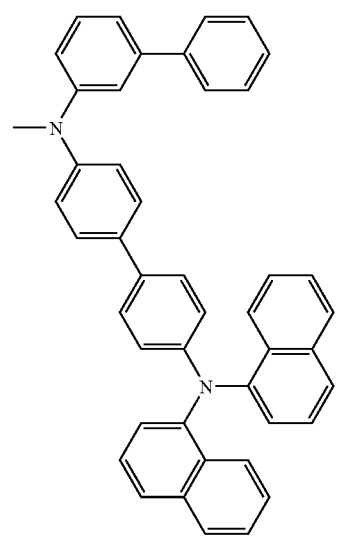
184
-continued
419
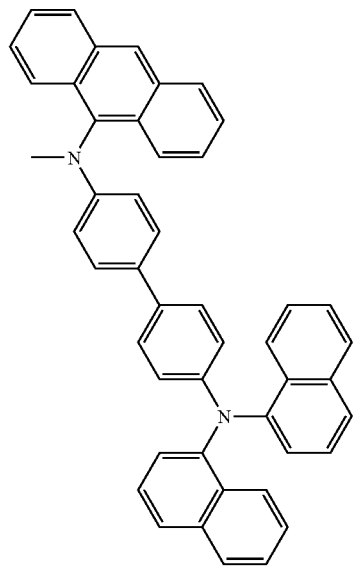
420
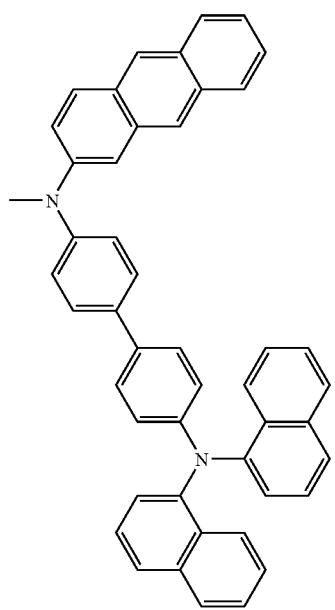

-continued
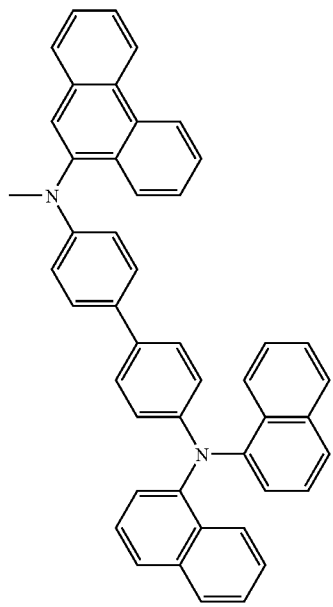
421
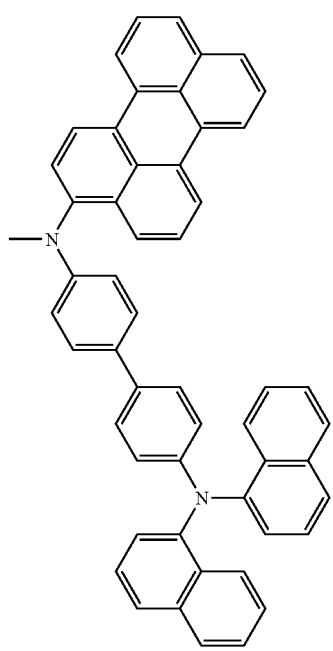
422
-continued
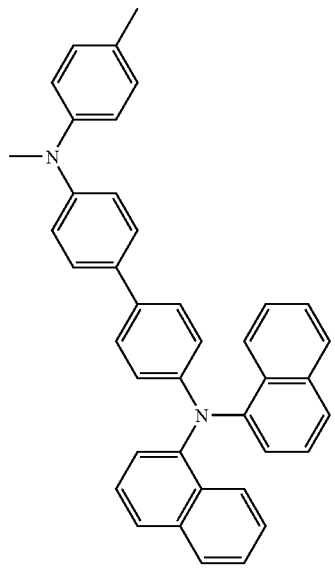
423
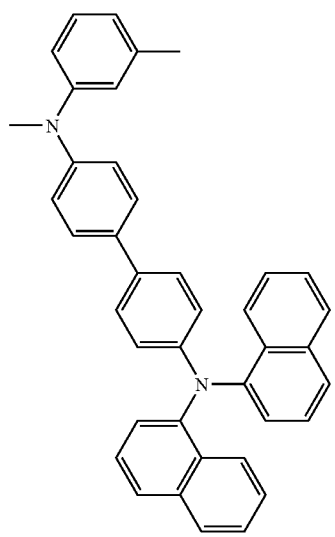
424

187 188
425
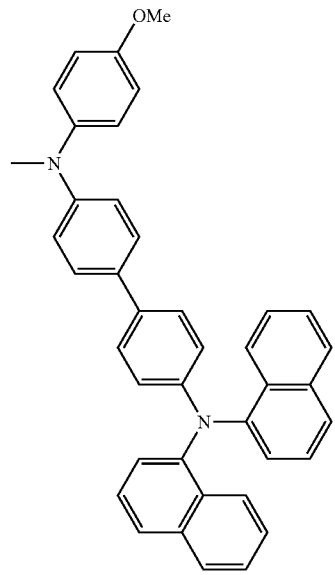
427
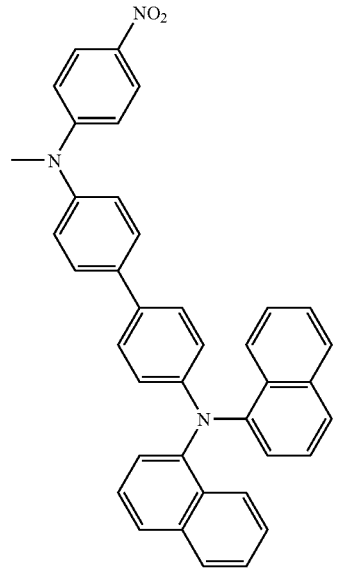
426
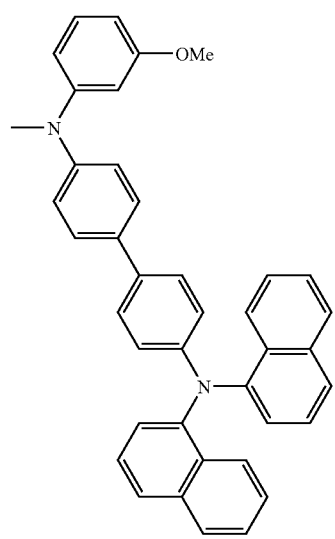
428
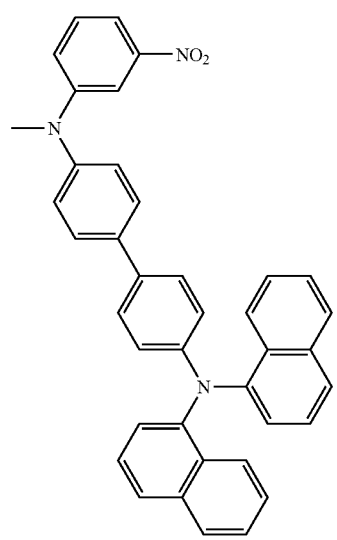

-continued
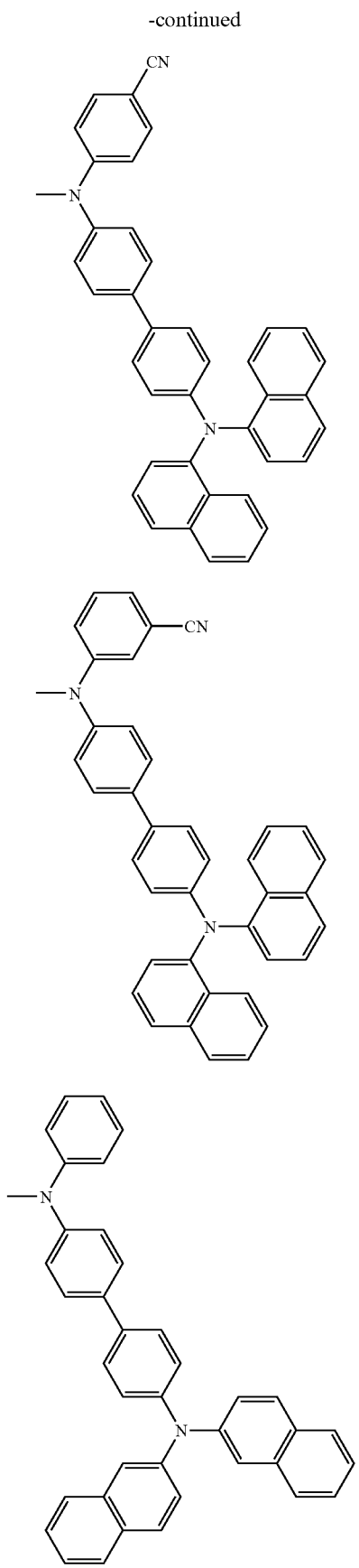
-continued
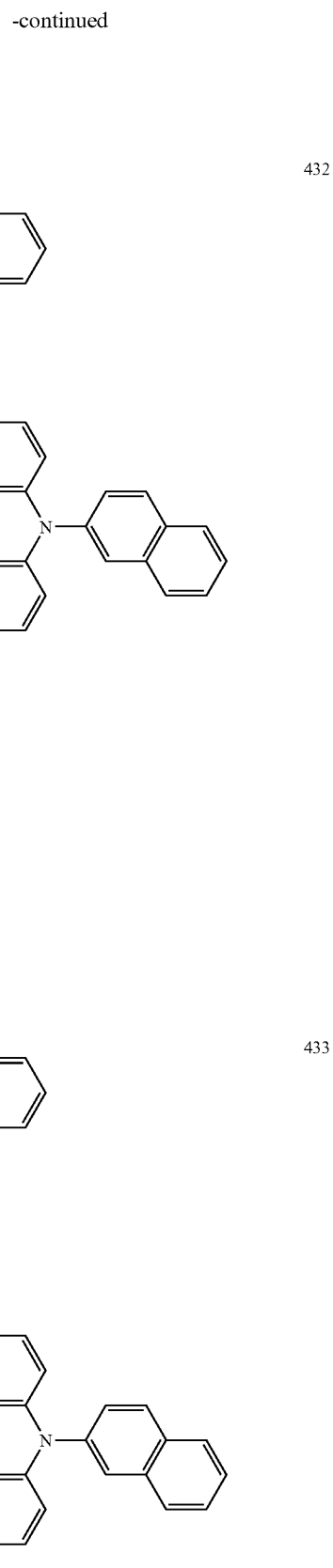

-continued
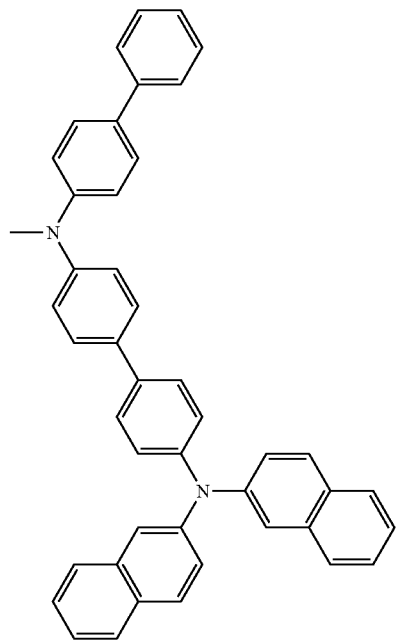
434
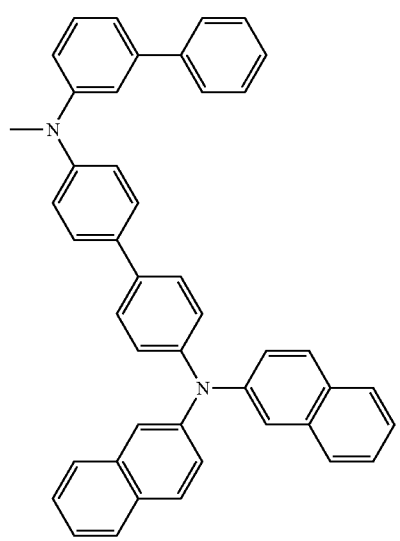
435
-continued
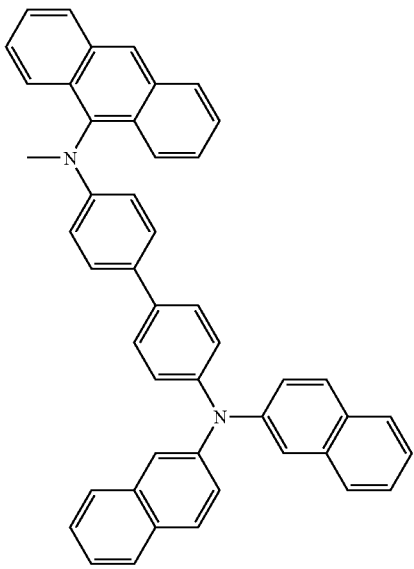
436
437

193
-continued
438
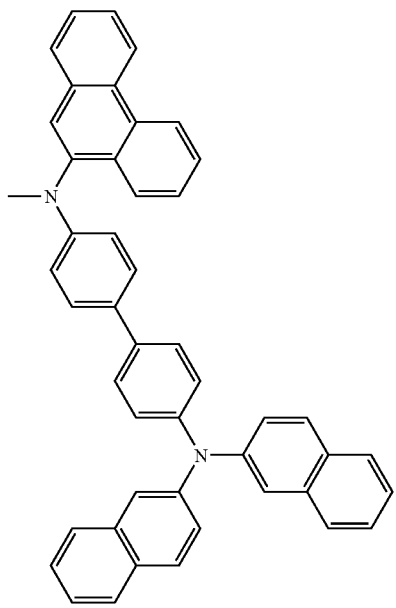
439
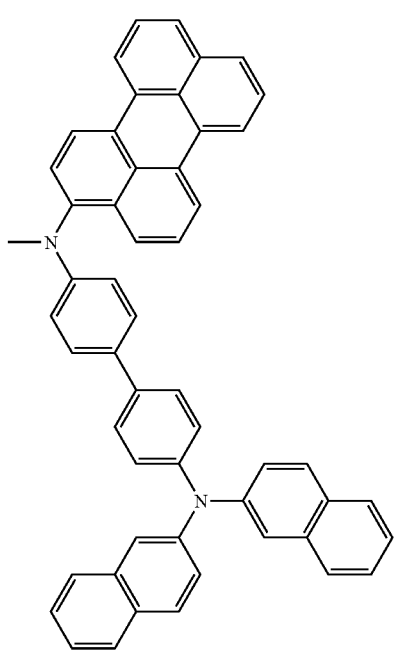
194
-continued
440
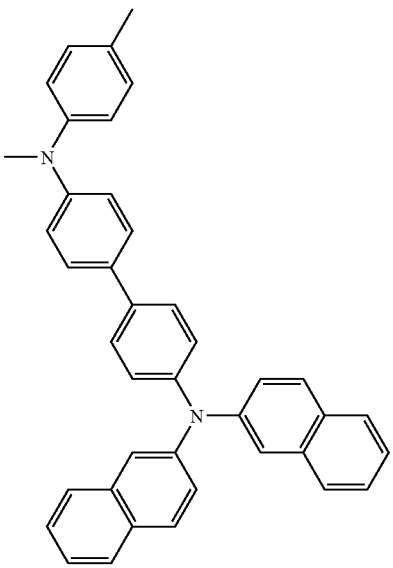
441
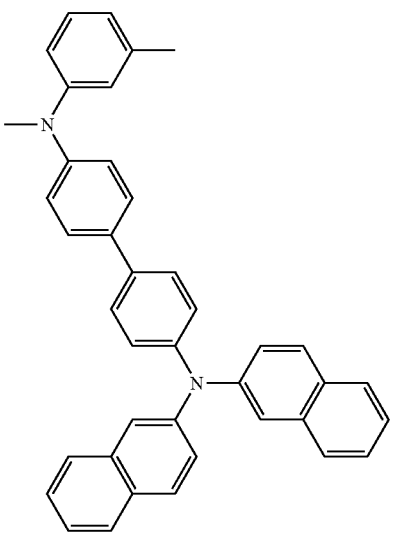

442
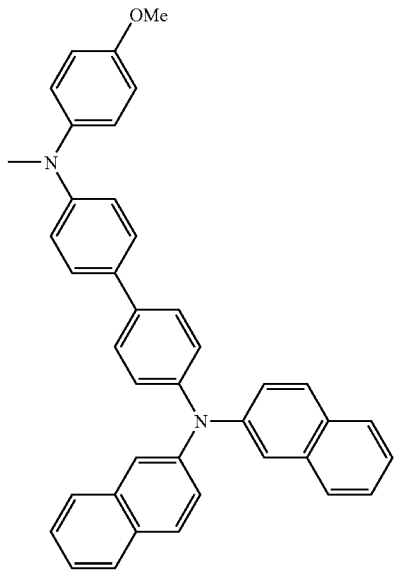
444
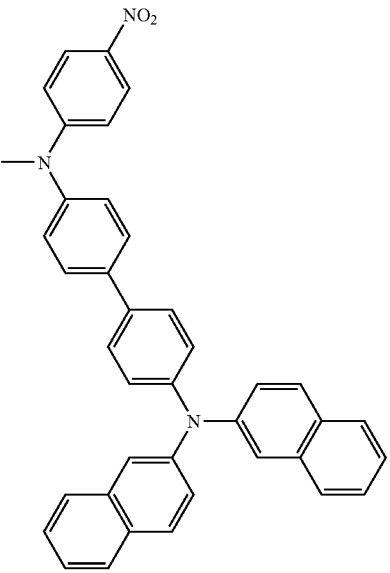
443
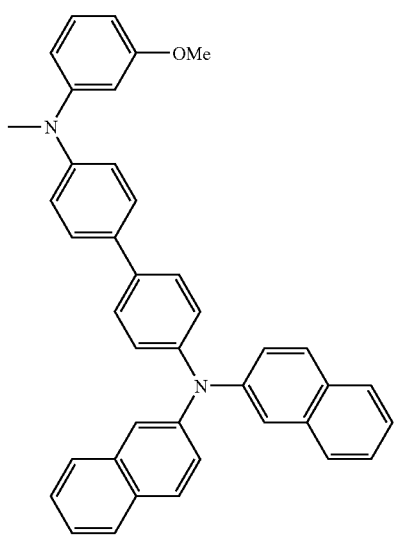
445
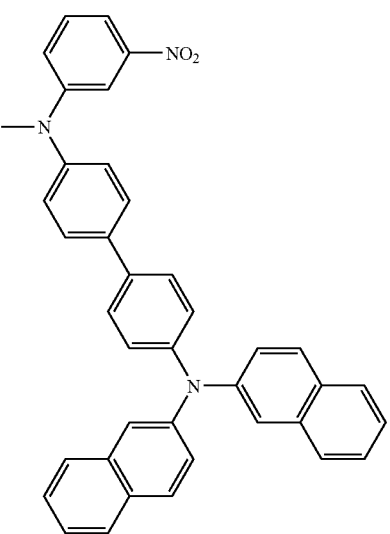

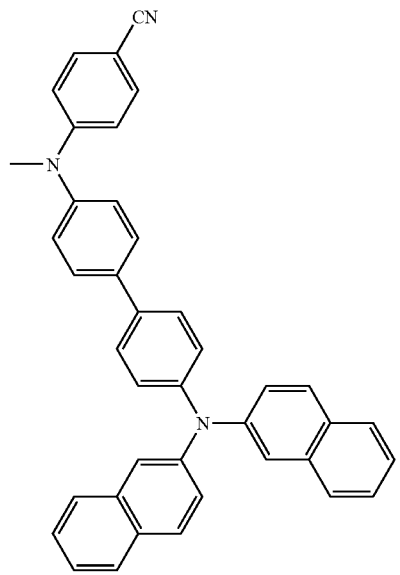
446
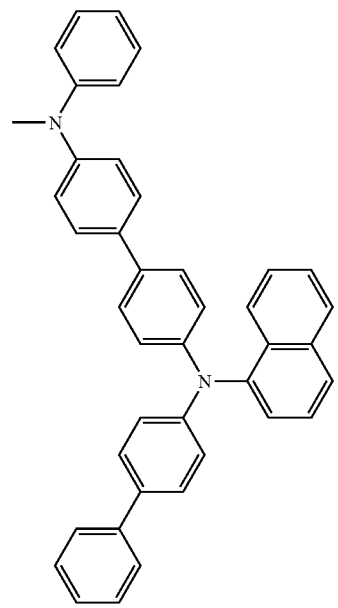
448
447
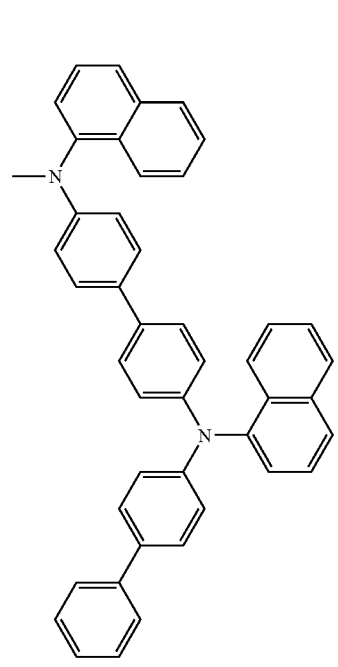
449

199
200
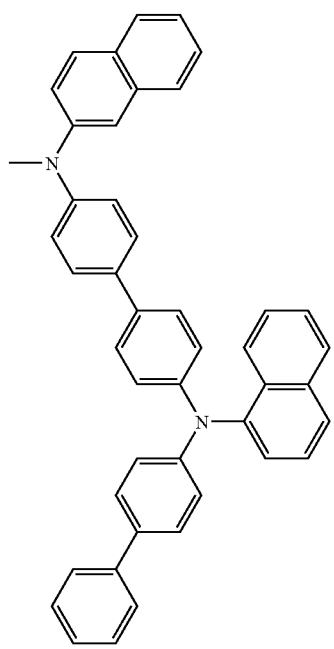
450
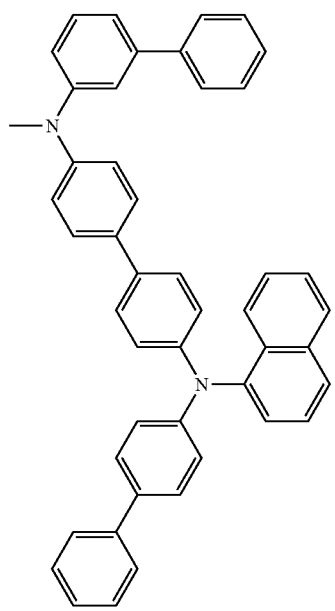
452
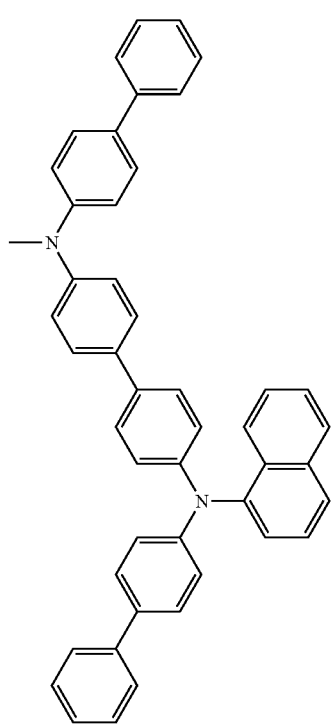
451
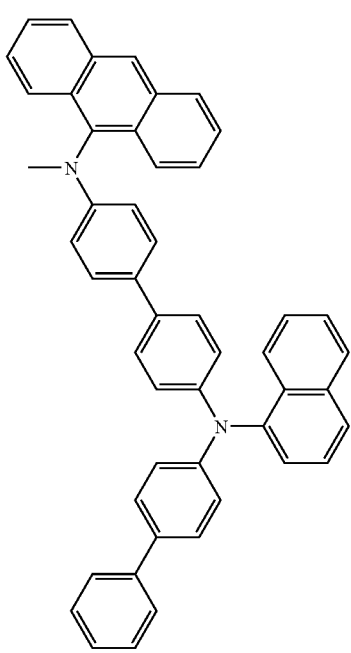
453

201
-continued
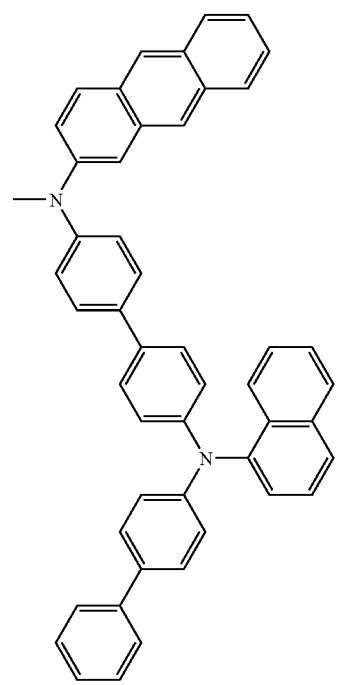
454
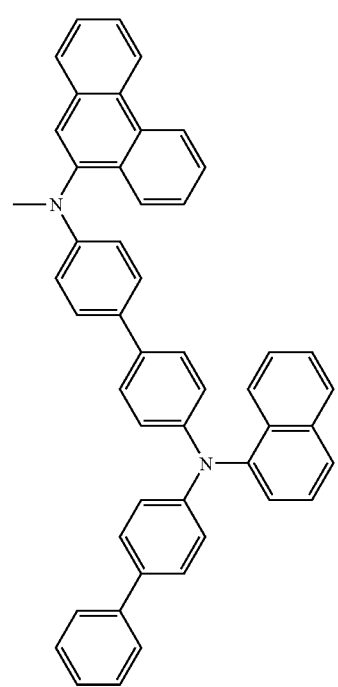
455
202
-continued
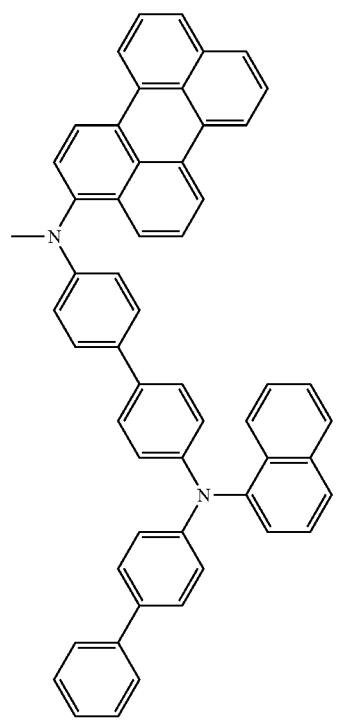
456
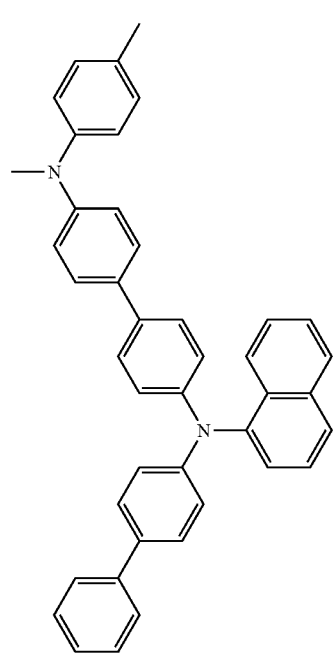
457

-continued
458
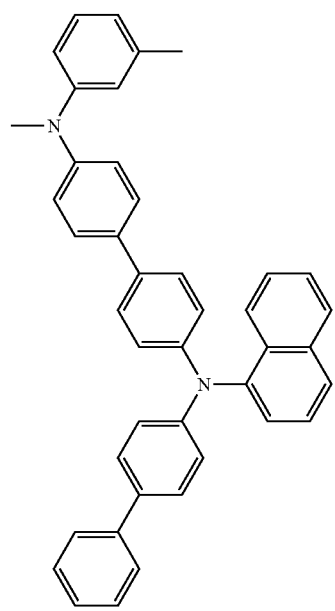
459
460
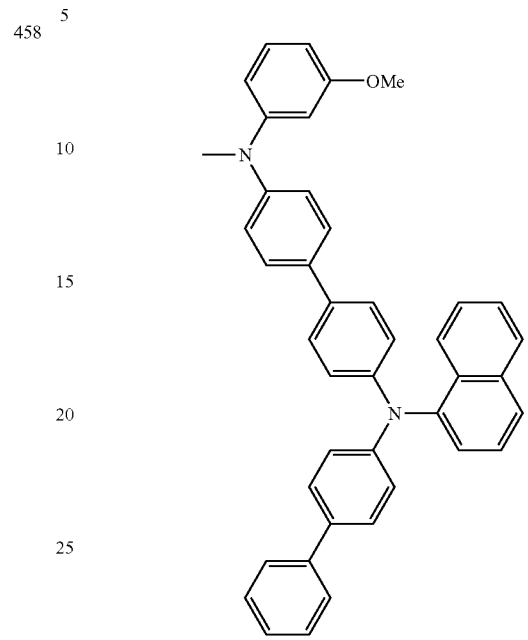
461
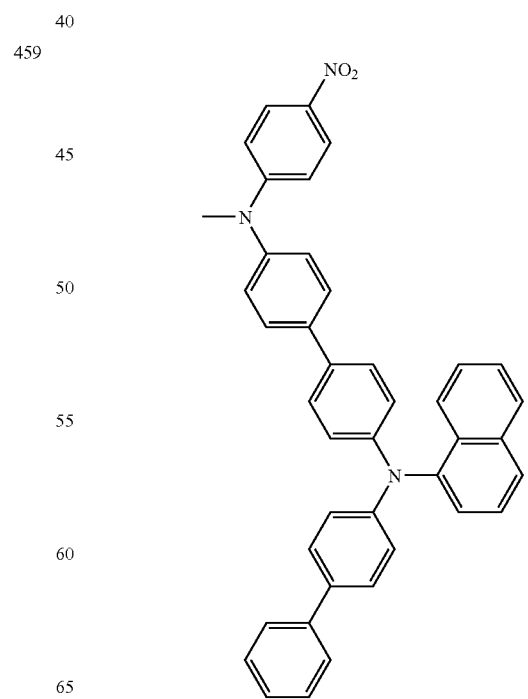

205
-continued
462
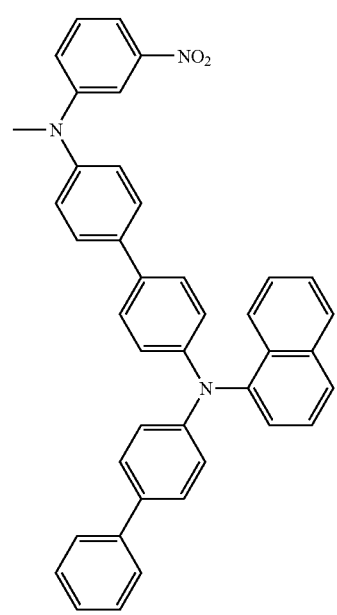
463
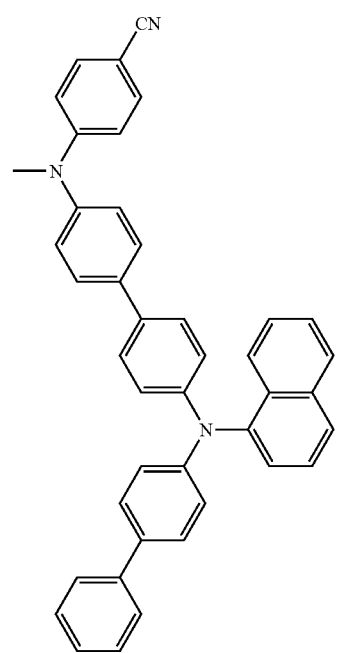
206
-continued
464
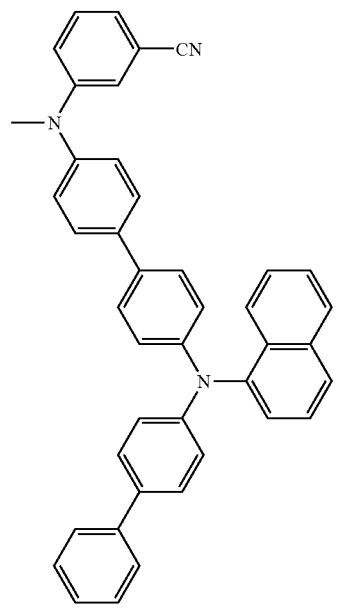
465
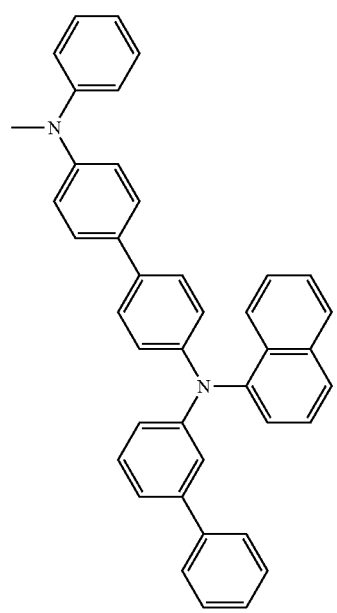

207
-continued
466
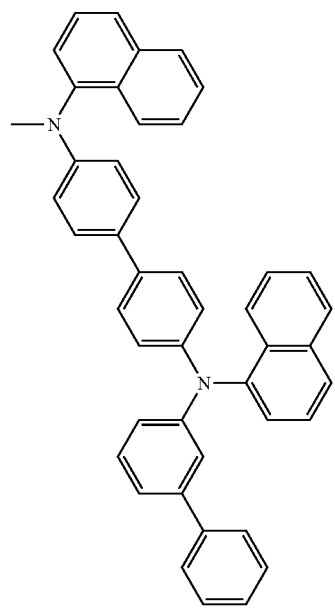
467
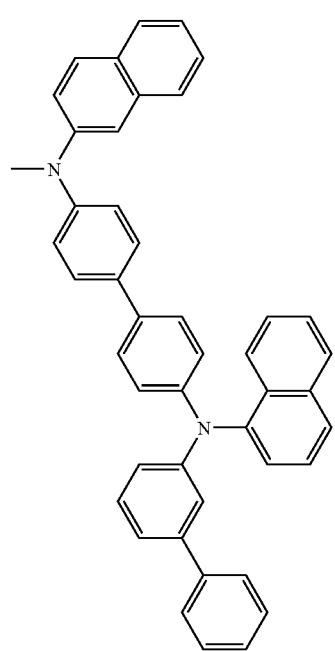
208
-continued
468
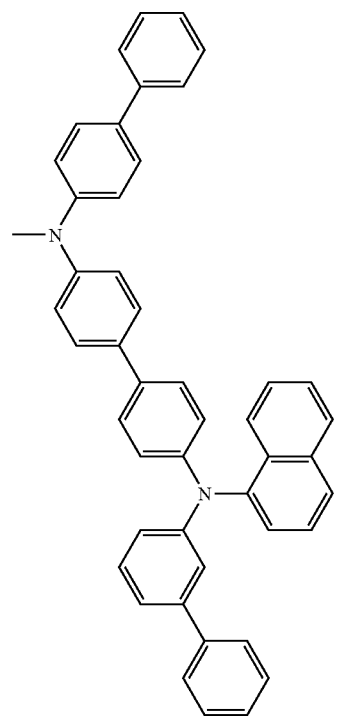
469
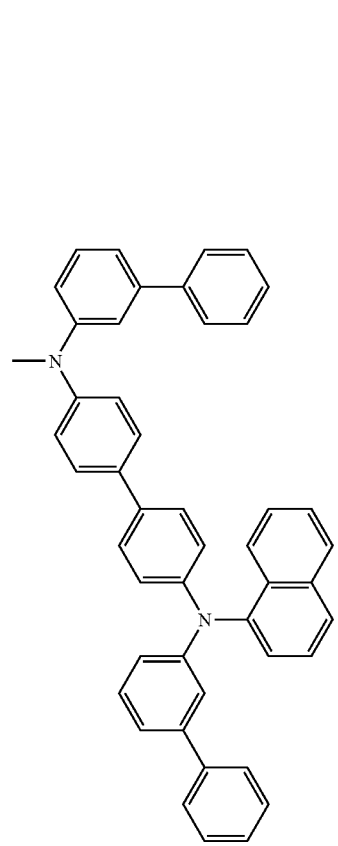

209
-continued
470
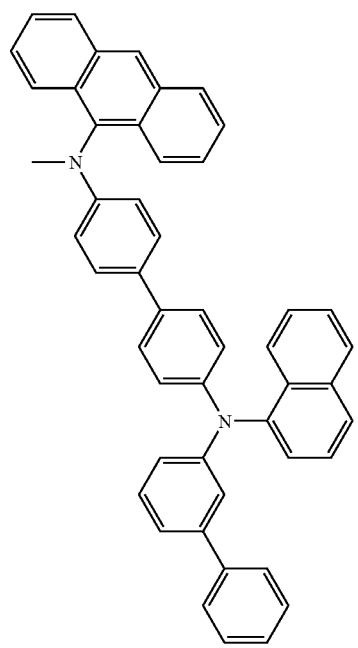
471
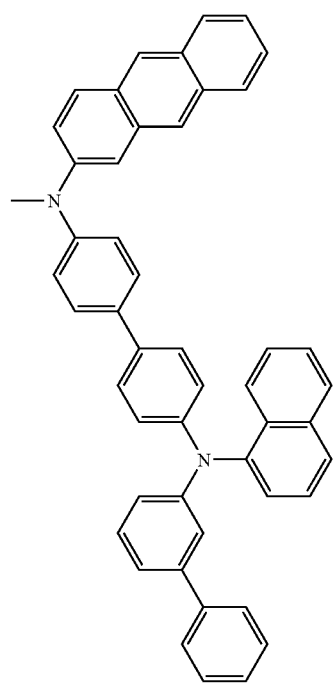
210
-continued
472
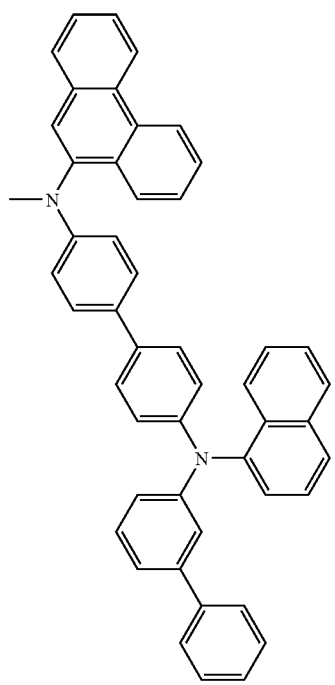
473
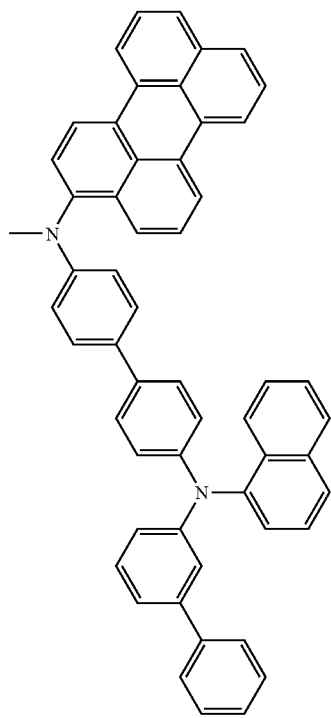

211
-continued
474
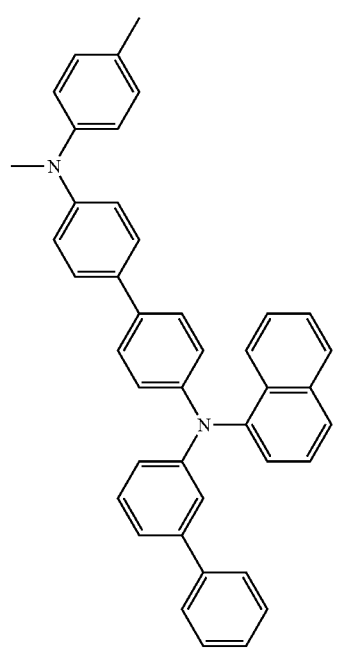
475
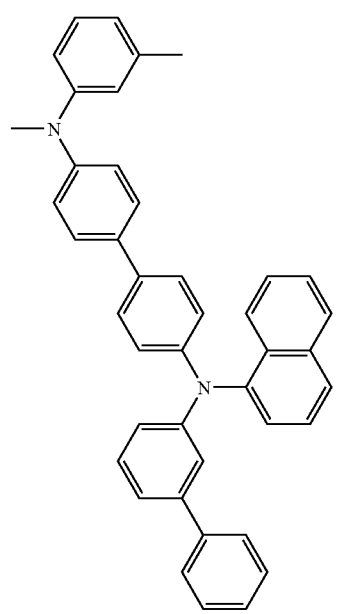
212
-continued
476
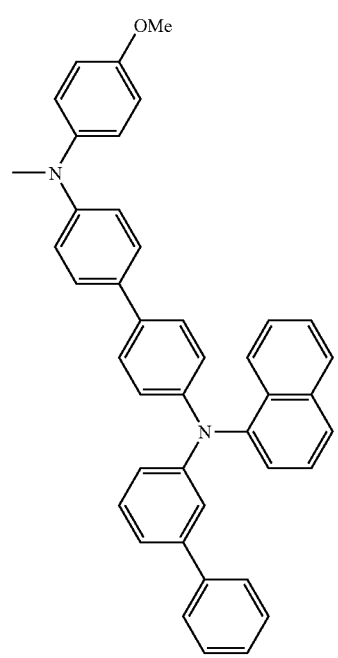
477
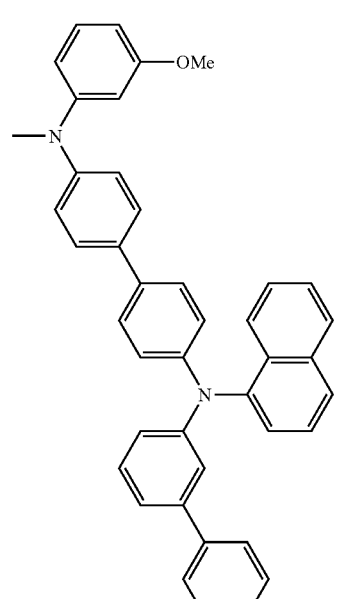

213 214
-continued -continued
478
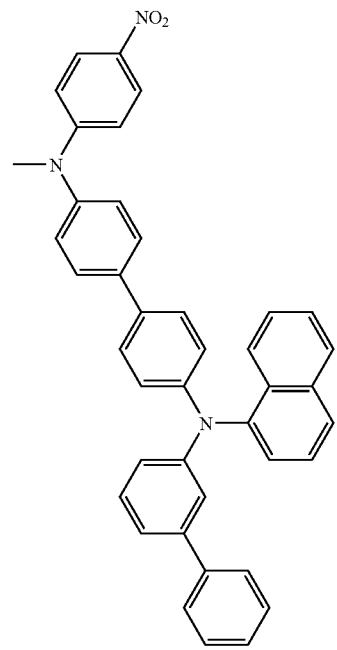
480
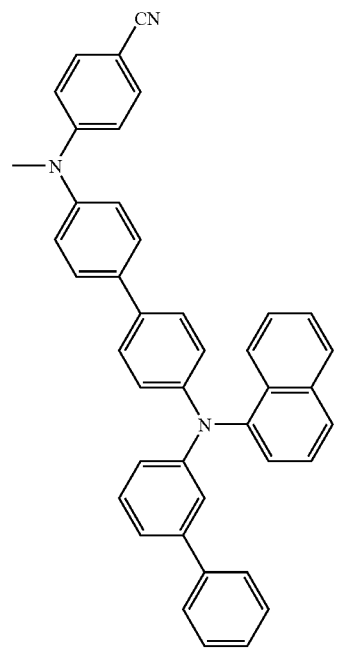
479
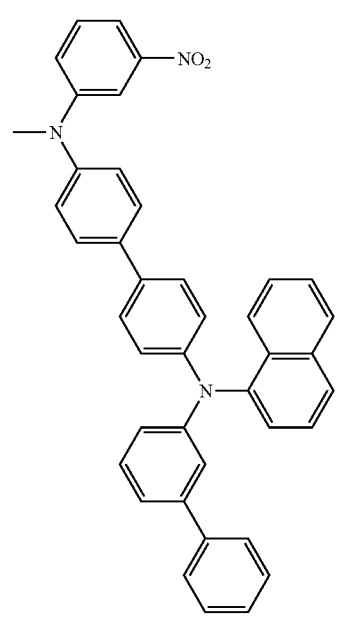
481
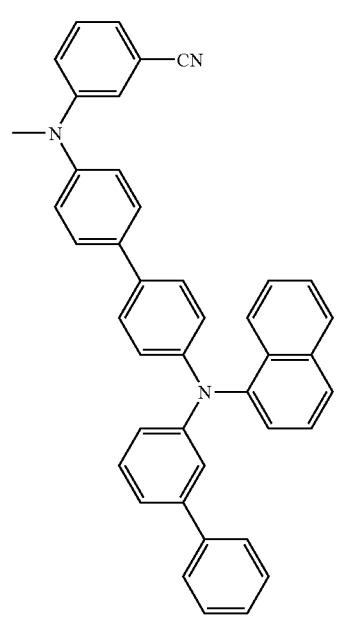

-continued
482
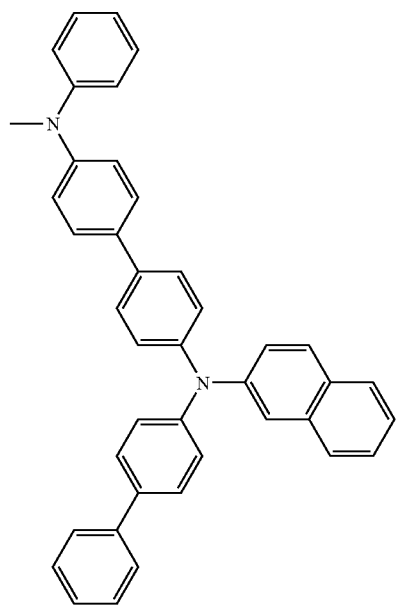
483
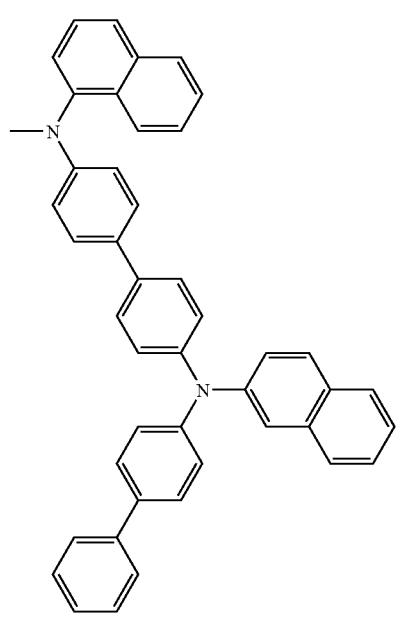
-continued
484
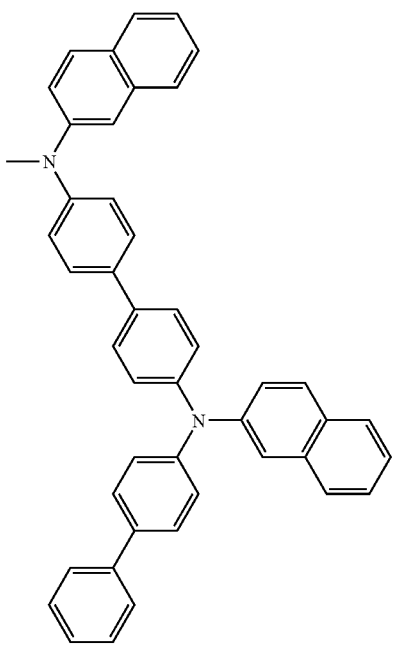
485
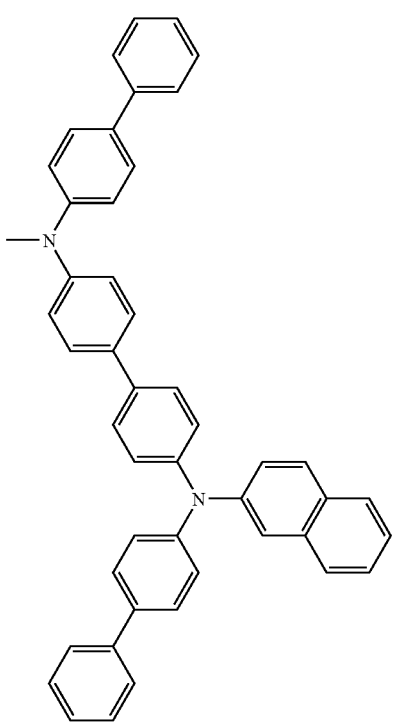

217
-continued
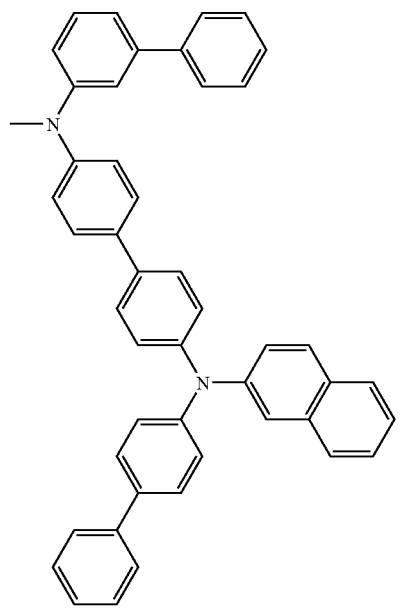
486
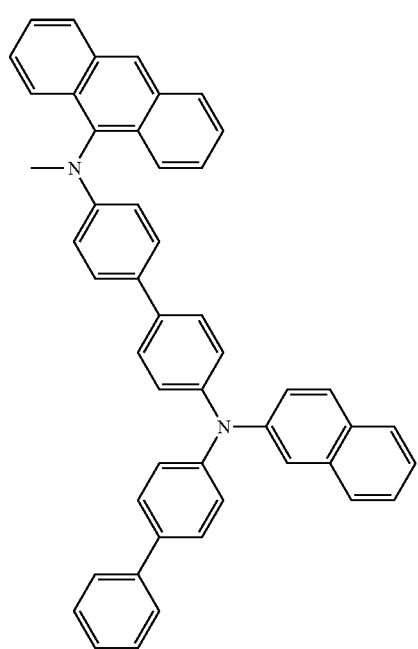
487
218
-continued
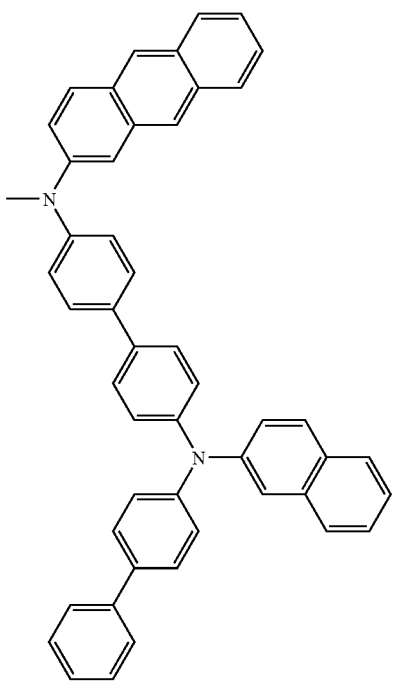
488
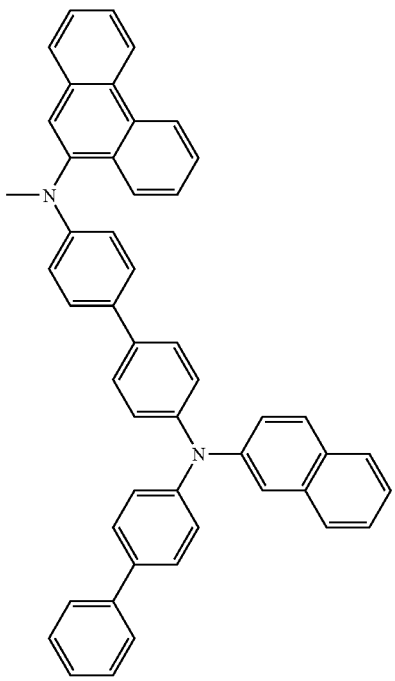
489

219                    220
-continued             -continued
490
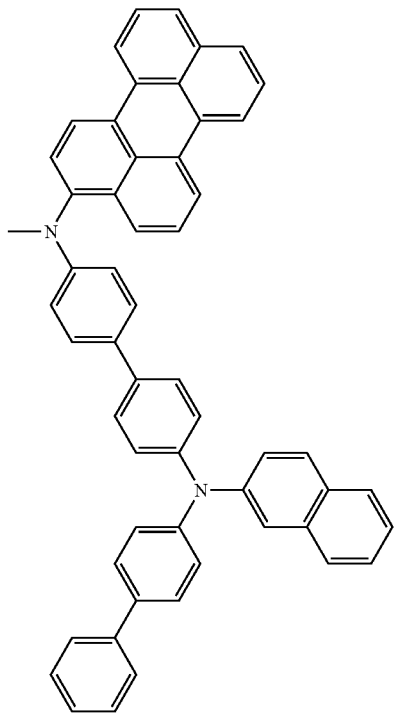
492
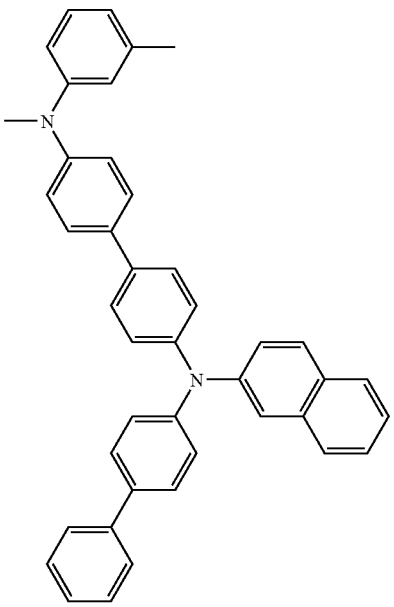
491
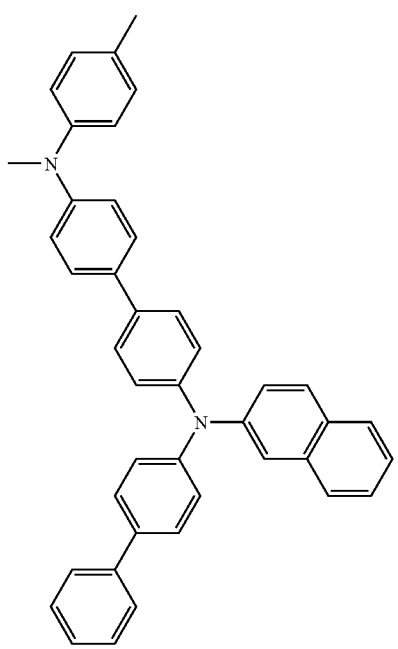
493
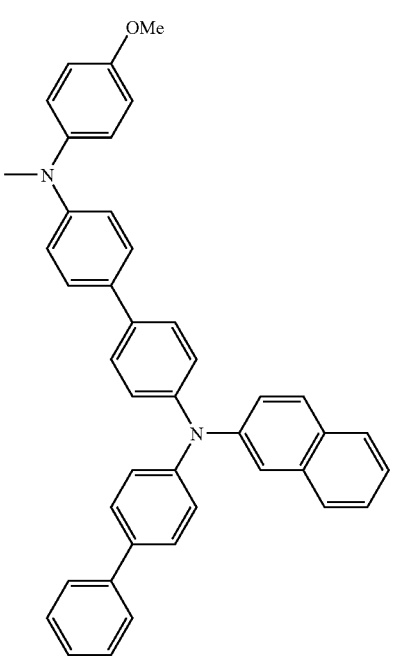

221
-continued
494
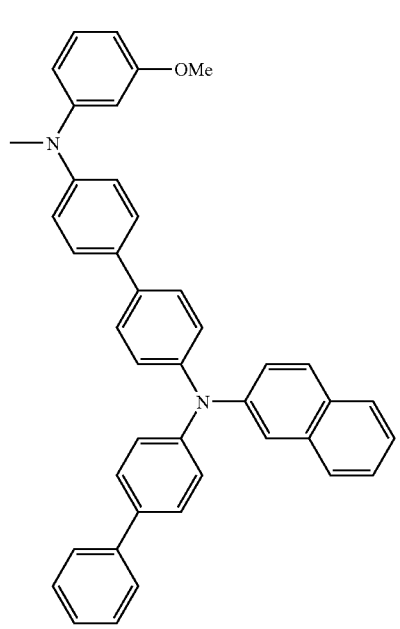
495
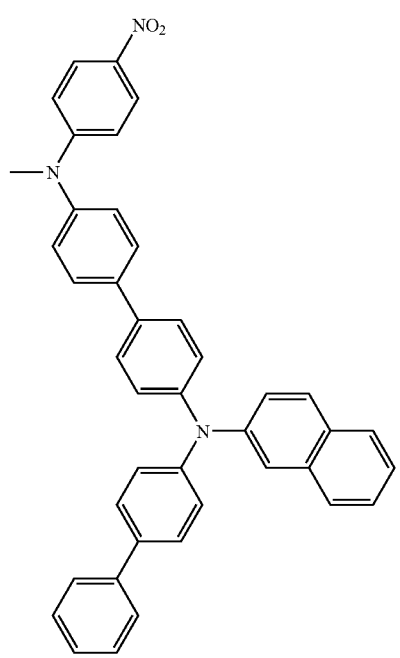
222
-continued
496
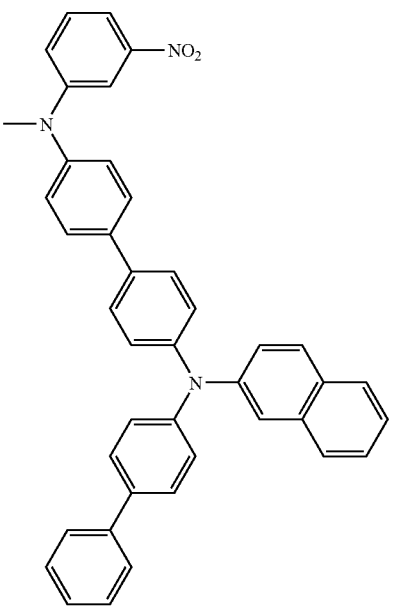
497
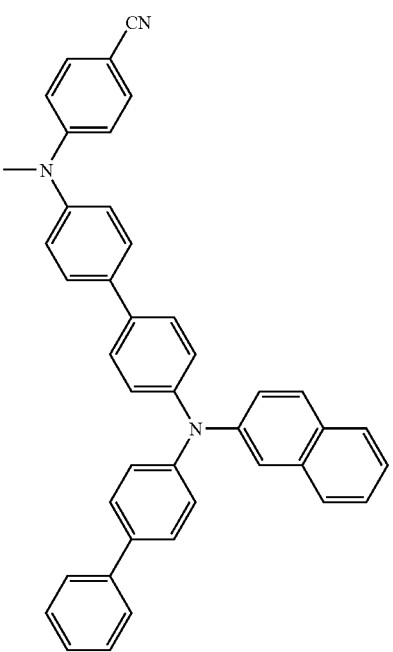

223
224
498
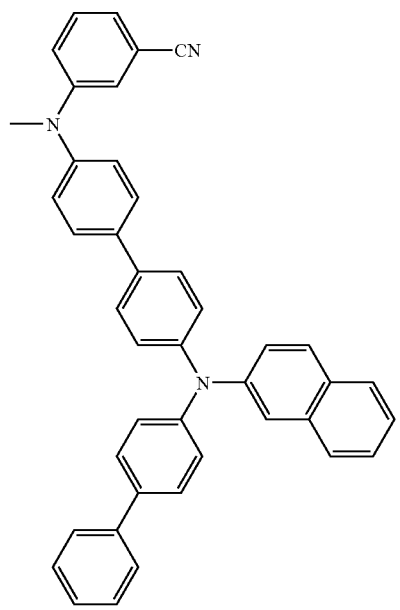
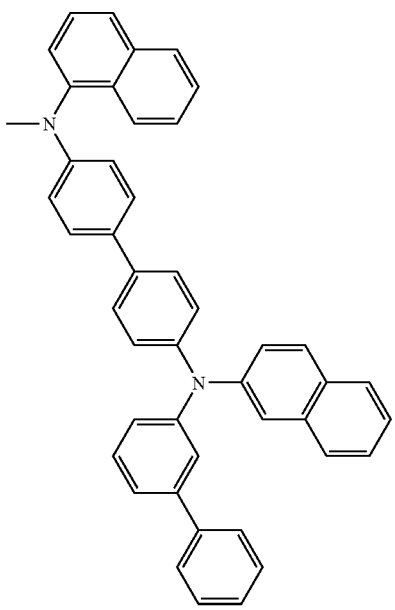
500
499
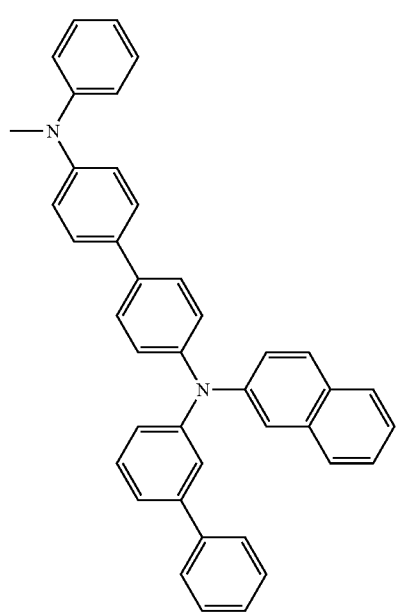
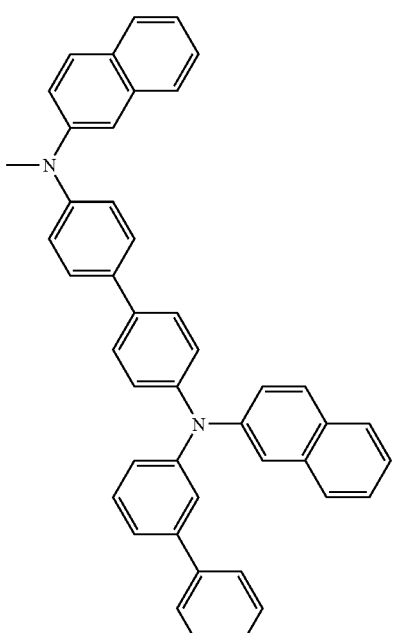
501

225
-continued
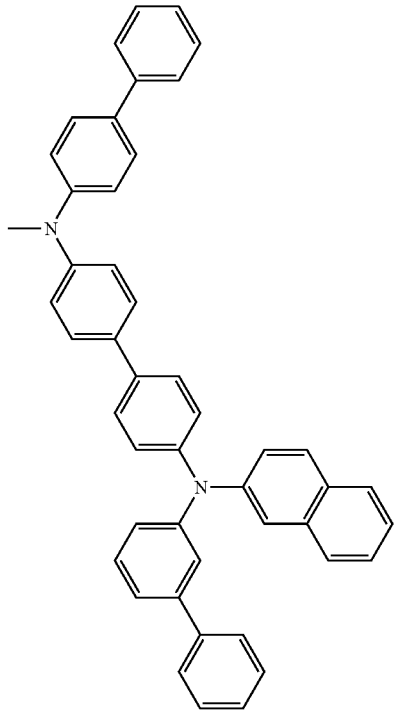
226
-continued
502
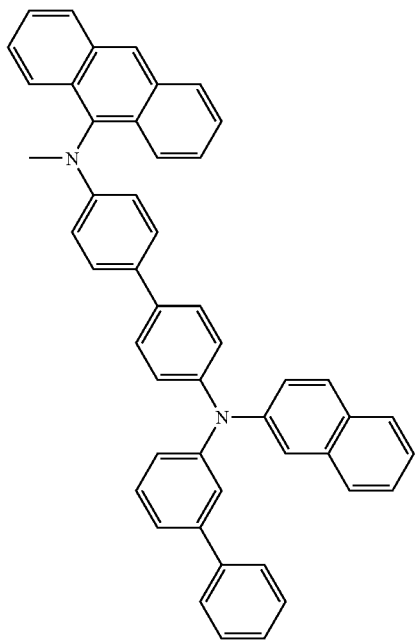
504
503
505
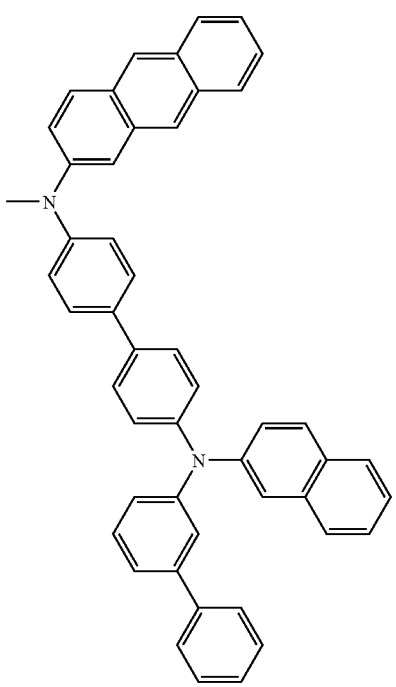

227                                                         228
-continued                                                  -continued
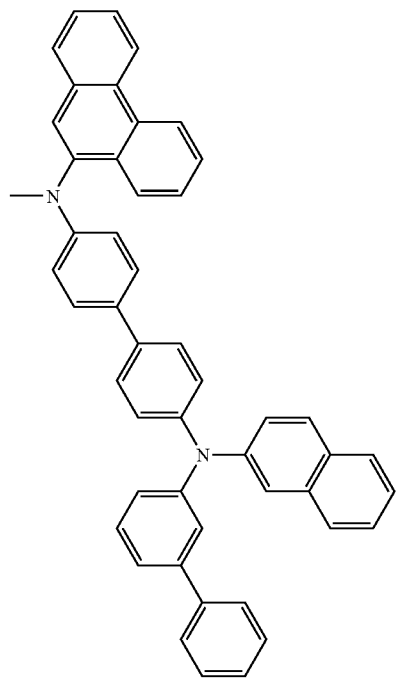
506
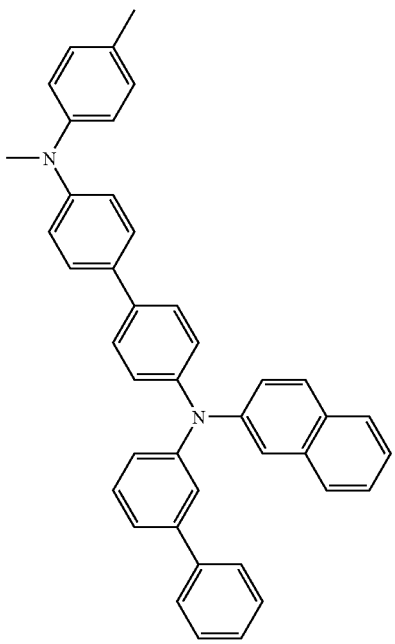
508
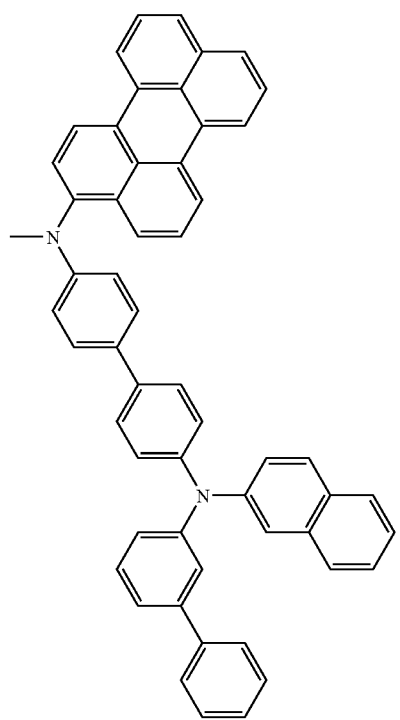
507
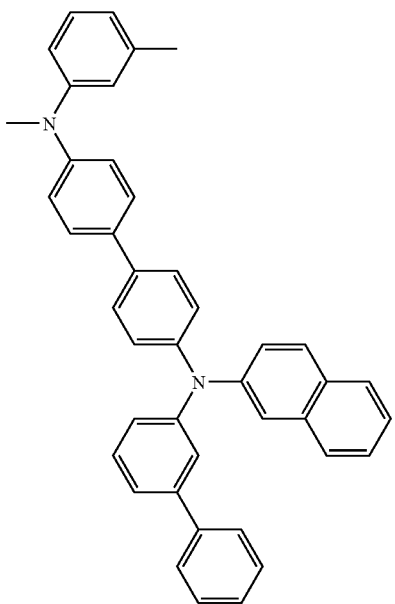
509

229
-continued
510
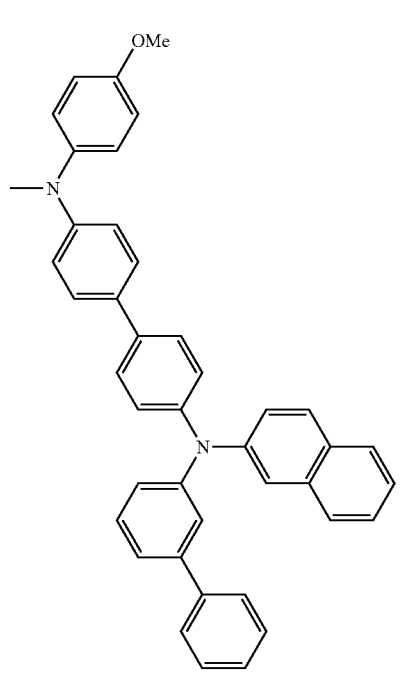
511
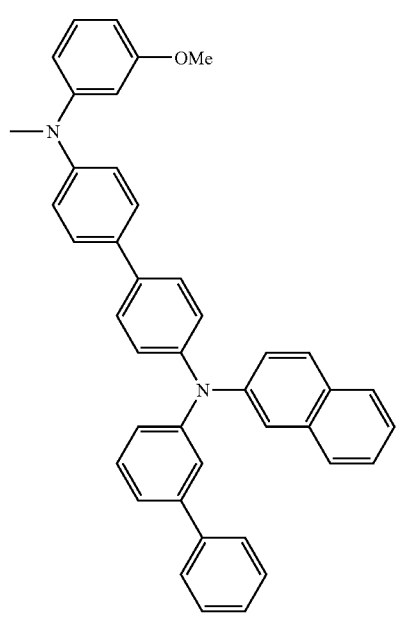
230
-continued
512
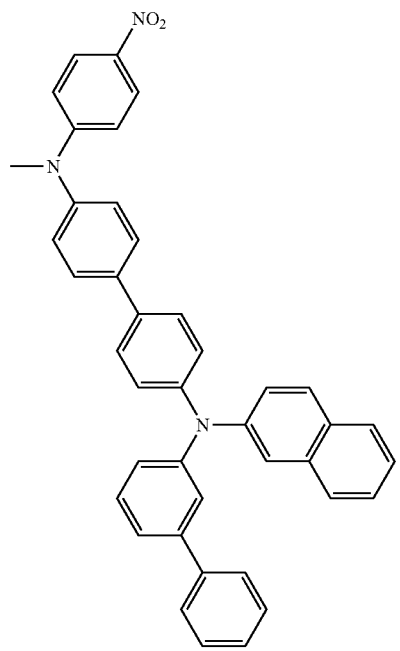
513
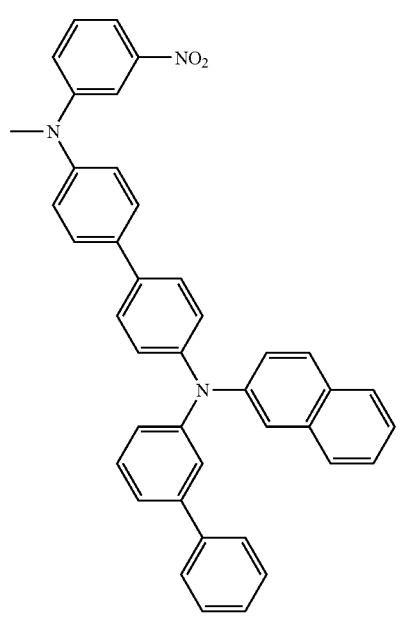

514
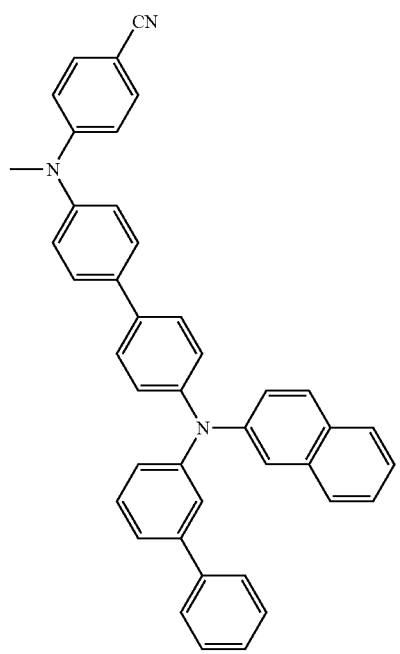
516
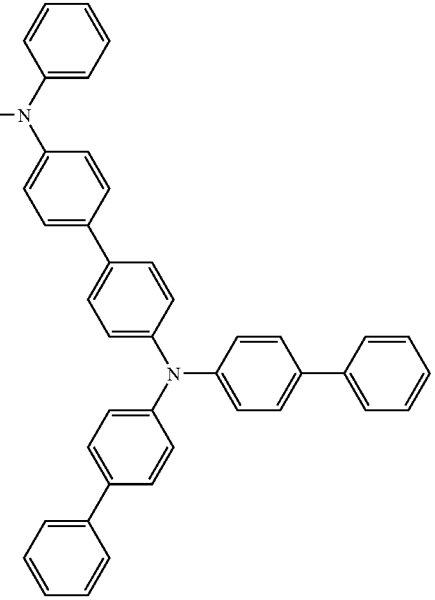
515
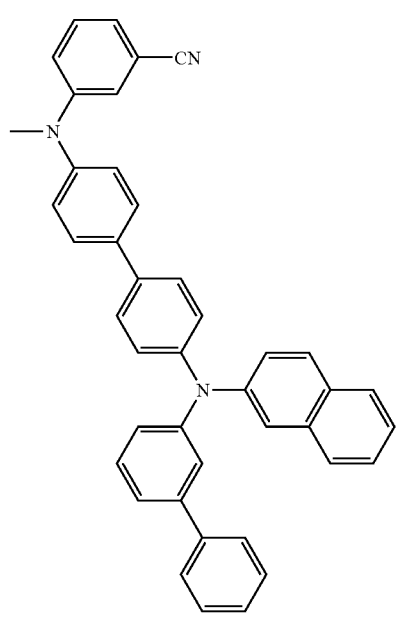
517
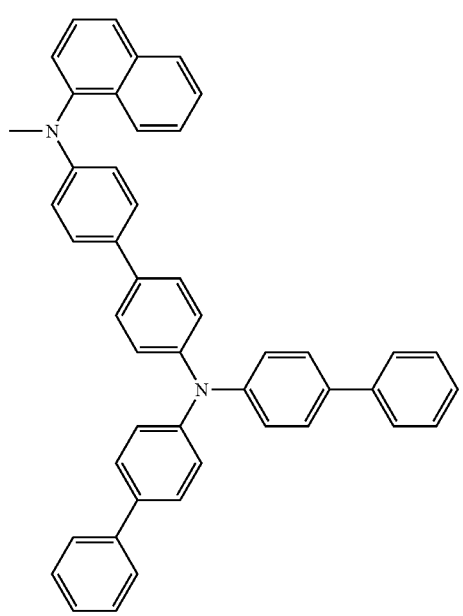

233 234
518 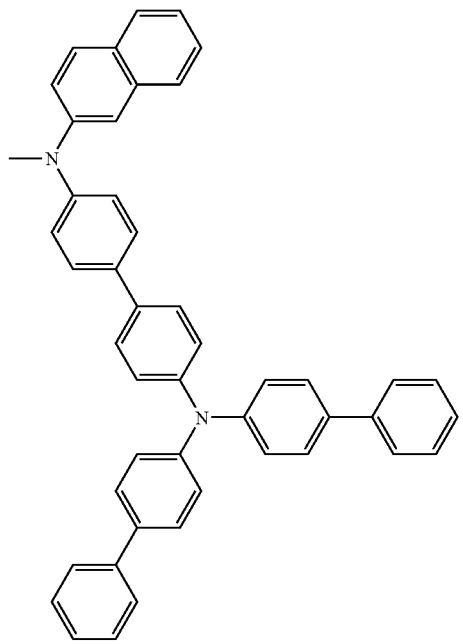
520 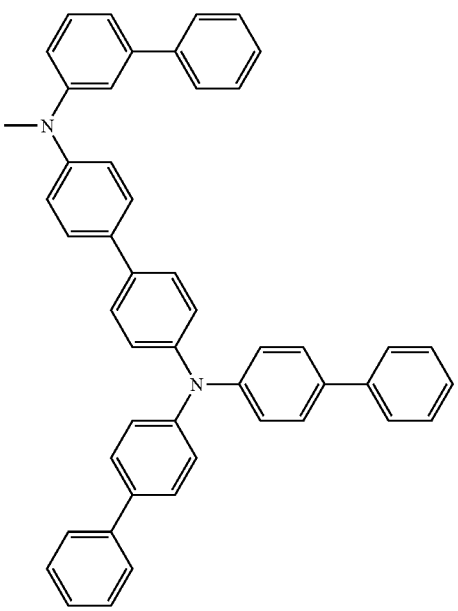
519 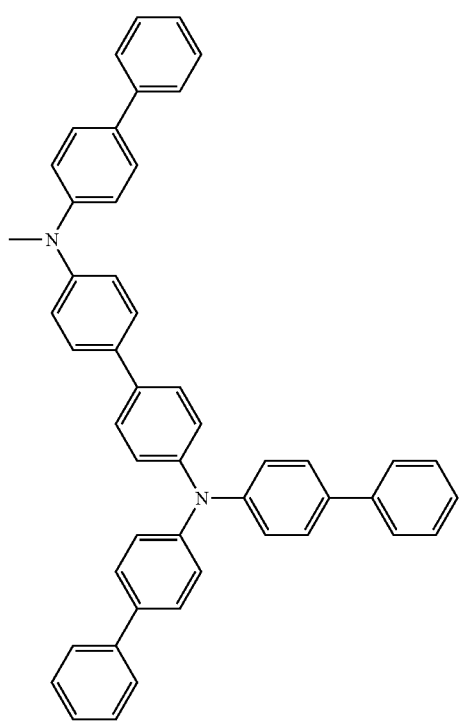
521 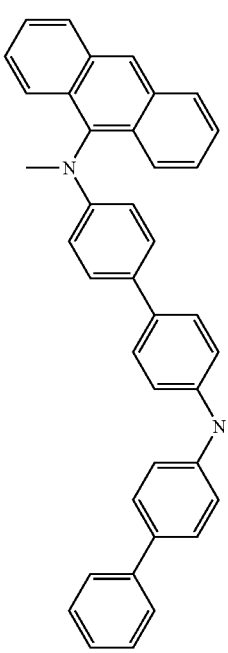

522
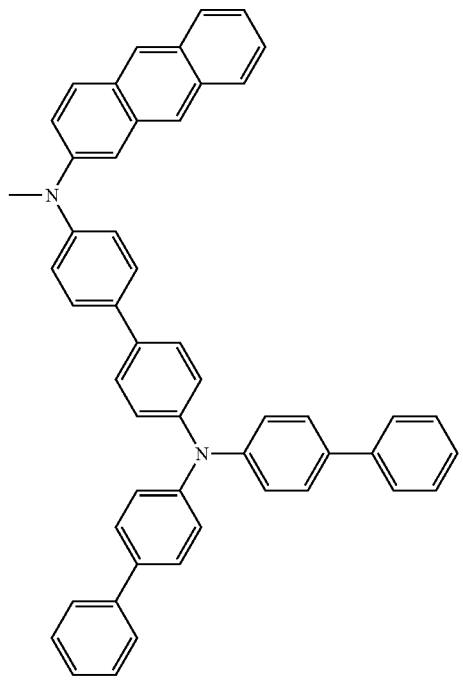
523
524
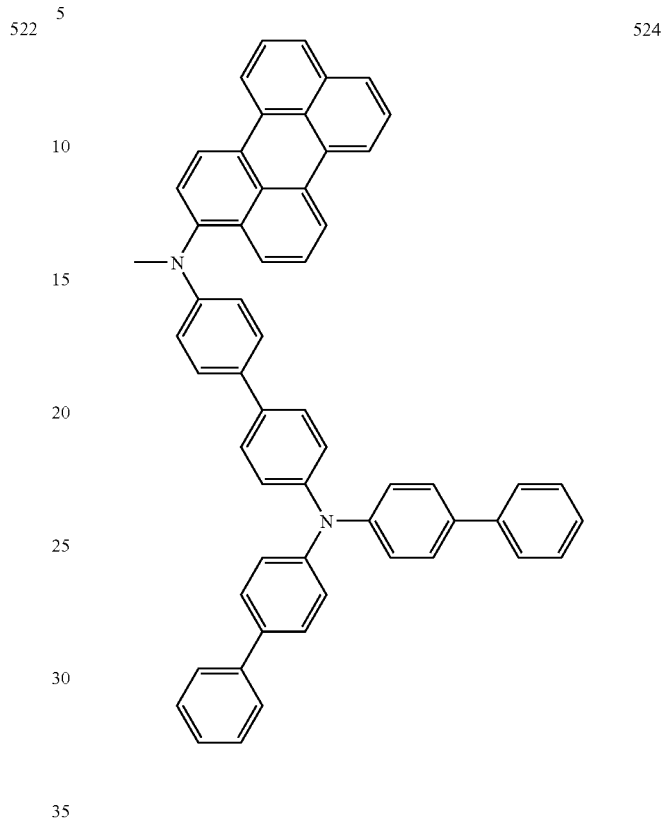
525
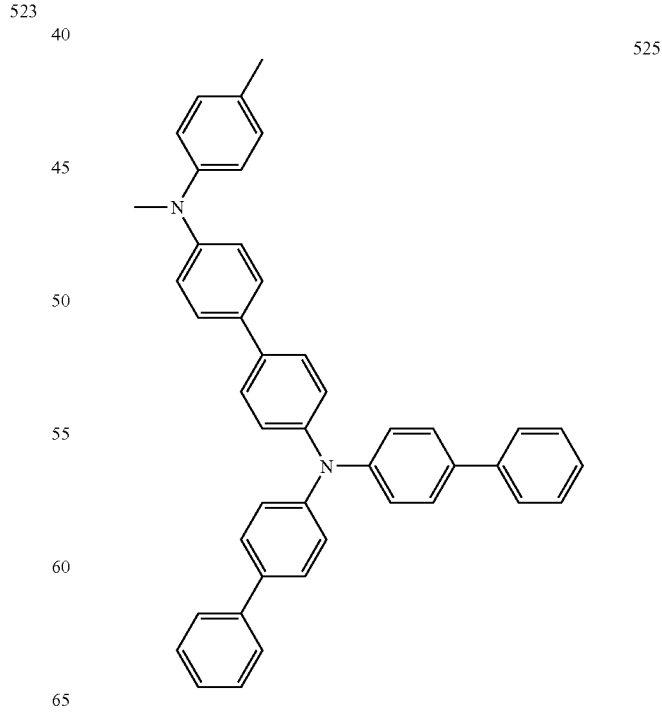

237
-continued
526
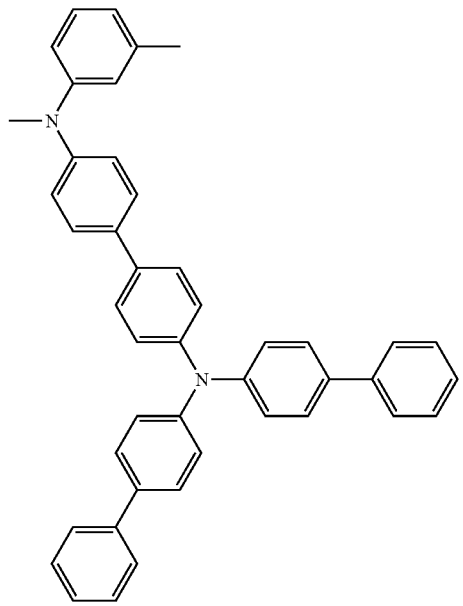
527
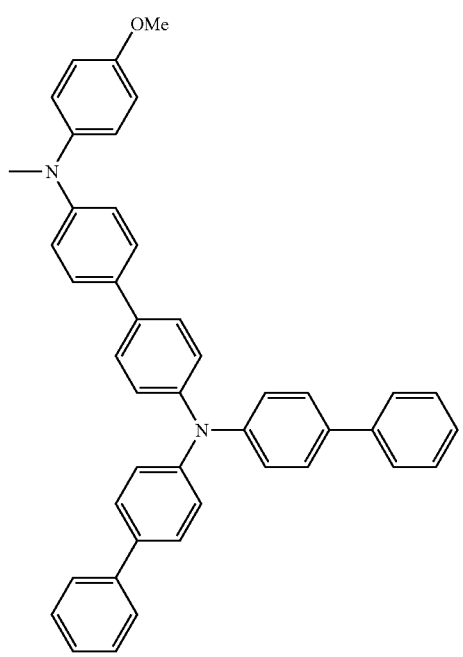
238
-continued
528
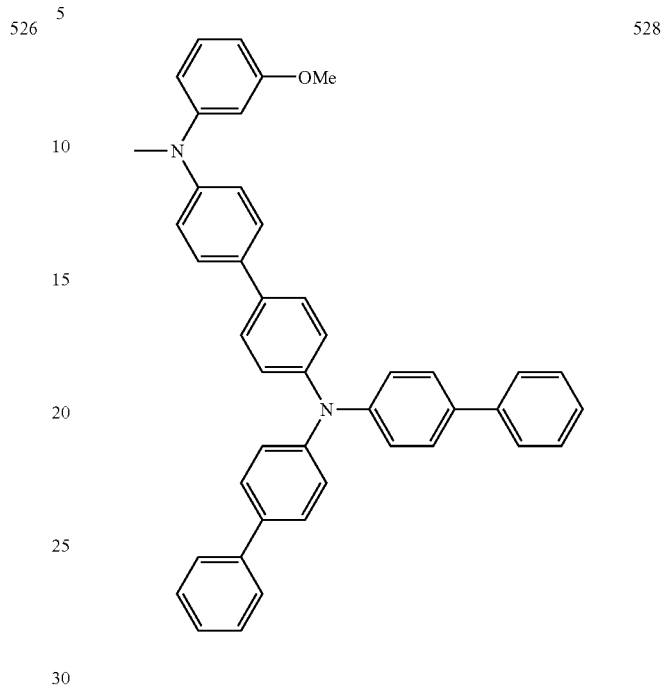
529
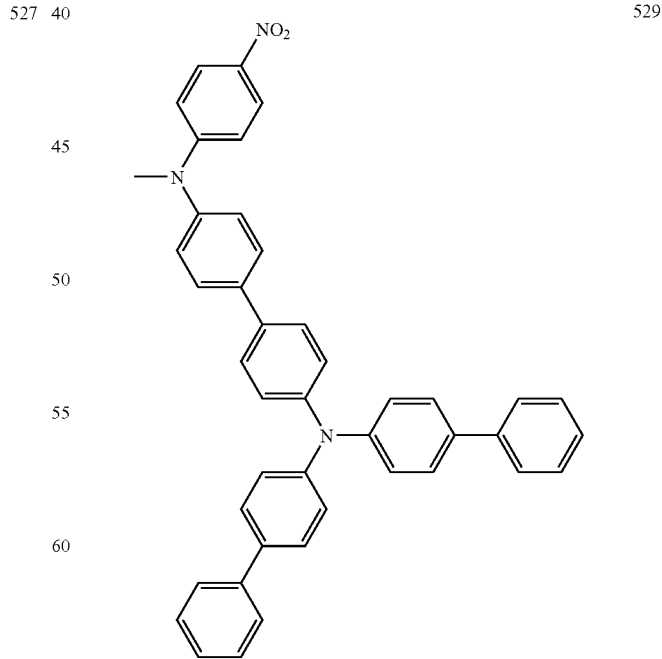

-continued
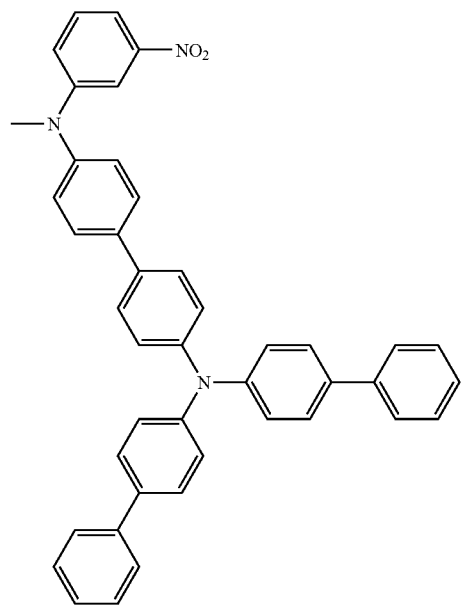
530
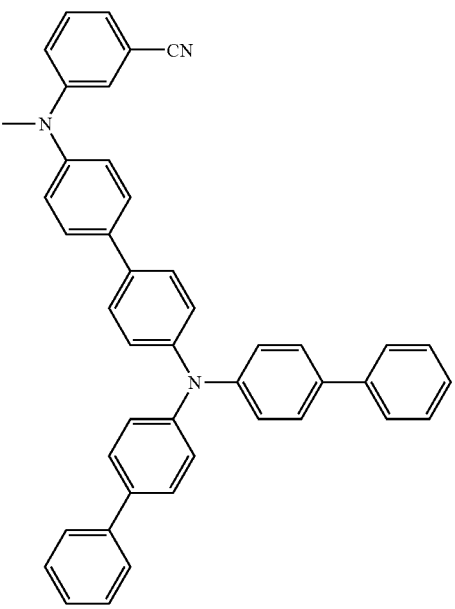
532
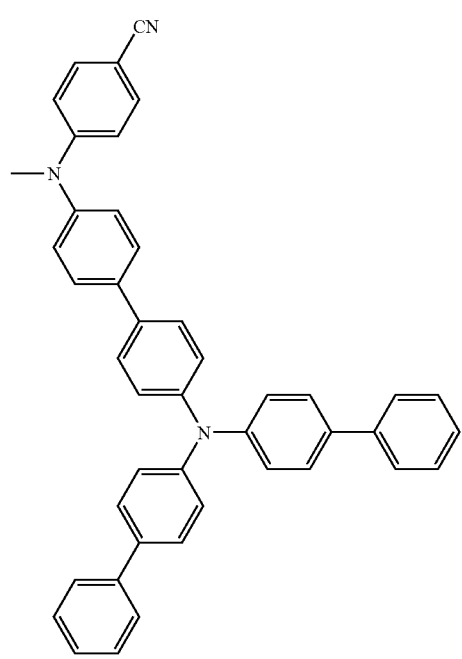
531
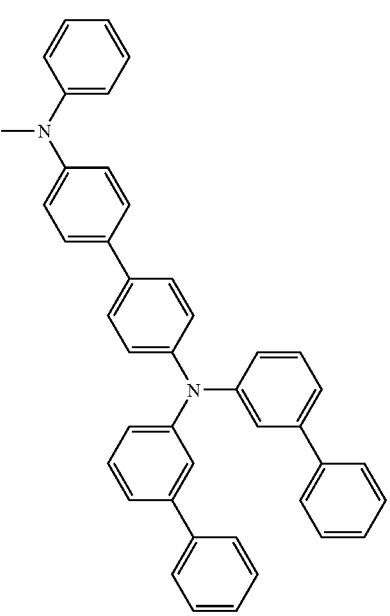
533

241
-continued
534
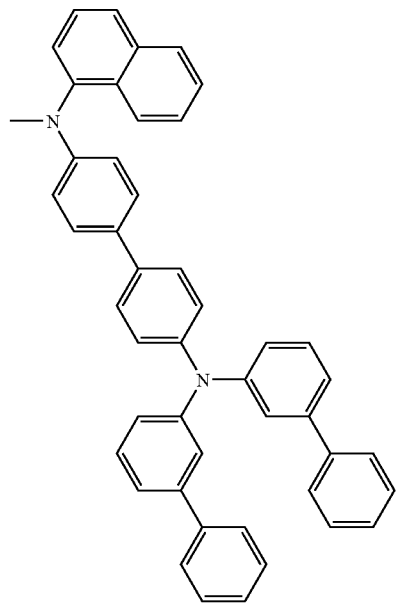
535
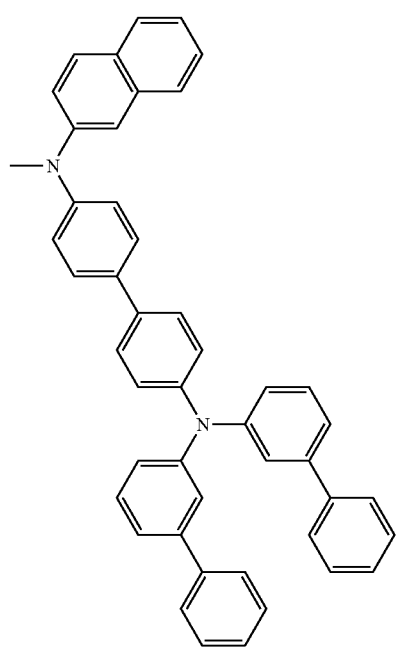
242
-continued
536
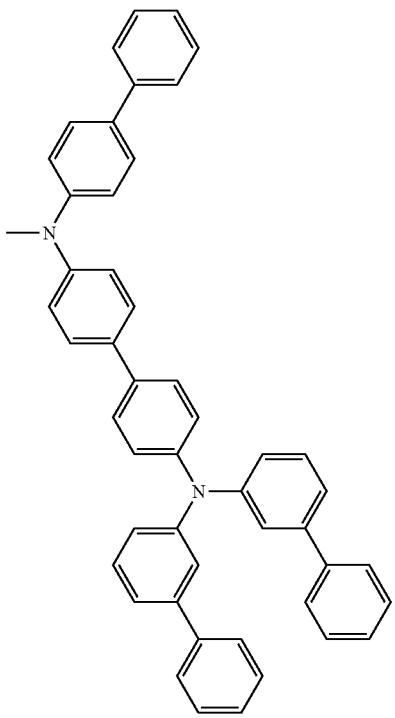
537
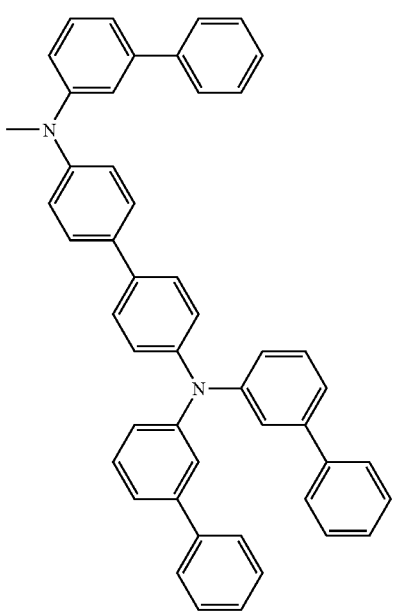

538
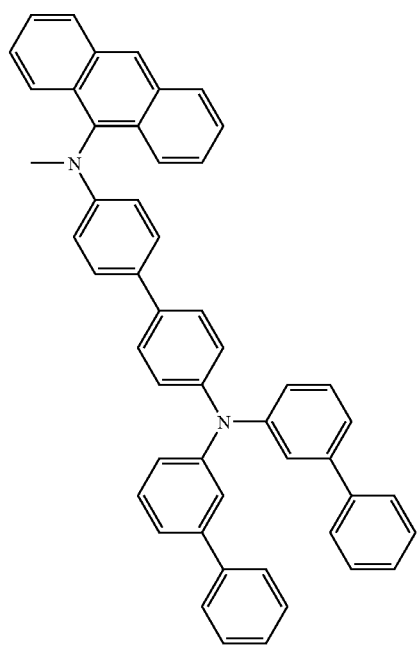
539
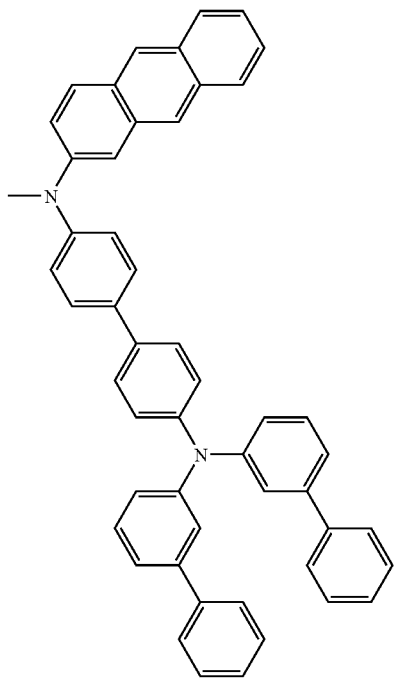
540
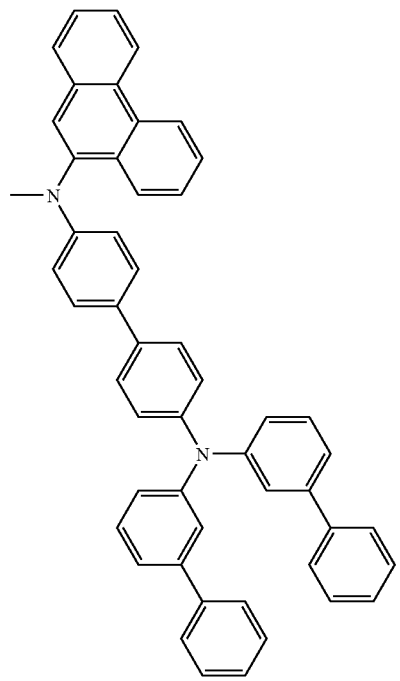
541
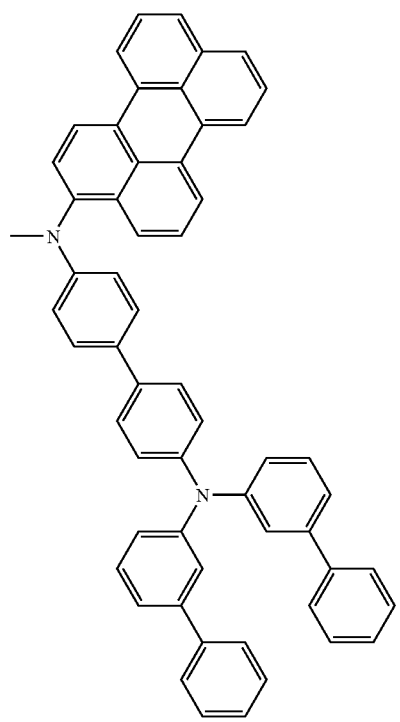

542
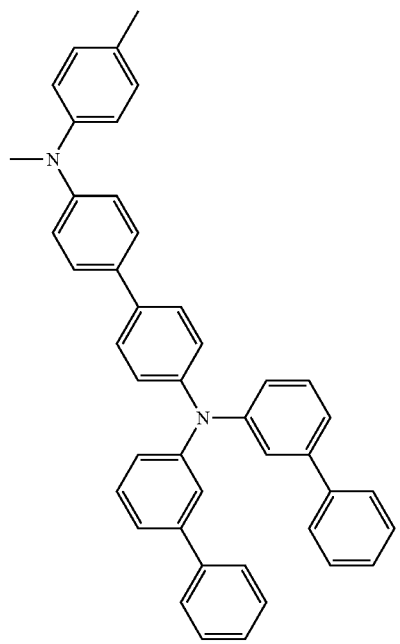
543
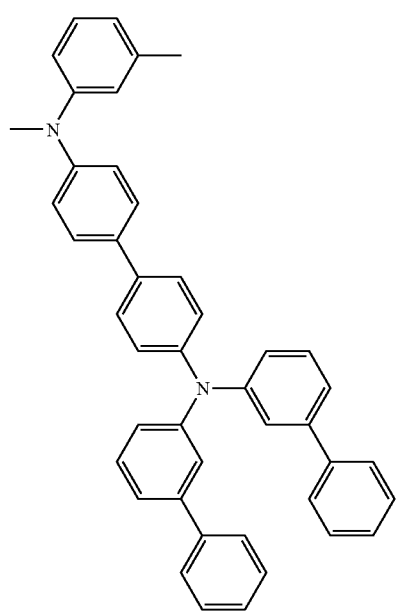
544
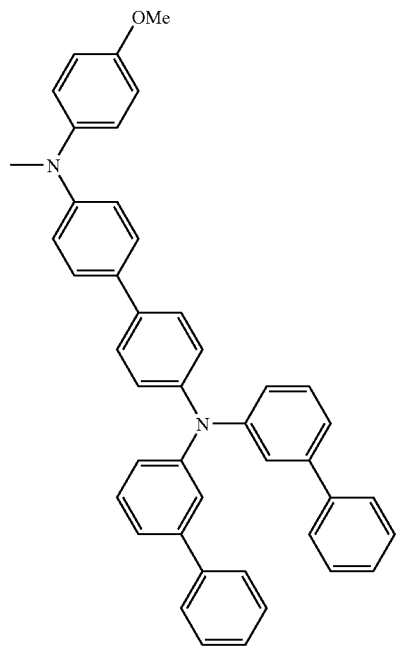
545
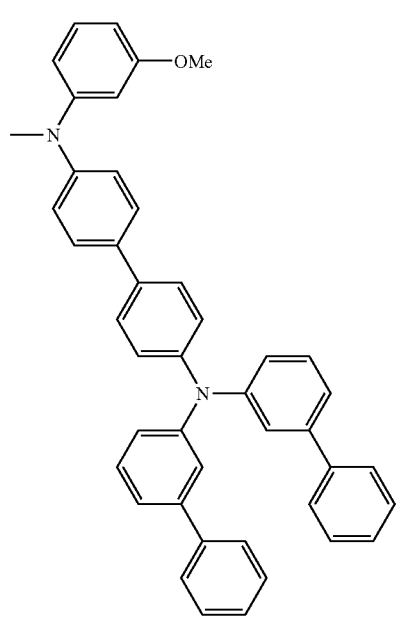

247
248
546 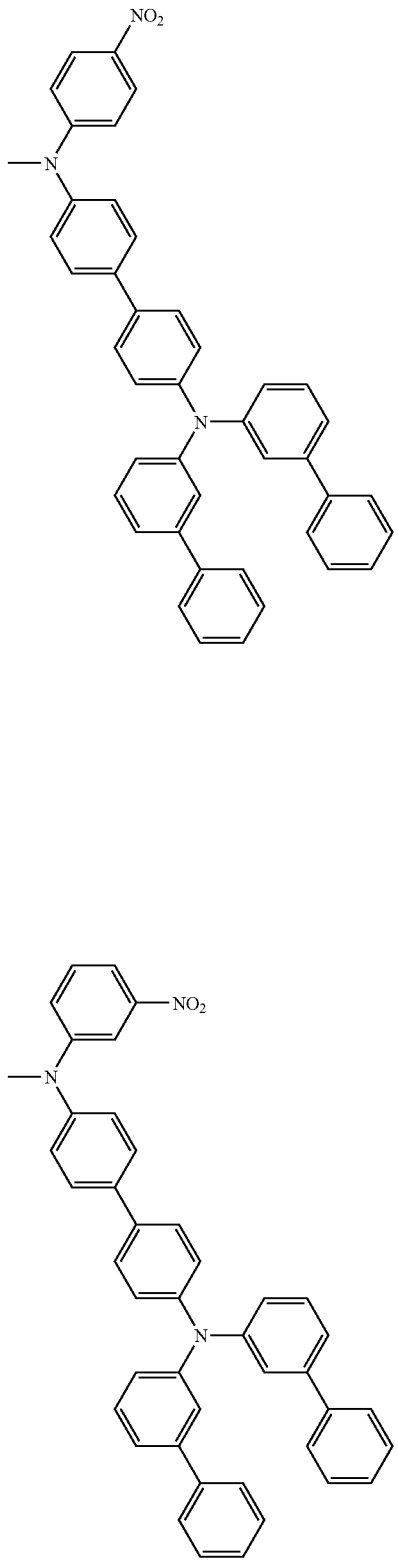
548 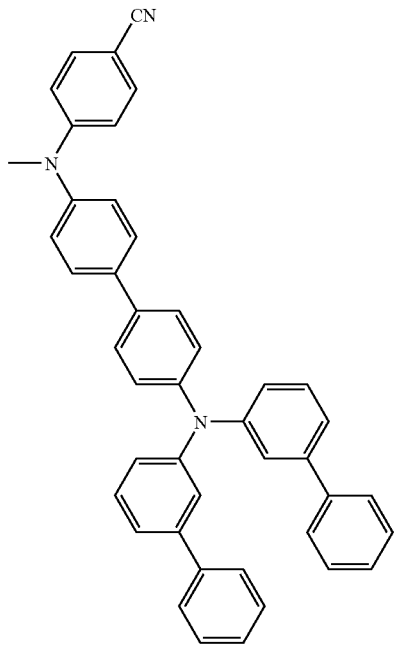
547
549
550
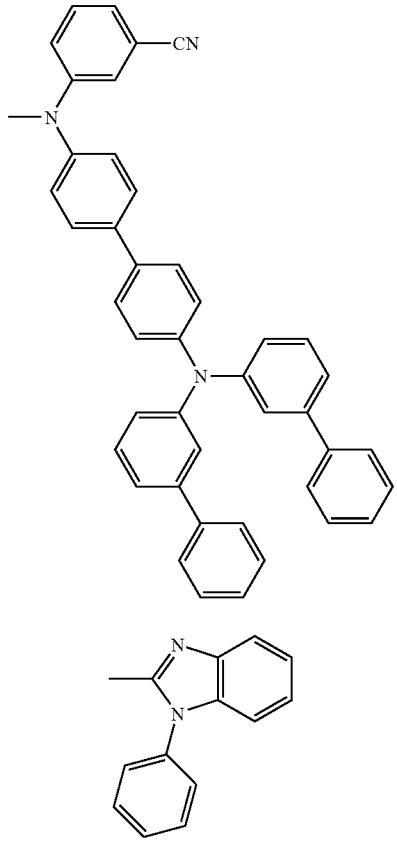

-continued
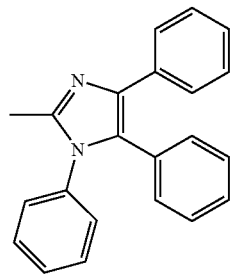 551
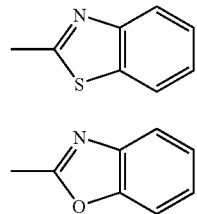 552
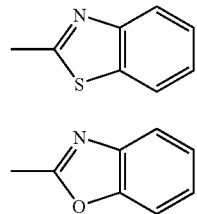 553
Illustrative, but non-limiting, examples of the compound of Formula 1 include the following compounds.
[compound 1]
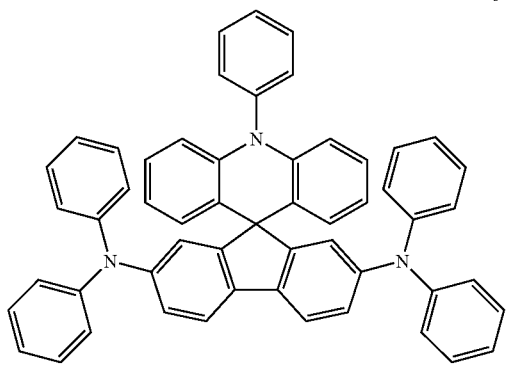
[compound 2]
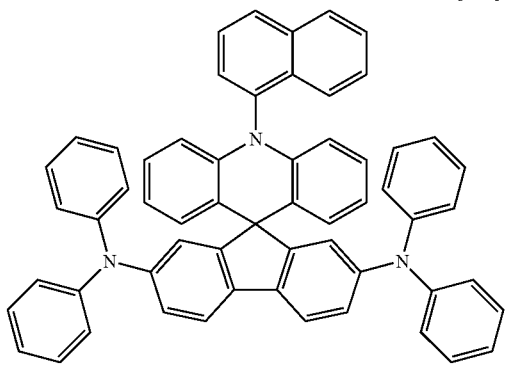
[compound 3]
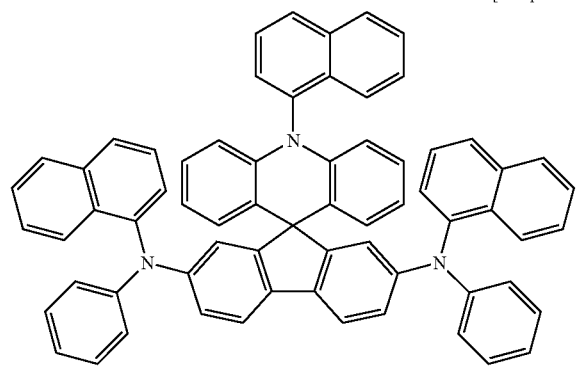
[compound 4]
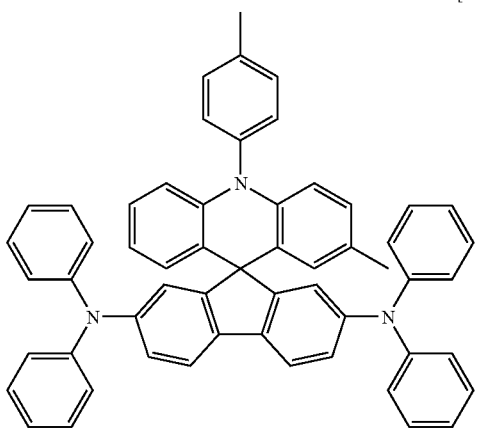

-continued
[compound 5]
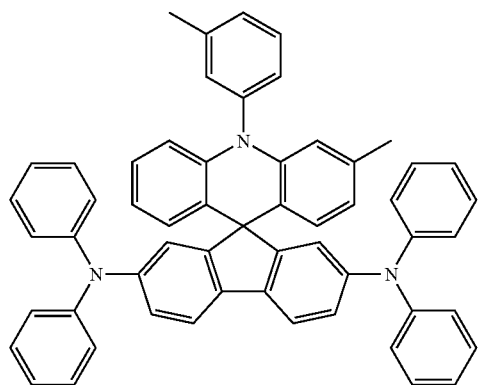
[compound 6]
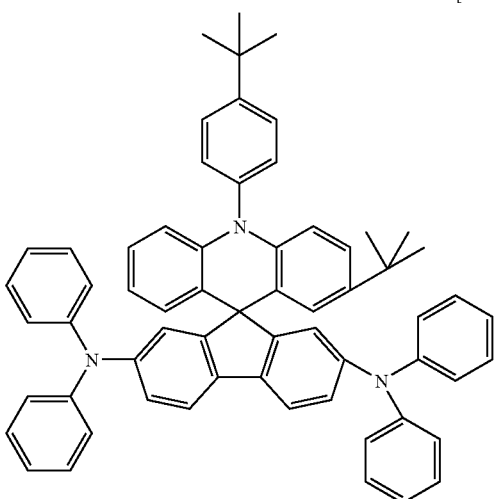
[compound 7]
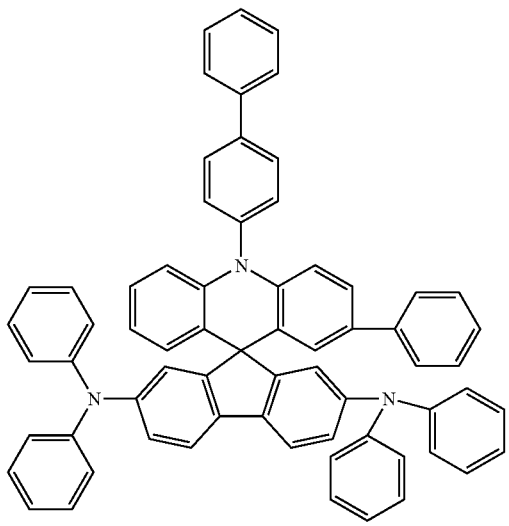
[compound 8]
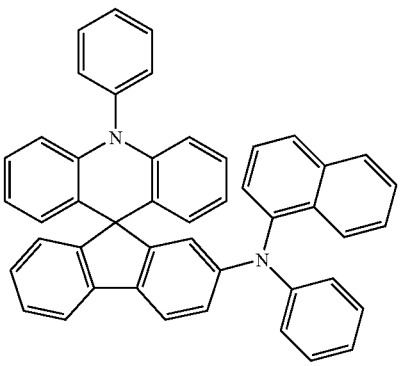
[compound 9]
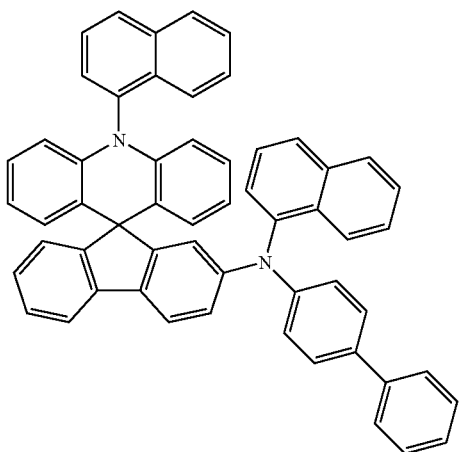

[compound 10]
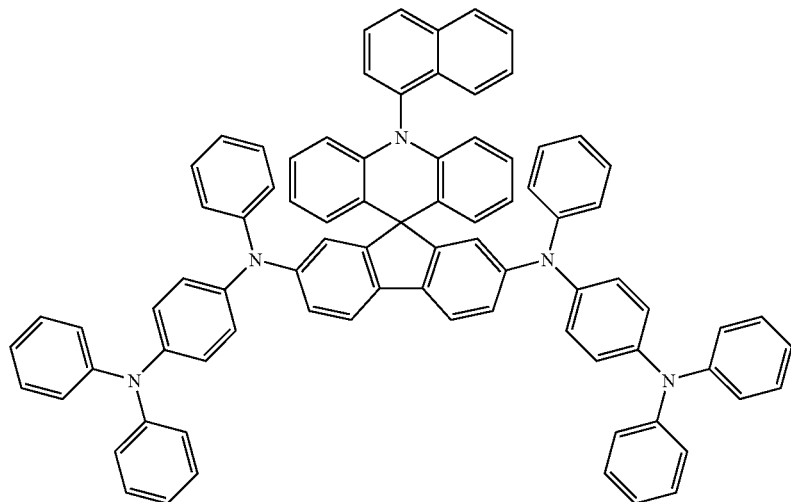
[compound 11]
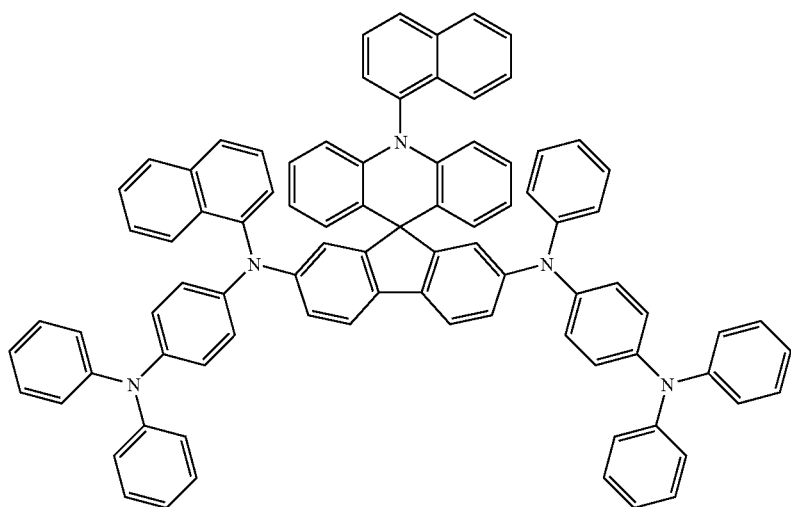
[compound 12]
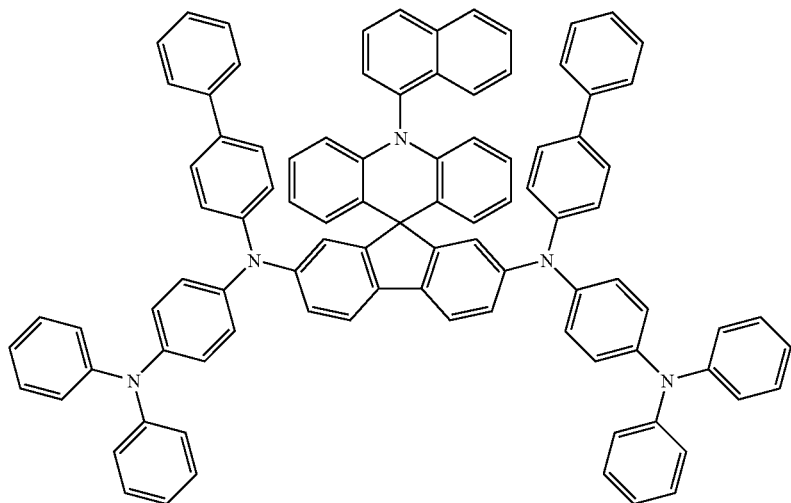

[compound 13]
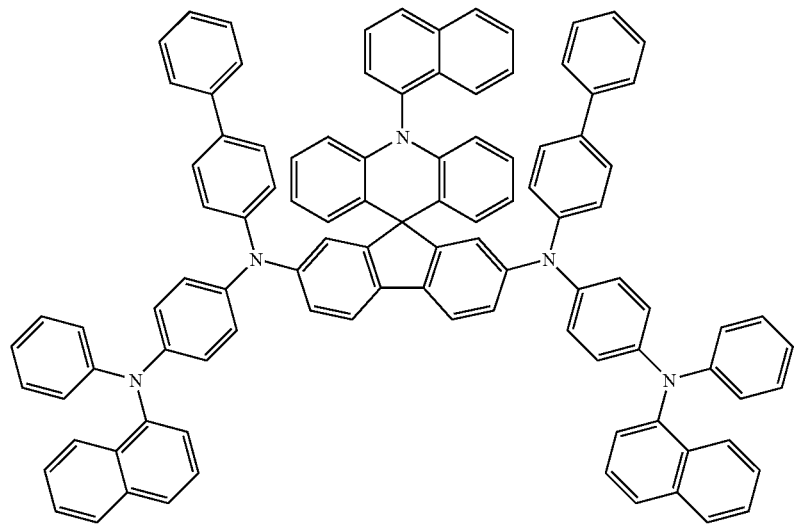
[compound 14]
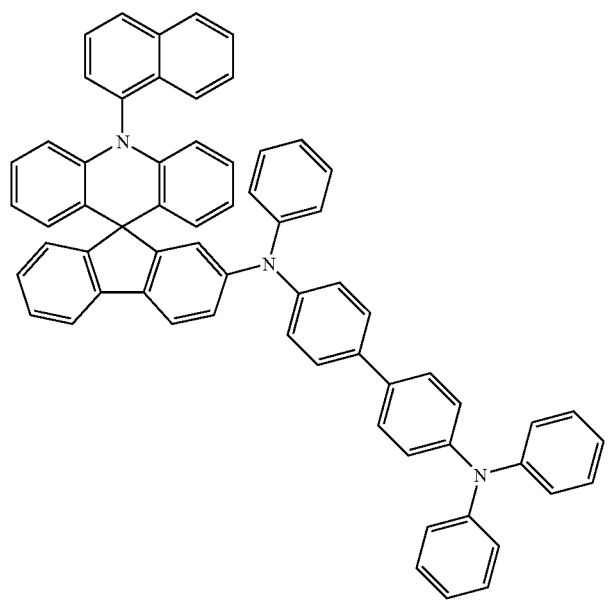

-continued

[compound 15]

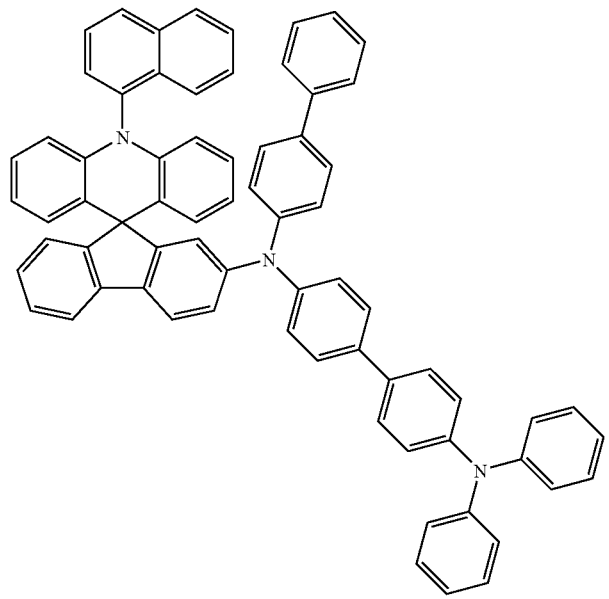

[compound 16]

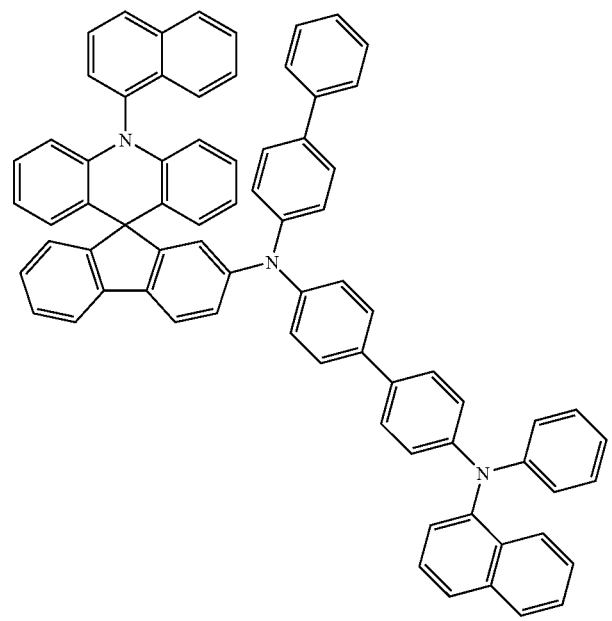

BRIEF DESCRIPTION OF THE DRAWINGS

FIG. 1 illustrates an organic light emitting device comprising a substrate 1, an anode 2, a light emitting layer 3, and a cathode 4; and FIG. 2 illustrates an organic light emitting device comprising a substrate 1, an anode 2, a hole injection layer 5, a hole transport layer 6, a light emitting layer 7, an electron transport layer 8, and a cathode 4.

BEST MODE FOR CARRYING OUT THE INVENTION

Hereinafter, a detailed description will be given of the present invention.

Various substituent groups are introduced into a core structure shown in Formula 1, in detail, the core structure in which a fluorene group is bonded to a combination of an acridine group and a carbazolyl group up to form a spiro structure, thereby the compound of Formula 1 has characteristics suitable for application to an organic material layer used in an organic light emitting device. This will be described in detail, below.

The steric core structure of the compound of Formula 1, for convenience of explanation, can be divided into two portions, A and B, as shown in the following Formula.

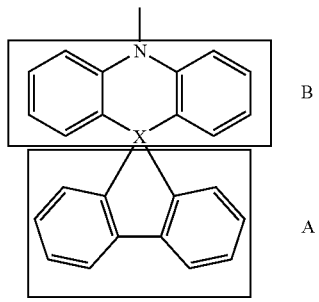

The compound of Formula 1 has the steric core structure in which a plane A meets with a plane B at right angles around X, and conjugation does not occur between the A and B portions around X. Furthermore, since one nitrogen atom is positioned among three aryl groups in the plane B, conjugation is limited in the plane B.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to R1 to R17 positions of the core structure having the large energy band gap so as to produce compounds having various energy band gaps. Generally, it is easy to control an energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into R1 to R17 of the core structure.

Additionally, by introducing various substituent groups into the core structure, compounds having intrinsic characteristics of the substituent groups can be obtained. For example, substituent groups, which are frequently applied to hole injection layer material, hole transport layer material, light emitting layer material, and electron transport layer materials during the production of the organic light emitting device, are introduced into the core structure so as to produce substances capable of satisfying the requirements of each organic material layer. Particularly, since the core structure of the compound of Formula 1 includes the arylamine structure, it has an energy level suitable for the hole injection and/or hole transport materials in the organic light emitting device. In the present invention, the compound having the proper energy level is selected depending on the substituent group among the compounds represented by Formula 1 to be used in the organic light emitting device, thereby it is possible to realize a device having a low actuating voltage and a high light efficiency.

Furthermore, various substituent groups are symmetrically or asymmetrically introduced into the core structure so as to precisely control the energy band gap, and to improve interfacial characteristics with organic materials, thereby apply the compound to various fields.

Additionally, various substituent groups are introduced into the steric structure of the compound of Formula 1 using spiro bonding to control the three-dimensional structure of the organic material so as to minimize π-π interaction in the organic material, thereby formation of excimers is prevented.

Meanwhile, since the compound of Formula 1 has a high glass transition temperature (Tg), it has excellent thermal stability. For example, the glass transition temperature of the compound of Formula 3-2 is 150° C., which is still higher than that of conventionally used NPB (Tg: 96° C.). Such increase in thermal stability is an important factor providing actuating stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

For example, the compound of Formula 2 has excellent solubility to a polar solvent, such as xylene, dichloroethane, or NMP, which is used during the production of the device, and forms a thin film very well through the process using a solution, thus the solution coating process may be applied to produce the device. Additionally, a light emitting wavelength of a thin film or a solid formed using the solution coating process is typically shifted to a longer wavelength due to interaction between molecules, in comparison with a light emitting wavelength in a solution state. Little shift in the wavelength occurs in the compound having the structure shown in Formula 1.

Tertiary alcohol, which is produced by a reaction of a lithiated aryl and keto group, is heated in the presence of an acid catalyst to form a hexagonal cyclic structure while water is removed, thereby producing the compound having a spiro structure according to the present invention. The above-mentioned procedure for producing the compound is well known in the art, and those skilled in the art can change the production conditions during the production of the compound of Formula 1. The production will be described in detail in the preparation examples later.

In the organic light emitting device of the present invention, a compound, in which a thermosetting or photo-crosslinkable functional group is introduced into the compound of Formula 1, for example the compound of Formula 12, may be used instead of the compound of Formula 1. The former compound has the basic physical properties of the compound of Formula 1, and may be used to form a thin film using a solution coating process and then be cured so as to form an organic material layer during the production of the device.

The method of forming the organic material layer, which comprises introducing the curable functional group into the organic material during the production of the organic light emitting device, forming the organic thin film using the solution coating process, and curing the resulting film, is disclosed in US Pat. No. 2003-0044518 and EP Pat. No. 1146574A2.

The above documents state that, if the organic material layer is formed through the above-mentioned method using a material having a thermosetting or photo-crosslinkable vinyl or acryl group so as to produce an organic light emitting device, it is possible to produce an organic light emitting device having a low voltage and high brightness as well as an organic light emitting device having a multilayered structure using the solution coating process. This operation mechanism may be applied to the compound of the present invention.

In the present invention, the thermosetting or photo-crosslinkable functional group may be a vinyl or an acryl group.

The organic light emitting device of the present invention can be produced using known materials through a known process, modified only in that at least one layer of organic material layer(s) include the compound of the present invention, that is, the compound of Formula 1.

The organic material layer(s) of the organic light emitting device according to the present invention may have a single layer structure, or alternatively, a multilayered structure in which at least two organic material layers are layered. For example, the organic light emitting device of the present invention may comprise a hole injection layer, a hole transport layer, a light emitting layer, an electron transport layer, and an electron injection layer as the organic material layer(s). However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

A method of producing the compound of Formula 1 and the production of the organic light emitting device using the same will be described in detail in the following preparation examples and examples. However, the following preparation examples and examples are set forth to illustrate, but are not to be construed to limit the present invention.

MODE FOR THE INVENTION

A better understanding of a method of producing an organic compound represented by Formula 1 and the production of an organic light emitting device using the same may be obtained in light of the following preparation examples and examples which are set forth to illustrate, but are not to be construed to limit the present invention.

In order to produce the compound represented by Formula 1, any one of the compounds of the following Formulae, a to g, may be used as a starting material.

[formula a]

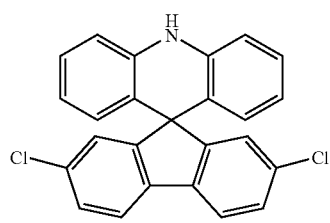

[formula b]

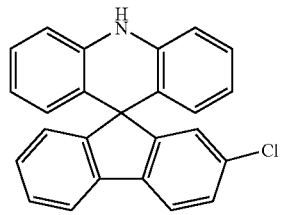

[formula c]

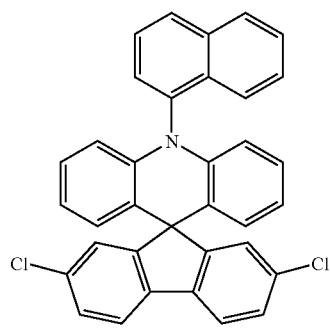

[formula d]

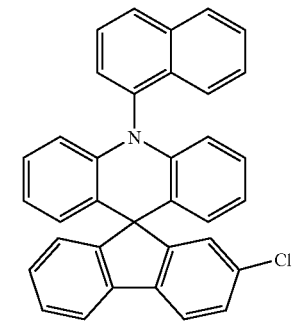

[formula e]

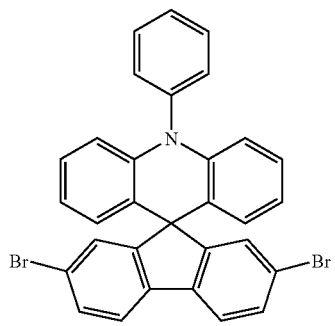

-continued

[formula f]

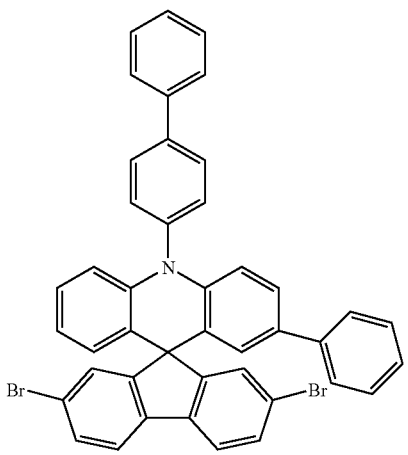

[formula g]

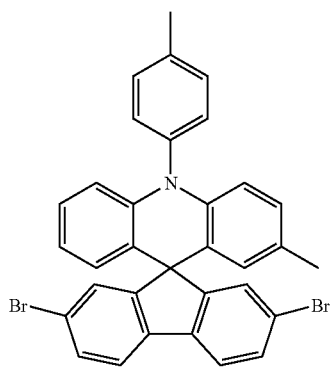

[formula h]

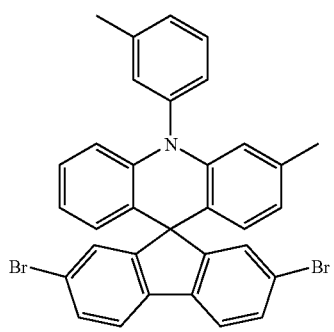

[formula i]

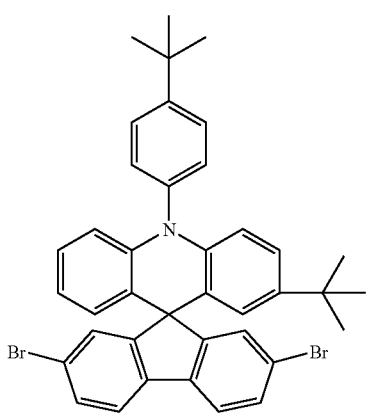

PREPARATION EXAMPLE 1

Preparation of a Starting Material Represented by Formula a

1) After 10 g of diphenylamine (59 mmol) and 8.04 ml of bromomethyl methyl ether (88.6 mmol) were dissolved in 100 ml of tetrahydrofuran, 12.4 ml of triethylamine (88.6 mmol) were added thereto. Stirring was conducted in a nitrogen atmosphere for 5 hours, and an organic layer was then extracted using distilled water. The extracted organic layer was subjected to a column separation process at a ratio of n-hexane/tetrahydrofuran of 15:1, and vacuum dried to produce 12 g of tertiary amine (yield 90%).

2) The amine compound produced in 1) (12.0 g, 56.3 mmol) was dissolved in 100 ml of purified THF and cooled to −78° C., and n-BuLi (2.5 M hexane solution, 22.5 ml, 56.3 mmol) was slowly dropped thereon. Stirring was conducted at the same temperature for 30 min, and a 2,7-dichloro-9-fluorenone compound (14.0 g, 56.3 mmol) was added thereto. After stirring at the same temperature for 40 min, the temperature was raised to normal temperature and stirring was carried out for an additional 3 hours. The reaction was completed in an ammonium chloride aqueous solution, and extraction was conducted with ethyl ether. Water was removed from an organic material layer using anhydrous magnesium sulfate, and an organic solvent was then removed therefrom. The produced solid was dispersed in ethanol, stirred for one day, filtered, and vacuum dried. After an intermediate material was dispersed in 100 ml of acetic acid, ten drops of concentrated sulfuric acid were added thereto and reflux was conducted for 4 hours. The resulting solid was filtered, washed with ethanol, and vacuum dried to produce 21.8 g of amine (96.8% yield). MS: [M+H]+=401.

PREPARATION EXAMPLE 2

Preparation of a Starting Material Represented by Formula b

1) After 10 g of diphenylamine (59 mmol) and 8.04 ml of bromomethyl methyl ether (88.6 mmol) were dissolved in 100 ml of tetrahydrofuran, 12.4 ml of triethylamine (88.6 mmol) were added thereto. Stirring was conducted in a nitrogen atmosphere for 5 hours, and an organic layer was then extracted using distilled water. The extracted organic layer was subjected to a column separation process at a ratio of n-hexane/tetrahydrofuran of 15:1, and vacuum dried to produce 12 g of tertiary amine (yield 90%).

2) The amine compound produced in 1) (12.0 g, 56.3 mmol) was dissolved in 100 ml of purified THF and cooled to −78° C., and n-BuLi (2.5 M hexane solution, 22.5 ml, 56.3 mmol) was slowly dropped thereon. Stirring was conducted at the same temperature for 30 min, and a 2-chloro-9-fluorenone compound (12.1 g, 56.3 mmol) was added thereto. After stirring at the same temperature for 40 min, the temperature was raised to normal temperature and stirring was carried out for an additional 3 hours. The reaction was completed in an ammonium chloride aqueous solution, and extraction was conducted with ethyl ether. Water was removed from an organic material layer using anhydrous magnesium sulfate, and an organic solvent was then removed therefrom. The produced solid was dispersed in ethanol, stirred for one day, filtered, and vacuum dried. After an intermediate material was dispersed in 100 ml of acetic acid, ten drops of concentrated sulfuric acid were added thereto and reflux was conducted for 4 hours. The resulting solid was filtered, washed with ethanol, and vacuum dried to produce 20 g of amine (97% yield). MS: [M+H]+=366.

PREPARATION EXAMPLE 3

Preparation of a Starting Material Represented by Formula c

A compound of Formula a (9.00 g, 22.5 mmol), 1-iodonaphthalene (11.4 g, 45.0 mmol), potassium carbonate (6.22 g, 45.0 mmol), copper iodide (214 mg, 1.13 mmol), and xylene (250 ml) were heated in a nitrogen atmosphere overnight. After cooling to normal temperature was conducted, a product was extracted with ethyl acetate, water was removed with anhydrous magnesium sulfate, and the solvent was removed at a reduced pressure. The resulting product was passed through a silica gel column using a hexane solvent to produce a compound, the solvent was removed at a reduced pressure, and vacuum drying was conducted to produce the compound of Formula b (5.0 g, 42% yield). MS: $[M+H]^+=$ 527.

PREPARATION EXAMPLE 4

Preparation of a Starting Material Represented by Formula d

A compound of Formula a (8.23 g, 22.5 mmol), iodobenzene (9.18 g, 45 mmol), potassium carbonate (6.22 g, 45.0 mmol), copper iodide (214 mg, 1.13 mmol), and xylene (250 ml) were heated in a nitrogen atmosphere overnight. After cooling to normal temperature was conducted, a product was extracted with ethyl acetate, water was removed with anhydrous magnesium sulfate, and the solvent was removed at a reduced pressure. The resulting product was passed through a silica gel column using a hexane solvent to produce a compound, the solvent was removed at a reduced pressure, and vacuum drying was conducted to produce the compound of Formula b (5.2 g, 47% yield). MS: $[M+H]^+=493$.

PREPARATION EXAMPLE 5

Preparation of a Starting Material Represented by Formula e 1) 5.08 ml of diphenylamine (30 mmol), 5.6 ml of 1-bromo-2-iodobenzene (45 mmol), 2.29 g of copper (36 mmol), and 4.98 g of potassium carbonate (36 mmol) were refluxed for 5 days. After cooling, extraction was conducted with water and ethyl acetate, water was removed with anhydrous magnesium sulfate, and a column separation process was conducted using n-hexane. Ethanol was added to achieve solidification, thereby creating 4.4 g of product (45% yield). MS: $[M+H]^+=323$.

2) 1.36 g of compound produced in 1) (4.19 mmol) were dissolved in 15 ml of THF in a dried flask, and a dry ice/acetone bath was provided therein. 6.18 ml (2.5 eq) of t-butyllithium (1.7 M pentane solution) were dropped thereon for 30 min and stirring was conducted for an additional 1 hour. 1.18 g of 2,7-dibromo-9-fluorenone (3.49 mmol) were dissolved in 20 ml of THF and then injected using a syringe into a reaction solution, and stirring was conducted for an additional 1 hour. After the stirring at normal temperature for the additional 1 hour, a saturated $NH_4Cl$ aqueous solution was added thereto and then stirred for 30 min. Extraction was conducted with water and ethyl acetate, water was removed with anhydrous magnesium sulfate, and vacuum drying was carried out to create a product.

3) The unpurified compound produced in 2) was dissolved in 5 ml of acetic acid, 5 drops of concentrated sulfuric acid were loaded therein, and stirring was conducted at 60° C. for one day. After cooling, filtration was conducted, washing was conducted using water and a 5% $NaHCO_3$ aqueous solution, and a column separation process was conducted using a solution of n-hexane and ethyl acetate at a ratio of 9:1. Ethanol was added to the resulting substance to achieve solidification, filtration was conducted, and vacuum drying was conducted to create 1.76 g of product (89.2%). MS: $[M+H]^+=566$.

PREPARATION EXAMPLE 6

Preparation of a Starting Material Represented by Formula f 1) 2.0 g of 4-aminobiphenyl (12 mmol) and 2.74 g of 4-bromobiphenyl (12.0 mmol) were dissolved in 50 ml of xylene, 1.72 g of sodium tert-butoxide (18 mmol), 0.11 g of tris(dibenzylideneacetone)dipalladium(0) (0.12 mmol), and 0.036 g of tri-t-butylphosphine (0.18 mmol) were added thereto, and reflux was conducted in a nitrogen atmosphere for 3 hours. Distilled water was loaded in a reaction solution to complete a reaction, an organic layer was extracted, and water was removed with anhydrous magnesium sulfate. The solvent was removed at a reduced pressure, recrystallization was conducted using hexane, and vacuum drying was conducted to create 2.2 g of product (57% yield). MS: $[M+H]^+=$ 322.

2) 2.2 g of compound produced in 1) (6.8 mmol), 1.25 ml of 1-bromo-2-iodobenzene (10 mmol), 1.2 g of potassium carbonate (8.8 mmol), and 0.56 g of copper (8.8 mmol) were refluxed in 5 ml of nitrobenzene in a nitrogen atmosphere for 30 hours, and then cooled to normal temperature. THF was added thereto, stirring was conducted for 30 min, an insoluble solid was filtered and thus removed, and the solvent was removed at a reduced pressure. A column separation process was conducted at a ratio of n-hexane/toluene of 3:1, recrystallization was conducted using ethanol, and vacuum drying was conducted to produce 2.4 g of compound (yield 74%). MS: $[M+H]^+=477$.

3) 2.30 g of compound produced in 2) (4.83 mmol) were dissolved in 30 ml of THF, and 5.68 ml (9.66 mmol) of t-BuLi (1.7 M pentane solution) were dropped thereon at −78° C. for 30 min. After stirring was conducted for 2 hours, 1.36 g of 2,7-dibromo-9-fluorenone compound (4.03 mmol), dissolved in 8 ml of THF, were added thereto. After stirring was conducted at the same temperature for 2 hours, a cooling bath (dry ice/acetone) was removed and stirring was conducted at normal temperature for 1 hour. 16 ml of saturated ammonium chloride aqueous solution were added thereto and stirring was conducted for 30 min to complete a reaction. A product was extracted with ethyl acetate and solidification was achieved using ethanol to produce a compound. The compound was vacuum dried and then dissolved in 5 ml of acetic acid, 5 drops of concentrated sulfuric acid solution were added thereto, and stirring was conducted at 60° C. overnight. After cooling to normal temperature, a solvent was removed at a reduced pressure and an organic layer was extracted with ethyl acetate. Byproducts contained in the product were removed through a column separation process using n-hexane and tetrahydrofuran at a ratio of 4:1. The product was recrystallized with ethanol and vacuum dried to create 0.77 g of product (27%). MS: [M+H]$^+$=718.

PREPARATION EXAMPLE 7

Preparation of a Starting Material Represented by Formula g 1) 1.97 g of 4,4-ditolylamine (10 mmol), 1.87 ml of 1-bromo-2-iodobenzene (15 mmol), 95 mg of copper iodide (0.5 mmol), and 4.15 g of potassium carbonate (30 mmol) were added to 100 ml of xylene and refluxed for 1 week. After cooling, water was added thereto, extraction was conducted with ethyl acetate, water was removed with anhydrous magnesium sulfate, and a column separation process was conducted using only n-hexane to create 2.219 g of product (yield 63%). MS: [M]$^+$=353.

3) The resulting compound (428 mg, 1.21 mmol) was dissolved in 6 ml of purified THF in a dried flask and a dry ice/acetone bath was provided therein. 1.43 ml of t-BuLi (1.7 M pentane solution, 2.43 mmol) were dropped thereon for 30 min and stirring was conducted at the same temperature for an additional 1 hour. A 2,7-dibromo-9-fluorenone compound (338 mg, 1.00 mmol) was dissolved in 6 ml of THF and then injected using a syringe into a reaction solution, and stirring was conducted for an additional 1 hour. After the stirring at normal temperature for the additional 1 hour, a saturated ammonium chloride aqueous solution was added thereto to complete the reaction, and then stirring was conducted for 30 min. Extraction was conducted with ethyl acetate, water was removed with anhydrous magnesium sulfate, and vacuum drying was carried out.

4) The compound produced in 3) was dissolved in 5 ml of acetic acid, 5 drops of concentrated sulfuric acid were loaded thereon, and stirring was conducted at 60° C. for one day. After cooling to normal temperature, filtration was conducted, washing was conducted using water and a 5% sodium bicarbonate aqueous solution, and a column separation process was conducted using a solution of n-hexane and tetrahydrofuran at a ratio of 9:1. Ethanol was used to achieve solidification, and filtration and drying were conducted (528 mg, yield 89%). MS: [M+H]$^+$=594.

PREPARATION EXAMPLE 8

Preparation of a Starting Material Represented by Formula h 1) 2.28 ml of m,m'-ditolylamine (12 mmol), 2.26 ml of 1-bromo-2-iodobenzene (18.0 mmol), 991 mg of copper (1.3 eq), 2.16 g of potassium carbonate (15.6 mmol), and 1 ml of nitrobenzene were refluxed for 3 days. After cooling, nitrobenzene was distilled at a reduced pressure and thus removed, extraction was conducted with water and ethyl acetate, and water was removed from an organic layer using anhydrous magnesium sulfate. After the organic solvent was removed, a column separation process was conducted using a solvent of n-hexane and ethyl acetate at a ratio of 50:1, and ethanol was used to achieve solidification. MS: [M+H]$^+$=353 (—Br), 400 (—I). Yield: 68% (2.9 g).

2) 779 mg of compound produced in 1) (2.21 mmol) were dissolved in 8 ml of purified THF in a dried flask, and a dry ice/acetone bath was provided therein. 2.6 ml (4.4 mmol) of t-butyllithium (1.7 M pentane solution) were dropped thereon for 30 min and stirring was conducted for an additional 1 hour. 0.622 g of 2,7-dibromo-9-fluorenone (1.83 mmol) were dissolved in 9 ml of THF and then injected using a syringe into a reaction solution, and stirring was conducted at the same temperature for an additional 1 hour. After the stirring at normal temperature for the additional 1 hour, a saturated ammonium chloride aqueous solution was added thereto and then stirred for 30 min. Extraction was conducted with water and ethyl acetate, water was removed from an organic layer using anhydrous magnesium sulfate, and vacuum drying was carried out.

3) The unpurified compound produced in 2) was dissolved in 5 ml of acetic acid, 5 drops of concentrated sulfuric acid were added thereto, and stirring was conducted at 60° C. for one day. After cooling, filtration was conducted, washing was conducted using water and a 5% NaHCO$_3$ aqueous solution, and a column separation process was conducted using a solution of n-hexane and ethyl acetate at a ratio of 9:1. Ethanol was used for solidification, and filtration and vacuum drying were conducted. MS: [M+H]$^+$=594. Yield: 73.9% (0.807 g).

PREPARATION EXAMPLE 9

Preparation of a Starting Material Represented by Formula i 1) 2-bromoaniline (800 mg, 4.70 mmol), 1-tert-butyl-4-iodobenzene (1 ml, 5.64 mmol), potassium hydroxide (1.06 g, 18.8 mmol), copper chloride (19 mg, 0.16 mmol), 1,10-phenanthroline (34 mg, 0.16 mmol), and xylene (16 ml) were heated in a nitrogen atmosphere overnight. After the resulting reactants were cooled to normal temperature, a product was extracted with ethyl acetate, water was removed with anhydrous magnesium sulfate, and the solvent was removed at a reduced pressure. The resulting product was passed through a silica gel column using a hexane solvent to produce secondary amine and tertiary amine. A mixture of secondary amine and tertiary amine was vacuum dried, added to toluene (15 ml) along with 1-tert-butyl-4-iodobenzene (0.8 mL, 4.42 mmol), copper iodide (35 mg, 0.18 mmol), and potassium carbonate (763 mg, 5.52 mmol), and heated in a nitrogen atmosphere overnight. They were cooled to normal temperature and extracted with ethyl acetate, water was removed with anhydrous magnesium sulfate, and the solvent was removed at a reduced pressure. The product was passed through a silica gel column using a hexane solvent, the solvent was removed at a reduced pressure, and vacuum drying was conducted to produce a desired white solid (0.67 g, 33%). MS: [M+H]$^+$=437.

2) 0.5 g of compound produced in 1) (1.2 mmol) were dissolved in 6 ml of purified THF in a dried flask, and a dry ice/acetone bath was provided therein. t-BuLi (1.7 M pentane solution, 1.35 ml, 2.3 mmol) was dropped thereon at −78° C. for 30 min. After the reactants were stirred for 1 hour, 338 mg of 2,7-dibromo-9-fluorenone (1 mmol) were dissolved in 5 ml of THF and then injected using a syringe into a reaction solution, and stirring was conducted at the same temperature for 1 hour. A dry ice/acetone bath was removed and stirring was conducted at normal temperature for 1 hour. Saturated ammonium chloride aqueous solution (10 ml) was added thereto and stirring was conducted for 30 min to complete a reaction. The resulting product was extracted with ethyl acetate and a column separation process was conducted using a solvent of n-hexane and ethyl acetate at a ratio of 9:1 to produce a compound.

3) The compound produced in 2) was vacuum dried and dissolved in acetic acid (5 ml), a concentrated sulfuric acid solution (3 drops) was added thereto, and stirring was conducted at 60° C. for one day. After the reactants were cooled to normal temperature, a product was filtered using a filter paper and washed with water. Byproducts contained in the product were removed through a column separation process using a solvent of n-hexane and ethyl acetate at a ratio of 9:1, and vacuum drying was conducted to create 0.31 g of product (yield 36%). MS: [M+H]$^+$=678.

EXAMPLE 1

Preparation of the Compound Represented by Formula 1

After 5.02 g of the compound of Formula e (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) we re added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 1 (5.2 g, yield 78.9%). MS: [M+H]$^+$=742.

EXAMPLE 2

Preparation of the Compound Represented by Formula 2

After 4.68 g of compound of Formula c (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 2 (5.1 g, yield 72.5%). MS: [M+H]$^+$=793.

EXAMPLE 3

Preparation of the Compound Represented by Formula 3

After 4.68 g of the compound of Formula c (8.88 mmol) and 2.34 g of N-phenyl-1-naphthylamine (10.7 mmol) were dissolved in 120 ml of toluene, 2.90 g of sodium-tert-butoxide (30.2 mmol), 0.12 g of bis(dibenzylidene acetone)palladium (0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 3 (5.6 g, yield 71%). MS: [M+H]$^+$=893.

EXAMPLE 4

Preparation of the Compound Represented by Formula 4

After 5.28 g of the compound of Formula g (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 4 (4.9 g, yield 71.7%). MS: [M+H]$^+$=771.

EXAMPLE 5

Preparation of the Compound Represented by Formula 5

After 5.27 g of the compound of Formula h (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 5 (5.0 g, yield 73%). MS: [M+H]$^+$=771.

EXAMPLE 6

Preparation of the Compound Represented by Formula 6

After 6.02 g of the compound of Formula i (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 6 (5.6 g, yield 73.8%). MS: [M+H]$^+$=855.

EXAMPLE 7

Preparation of the Compound Represented by Formula 7

After 6.37 g of the compound of Formula f (8.88 mmol) and 1.81 g of diphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 7 (6.2 g, yield 77%). MS: $[M+H]^+=895$.

EXAMPLE 8

Preparation of the Compound Represented by Formula 8

After 4.37 g of the compound of Formula d (8.88 mmol) and 2.34 g of N-phenyl-1-naphthylamine (10.7 mmol) were dissolved in 120 ml of toluene, 2.90 g of sodium-tert-butoxide (30.2 mmol), 0.12 g of bis(dibenzylidene acetone)palladium (0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 8 (5.2 g, yield 86.8%). MS: $[M+H]^+=675$.

EXAMPLE 9

Preparation of the Compound Represented by Formula 9

1) Synthesis of arylamine (1,4-naphthylbiphenylamine) to produce the compound represented by Formula 9: 1-aminonaphthalene (7.4 g, 51.48 mmol) and 4-bromobiphenyl (12 g, 51.48 mmol) were dissolved in 200 ml of toluene, and bis (dibenzylidene acetone)palladium(0) (Pd(dba)$_2$, 0.89 g, 1.54 mmol), 50 wt % tri-tert-butylphosphine (0.60 ml, 1.54 mmol), and sodium-tert-butoxide (9.90 g, 103.0 mmol) were added thereto. Reflux was conducted in a nitrogen atmosphere for 2 hours, and distilled water was added to the reaction solution to complete the reaction. The organic layer was extracted, a column separation process was conducted using a developing solvent of n-hexane and tetrahydrofuran (n-hexane/THF=15/1), stirring was conducted using petroleum ether, and vacuum drying was conducted to produce arylamine (6.3 g, yield 42%). MS: $[M+H]^+=295$.

2) After 4.37 g of the compound of Formula d (8.88 mmol) and 3.16 g of naphthylbiphenylamine (10.7 mmol) were dissolved in 120 ml of toluene, 2.90 g of sodium-tert-butoxide (30.2 mmol), 0.12 g of bis(dibenzylidene acetone)palladium (0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 9 (4.5 g, yield 67.5%). MS: $[M+H]^+=751$.

EXAMPLE 10

Preparation of the Compound Represented by Formula 10

1) Synthesis of arylamine (4-(N-phenyl-N-phenylamino)phenyl-1-phenylamine) to produce the compound represented by Formula 10: 13.5 g of 4-bromophenyl-N-phenyl-N-phenylamine (41.6 mmol) and 3.98 ml of aniline (43.7 mmol) were dissolved in 120 ml of toluene, 10.00 g of sodium-tert-butoxide (104.1 mmol), 0.48 g of bis(dibenzylidene acetone)palladium(0) (0.83 mmol), and 0.58 ml of 50 wt % tri-tert-butylphosphine toluene solution (1.25 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (9.6 g, yield 69%). MS: $[M+H]^+=336$.

2) 4.68 g of compound of Formula c (8.88 mmol) and 6.86 g of 4-(N-phenyl-N-phenylamino)phenyl-1-phenylamine (20.4 mmol) were dissolved in 120 ml of toluene, 5.89 g of sodium-tert-butoxide (61.3 mmol), 0.24 g of tris(dibenzylidene acetone)dipalladium(0) (0.41 mmol), and 0.25 ml of 50 wt % tri-tert-butylphosphine toluene solution (0.61 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 10 (5.2 g, yield 52%). MS: $[M+H]^+=1127$.

EXAMPLE 11

Preparation of the Compound Represented by Formula 11

1) Synthesis of arylamine (4-(N-phenyl-N-phenylamino)phenyl-1-naphthylamine) to produce the compound represented by Formula 11: 15.0 g of 4-bromophenyl-N-phenyl-N-phenylamine (46.3 mmol) and 7.29 g of 1-naphthylamine (50.9 mmol) were dissolved in 200 ml of toluene, 13.34 g of sodium-tert-butoxide (138.8 mmol), 0.53 g of bis(dibenzylidene acetone)palladium(0) (0.93 mmol), and 0.56 ml of 50 wt % tri-tert-butylphosphine toluene solution (1.39 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (13 g, yield 73%). MS: $[M+H]^+=386$.

2) 4.68 g of compound of Formula c (8.88 mmol) and 7.88 g of 4-(N-phenyl-N-phenylamino)phenyl-1-naphthylamine (20.4 mmol) were dissolved in 120 ml of toluene, 5.89 g of sodium-tert-butoxide (61.3 mmol), 0.24 g of tris(dibenzylidene acetone)dipalladium(0) (0.41 mmol), and 0.25 ml of 50 wt % tri-tert-butylphosphine toluene solution (0.61 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 11 (5.4 g, yield 50%). MS: $[M+H]^+=1227$.

EXAMPLE 12

Preparation of the Compound Represented by Formula 12

1) Synthesis of arylamine (4-(N-phenyl-N-phenylamino)phenyl-1-biphenylamine) to produce the compound represented by Formula 12: 17.4 g of 4-bromophenyl-N-phenyl-N-phenylamine (53.7 mmol) and 9.99 g of 4-aminobiphenyl (59.0 mmol) were dissolved in 250 ml of toluene, 17.02 g of sodium-tert-butoxide (177.1 mmol), 0.68 g of bis(dibenzylidene acetone)palladium(0) (1.2 mmol), and 0.72 ml of 50 wt % tri-tert-butylphosphine toluene solution (1.8 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (16 g, yield 73%). MS: $[M+H]^+=412$.

2) 4.68 g of compound of Formula c (8.88 mmol) and 8.42 g of 4-(N,N-diphenylamino)phenyl-4-biphenylamine (20.4 mmol) were dissolved in 120 ml of toluene, 5.89 g of sodium-tert-butoxide (61.3 mmol), 0.24 g of tris(dibenzylidene acetone)dipalladium(0) (0.41 mmol), and 0.25 ml of 50 wt % tri-tert-butylphosphine toluene solution (0.61 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 12 (5.2 g, yield 45.8%). MS: $[M+H]^+=1279$.

EXAMPLE 13

Preparation of the Compound Represented by Formula 13

1) Synthesis of arylamine (4-(N-phenyl-N-naphthylamino)phenyl-1-biphenylamine) to produce the compound represented by Formula 13: 14.0 g of 4-bromophenyl-N-phenyl-N-naphthylamine (37.4 mmol) and 6.96 g of 4-aminobiphenyl (41.2 mmol) were dissolved in 200 ml of toluene, and 0.47 g of bis(dibenzylidene acetone)palladium(0) (0.82 mmol), 0.50 ml of 50 wt % tri-tert-butylphosphine toluene solution (1.2 mmol), and 11.86 g of sodium-tert-butoxide (123.4 mmol) were added thereto. After reflux was conducted in a nitrogen atmosphere for 2 hours, distilled water was added to the reaction solution to complete the reaction. The organic layer was extracted, a column separation process was conducted using a developing solvent of n-hexane and tetrahydrofuran at a ratio of 10:1, stirring was conducted using petroleum ether, and vacuum drying was conducted to produce an arylamine connection group (7.5 g, yield 43%). MS: $[M+H]^+=462$.

2) 4.68 g of compound of Formula c (8.88 mmol) and 9.44 g of 4-(N-phenyl-1-naphthylamino)phenyl-4-biphenylamine (20.4 mmol) were dissolved in 120 ml of toluene, 5.89 g of sodium-tert-butoxide (61.3 mmol), 0.24 g of tris(dibenzylidene acetone)dipalladium(0) (0.41 mmol), and 0.25 ml of 50 wt % tri-tert-butylphosphine toluene solution (0.61 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 4:1, stirring was conducted using petroleum ether, and vacuum drying was conducted to produce the compound of Formula 13 (5.5 g, yield 45%). MS: $[M+H]^+=1379$.

EXAMPLE 14

Preparation of the Compound Represented by Formula 14

1) Synthesis of arylamine (4-(N,N-diphenylamino)-biphenyl-N-phenylamine) to produce the compound represented by Formula 14: 4.00 g of 4-chlorobiphenyl-N,N-diphenylamine (11.2 mmol) and 1.13 ml of aniline (12.4 mmol) were dissolved in 100 ml of toluene, 2.70 g of sodium-tert-butoxide (28.1 mmol), 0.13 g of bis(dibenzylidene acetone)palladium(0) (0.23 mmol), and 0.17 ml of 50 wt % tri-tert-butylphosphine toluene solution (0.34 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.8 g, yield 81%). MS: $[M+H]^+=413$.

2) 4.369 g of compound of Formula d (8.88 mmol) and 4.414 g of 4-(N,N-diphenylamino)-biphenyl-N-phenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 14 (5.2 g, yield 65%). MS: $[M+H]^+=869$.

EXAMPLE 15

Preparation of the Compound Represented by Formula 15

1) Synthesis of arylamine (4-(N,N-diphenylamino)-biphenyl-N-biphenylamine) to produce the compound represented by Formula 15: 8.80 g of 4-chlorobiphenyl-N,N-diphenylamine (24.7 mmol) and 6.28 g of 4-aminobiphenyl (37.1 mmol) were dissolved in 200 ml of toluene, 5.94 g of sodium-tert-butoxide (61.8 mmol), 0.43 g of bis(dibenzylidene acetone)palladium(0) (0.74 mmol), and 0.61 ml of 50 wt % tri-tert-butylphosphine toluene solution (1.24 mmol) were added thereto, and reflux was conducted in a nitrogen atmosphere for 5 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (7.0 g, yield 58%). MS: [M+H]$^+$=489.

2) 4.37 g of compound of Formula d (8.88 mmol) and 5.23 g of 4-(N,N-diphenylamino)-biphenyl-N-biphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 15 (5.4 g, yield 64%). MS: [M+H]$^+$=943.

EXAMPLE 16

Preparation of the Compound Represented by Formula 16

1) Synthesis of arylamine (4-(N-phenyl-N-naphthylamino)-biphenyl-N-biphenylamine) to produce the compound represented by Formula 16: 4.08 g of 4-chlorobiphenyl-N-phenyl-N-naphthylamine (10.1 mmol) and 2.55 g of 4-aminobiphenyl (15.1 mmol) were dissolved in 100 ml of toluene, 2.90 g of sodium-tert-butoxide (30.2 mmol), 0.17 g of bis(dibenzylidene acetone)palladium(0) (0.30 mmol), and 0.26 ml of 50 wt % tri-tert-butylphosphine toluene solution (0.53 mmol) were added thereto, and reflux was conducted in a nitrogen atmosphere for 7 hours. Distilled water was added to the reaction solution to complete the reaction, and the organic layer was extracted. A column separation process was conducted using a solvent of n-hexane and tetrahydrofuran at a ratio of 10:1, stirring was conducted using petroleum ether, and vacuum drying was conducted to produce an arylamine connection group (3.8 g, yield 70%). MS: [M+H]$^+$=539.

2) 4.369 g of compound of Formula d (8.88 mmol) and 5.76 g of 4-(N-phenyl-N-naphthylamino)-biphenyl-N-biphenylamine (10.7 mmol) were dissolved in 120 ml of toluene, 2.90 g of sodium-tert-butoxide (30.2 mmol), 0.12 g of bis(dibenzylidene acetone)palladium(0) (0.21 mmol), and 0.16 ml of 50 wt % tri-tert-butylphosphine toluene solution (0.32 mmol) were added thereto, and reflux was conducted in a nitrogen atmosphere for 2 hours. Distilled water was added to the reaction solution to complete the reaction, and the organic layer was extracted. A column separation process was conducted using a solvent of n-hexane and tetrahydrofuran at a ratio of 9:1, stirring was conducted using petroleum ether, and vacuum drying was conducted to produce the compound of Formula 16 (4.9 g, yield 56%). MS: [M+H]$^+$=995.

EXAMPLE 17

Production of an Organic Light Emitting Device

A glass substrate (corning 7059 glass), on which ITO (indium tin oxide) was applied to a thickness of 1000 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. The substrate was dry washed using nitrogen plasma under a pressure of 14 mtorr at 85 W for 5 min, and then transported to a vacuum evaporator.

Hexanitrile hexaazatriphenylene (hereinafter, referred to as "HAT") of the following Formula was vacuum deposited to a thickness of 500 Å by heating on a transparent ITO electrode, which was prepared through the above procedure, so as to form an anode including an ITO conductive layer and an N-type organic material.

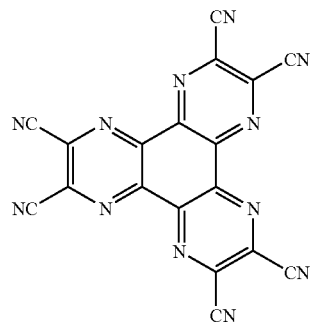

[HAT]

The compound of Formula 6 (400 Å) was vacuum deposited thereon to form a hole transport layer. Alq3 was vacuum deposited to a thickness of 300 Å on the hole transport layer to form a light emitting layer. An electron transport layer material of the following Formula was deposited to a thickness of 200 Å on the light emitting layer to form an electron transport layer.

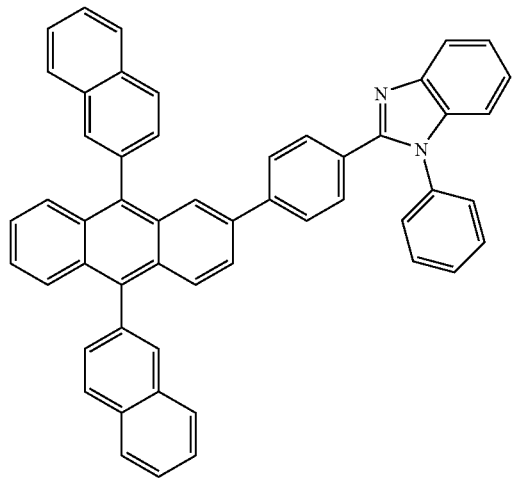

Electron transport layer material

Lithium fluoride (LiF) having a thickness of 12 Å and aluminum having a thickness of 2000 Å were sequentially deposited on the electron transport layer to form a cathode.

277

In the above procedure, the deposition speed of an organic material was maintained at 0.3-0.8 Å/sec. Furthermore, lithium fluoride and aluminum were deposited at speeds of 0.3 Å/sec and 1.5-2.5 Å/sec, respectively, on the cathode. During the deposition, a vacuum was maintained at $1-3\times10^{-7}$.

The resulting device had an electric field of 5.47 V at a forward current density of 100 mA/cm², and emitted green light at a light efficiency of 2.91 lm/W. The operation and light emission of the device at the above-mentioned actuating voltage mean that the compound of Formula 6, which formed the layer between the hole injection layer and the light emitting layer, functions to transport holes.

EXAMPLE 18

Production of an Organic Light Emitting Device

The procedure of example 1 was repeated to produce an organic light emitting device except that a HAT thin film (80 Å: used to improve interfacial characteristics) was formed on an ITO transparent electrode which was prepared through the same procedure as example 17 and a compound of Formula 6 was deposited thereon to a thickness of 1100 Å to form a layer for both injecting and transporting holes.

The resulting device had an electric field of 6.75 V at a forward current density of 100 mA/cm², and emitted green light at a light efficiency of 2.19 lm/W. The operation and light emission of the device at the above-mentioned actuating voltage mean that the compound of Formula 1-4 functions to inject and transport the holes, and it can be seen that, even when the layer for both injecting and transporting the holes is formed using the compound of the present invention, it is possible to assure actuation at low voltage and excellent light efficiency.

INDUSTRIAL APPLICABILITY

The compound of the present invention can be used as an organic material layer material, particularly, hole injection and/or transport materials in an organic light emitting device, and when applied to an organic light emitting device it is possible to reduce the actuating voltage of the device, to improve the light efficiency thereof, and to improve the lifespan of the device through the thermal stability of the compound.

What is claimed is:
1. A compound represented by Formula 1:

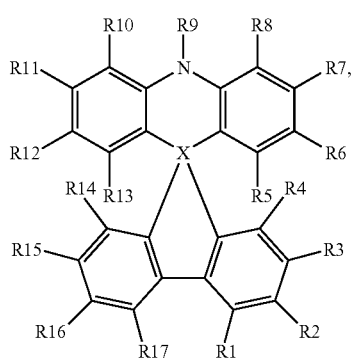

Formula 1 wherein X is C;
R1 to R8 and R10 to R17 are each independently selected from the group consisting of hydrogen; an alkyl group,

278 which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an alkoxy group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an alkenyl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an aryl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; an arylamine group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; a hetero arylamine group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; a heterocyclic group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group and which includes O, N, or S as a heteroatom; an amino group, which is substituted with at least one substituent group selected from the group consisting of an alkyl group, an alkenyl group, a substituted or unsubstituted aryl group, a substituted or unsubstituted arylalkyl group, and a substituted or unsubstituted arylalkenyl group; a nitrile group; a nitro group; a halogen group; an amide group; and an ester group, R1 to R8 and R10 to R17 may form aliphatic or hetero condensation rings along with adjacent groups;

with a proviso that at least one of R1 to R4 and R14 to R17 is the arylamine group, which is unsubstituted or substituted with at least one substituent group selected from the group consisting of the halogen group, the alkyl group, the alkenyl group, the alkoxy group, the substituted or unsubstituted arylamine group, the substituted or unsubstituted aryl group, the substituted or unsubstituted arylalkyl group, the substituted or unsubstituted arylalkenyl group, the substituted or unsubstituted heterocyclic group, the nitrile group, and the acetylene group;

R9 is an aryl group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group; or a heterocyclic group, which is substituted or unsubstituted with at least one substituent group selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and an acetylene group and which includes O, N, or S as a heteroatom; and with a proviso that carbon at an ortho-position of the aryl or heterocyclic group of R9 and R8 or R10 independently may form a condensation ring along with a group selected from the group consisting of O, S, NR, PR, C=O, CRR', and SiRR', wherein R and R' are independently or collectively selected from the group consisting of hydrogen, oxygen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a nitrile group, an amide group, and an ester group, and form a condensation ring to form a spiro compound.

2. The compound as set forth in claim 1, wherein carbon at the ortho-position of the aryl or heterocyclic group of R9 and R8 or R10 independently form a condensation ring along with a group selected from the group consisting of O, S, NR, PR, C=O, CRR', and SiRR'.

3. The compound as set forth in claim 1, wherein any one of R1 to R4 and/or any one of R14 to R17 is a diphenylamine group, a dinaphthylamine group, a dibiphenylamine group, a phenylnaphthylamine group, a phenyldiphetylamine group, a ditolylamine group, a phenyltolylamine group, a carbazolyl group, or a triphenylamine group.

4. The compound as set forth in claim 1, wherein the compound of Formula 1 is any one of following compounds 1 to 16:

[compound 1]

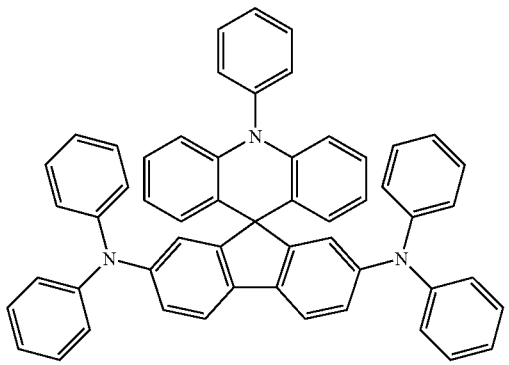

[compound 2]

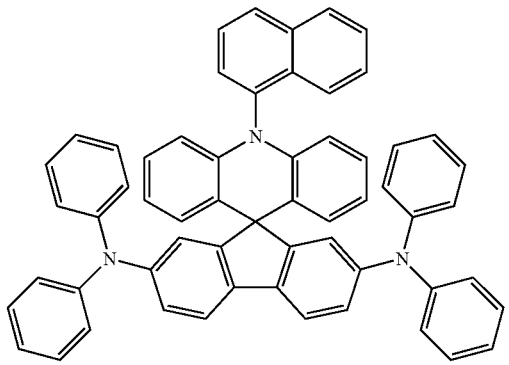

[compound 3]

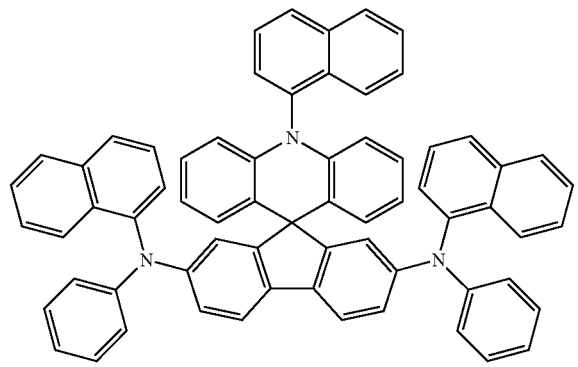

[compound 4]

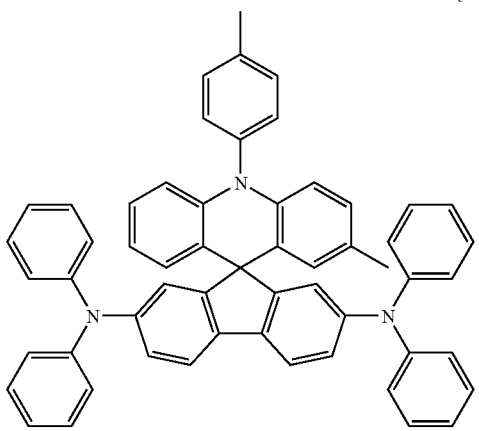

-continued
[compound 5]
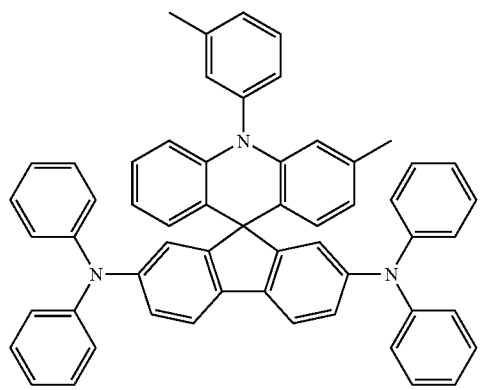
[compound 6]
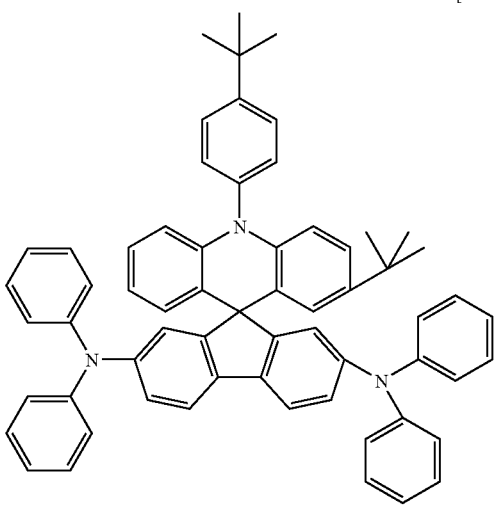
[compound 7]
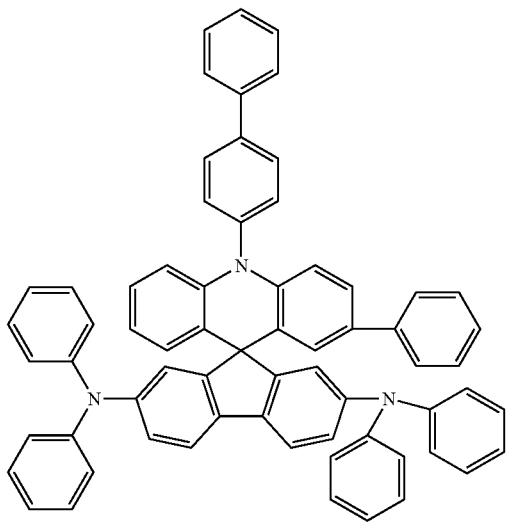
[compound 8]
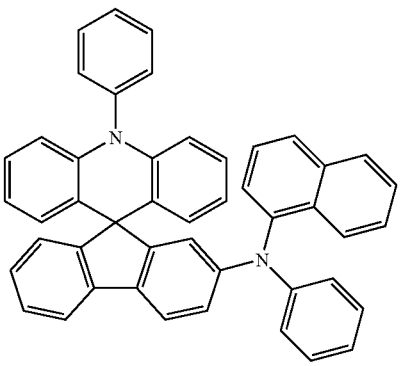
[compound 9]
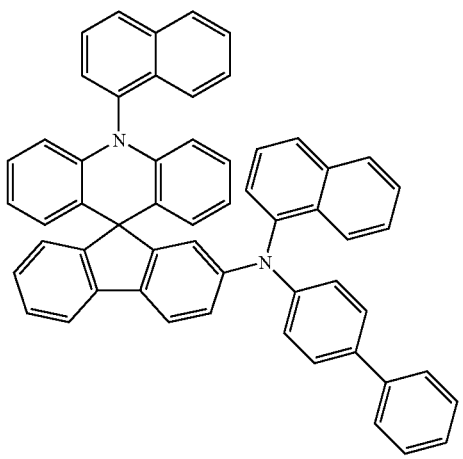

[compound 10]
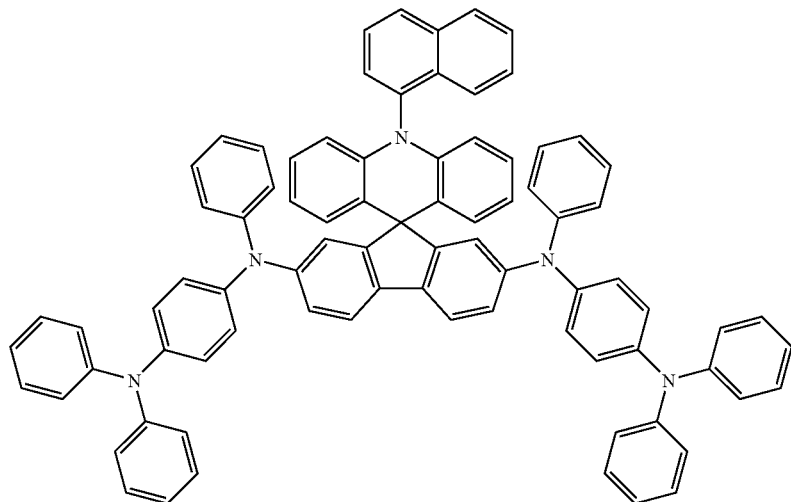
[compound 11]
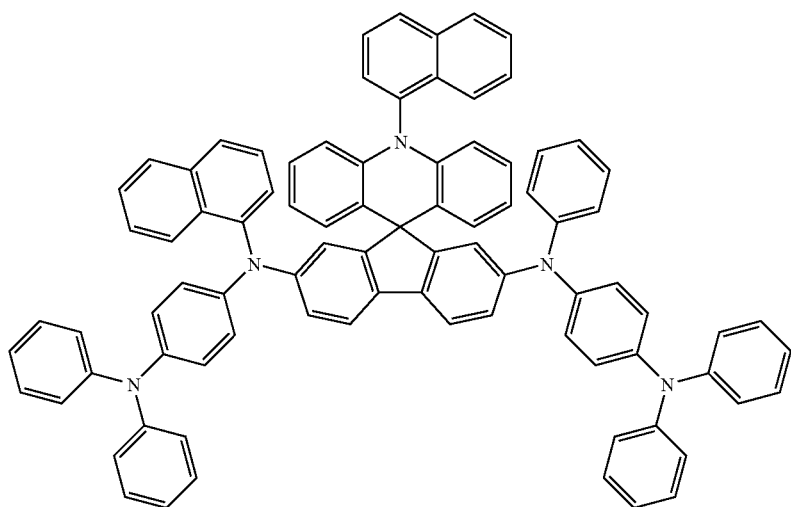
[compound 12]
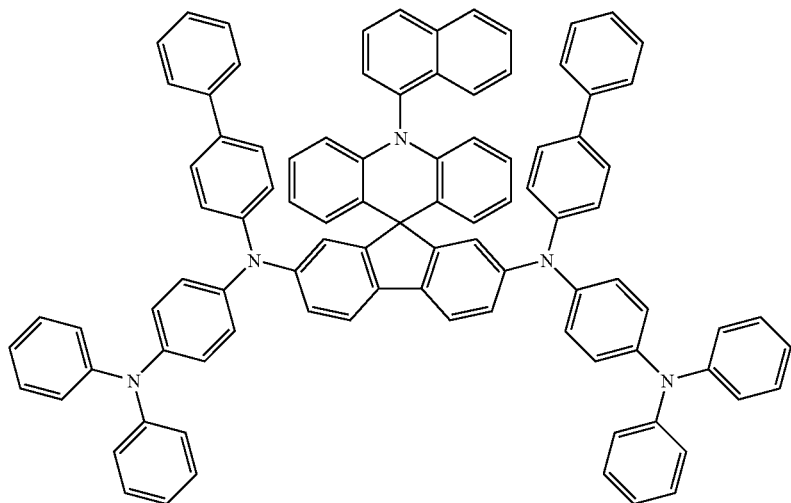

[compound 13]
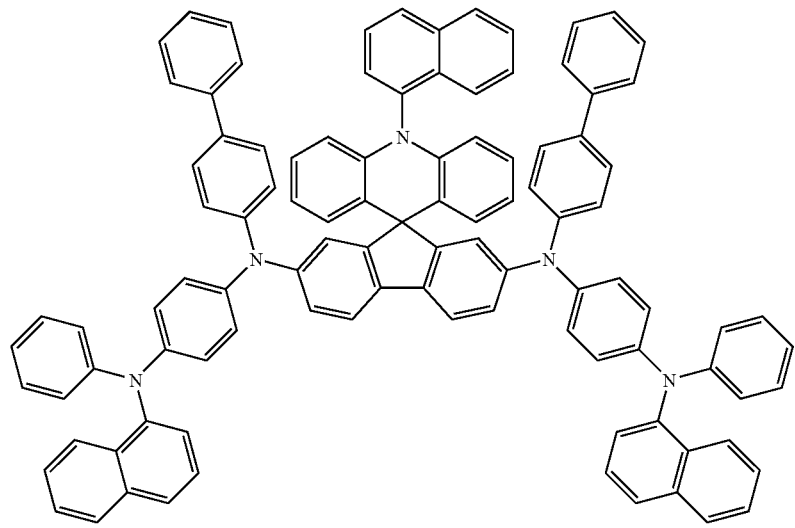
[compound 14]
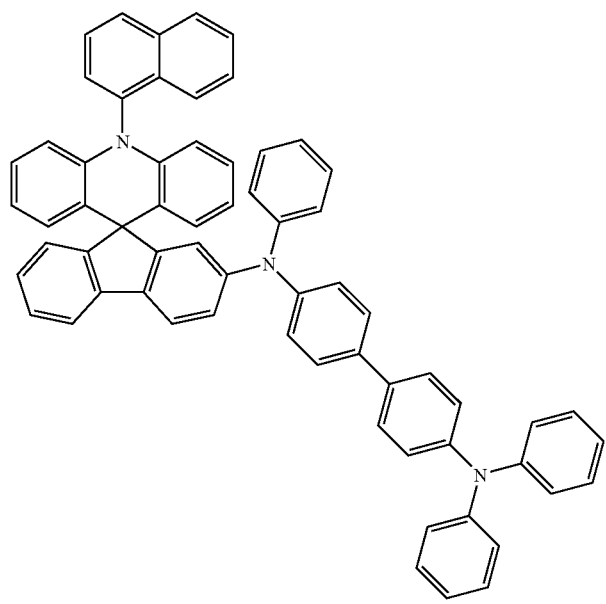

-continued

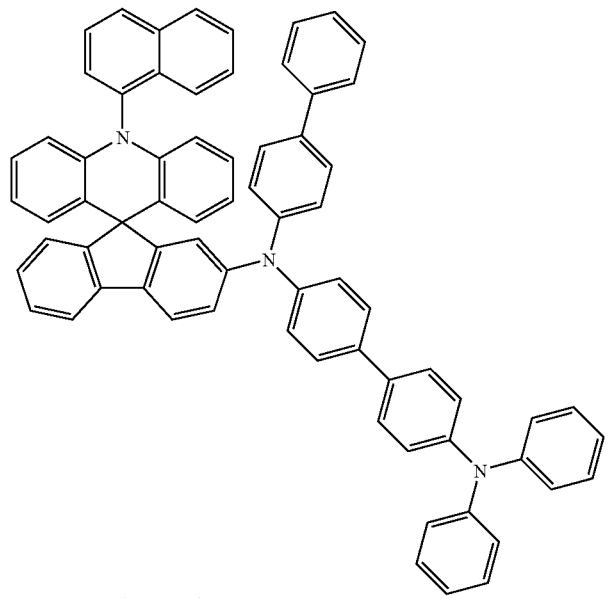

[compound 15]

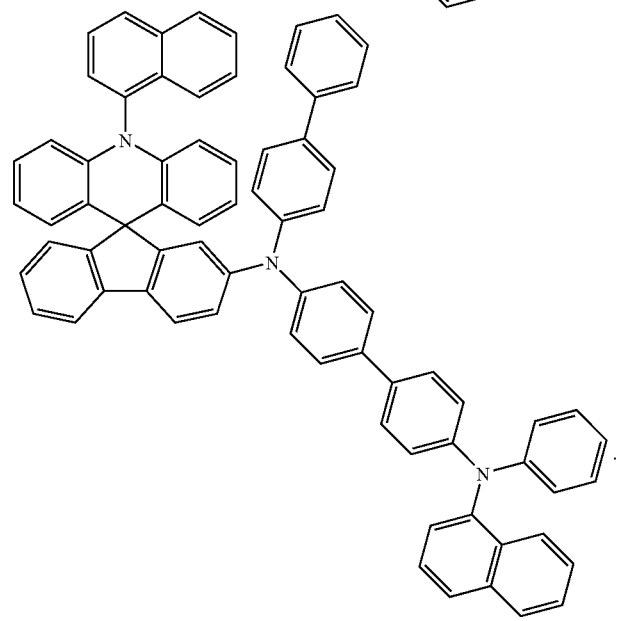

[compound 16]

5. An organic light emitting device, comprising:
a first electrode;
organic material layer(s) comprising a light emitting layer, wherein at least one layer of the organic material layer(s) includes the compound of Formula 1 as set forth in claim 1; and
a second electrode;
wherein the first electrode, the organic material layer(s), and the second electrode form a layered structure.

6. The organic light emitting device as set forth in claim 5, wherein the organic material layer(s) comprise a hole transport layer, and the hole transport layer that includes the compound of Formula 1.

7. The organic light emitting device as set forth in claim 5, wherein the organic material layer(s) comprise a hole injection layer, and the hole injection layer includes the compound of Formula 1.

8. The organic light emitting device as set forth in claim 5, wherein the organic material layer(s) comprise a layer which both injects and transports holes and which includes the compound of Formula 1.

9. The organic light emitting device as set forth in claim 5, wherein the organic material layer(s) comprise a layer which both injects and transports electrons and which includes the compound of Formula 1.

10. The organic light emitting device as set forth in claim 5, wherein the light emitting layer includes the compound of Formula 1.

* * * * *